US009803217B2

(12) United States Patent
Choi et al.

(10) Patent No.: US 9,803,217 B2
(45) **Date of Patent: *Oct. 31, 2017**

(54) VIRAL VECTORS FOR THE TREATMENT OF RETINAL DYSTROPHY

(71) Applicant: Novartis AG, Basel (CH)

(72) Inventors: Vivian Choi, Waltham, MA (US); Chad Eric Bigelow, Somerville, MA (US); Thaddeus Peter Dryja, Milton, MA (US); Seshidhar Reddy Police, Burlington, MA (US)

(73) Assignee: NOVARTIS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/881,960

(22) Filed: Oct. 13, 2015

(65) Prior Publication Data

US 2016/0097061 A1 Apr. 7, 2016

Related U.S. Application Data

(63) Continuation of application No. 13/873,558, filed on Apr. 30, 2013, now Pat. No. 9,163,259.

(60) Provisional application No. 61/776,167, filed on Mar. 11, 2013, provisional application No. 61/642,630, filed on May 4, 2012.

(51) Int. Cl.

| | |
|---|---|
| ***C12N 15/63*** | (2006.01) |
| ***C07H 21/04*** | (2006.01) |
| ***C12N 15/86*** | (2006.01) |
| ***A61K 48/00*** | (2006.01) |
| ***A61K 38/17*** | (2006.01) |
| ***C07K 14/47*** | (2006.01) |
| ***C12N 7/00*** | (2006.01) |
| *C12N 15/79* | (2006.01) |

(52) U.S. Cl.

CPC .......... *C12N 15/86* (2013.01); *A61K 38/1709* (2013.01); *A61K 48/005* (2013.01); *A61K 48/0058* (2013.01); *C07K 14/47* (2013.01); *C12N 7/00* (2013.01); *C07H 21/04* (2013.01); *C12N 15/79* (2013.01); *C12N 2750/14143* (2013.01); *C12N 2750/14171* (2013.01); *C12N 2750/14343* (2013.01); *C12N 2750/14345* (2013.01); *C12N 2750/14371* (2013.01); *C12N 2800/22* (2013.01); *C12N 2810/6027* (2013.01); *C12N 2810/85* (2013.01)

(58) Field of Classification Search

CPC .......... C12N 15/86; C12N 2750/14143; C12N 2750/14343; C07H 21/04

USPC .......................... 435/320.1; 536/23.72, 24.1

See application file for complete search history.

(56) References Cited

U.S. PATENT DOCUMENTS

| | | | |
|---|---|---|---|
| 7,339,042 | B2 | 3/2008 | Sullivan et al. |
| 9,163,259 | B2 | 10/2015 | Choi et al. |
| 2004/0208847 | A1 | 10/2004 | Rolling et al. |
| 2005/0090646 | A1 | 4/2005 | Sullivan |
| 2007/0258950 | A1 | 11/2007 | Auricchio et al. |
| 2010/0184838 | A1 * | 7/2010 | Kumar-Singh et al. |
| 2010/0297084 | A1 | 11/2010 | Bennett et al. |
| 2012/0141422 | A1 | 6/2012 | Barkats |

FOREIGN PATENT DOCUMENTS

| | | | |
|---|---|---|---|
| EP | 2287323 | A1 | 2/2011 |
| WO | 00/15822 | A2 | 3/2000 |
| WO | WO 00/15822 | * | 3/2000 |
| WO | 01/92551 | | 12/2001 |
| WO | 2004/084951 | A2 | 3/2004 |
| WO | WO 2004/084951 | A2 * | 10/2004 |
| WO | 2007/078599 | | 7/2007 |
| WO | 2008127675 | A1 | 10/2008 |
| WO | 2011/034947 | A2 | 3/2011 |

OTHER PUBLICATIONS

Aartsen et al.; "GFAP-Driven GFP Expression in Activated Mouse Muller Glial Cells Aligning Retinal Blood Vessels Following Intravitreal Injection of AAV2/6 Vectors" PLoS ONE, vol. 5, Issue 8, e12387: 1-12 (Aug. 2010).

Burstedt et al., Self-reported quality of life in patients with retinitis pigmentosa and maculopathy of Bothnia type. Clin Ophthalmol. Mar. 24, 2010;4:147-54.

Burstedt, et al., Ocular phenotype of bothnia dystrophy, an autosomal recessive retinitis pigmentosa associated with an R234W mutation in the RLBP1 gene. Arch Ophthalmol. Feb. 2001;119(2):260-7.

Choi et al., AAV hybrid serotypes: improved vectors for gene delivery. Curr Gene Ther. Jun. 2005;5(3):299-310.

Choi et al., Production of recombinant adeno-associated viral vectors for in vitro and in vivo use. Curr Protoc Mol Biol. Apr. 2007;Chapter 16:Unit 16.25, Supplement 78.

Demirci et al., A novel compound heterozygous mutation in the cellular retinaldehyde-binding protein gene (RLBP1) in a patient with retinitis punctata albescens. Am J Ophthalmol. Jul. 2004;138(1):171-3.

Eichers et al., Newfoundland rod-cone dystrophy, an early-onset retinal dystrophy, is caused by splice-junction mutations in RLBP1. Am J Hum Genet. Apr. 2002;70(4):955-64.

Ferrari et al., New developments in the generation of Ad-free, high-titer rAAV gene therapy vectors. Nat Med. Nov. 1997;3(11):1295-7.

(Continued)

*Primary Examiner* — Shin Lin Chen

(74) *Attorney, Agent, or Firm* — Sherwin Y. Chan

(57) ABSTRACT

The present invention relates to viral vectors that are capable of delivering a heterologous gene to the retina and in particular delivering RLBP1 to RPE and Müller cells of the retina. The invention also relates nucleic acids useful for producing viral vectors, compositions comprising the viral vectors and uses of the compositions and viral vectors. The invention also relates to methods of delivering and/or expressing a heterologous gene to the retina, improving the rate of dark adaption in a subject and treating RLBP1-associated retinal dystrophy.

12 Claims, 7 Drawing Sheets

(56) References Cited

OTHER PUBLICATIONS

Fishman et al., Novel mutations in the cellular retinaldehyde-binding protein gene (RLBP1) associated with retinitis punctata albescens: evidence of interfamilial genetic heterogeneity and fundus changes in heterozygotes. Arch Ophthalmol. Jan. 2004;122(1):70-5.
Geller et al., "In vitro analysis of promoter activity in Muller cells" Molecular Vision 2008, 14: 691-705 (Apr. 2008).
Giove et al., "Transduction of the inner mouse retina using AAVrh8 and AAVrh10 via intravitreal injection" Experimental Eye Research 91: 652-659 (Nov. 2010).
Golovleva et al., Mutation spectra in autosomal dominant and recessive retinitis pigmentosa in northern Sweden. Adv Exp Med Biol. 2010;664:255-62.
Golovleva et al., Retinitis Pigmentosa in Northern Sweden—From Gene to Treatment. Advances in Ophthalmology. Mar 2012;25:451-72.
Grieger et al., Production and characterization of adeno-associated viral vectors. Nat Protoc. 2006;1(3):1412-28.
He et al., Bothnia dystrophy is caused by domino-like rearrangements in cellular retinaldehyde-binding protein mutant R234W. Proc Natl Acad Sci U S A. Nov. 3, 2009;106(44):18545-50.
Hollander et al., Journal of Clinical Investigation; vol. 120; No. 9: 3042-3053 (Sep. 2010).
Humbert et al. "Homozygous Deletion Related to Alu Repeats in RLBP1 Causes Retinitis Punctata Albescens" IOVS, vol. 47, No. 11: 4719-4724 (Nov. 2006).
Jacobson et al., Safety of recombinant adeno-associated virus type 2-RPE65 vector delivered by ocular subretinal injection. Mol Ther. Jun. 2006;13(6):1074-84.
Katsanis et al., Fundus albipunctatus and retinitis punctata albescens in a pedigree with an R150Q mutation in RLBP1. Clin Genet. Jun. 2001;59(6):424-9.
Klimczak et al.; "A Novel Adeno-Associated Viral Variant for Efficient and Selective Intravitreal Transduction of Rat Muller Cells" PLoS ONE, vol. 4, Issue 10, e7467: 1-10 (Oct. 2009).
Köhn et al., Carrier of R14W in carbonic anhydrase IV presents Bothnia dystrophy phenotype caused by two allelic mutations in RLBP1. Invest Ophthalmol Vis Sci. Jul. 2008;49(7):3172-7.
Lock et al., Rapid, simple, and versatile manufacturing of recombinant adeno-associated viral vectors at scale. Hum Gene Ther. Oct. 2010;21(10):1259-71.
Maw et al., Mutation of the gene encoding cellular retinaldehyde-binding protein in autosomal recessive retinitis pigmentosa. Nat Genet. Oct. 1997;17(2):198-200.
McCarty et al., Adeno-associated virus terminal repeat (TR) mutant generates self-complementary vectors to overcome the rate-limiting step to transduction in vivo. Gene Ther. Dec. 2003;10(26):2112-8.
McCarty, "Self-complementary AAV Vectors; Advances and Applications" www.moleculartherapy.org, vol. 16, No. 10: 1648-1656 (Oct. 2008).
Morimura et al., Recessive mutations in the RLBP1 gene encoding cellular retinaldehyde-binding protein in a form of retinitis punctate albescens. Invest Ophthalmol Vis Sci. Apr. 1999;40(5):1000-4.
Muzyczka et al., Chapter 69: Parvoviridae: The viruses and their replication. Fields Virology. Aug. 2001, 4th Edition. Lippincott Williams & Wilkins. 27 pages.
Naz et al., Mutations in RLBPlassociated with fundus albipunctatus in consanguineous Pakistani families. Br J Ophthalmol. Jul. 2011;95(7):1019-24.
Nojima et al., Clinical features of a Japanese case with Bothnia dystrophy. Ophthalmic Genet. Jun. 2012;33(2):83-8.
Phelan et al., A brief review of retinitis pigmentosa and the identified retinitis pigmentosa genes. Mol Vis. Jul. 8, 2000;6:116-24.
Roman et al., Electroretinographic analyses of Rpe65-mutant rd12 mice: developing an in vivo bioassay for human gene therapy trials of Leber congenital amaurosis. Mol Vis. Sep. 18, 2007;13:1701-10.
Saari et al., Cellular retinaldehyde-binding protein is expressed by oligodendrocytes in optic nerve and brain. Glia. Nov. 1997;21(3):259-68.
Saari et al., Visual cycle impairment in cellular retinaldehyde binding protein (CRALBP) knockout mice results in delayed dark adaptation. Neuron. Mar. 2001;29(3):739-48.
Samulski et al., Rescue of adeno-associated virus from recombinant plasmids: gene correction within the terminal repeats of AAV. Cell. May 1983;33(1):135-43.
Schmidt et al., Adeno-associated virus type 12 (AAV12): a novel AAV serotype with sialic acid-and heparan sulfate proteoglycan-independent transduction activity. J. Virol. Feb. 2008;82(3):1399-406.
Smith et al., A simplified baculovirus-AAV expression vector system coupled with one-step affinity purification yields high-titer rAAV stocks from insect cells. Mol Ther. Nov. 2009;17(11):1888-96.
Travis et al., Diseases caused by defects in the visual cycle: retinoids as potential therapeutic agents. Annu Rev Pharmacol Toxicol. 2007;47:469-512.
Trinklein et al., 2009, GenEmbl Accession No. JB105613, computer printout pp. 8-9.
Vandenberghe et al., Efficient serotype-dependent release of functional vector into the culture medium during adeno-associated virus manufacturing. Hum Gene Ther. Oct. 2010;21(10):1251-7.
Vazquez-Chona et al.; "RIbp1 Promoter Drives Robust Muller Glial GFP Expression in Transgenic Mice" IOVS, vol. 50, No. 8: 3996-4003 (Aug. 2009).
Wang et al., The cone-specific visual cycle. Prog Retin Eye Res. Mar. 2011;30(2):115-28.
Yin et al.; "Intraviteral Injection of AAV2 Transduces Macaque Inner Retina" IOVS, vol. 52, No. 5: 2775-2783 (Apr. 2011).
Yokoi et al.; "Ocular Gene Transfer with Self-Complementary AAV Vectors" IOVS, vol. 48, No. 7: 3324-3328 (Jul. 2007).
Weber Michel et al., "Recombinant adeno-associated virus serotype 4 madiates unique and exclusive long-term transduction of retinal pigmented apithelium in rat, dog, and nonhuman primate after subretinal delivery", Molecular Therapy, 7(6):774-781. (2003).
Database DDBJ/EMBL/GenBank [online], Accession No. BV703725, <http://www.ncbi.nlm.nih.gov/nuccore/209625?sat=4&satkey=58724> Apr. 27, 1993 uploaded, Lefbvre, R.B. et al., Definition:Adeno-associated virus 2 left terminal sequence.Adeno-associated virus 2 right terminal sequence [retrieved on Jan. 17, 2017].

* cited by examiner

Dark adaptation in RLBP1 -/- and +/+ mice.

VIRAL VECTORS FOR THE TREATMENT OF RETINAL DYSTROPHY

RELATED APPLICATIONS

This application is a continuation of U.S. application Ser. No. 13/873,558, filed Apr. 30, 2013, which claims priority to U.S. Provisional Application No. 61/642,630 filed May 4, 2012 and U.S. Provisional Application No. 61/776,167 filed Mar. 11, 2013, the contents of which are incorporated herein by reference in their entireties.

SEQUENCE LISTING

The instant application contains a Sequence Listing which was submitted in ASCII format via EFS-Web on Sep. 18, 2013, in U.S. patent application Ser. No. 13/873,558, and is hereby incorporated by reference in its entirety.

BACKGROUND OF THE INVENTION

Retinitis pigmentosa (RP) refers to a group of inherited degenerations of the photoreceptor cells (rods and cones) of the retina leading to visual loss and blindness. Mutations in any of a wide variety of genes can cause RP, including genes encoding proteins that are involved in phototransduction (the process by which the energy of a photon of light is converted in the photoreceptor cell outer segment into a neuronal signal), the visual cycle (production and recycling of vitamin A in the retina), photoreceptor structure, and transcription factors (Phelan and Bok, 2000).

RLBP1-associated retinal dystrophy is a rare form of RP caused by mutations in the retinaldehyde binding protein 1 (RLBP1) gene on chromosome 15. Mutations in this gene cause absence of or dysfunction of cellular retinaldehyde-binding protein (CRALBP), a protein that is important in the visual cycle (He et al 2009). CRALBP is expressed in retinal pigment epithelium (RPE) and Müller cells, ciliary epithelium, iris, cornea, pineal gland and a subset of oligodendrocytes of the optic nerve and brain (Saari et al 1997). CRALBP accepts 11-cis-retinol from the isomerase RPE65 and acts as a carrier of this substrate for 11-cis-retinol dehydrogenase (RDH5) to convert the substrate into 11-cis-retinal. The rate of chromophore regeneration is severely reduced in the absence of functional CRALBP (Travis et al 2007). The function of CRALBP outside the RPE is not well understood, but it has been suggested that CRALBP in the Müller cells supports a cone-specific visual pathway that permits cone cells to quickly adapt to a wide range of light intensities (Wang and Kefalov 2011).

RLBP1-associated retinal dystrophy is characterized by early severe night blindness and slow dark adaptation, followed by progressive loss of visual acuity, visual fields and color vision leading to legal blindness typically around middle adulthood. The fundus appearance is characterized by yellow or white spots in the retina. The reduction in visual acuity and visual field significantly impacts patients' quality of life (Burstedt and Mönestam, 2010).

The most common RLBP1 mutations leading to RLBP1-associated retinal dystrophy are recessive mutations, designated R234W and M226K (Golovleva I and Burstedt M 2012). RLBP1-associated retinal dystrophy caused by 1 or both of these recessive missense mutations is also known as Bothnia Dystrophy. Several other loss-of-function mutations in the RLBP1 gene have been reported to lead to RLBP1-associated retinal dystrophy. For example, splice-junction mutations in RLBP1 cause rod-cone dystrophy in Newfoundland. Currently there is no treatment available for RLBP1-associated retinal dystrophy (Eichers et al 2002).

The present invention is based in part on the discovery that expression of RLBP1 from recombinant adeno-associated viral vectors (rAAV) having a combination of selected promoter, AAV genome and capsid serotype provides a potent and efficacious treatment for RLBP1-associated retinal dystrophy.

SUMMARY OF THE INVENTION

The present invention relates generally to recombinant viral vectors and methods of using recombinant viral vectors to express proteins in the retina of subjects suffering from retinal diseases and blindness.

The present invention relates to viral vectors that are capable of delivering a heterologous gene to the retina. The present invention also relates to viral vectors that are capable of directing a heterologous gene to RPE and Müller cells of the retina. The present invention further relates to viral vectors that are recombinant adeno-associated viral vectors (rAAV). In certain embodiments the rAAV viral vector may be selected from among any AAV serotype known in the art, including, without limitation, AAV1-AAV12. In certain embodiments, the rAAV vector capsid is an AAV2 serotype. In certain other embodiments, the rAAV vector capsid is an AAV8 serotype.

The invention relates, in part, to viral vectors carrying a single stranded vector genome. In the single stranded viral vector, the vector genome can include a 5' ITR, a recombinant nucleotide sequence comprising an RLBP1 coding sequence, and a 3' ITR.

The recombinant nucleic acid sequence of the vector genome can also include a promoter as described herein. In one aspect, the promoter is an RLBP1 (long) promoter (SEQ ID NO: 10), in another aspect the promoter is an RLBP1 (short) promoter (SEQ ID NO: 3). In certain specific aspects of the invention, the vector genome comprises, in the 5' to 3' direction, nucleic acid sequences selected from: a) SEQ ID NO: 2, 10, 5, 6, 8, and 9; b) SEQ ID NO: 2, 11, 5, 6, 8, 14, 9; c) SEQ ID NO: 2, 22, 5, 6, 8, 23, and 9; and d) SEQ ID NO: 2, 3, 4, 5, 6, 8, 23, and 9.

The invention also relates, in part, to viral vectors carrying a self-complementary genome. The self-complementary vector genome can include, from 5' to 3', a 5' ITR, a first recombinant nucleotide sequence, a non-resolvable ITR (e.g.: ΔITR), a second recombinant nucleotide sequence, and a 3' ITR, wherein the first and second recombinant nucleotide sequences are self-complementary. The second recombinant nucleotide sequence comprises in the 5' to 3' direction, a promoter, an RLBP1 coding sequence and an SV40 polyA sequence. The promoter can be an RLBP1 promoter and, further, can be the RLBP1 (short) promoter (SEQ ID NO: 3). In certain aspects of the invention, the second recombinant nucleotide sequence comprises nucleic acid sequences in the 5' to 3' direction of SEQ ID NO: 3, 4, 5, 6, and 8 and the first recombinant nucleotide sequence comprises sequences that are self-complementary to, or the reverse complement of, the second recombinant sequence, for example, SEQ ID NOs: 62, 63, 64, 65, and 66. The invention also relates to a viral vector comprising a self-complementary vector genome wherein the genome comprises, nucleic acid sequences in the 5' to 3' direction of: SEQ ID NOs: 36, 62, 63, 64, 65, 66, 1, 3, 4, 5, 6, 8, and 9. The self-complementary vector genome described above can be packaged in an AAV capsid that is selected from any AAV serotype known in the art, including but not limited to AAV1-12. In one aspect, the self-complementary genome is packaged in an AAV8 capsid. In another aspect, the self-complementary genome is packaged in an AAV2 capsid.

The present invention also relates to a viral vector capable of directing expression of a heterologous gene to RPE and Müller cells of the retina. It is contemplated that the viral vector capsid is an AAV2 or an AAV8 serotype capsid and that the viral vector comprises a vector genome, wherein the heterologous gene is operably linked to an RLBP1 promoter. It is further contemplated that the RLBP1 promoter is the RLBP1 (short) promoter (SEQ ID NO: 3) or the RLBP1 (long) promoter (SEQ ID NO: 10). In another aspect of the invention it is contemplated that the heterologous gene to be expressed in RPE and Müller cells is an RLBP1 coding sequence having for example, the sequence of SEQ ID NO: 6.

The present invention also relates to a viral vector capable of directing expression of a heterologous gene to RPE and Müller cells of the retina, wherein the viral vector capsid is an AAV8 serotype capsid and that the viral vector comprises a self-complementary vector genome wherein a heterologous gene is operably linked to an RLBP1 promoter. It is further contemplated that the RLBP1 promoter is the RLBP1 (short) promoter (SEQ ID NO: 3). In another aspect of the invention it is contemplated that the heterologous gene to be expressed in RPE and Müller cells is an RLBP1 coding sequence having for example, the sequence of SEQ ID NO: 6.

The invention also relates to a composition comprising a viral vector described herein, as well as viral vector compositions in combination with a pharmaceutically acceptable carrier. Specifically, the invention further relates to compositions comprising the viral vectors as described in Table 4. The invention still further relates to compositions comprising viral vectors that can be generated using the plasmids described in Table 2, in conjunction with rAAV production methods known in the art and described herein. The compositions described herein are useful for treating a subject having RLBP1 associated retinal dystrophy and/or improving the rate of dark adaption in a subject having RLBP1-associated retinal dystrophy.

The present invention also relates to nucleic acids that can be used, with the rAAV production methods known in the art and described herein, for the generation of the viral vectors described herein. The invention relates to nucleic acids comprising a gene cassette, wherein the gene cassette comprises, in the 5' to 3' direction: (i) a 5' ITR or a non-resolvable ITR, (ii) a recombinant nucleotide sequence comprising an RLBP1 coding sequence, and (iii) a 3' ITR. It is contemplated that the nucleic acid may comprise a gene cassette comprising a nucleic acid sequence selected from SEQ ID NOs: 51, 52, 53, 54, and 55. It is contemplated that the nucleic acids of the invention may be plasmids. It is further contemplated that the nucleic acid may be a plasmid comprising a nucleic acid sequence selected from SEQ ID NOs: 26, 27, 28, 29, 30 and 50.

In certain specific aspects of the invention, the nucleic acid can comprise a gene cassette comprising sequences in the 5' to 3' direction that are selected from: a) a) SEQ ID NO: 2, 10, 5, 6, 8, and 9, b) SEQ ID NO: 2, 11, 5, 6, 8, 14 and 9, c) SEQ ID NO: 2, 22, 5, 6, 8, 23 and 9, d) SEQ ID NO: 2, 3, 4, 5, 6, 8, 23 and 9, or e) SEQ ID NO: 1, 3, 4, 5, 6, 8, and 9.

The invention also relates to nucleic acids comprising a gene cassette, wherein the gene cassette comprises, in the 5' to 3' direction: (i) a 5' ITR, (ii) a recombinant nucleotide sequence comprising a promoter operably linked to reporter gene, and (iii) a 3' ITR. It is contemplated that the nucleic acid may comprise a gene cassette comprising a nucleic acid sequence selected from SEQ ID NOs: 56, 57, 59 and 60. It is further contemplated that nucleic acid may be a plasmid comprising a nucleic acid sequence selected from SEQ ID NOs: 31, 32, 34 and 35.

The invention also relates to methods of treating a subject having RLBP1-associated retinal dystrophy wherein the method comprises administering to a subject in need thereof, a composition comprising a viral vector as described herein.

The invention also relates to a method of improving the rate of dark adaption in a subject having RLBP1-associated retinal dystrophy, wherein the method comprises administering to a subject in need thereof, a composition comprising a viral vector as described herein.

The invention still further relates to a method of directing expression of an RLBP1 coding sequence in RPE and Müller cells in the retina of a subject having RLBP1-associated retinal dystrophy, wherein the method comprises the step of contacting the retina of the subject, with a viral vector comprising an AAV8 or AAV2 serotype capsid and a vector genome comprising an RLBP1 coding sequence operably linked to an RLBP1 promoter, such as, for example, the RLBP1(short) (SEQ ID NO: 3) or RLBP1 (long) (SEQ ID NO: 10) promoters as described herein.

The invention still further relates to a method of delivering an RLBP1 coding sequence in RPE and Müller cells in the retina of a subject having RLBP1-associated retinal dystrophy, wherein the method comprises the step of contacting the retina of the subject, with a viral vector comprising an AAV8 or AAV2 serotype capsid and a vector genome comprising an RLBP1 coding sequence operably linked to an RLBP1 promoter, such as, for example, the RLBP1(short) (SEQ ID NO: 3) or RLBP1(long) (SEQ ID NO: 10) promoters as described herein.

The invention also includes a viral vector as described in Table 1, or 4, as well as a plasmid described in Table 2.

DEFINITIONS

Unless defined otherwise, all technical and scientific terms used herein have the same meaning as commonly understood by those of ordinary skill in the art to which this invention pertains.

The term "capsid" refers to the protein coat of the virus or viral vector. The term "AAV capsid" refers to the protein coat of the adeno-associated virus (AAV), which is composed of a total of 60 subunits; each subunit is an amino acid sequence, which can be viral protein 1(VP1), VP2 or VP3 (Muzyczka N and Berns K I 2001).

The term "gene cassette" refers to a manipulatable fragment of DNA carrying, and capable of expressing, one or more genes, or coding sequences, of interest between one or more sets of restriction sites. A gene cassette can be transferred from one DNA sequence (often in a plasmid vector) to another by 'cutting' the fragment out using restriction enzymes and ligating it back into a new context, for example into a new plasmid backbone.

The term "heterologous gene" or "heterologous nucleotide sequence" will typically refer to a gene or nucleotide sequence that is not naturally-occurring in the virus. Alternatively, a heterologous gene or nucleotide sequence may refer to a viral sequence that is placed into a non-naturally occurring environment (e.g.: by association with a promoter with which it is not naturally associated in the virus).

The terms "ITR" or "inverted terminal repeat" refer to the stretch of nucleic acid sequences that exist in Adeno- Associated Viruses (AAV) and/or recombinant Adeno-Associated Viral Vectors (rAAV) that can form a T-shaped palindromic structure, that is required for completing AAV lytic and latent life cycles (Muzyczka N and Berns K I 2001). The term "non-resolvable ITR" refers to a modified ITR such that the resolution by the Rep protein is reduced. A non-resolvable ITR can be an ITR sequence without the terminal resolution site (TRS) which leads to low or no resolution of the non-resolvable ITR and would yield 90-95% of self-complementary AAV vectors (McCarty et al 2003). A specific example of a non-resolvable ITR is "ΔITR", having a sequence of SEQ ID NO: 1.

The term "operably linked" refers to a functional relationship between two or more polynucleotide (e.g., DNA) segments. Typically, the term refers to the functional relationship of a transcriptional regulatory sequence to a sequence to be transcribed. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribable sequence are contiguous to the transcribable sequence, i.e., they are cis-acting. However, some transcriptional regulatory sequences, such as enhancers, need not be physically contiguous or located in close proximity to the coding sequences whose transcription they enhance.

The term "promoter" refers to a sequence that regulates transcription of an operably-linked gene, or nucleotide sequence encoding a protein, etc. Promoters provide the sequence sufficient to direct transcription, as well as, the recognition sites for RNA polymerase and other transcription factors required for efficient transcription and can direct cell specific expression. In addition to the sequence sufficient to direct transcription, a promoter sequence of the invention can also include sequences of other regulatory elements that are involved in modulating transcription (e.g.: enhancers, kozak sequences and introns). Examples of promoters known in the art and useful in the viral vectors described herein, include the CMV promoter, CBA promoter, smCBA promoter and those promoters derived from an immunoglobulin gene, SV40, or other tissue specific genes (e.g: RLBP1, RPE, VMD2). Specific promoters may also include those described in Table 1, for example, the "RLBP1 (short)" promoter (SEQ ID NO: 3), the "RLBP1 (long)" promoter (SEQ ID NO: 10), RPE65 promoter (SEQ ID NO: 11), VMD2 promoter (SEQ ID NO: 12), and the CMV enhancer+CBA promoter (SEQ ID NO: 22). In addition, standard techniques are known in the art for creating functional promoters by mixing and matching known regulatory elements. "Truncated promoters" may also be generated from promoter fragments or by mix and matching fragments of known regulatory elements; for example the smCBA promoter is a truncated form of the CBA promoter.

The term "RLBP1" refers to the "Retinaldehyde Binding Protein 1". The human RLBP1 gene is found on chromosome 15 and has the nucleic acid coding sequence as set out in Table 1: SEQ ID NO: 6. The "RLBP1 gene product" is also known as, "cellular retinaldehyde binding protein" or "CRALBP" and is the protein encoded by the RLBP1 gene. The human RLBP1 gene product (hCRALBP) has the amino acid sequence as set out in Table 1: SEQ ID NO: 7. Examples of RLBP1 coding sequences and RLBP1 gene products from other species can be found in Table 1 (e.g.: SEQ ID NOs: 37-48). The term "RLBP1 coding sequence" or "RLBP1 GENE CDS" or "RLBP1 CDS" refers to the nucleic acid sequence that encodes the RLBP1 gene product. One of skill in the art would understand that an RLBP1 coding sequence may include any nucleic acid sequence that encodes an RLBP1 gene product. The RLBP1 coding sequence may or may not include intervening regulatory elements (e.g.: introns, enhancers, or other non-coding sequences).

The term "subject" includes human and non-human animals. Non-human animals include all vertebrates (e.g.: mammals and non-mammals) such as, non-human primates (e.g.: cynomolgus monkey), mice, rats, sheep, dogs, cows, chickens, amphibians, and reptiles. Except when noted, the terms "patient" or "subject" are used herein interchangeably.

As used herein, the term "treating" or "treatment" of any disease or disorder (e.g., retinitis pigmentosa, RBLP1-associated retinal dystrophy) refers, to ameliorating the disease or disorder such as by slowing or arresting or reducing the development of the disease or at least one of the clinical symptoms thereof. "Treating" or "treatment" can also refer to alleviating or ameliorating at least one physical parameter including those which may not be discernible by the patient. "Treating" or "treatment" can also refer to modulating the disease or disorder, either physically, (e.g., stabilization of a discernible symptom), physiologically, (e.g., stabilization of a physical parameter), or both. More specifically, "treatment" of RLBP1-associated retinal dystrophy means any action that results in the improvement or preservation of visual function and/or regional anatomy in a subject having RLBP1-associated retinal dystrophy. "Preventing" or "prevention" as used herein, refers to preventing or delaying the onset or development or progression of the disease or disorder. "Prevention" as it relates to RLBP1-associated retinal dystrophy means any action that prevents or slows a worsening in visual function, retinal anatomy, and/or an RLBP1-associated retinal dystrophy disease parameter, as described below, in a patient with RLBP1-associated retinal dystrophy and at risk for said worsening. Methods for assessing treatment and/or prevention of disease are known in the art and described herein below.

The term "virus vector" or "viral vector" is intended to refer to a non-wild-type recombinant viral particle (e.g.: a parvovirus, etc.) that functions as a gene delivery vehicle and which comprises a recombinant viral genome packaged within a viral (e.g.: AAV) capsid. A specific type of virus vector may be a "recombinant adeno-associated virus vector", or "rAAV vector". The recombinant viral genome packaged in the a viral vector is also referred to herein as the "vector genome".

DETAILED DESCRIPTION

Figure 1A:
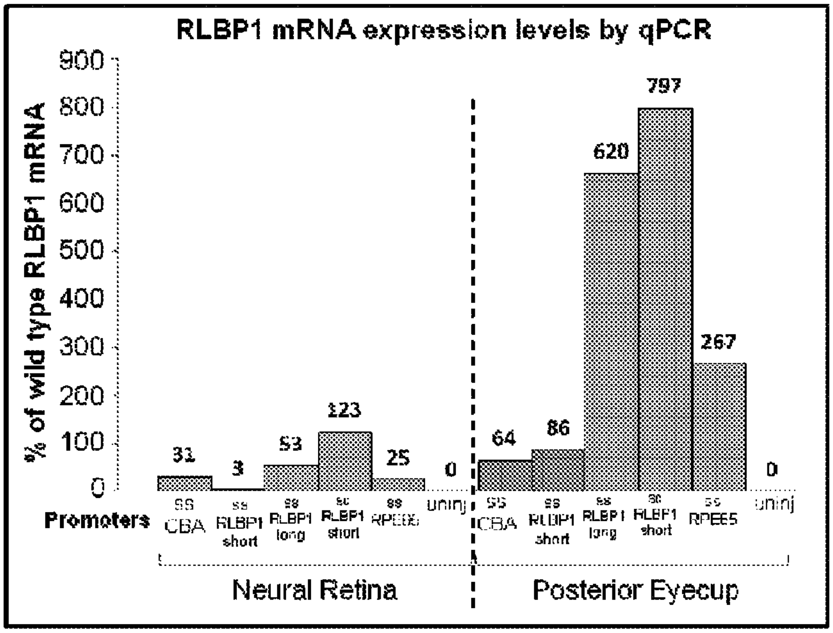
FIGS. 1A-1B. Relative expression of vector-mediated human RLBP1 mRNA compared to endogenous mouse RLBP1 mRNA in eyes injected with various viral vectors at the dosage of $1\times10^9$ (1A) and $1\times10^8$ (1B) vector genome (vg) particles per eye.

The present invention is based, in part, on the discovery of viral vectors that express a heterologous gene in RPE and Müller cells of the retina. The invention also relates both to single stranded and self-complementary viral vectors with a heterologous gene expressing the RLBP1 gene product (CRALBP).

Accordingly, the present invention provides recombinant viral vectors that direct expression of the RLBP1 coding sequence to the retina, viral vector compositions, plasmids useful for generating the viral vectors, methods of delivering an RLBP1 coding sequence to the retina, methods of expressing an RLBP1 coding sequence in RPE and Müller cells of the retina, and methods of use of such viral vectors.

Except as otherwise indicated, standard methods known to those skilled in the art may be used for the construction of recombinant parvovirus and rAAV vectors, using recombinant plasmids carrying a viral gene cassette, packaging plasmids expressing the parvovirus rep and/or cap sequences, as well as transiently and stably transfected packaging cells. Such techniques are known to those skilled in the art. (e.g.: SAMBROOK et al., MOLECULAR CLONING: A LABORATORY MANUAL 2nd Ed. (Cold Spring Harbor, N. Y., 1989); Choi V W et al. CURRENT PROTOCOLS IN MOLECULAR BIOLOGY (2007)).

1. Viral Vectors

The present invention is related to viral vectors that direct expression of a heterologous gene to the retina. In certain aspects of the invention, expression is directed to RPE and Müller cells of the retina. A variety of viral vectors known in the art may be adapted by one of skill in the art for use in the present invention, for example, recombinant adeno-associated viruses, recombinant adenoviruses, recombinant retroviruses, recombinant poxviruses, recombinant baculoviruses, etc.

In particular, it is contemplated that the viral vector of the invention may be a recombinant adeno-associated (rAAV) vector. AAVs are small, single-stranded DNA viruses which require helper virus to facilitate efficient replication (Muzyczka N and Berns K I 2001). The viral vector comprises a vector genome and a protein capsid. The viral vector capsid may be supplied from any of the AAV serotypes known in the art, including presently identified human and non-human AAV serotypes and AAV serotypes yet to be identified (See: Choi V W et al 2005, Schmidt et al 2008). Virus capsids may be mixed and matched with other vector components to form a hybrid viral vector, for example the ITRs and capsid of the viral vector may come from different AAV serotypes. In one aspect, the ITRs can be from an AAV2 serotype while the capsid is from, for example, an AAV2 or AAV8 serotype. In addition, one of skill in the art would recognize that the vector capsid may also be a mosaic capsid (e.g.: a capsid composed of a mixture of capsid proteins from different serotypes), or even a chimeric capsid (e.g.: a capsid protein containing a foreign or unrelated protein sequence for generating markers and/or altering tissue tropism). It is contemplated that the viral vector of the invention may comprise an AAV2 capsid. It is further contemplated that the invention may comprise an AAV8 capsid.

The invention relates, in part, to viral vectors wherein the vector genome is single stranded. In certain aspects, the invention is related to a single stranded vector genome comprising, in the 5' to 3' direction: (i) a 5' ITR, (ii) a recombinant nucleotide sequence comprising an RLBP1 coding sequence, and (iii) a 3' ITR. In certain aspects of the invention the recombinant nucleotide sequence comprises in the 5' to 3' direction: (i) a promoter, (ii) an RLBP1 coding sequence, and (iii) an SV40 polyA sequence. In certain aspects, the promoter may be an RLBP1 (short) promoter, an RLBP1 (long) promoter, or a truncated promoter of RLBP1. In particular, the invention relates to a single stranded vector genome comprising a recombinant nucleotide sequence comprising in the 5' to 3' direction: an RLBP1 (long) promoter (SEQ ID NO:10), an RLBP1 coding sequence, and an SV40 polyA sequence. In addition, the invention also relates to a single stranded vector genome comprising a recombinant nucleotide sequence comprising in the 5' to 3' direction: an RLBP1 (short) promoter (SEQ ID NO: 3), an RLBP1 coding sequence, and an SV40 polyA sequence. Certain aspects of the invention further relate to a single stranded vector genome comprising a recombinant nucleotide sequence packaged in an AAV2 or AAV8 capsid.

In certain aspects of the invention the viral vector comprises an AAV2 capsid (encoded by SEQ ID NO: 18) and a vector genome comprising in the 5' to 3 direction nucleotide sequences selected from the following: a) SEQ ID NO: 2, 10, 5, 6, 8, and 9; b) SEQ ID NO: 2, 11, 5, 6, 8, 14, 9; c) SEQ ID NO: 2, 22, 5, 6, 8, 23, and 9; and d) SEQ ID NO: 2, 3, 4, 5, 6, 8, 23, and 9. In certain aspects the AAV2 capsid comprises capsid proteins VP1, VP2 and VP3 having an amino acid sequence of SEQ ID NO: 19, 68, and 69, respectively. In certain other aspects the AAV2 capsid may comprise subcombinations of capsid proteins VP1, VP2 and/or VP3.

In certain aspects of the invention the viral vector comprises an AAV8 capsid (encoded by SEQ ID NO: 20) and a vector genome comprising in the 5' to 3' direction nucleotide sequences selected from the following: a) SEQ ID NO: 2, 10, 5, 6, 8, and 9; b) SEQ ID NO: 2, 11, 5, 6, 8, 14, 9; c) SEQ ID NO: 2, 22, 5, 6, 8, 23, and 9; and d) SEQ ID NO: 2, 3, 4, 5, 6, 8, 23, and 9. In certain aspects the AAV8 capsid comprises capsid proteins VP1, VP2 and VP3 having an amino acid sequence of SEQ ID NO: 21, 70, and 71. In certain other aspects the AAV8 capsid may comprise subcombinations of capsid proteins VP1, VP2 and/or VP3.

The viral vector can also be an AAV vector comprising a self-complementary genome. Self-complementary rAAV vectors have been previously described in the art (U.S. Pat. No. 7,465,583 and McCarty 2008) and may be adapted for use in the present invention. A self-complementary genome comprises a 5' ITR and a 3' ITR (i.e.: resolvable ITR or wild-type ITR) at either end of the genome and a non-resolvable ITR (e.g.: ΔITR, as described herein) interposed between the 5' and 3' ITRs. Each portion of the genome (i.e. between each resolvable ITR and non-resolvable ITR) comprises a recombinant nucleotide sequence, wherein each half (i.e.: the first recombinant nucleotide sequence and the second recombinant nucleotide sequence) is complementary to the other, or self-complementary. In other words, the self-complementary vector genome is essentially an inverted repeat with the two halves joined by the non-resolvable ITR. In certain aspects the invention is related to a self-complementary vector genome comprising, in the 5' to 3' direction, (i) a 5' ITR, (ii) a first recombinant nucleotide sequence, (iii)

a non-resolvable ITR, (iv) a second recombinant nucleotide sequence, and (v) a 3' ITR. In a certain aspect of the invention the second recombinant nucleotide sequence of the vector genome comprises, an RLBP1 promoter, an RLBP1 coding sequence, and an SV40 polyA sequence and the first recombinant nucleotide sequence is self-complementary to the second nucleotide sequence. In certain specific aspects the RLBP1 promoter has the nucleotide sequence of SEQ ID NO: 3. In certain aspects of the invention, the second recombinant nucleotide sequence comprises nucleic acid sequences in the 5' to 3' direction of SEQ ID NO: 3, 4, 5, 6, and 8 and the first recombinant nucleotide sequence comprises sequences that are self-complementary to, or the reverse complement of, the second recombinant sequence, for example, SEQ ID NOs: 62, 63, 64, 65, and 66. It is also contemplated that the viral vector of the invention may comprise a self-complementary genome wherein the first recombinant nucleotide sequence of the vector genome comprises, an RLBP1 promoter, an RLBP1 coding sequence, and an SV40 polyA sequence and the second recombinant nucleotide sequence is self-complementary to the first recombinant nucleotide sequence.

In certain aspects of the invention the self-complementary viral vector comprises an AAV2 capsid (encoded by SEQ ID NO: 18) and a vector genome comprising a nucleotide sequence comprising sequences in the 5' to 3' direction SEQ ID NO: 36, SEQ ID NO: 62, SEQ ID NO: 63, SEQ ID NO: 64, SEQ ID NO: 65, SEQ ID NO: 66, SEQ ID NO: 1, SEQ ID NO: 3, SEQ ID NO: 4, SEQ ID NO: 5, SEQ ID NO: 6, SEQ ID NO: 8, and SEQ ID NO: 9. In certain aspects the AAV2 capsid comprises capsid proteins VP1, VP2 and VP3 having an amino acid sequence of SEQ ID NO: 19, 68, and 69, respectively. In certain other aspects the AAV2 capsid may comprise subcombinations of capsid proteins VP1, VP2 and/or VP3.

In certain aspects of the invention the self-complementary viral vector comprises an AAV8 capsid (encoded by SEQ ID NO: 20) and a vector genome comprising a nucleotide sequence comprising sequences in the 5' to 3' direction SEQ ID NO: 36, SEQ ID NO: 62, SEQ ID NO: 63, SEQ ID NO: 64, SEQ ID NO: 65, SEQ ID NO: 66, SEQ ID NO: 1, SEQ ID NO: 3, SEQ ID NO: 4, SEQ ID NO: 5, SEQ ID NO: 6, SEQ ID NO: 8, and SEQ ID NO: 9. In certain aspects the AAV8 capsid comprises capsid proteins VP1, VP2 and VP3 having an amino acid sequence of SEQ ID NO: 21, 70, and 71. In certain other aspects the AAV8 capsid may comprise subcombinations of capsid proteins VP1, VP2 and/or VP3.

Thus, the invention also relates to viral vectors as described herein, comprising a truncated promoter of RLBP1.

The invention further relates to a viral vector that directs expression of a heterologous gene to RPE and Müller cells of the retina, wherein the viral vector comprises an AAV8 capsid and a vector genome comprising an RLBP1 (short) promoter (SEQ ID NO:3) operably linked to a heterologous gene. In certain aspects of the invention, the vector genome is a self-complementary genome.

The invention also relates to methods of expressing RLBP1 in RPE cells and Müller cells of the retina. In certain aspects of the invention the method comprises contacting the retinal cells with a viral vector comprising an AAV capsid and a vector genome comprising an RLBP1 coding sequence operably linked to an RLBP1 promoter, which may be an RLBP1 (short) promoter (SEQ ID NO:3). In certain aspects of the invention the AAV capsid is AAV2. In certain other aspects, the AAV capsid is AAV8. In other aspects of the invention the method comprises contacting the retinal cells with a viral vector comprising an AAV capsid and a vector genome comprising an RLBP1 coding sequence operably linked to an RLBP1 promoter, which may be an RLBP1 (long) promoter (SEQ ID NO: 10). In certain aspects of the invention the AAV capsid is AAV2. In certain other aspects, the AAV capsid is AAV8.

Methods for generating viral vectors are well known in the art and would allow for the skilled artisan to generate the viral vectors of the invention (see, e.g., U.S. Pat. No. 7,465,583), including the viral vectors described in Table 4, using the plasmids described in Table 2 and the Examples.

In general, methods of producing rAAV vectors are applicable to producing the viral vectors of the invention; the primary difference between the methods is the structure of the genetic elements to be packaged. To produce a viral vector according to the present invention, sequences of the genetic elements and plasmids as described in table 2 can be used to produce the encapsidated viral genome.

The genetic elements as described in table 2 are in the context of a circular plasmid, but one of skill in the art will appreciated that a DNA substrate may be provided in any form known in the art, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the genetic elements in table 2 necessary to produce the viral vectors described herein may be stably incorporated into the genome of a packaging cell.

The viral vector particles according to the invention may be produced by any method known in the art, e.g., by introducing the sequences to be replicated and packaged into a permissive or packaging cell, as those terms are understood in the art (e.g., a "permissive" cell can be infected or transduced by the virus; a "packaging" cell is a stably transformed cell providing helper functions).

In one embodiment, a method is provided for producing an RLBP1 viral vector, wherein the method comprises providing to a cell permissive for parvovirus replication: (a) a nucleotide sequence containing the genetic elements for producing a vector genome of the invention (as described in detail below and in table 2); (b) nucleotide sequences sufficient for replication of the vector genome sequence in (a) to produce a vector genome; (c) nucleotide sequences sufficient to package the vector genome into a parvovirus capsid, under conditions sufficient for virus vectors comprising the vector genome encapsidated within the parvovirus capsid to be produced in the cell. Preferably, the parvovirus replication and/or capsid coding sequences are AAV sequences.

Any method of introducing the nucleotide sequence carrying the gene cassettes described below into a cellular host for replication and packaging may be employed, including but not limited to, electroporation, calcium phosphate precipitation, microinjection, cationic or anionic liposomes, and liposomes in combination with a nuclear localization signal.

Viral vectors described herein may be produced using methods known in the art, such as, for example, triple transfection or baculovirus mediated virus production. Any suitable permissive or packaging cell known in the art may be employed to produce the vectors. Mammalian cells are preferred. Also preferred are trans-complementing packaging cell lines that provide functions deleted from a replication-defective helper virus, e.g., 293 cells or other E1a trans-complementing cells. Also preferred are mammalian cells or cell lines that are defective for DNA repair as known in the art, as these cell lines will be impaired in their ability to correct the mutations introduced into the plasmids described herein.

The gene cassette may contain some or all of the parvovirus (e.g., AAV) cap and rep genes. Preferably, however, some or all of the cap and rep functions are provided in trans by introducing a packaging vector(s) encoding the capsid and/or Rep proteins into the cell. Most preferably, the gene cassette does not encode the capsid or Rep proteins. Alternatively, a packaging cell line is used that is stably transformed to express the cap and/or rep genes (see, e.g., Gao et al., (1998) Human Gene Therapy 9:2353; Inoue et al., (1998) J. Virol. 72:7024; U.S. Pat. No. 5,837,484; WO 98/27207; U.S. Pat. No. 5,658,785; WO 96/17947).

In addition, helper virus functions are preferably provided for the virus vector to propagate new virus particles. Both adenovirus and herpes simplex virus may serve as helper viruses for AAV. See, e.g., BERNARD N. FIELDS et al., VIROLOGY, volume 2, chapter 69 (3d ed., Lippincott-Raven Publishers). Exemplary helper viruses include, but are not limited to, Herpes simplex (HSV) varicella zoster, cytomegalovirus, and Epstein-Barr virus. The multiplicity of infection (MOI) and the duration of the infection will depend on the type of virus used and the packaging cell line employed. Any suitable helper vector may be employed. Preferably, the helper vector is a plasmid, for example, as described by Xiao et al., (1998) J. Virology 72:2224. The vector can be introduced into the packaging cell by any suitable method known in the art, as described above.

Vector stocks free of contaminating helper virus may be obtained by any method known in the art. For example, recombinant single stranded or self complementary virus and helper virus may be readily differentiated based on size. The viruses may also be separated away from helper virus based on affinity for a heparin substrate (Zolotukhin et al. (1999) Gene Therapy 6:973). Preferably, deleted replication-defective helper viruses are used so that any contaminating helper virus is not replication competent. As a further alternative, an adenovirus helper lacking late gene expression may be employed, as only adenovirus early gene expression is required to mediate packaging of the duplexed virus. Adenovirus mutants defective for late gene expression are known in the art (e.g., ts100K and ts149 adenovirus mutants).

One method for providing helper functions employs a non-infectious adenovirus miniplasmid that carries all of the helper genes required for efficient AAV production (Ferrari et al., (1997) Nature Med. 3:1295; Xiao et al., (1998) J. Virology 72:2224). The rAAV titers obtained with adenovirus miniplasmids are forty-fold higher than those obtained with conventional methods of wild-type adenovirus infection (Xiao et al., (1998) J. Virology 72:2224). This approach obviates the need to perform co-transfections with adenovirus (Holscher et al., (1994), J. Virology 68:7169; Clark et al., (1995) Hum. Gene Ther. 6:1329; Trempe and Yang, (1993), in, Fifth Parvovirus Workshop, Crystal River, Fla.).

Other methods of producing rAAV stocks have been described, including but not limited to, methods that split the rep and cap genes onto separate expression cassettes to prevent the generation of replication-competent AAV (see, e.g., Allen et al., (1997) J. Virol. 71:6816), methods employing packaging cell lines (see, e.g., Gao et al., (1998) Human Gene Therapy 9:2353; Inoue et al., (1998) J. Virol. 72:7024; U.S. Pat. No. 5,837,484; WO 98/27207; U.S. Pat. No. 5,658,785; WO 96/17947), and other helper virus free systems (see, e.g., U.S. Pat. No. 5,945,335 to Colosi).

Herpesvirus may also be used as a helper virus in AAV packaging methods. Hybrid herpesviruses encoding the AAV Rep protein(s) may advantageously facilitate for more scalable AAV vector production schemes. A hybrid herpes simplex virus type I (HSV-1) vector expressing the AAV-2 rep and cap genes has been described (Conway et al., (1999) Gene Therapy 6:986 and WO 00/17377).

In summary, the gene cassette to be replicated and packaged, parvovirus cap genes, appropriate parvovirus rep genes, and (preferably) helper functions are provided to a cell (e.g., a permissive or packaging cell) to produce rAAV particles carrying the vector genome. The combined expression of the rep and cap genes encoded by the gene cassette and/or the packaging vector(s) and/or the stably transformed packaging cell results in the production of a viral vector particle in which a viral vector capsid packages a viral vector genome according to the invention. The single stranded or self-complementary viral vectors are allowed to assemble within the cell, and may then be recovered by any method known by those of skill in the art and described in the examples. For example, viral vectors may be purified by standard CsCl centrifugation methods (Grieger J C et al 2006) or by various methods of column chromatography known to the skilled artisan (see: Lock M et al (2010), Smith R H et al (2009) and Vadenberghe L H et al (2010)).

The reagents and methods disclosed herein may be employed to produce high-titer stocks of the inventive viral vectors, preferably at essentially wild-type titers. It is also preferred that the parvovirus stock has a titer of at least about $10^5$ transducing units (tu)/ml, more preferably at least about $10^6$ tu/ml, more preferably at least about $10^7$ tu/ml, yet more preferably at least about $10^6$ tu/ml, yet more preferably at least about $10^9$ tu/ml, still yet more preferably at least about $10^{10}$ tu/ml, still more preferably at least about $10^{11}$ tu/ml, or more.

Further, the RLBP1 viral vectors of the invention, may have an improved transducing unit/particle ratio over conventional AAV vectors. Preferably, the tu/particle ratio is less than about 1:50, less than about 1:20, less than about 1:15, less than about 1:10, less than about 1:8, less than about 1:7, less than about 1:6, less than about 1:5, less than about 1:4, or lower. Typically, the tu/particle ratio will be greater than about 1:1, 1:2, 1:3 or 1:4.

2. Nucleic Acids for Use in Generating the Viral Vector

The invention also relates to nucleic acids useful for the generation of viral vectors. In certain aspects of the invention, the nucleic acids useful for the generation of viral vectors may be in the form of plasmids. Plasmids useful for the generation of viral vectors, also referred to as a viral vector plasmid, may contain a gene cassette. At a minimum, a gene cassette of a viral vector plasmid contains: a heterologous gene and its regulatory elements (e.g.: promoter, enhancer, and/or introns, etc.), and 5' and 3' AAV inverted terminal repeats (ITRs).

The composition of the heterologous gene and its regulatory elements will depend upon the use to which the resulting vector will be put. For example, one type of heterologous gene sequence includes a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc. For example, where the reporter sequence is the LacZ gene, the presence of the vector carrying the signal is detected by assays for beta-galactosidase activity. Where the reporter sequence is green fluorescent protein or luciferase, the vector carrying the signal may be measured visually by color or light production in a luminometer.

The heterologous gene sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry.

The heterologous gene may also be a non-marker sequence encoding a product which is useful in biology and medicine, such as proteins, peptides, RNA, enzymes, dominant negative mutants, or catalytic RNAs. Desirable RNA molecules include tRNA, dsRNA, ribosomal RNA, catalytic RNAs, siRNA, small hairpin RNA, trans-splicing RNA, and antisense RNAs. One example of a useful RNA sequence is a sequence which inhibits or extinguishes expression of a targeted nucleic acid sequence in the treated animal.

The heterologous gene may also be used to correct or ameliorate gene deficiencies, which may include deficiencies in which normal genes are expressed at less than normal levels or deficiencies in which the functional gene product is not expressed. It is contemplated in the present invention that the heterologous gene sequence may be an RLBP1 coding sequence. Examples of RLBP1 coding sequences are provided in Table 1: SEQ ID NOs: 6, 37, 39, 41, 43, 45 or 47.

In addition to the heterologous gene, the gene cassette may include regulatory elements operably linked to the heterologous gene. These regulatory elements may include appropriate transcription initiation, termination, promoter and enhancer sequences, efficient RNA processing signals such as splicing and polyadenylation (polyA) signals; sequences that stabilize cytoplasmic mRNA; sequences that enhance translation efficiency; sequences that enhance protein stability; and when desired, sequences that enhance secretion of the encoded product. A great number of regulatory sequences, including promoters which are native, constitutive, inducible and/or tissue-specific, are known in the art and may be utilized. Regulatory element sequences of the invention include those described in Table 1, for example SEQ ID NO: 3, 4, 5, 8, 10, 11, 12 and 22.

The gene cassette may include an RLBP1 promoter with a nucleic acid sequence of SEQ ID NO: 3 or 10 operably linked to a heterologous gene. In particular, the RLBP1 short promoter (SEQ ID NO: 3) is operably linked to an RLBP1 coding sequence (SEQ ID NO: 6, 37, 39, 41, 43, 45 or 47). Alternatively, the RLBP1 long promoter (SEQ ID NO: 10) is operably linked to an RLBP1 coding sequence (SEQ ID NO: 6, 37, 39, 41, 43, 45 or 47).

It is contemplated that the ITRs of AAV serotype 2 may be used (e.g.: SEQ ID NO: 2, 9, 16, 17, 36). However, ITRs from other suitable serotypes may be selected from among any AAV serotype known in the art, as described herein. These ITRs or other AAV components may be readily isolated using techniques available to those of skill in the art from any AAV serotype known, or yet to be identified serotypes, for example, the AAV sequences may be obtained through synthetic or other suitable means by reference to published sequences such as are available in the literature or in databases such as, e.g., GenBank, PubMed, or the like. Alternatively, such AAV components may also be isolated or obtained from academic, commercial, or public sources (e.g., the American Type Culture Collection, Manassas, Va.).

It is contemplated that in certain aspects of the invention, one ITR of the gene cassette may be a modified ITR, or non-resolvable ITR, sequence without the terminal resolution site (TRS). During replication of a gene cassette comprising a non-resolvable ITR, the inability of Rep protein to resolve the non-resolvable ITRs will result in a dimeric inverted repeat sequence (i.e.: self-complementary) with a non-resolvable ITR (e.g.: ΔITR) in the middle and a wild-type ITR at each end. The resulting sequence is a self-complementary viral genome sequence such that the genome is capable of forming a hairpin structure upon release from the capsid (see also: U.S. Pat. No. 7,465,583 and McCarty (2008)) A non-resolvable ITR may be produced by any method known in the art. For example, insertion into the ITR will displace the TRS and result in a non-resolvable ITR. Preferably, the insertion is in the region of the TRS site. Alternatively, the ITR may be rendered non-resolvable by deletion of the TRS site, a specific example includes ΔITR (SEQ ID NO: 1).

The invention relates to nucleic acids that comprise a gene cassette comprising in the 5' to 3' direction nucleic acid sequences selected from the following: a) SEQ ID NOs: 2, 10, 5, 6, 8, and 9; b) SEQ ID NOs: 2, 11, 5, 6, 8, 14 and 9; c) SEQ ID NOs: 2, 22, 5, 6, 8, 23 and 9; d) SEQ ID NOs: 2, 3, 4, 5, 6, 8, 23 and 9; e) SEQ ID NOs: 2, 10, 5, 24, 8, and 9; f) SEQ ID NOs: 2, 11, 24, 8, 14, and 9; and g) SEQ ID NOs: 2, 12, 24, 8, 14, and 9. In certain aspects the nucleic acid comprising the gene cassette may be a plasmid. In particular, the sequence of the plasmid may have a sequence selected from SEQ ID NOs: 27, 28, 29, 30, 32, 33, 34 and 35.

The invention also relates to nucleic acids that comprise a gene cassette comprising in the 5' to 3' direction nucleic acid sequences selected from the following: a) SEQ ID NOs: 1, 3, 4, 5, 6, 8, and 9; and b) SEQ ID NOs: 1, 3, 4, 5, 24, 8 and 9. In certain aspects the nucleic acid comprising the gene cassette may be a plasmid. In particular, the sequence of the plasmid may have a sequence selected from SEQ ID NOs: 26, 31 and 50.

Methods for incorporating the elements in Table 2 are well known in the art and would allow for the skilled artisan to generate the nucleic acids and plasmids of the invention using the methods outlined in Table 3 and the Examples.

3 Pharmaceutical Compositions

The invention provides pharmaceutical compositions comprising the viral vectors of the invention formulated together with a pharmaceutically acceptable carrier. The compositions can additionally contain one or more other therapeutic agents that are suitable for treating or preventing, for example, RLBP1-associated retinal dystrophy, and/or retinal pigmentosa (RP). Pharmaceutically acceptable carriers enhance or stabilize the composition, or can be used to facilitate preparation of the composition. Pharmaceutically acceptable carriers include solvents, surfactants, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. It is preferred that administration be subretinal. The pharmaceutically acceptable carrier should be suitable for subretinal, intravitreal, intravenous, subcutaneous or topical administration.

The composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

Pharmaceutical compositions of the invention can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the viral vector is employed in the pharmaceutical compositions of the invention. The viral vectors may be formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician or veterinarian can start doses of the viral vectors of the invention employed in the pharmaceutical composition at levels lower than that required to achieve the desired therapeutic effect and gradually increase the dosage until the desired effect is achieved. In general, effective doses of the compositions of the present invention, for the treatment of RLBP1-associated retinal dystrophy as described herein vary depending upon many different factors, including means of administration, target site, physiological state of the patient, whether the patient is human or an animal, other medications administered, and whether treatment is prophylactic or therapeutic. Treatment dosages need to be titrated to optimize safety and efficacy. For subretinal administration with a viral vector, the dosage may range from $1\times10^8$ vector genomes (vg)/eye to $1\times10^{12}$ vg/eye. For example the dosage may be, $1\times10^8$ vg/eye, $2.5\times10^8$ vg/eye, $5\times10^8$ vg/eye, $7.5\times10^8$ vg/eye, $1\times10^9$ vg/eye, $2.5\times10^9$ vg/eye, $5\times10^9$ vg/eye, $7.5\times10^9$ vg/eye, $1\times10^{10}$ vg/eye, $2.5\times10^{10}$ vg/eye, $5\times10^{10}$ vg/eye, $7.5\times10^{10}$ vg/eye, $1\times10^{11}$ vg/eye, $2.5\times10^{11}$ vg/eye, $5\times10^{11}$ vg/eye, $7.5\times10^{11}$ vg/eye, $1\times10^{12}$ vg/eye.

The viral vectors described herein are mainly used as one time doses per eye, with the possibility of repeat dosing to treat regions of the retina that are not covered in the previous dosing. The dosage of administration may vary depending on whether the treatment is prophylactic or therapeutic.

The various features and embodiments of the present invention, referred to in individual sections and embodiments above apply, as appropriate, to other sections and embodiments, mutatis mutandis. Consequently features specified in one section or embodiment may be combined with features specified in other sections or embodiments, as appropriate.

4. Therapeutic Uses

Viral vectors as described herein, can be used at a therapeutically useful concentration for the treatment of eye related diseases, by administering to a subject in need thereof, an effective amount of the viral vectors of the invention. More specifically, the present invention provides a method of treating RLBP1-associated retinal dystrophy, by administering to a subject in need thereof an effective amount of a viral vector comprising an RLBP1 coding sequence.

The present invention provides a viral vector comprising an RLBP1 coding sequence for use in treating RLBP1-associated retinal dystrophy in a subject.

Table A: RLBP1 Mutations and Associated Phenotypes of RLBP1-Associated Retinal Dystrophy. Disease phenotypes of RLBP1-associated retinal dystrophy include: Autosomal recessive retinitis pigmentosa (AARP), Bothnia dystrophy (BD), Newfoundland rod-cone dystrophy (NFRCD), Retinitis *punctata albescens* (RPA) and Fundus albipunctatus (FA).

TABLE A

| # pts | Mutation | Region | Disease | Night Blind | Yellow Dots | Pigment Deposits | Atrophy | Reference |
|---|---|---|---|---|---|---|---|---|
| | | | | Missense Mutations | | | | |
| 67 | R234W | Sweden | BD | Yes | Perifoveal, midperiphery | In advanced | Advanced | Burstedt et al 2001; Golovleva et al 2010; Golovleva et al 2012 |
| 10 | R234W/M226K | Sweden | BD | Yes | Perifoveal, midperiphery | In advanced | Advanced | Kohn et al 2008; Golovleva et al 2010; Golovleva et al 2012 |
| 2 | M226K | Sweden | BD | Yes | Perifoveal, midperiphery | In advanced | Advanced | Golovleva et al 2010; Golovleva et al 2012 |

TABLE A-continued

| # pts | Mutation | Region | Disease | Night Blind | Yellow Dots | Pigment Deposits | Atrophy | Reference |
|---|---|---|---|---|---|---|---|---|
| 4 | G116R | Pakistan | FA | Yes | Midperiphery | No | No | Naz et al 2011 |
| 4 | R151Q | Saudi Arabia | FA | Yes | Whole fundus | No | No | Katsaris et al 2001 |
| 4 | R151Q | India | ARRP | Yes | Whole fundus | Yes | Yes | Maw et al 1997 |
| 1 | R234W | Japan | BD | Yes | Perifoveal, midperiphery | In advanced | Advanced | Nojima et al 2011 |
| 1 | R103W R234W | Japan | RPA | Yes | Perifoveal, midperiphery | In advanced | Yes | Nakamura et al 2011 |
| 1 | G146D I201T | USA | RPA | No | Midperiphery | No | No | Demirci et al 2004 |
| 1 | R103W | USA | RPA | Yes | Midperiphery | No | Yes | Demirci et al 2004 |
| | | | | Truncating Mutations | | | | |
| 26 | 324G_A IVS3_2T 3 C | Canada | NFRCD | Yes | Perifoveal, midperiphery | No | Yes | Eichers et al 2002 |
| 6 | R156X | Pakistan | FA | Yes | Midperiphery | No | No | Naz et al 2011 |
| 4 | R151W Gly31 (2-bp del) | USA | RPA | Yes | Midperiphery | Few, peripheral | No | Fishman et al 2004 |
| 6 | Exons 7_9 del | Morocco | RPA | Yes | Perifoveal, midperiphery | No | No | Humbert et al 2006 Littink et al 2012 |
| 1 | IVS3_2T 3 C M226K | USA | RPA | Yes | Perifoveal, midperiphery | No | No | Morimura et al 1999 |
| 1 | Q278(1-bp del) | USA | RPA | Yes | Perifoveal | Few, peripheral | Yes | Morimura et al 1999 |

Use of recombinant AAV has been shown to be feasible and safe for the treatment of retinal disease (See, e.g., Bainbridge et al. 2008, Houswirth et al 2008, Maguire et al 2008). The viral vectors of the invention can be used, inter alia, to treat and prevent progression of RLBP1-associated retinal dystrophy and improve vision loss. Viral vectors of the invention can also be used in patients where other retinal dystrophy is caused by other loss of function mutations in the RLBP1 gene, for example, Autosomal recessive retinitis pigmentosa, Retinitis *punctata albescens* and Fundus albipunctatus.

The present invention is also relates to a method of expressing an RLBP1 coding sequence in RPE and Müller cells of the retina, by administering viral vectors of the invention to a subject in need thereof. The present invention also relates to viral vectors of the invention for use in expressing an RLBP1 coding sequence in RPE and/or Müller cells of the retina of the subject in need thereof. The invention also contemplates a method of delivering an RLBP1 coding sequence to the retina, specifically to RPE and/or Müller cells in the retina, of a subject having RLBP1-associated retinal dystrophy. It is contemplated that the an RLBP1 coding sequence is delivered to the subject in need thereof by contacting the retina, RPE and/or Müller cells of the subject with a viral vector as described herein. Alternatively, an RLBP1 coding sequence is delivered to a subject by administering to the subject a viral vector as described herein.

The present invention further includes methods of expressing an RLBP1 coding sequence in RPE and/or Müller cells in the retina of a subject having RLBP1-associated retinal dystrophy, by contacting the retina of the subject with viral vectors of the invention. In certain aspects RPE and/or Müller cells of the retina of the subject are contacted with viral vectors of the invention.

It is further contemplated that the viral vectors used in the methods described herein comprise an AAV2 or AAV8 capsid, and the vector genome comprises an RLBP1 coding sequence operably linked to an RLBP1 promoter with a nucleotide sequence selected from SEQ ID NO: 3 or 10. It is further contemplated that the vector genome can be self-complementary.

In one aspect the viral vectors described herein can be administered subretinally or intravitreally using methods known to those of skill in the art.

Treatment and/or prevention of ocular disease such as RLBP1-associated retinal dystrophy can be determined by an ophthalmologist or health care professional using clinically relevant measurements of visual function and/or retinal anatomy. Treatment of RLBP1-associated retinal dystrophy means any action (e.g., administration of a viral vector described herein) contemplated to improve or preserve visual function and/or retinal anatomy. In addition, prevention as it relates to RLBP1-associated retinal dystrophy means any action (e.g., administration of a viral vector described herein) that prevents or slows a worsening in visual function, retinal anatomy, and/or RLBP1-associated retinal dystrophy disease phenotype, as defined herein, in a patient at risk for said worsening.

Visual function may include, for example, visual acuity, visual acuity with low illumination, visual field, central visual field, peripheral vision, contrast sensitivity, dark adaptation, photostress recovery, color discrimination, reading speed, dependence on assistive devices (e.g., large typeface, magnifying devices, telescopes), facial recognition, proficiency at operating a motor vehicle, ability to perform one or more activities of daily living, and/or patient-reported satisfaction related to visual function. Thus, treatment of retinitis pigmentosa (RP), specifically RLBP1-associated retinal dystrophy, can be said to occur where a subject has an at least 10% decrease or lack of a 10% or more increase in time to a pre-specified degree of dark adaptation. In addition, treatment of RLBP1-associated retinal dystrophy can be said to occur where a subject exhibits early severe night blindness and slow dark adaptation in young age, followed by progressive loss of visual acuity, visual fields and color vision, leading to legal blindness, determined by a qualified health care professional (i.e., ophthalmologist) (Burstedt and Mönestam, 2010).

Exemplary measures of visual function include Snellen visual acuity, ETDRS visual acuity, low-luminance visual acuity, Amsler grid, Goldmann visual field, standard automated perimetry, microperimetry, Pelli-Robson charts, SKILL card, Ishihara color plates, Farnsworth D15 or D100 color test, standard electroretinography, multifocal electroretinography, validated tests for reading speed, facial recognition, driving simulations, and patient reported satisfaction. Thus, treatment of RLBP1-associated retinal dystrophy can be said to be achieved upon a gain of or failure to lose 2 or more lines (or 10 letters) of vision on an ETDRS scale. In addition, treatment of RLBP1-associated retinal dystrophy can be said to occur where a subject exhibits at least a 10% increase or lack of 10% decrease in reading speed (words per minute). In addition, treatment of RLBP1-associated retinal dystrophy can be said to occur where a subject exhibits at least a 20% increase or lack of a 20% decrease in the proportion of correctly identified plates on an Ishihara test or correctly sequenced disks on a Farnsworth test. Thus, treatment of, for example, RLBP1-associated retinal dystrophy can be determined by, for example, improvement of rate of dark adaptation, or an improvement in, or slowing of the rate of, visual acuity loss.

Undesirable aspects of retinal anatomy that may be treated or prevented include, for example, retinal atrophy, retinal pigment epithelium atrophy, narrowing of retinal vessels, pigmentary clumping, retinal yellow/white spots, subretinal fluid.

Exemplary means of assessing retinal anatomy include fundoscopy, fundus photography, fluorescein angiography, indocyanine green angiography, optical coherence tomography (OCT), spectral domain optical coherence tomography, scanning laser ophthalmoscopy, confocal microscopy, adaptive optics, fundus autofluorescence, biopsy, necropsy, and immunohistochemistry. Thus, RLBP1-associated retinal dystrophy can be said to be treated in a subject as determined by, for example, a reduction in the rate of development of retinal atrophy.

Subjects to be treated with therapeutic agents of the present invention can also be administered other therapeutic agents or devices with known efficacy for treating retinal dystrophy such as vitamin and mineral preparations, low-vision aids, guide dogs, or other devices known to assist patients with low vision.

Currently there are no other approved therapeutic agents for the treatment of RLBP1-associated retinal dystrophy. As other new therapies emerge, the two can be administered sequentially in either order or simultaneously as clinically indicated.

EXAMPLES

The following examples are provided to further illustrate the invention but not to limit its scope. Other variants of the invention will be readily apparent to one of ordinary skill in the art and are encompassed by the appended claims.

Example 1

Construction of AAV-ITR Plasmids 1.1 Cloning of AAV-ITR Plasmids:

The nucleic acid sequences of the individual plasmid elements are described in Table 1. The sequences were either synthesized or purchased commercially. Table 2 describes the elements that exist in each plasmid that was constructed. Standard molecular biology cloning techniques were used in generating the plasmids as described in Table 3. The plasmid backbone pAAV-MCS (Stratagene®) with Ampicillin resistance or pUC57 with Kanamycin resistance was used as the backbone and starting material. The individual sequence elements were cloned in at restriction enzyme sites or using blunt end cloning.

Because the antibiotic resistance gene cassette contained in the plasmid backbone does not play a role in the production of the AAV vectors, one of skill in the art could use alternate plasmid backbones and/or antibiotic resistance gene cassettes and yield the same viral vectors. We have demonstrated that functionally equivalent NVS2 vectors can be generated using plasmids with different backbones. For example, plasmid sequences SEQ ID NO: 26 and SEQ ID NO: 50 produce functionally equivalent NVS2 vectors.

1.2. Triple Plasmid Transfection to Produce rAAV Vectors:

Recombinant AAV (rAAV) viral vectors were generated by triple transfection methods. Methods for triple transfection are known in the art (Ferrari F K et al 1997). Briefly, AAV-ITR-containing plasmids (described in Table 2), AAV-RepCap containing plasmid (carrying Rep2 and Cap2 or Cap8) and Adeno-helper plasmid (carrying genes that assist in completing AAV replication cycle) were co-transfected into 293 cells. Cells were cultured for 4 days. At the end of the culture period the cells were lysed and the vectors in the culture supernatant and in the cell lysate were purified by a standard CsCl gradient centrifugation method (method modified based on Grieger J C et al 2006). The purified viral vectors are described in Table 4.

Alternatively, GMP-like rAAV vectors were generated by the cell transfection and culture methods described above. The harvested cell culture material was then processed by column chromatography based on methods described by Lock M et al (2010), Smith R H et al (2009) and Vandenberghe L H et al (2010).

1.3. Variation of 5' ITR Sequences:

As described previously (Samulski et al, 1983; Muzyczka et al, 1984), mutations within the terminal repeat sequences of AAV plasmids are well tolerated in generating functional AAV vectors. Even plasmids with one of the two ITRs deleted, the AAV sequences could be rescued, replicated, and infectious virions be produced, as long as the existing ITR in the construct contains the full AAV ITR sequence (Samulski et al, 1983; Muzyczka et al, 1984). Therefore, even though SEQ. ID. NO.2 is used as the 5' ITR sequence of all single-stranded AAV vectors described in this document, it is expected that any 5'ITR sequence that carries the terminal resolution site (i.e.: SEQ. ID. NOS. 2, 16 and 17) would produce vectors with the same functionality.

TABLE 1

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:) AND SEQUENCE |
|---|---|
| ΔITR | 1<br>cgcgctcgctcgctcactgaggccgcccgggcaaagcccgggcg<br>tcgggcgacctttggtcgcccggcctcagtgagcgagcgagcgc<br>gcagagagggagtgg |
| 5' ITR | 2<br>ctgcgcgctcgctcgctcactgaggccgcccgggcgtcgggcga<br>cctttggtcgcccggcctcagtgagcgagcgagcgcgcagagag<br>ggagtggccaactccatcactaggggttcct |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:) AND SEQUENCE |
|---|---|
| Human RLBP1 Promoter(short) (NT_010274.17) | 3<br>ttgtcctctccctgcttggccttaaccagccacatttctcaact<br>gaccccactcactgcagaggtgaaaactaccatgccaggtcctg<br>ctggctgggggaggggtgggcaataggcctggatttgccagagc<br>tgccactgtagatgtagtcatatttacgatttcccttcacctct<br>tattaccctggtggtggtggtgggggggggggggtgctctctca<br>gcaaccccaccccgggatcttgaggagaaagagggcagagaaaa<br>gagggaatgggactggcccagatcccagccccacagccgggctt<br>ccacatggccgagcaggaactccagagcaggagcacacaaagga<br>gggctttgatgcgcctccagccaggcccaggcctctcccctctc<br>ccctttctctctgggtcttcctttgccccactgagggcctcctg<br>tgagcccgatttaacggaaactgtgggcggtgagaagttcctta<br>tgacacactaatcccaacctgctgaccggaccacgcctccagcg<br>gagggaacctctagagctccaggacattcaggtaccaggtagcc<br>ccaaggaggagctgccga |
| MODIFIED SV40INTRON (MODIFIED EF579804) | 4<br>aactgaaaaaccagaaagttaactggtaagtttagtctttttgt<br>cttttatttcaggtcccggatccggtggtggtgcaaatcaaaga<br>actgctcctcagtggatgttgcctttacttctaggcctgtacgg<br>aagtgttacttctgctctaaaagctgcggaattgtacccgcccc<br>gggatcc |
| ADDED-KOZAK | 5<br>gccacc |
| HUMAN RLBP1 GENE CDS NM_000326.4 | 6<br>atgtcagaaggggtgggcacgttccgcatggtacctgaagagga<br>acaggagctccgtgcccaactggagcagctcacaaccaaggacc<br>atggacctgtctttggcccgtgcagccagctgccccgccacacc<br>ttgcagaaggccaaggatgagctgaacgagagagaggagacccg<br>ggaggaggcagtgcgagagctgcaggagatggtgcaggcgcagg<br>cggcctcgggggaggagctggcggtggccgtggcggagagggtg<br>caagagaaggacagcggcttcttcctgcgcttcatccgcgcacg<br>gaagttcaacgtgggccgtgcctatgagctgctcagaggctatg<br>tgaatttccggctgcagtaccctgagctctttgacagcctgtcc<br>ccagaggctgtccgctgcaccattgaagctggctaccctggtgt<br>cctctctagtcgggacaagtatggccgagtggtcatgctcttca<br>acattgagaactggcaaagtcaagaaatcacctttgatgagatc<br>ttgcaggcatattgcttcatcctggagaagctgctggagaatga<br>ggaaactcaaatcaatggcttctgcatcattgagaacttcaagg<br>gctttaccatgcagcaggctgctagtctccggacttcagatctc<br>aggaagatggtggacatgctccaggattccttcccagcccggtt<br>caaagccatccacttcatccaccagccatggtacttcaccacga<br>cctacaatgtggtcaagcccttcttgaagagcaagctgcttgag<br>agggtctttgtccacggggatgacctttctggtttctaccagga<br>gatcgatgagaacatcctgccctctgacttcgggggcacgctgc<br>ccaagtatgatggcaaggccgttgctgagcagctctttggcccc<br>caggcccaagctgagaacacagccttctga |
| HUMAN RLBP1 GENE PRODUCT (CELLULAR RETINALDEHYDE BINDING PROTEIN - CRALBP) | 7<br>MSEGVGTFRMVPEEEQELRAQLEQLTTKDHGPVFGPCSQLPRHT<br>LQKAKDELNEREETREEAVRELQEMVQAQAASGEELAVAVAERV<br>QEKDSGFFLRFIRARKFNVGRAYELLRGYVNFRLQYPELFDSLS<br>PEAVRCTIEAGYPGVLSSRDKYGRVVMLFNIENWQSQEITFDEI<br>LQAYCFILEKLLENEETQINGFCIIENFKGFTMQQAASLRTSDL<br>RKMVDMLQDSFPARFKAIHFIHQPWYFTTTYNVVKPFLKSKLLE<br>RVFVHGDDLSGFYQEIDENILPSDFGGTLPKYDGKAVAEQLFGP<br>QAQAENTAF |
| SV40 POLYA (EF579804) | 8<br>gatcataatcagccataccacatttgtagaggttttacttgctt<br>taaaaaacctcccacacctccccctgaacctgaaacataaaatg<br>aatgcaattgttgttgttaacttgtttattgcagcttataatgg<br>ttacaaataaagcaatagcatcacaaatttcacaaataaagcat<br>ttttttcactgcattctagttgtggtttgtccaaactcatcaat<br>gtatcttatcatgtct |
| 3' ITR (AF043303) | 9<br>aggaacccctagtgatggagttggccactccctctctgcgcgct<br>cgctcgctcactgaggccgggcgaccaaaggtcgcccgacgccc<br>gggctttgcccgggcggcctcagtgagcgagcgagcgcgcag |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:)AND SEQUENCE |
|---|---|
| Human RLBP1 Promoter(long) (NT_010274.17) | 10<br>ttgtcctctccctgcttggccttaaccagccacatttctcaact<br>gaccccactcactgcagaggtgaaaactaccatgccaggtcctg<br>ctggctgggggaggggtgggcaataggcctggatttgccagagc<br>tgccactgtagatgtagtcatatttacgatttcccttcacctct<br>tattaccctggtggtggtggtggggggggggggggtgctctctca<br>gcaaccccaccccgggatcttgaggagaaagagggcagagaaaa<br>gagggaatgggactggcccagatcccagccccacagccgggctt<br>ccacatggccgagcaggaactccagagcaggagcacacaaagga<br>gggctttgatgcgcctccagccaggcccaggcctctcccctctc<br>ccctttctctctgggtcttcctttgccccactgagggcctcctg<br>tgagcccgatttaacggaaactgtgggcggtgagaagttcctta<br>tgacacactaatcccaacctgctgaccggaccacgcctccagcg<br>gagggaacctctagagctccaggacattcaggtaccaggtagcc<br>ccaaggaggagctgccgacctggcaggtaagtcaatacctgggg<br>cttgcctgggccagggagcccaggactggggtgaggactcaggg<br>gagcagggagaccacgtcccaagatgcctgtaaaactgaaacca<br>cctggccattctccaggttgagccagaccaatttgatggcagat<br>ttagcaaataaaaatacaggacacccagttaaatgtgaatttca<br>gatgaacagcaaatacttttttagtattaaaaaagttcacattt<br>aggctcacgcctgtaatcccagcactttgggaggccgaggcagg<br>cagatcacctgaggtcaggagttcgagaccagcctggccaacat<br>ggtgaaaccccatctccactaaaaataccaaaaattagccaggc<br>gtgctggtgggcacctgtagttccagctactcaggaggctaagg<br>caggagaattgcttgaacctgggaggcagaggttgcagtgagct<br>gagatcgcaccattgcactctagcctgggcgacaagaacaaaac<br>tccatctcaaaaaaaaaaaaaaaaaaaaagttcacatttaactg<br>ggcattctgtatttaattggtaatctgagatggcagggaacagc<br>atcagcatggtgtgagggataggcattttttcattgtgtacagc<br>ttgtaaatcagtatttttaaaactcaaagttaatggcttgggca<br>tatttagaaaagagttgccgcacggacttgaaccctgtattcct<br>aaaatctaggatcttgttctgatggtctgcacaactggctgggg<br>gtgtccagccactgtccctcttgcctgggctccccagggcagtt<br>ctgtcagcctctccatttccattcctgttccagcaaaacccaac<br>tgatagcacagcagcatttcagcctgtctacctctgtgcccaca<br>tacctggatgtctaccagccagaaaggtggcttagatttggttc<br>ctgtgggtggattatggcccccagaacttccctgtgcttgctgg<br>gggtgtggagtggaaagagcaggaaatgggggaccctccgatac<br>tctatgggggtcctccaagtctctttgtgcaagttagggtaata<br>atcaatatggagctaagaaagagaaggggaactatgctttagaa<br>caggacactgtgccaggagcattgcagaaattatatggttttca<br>cgacagttctttttggtaggtactgttattatcctcagtttgca<br>gatgaggaaactgagacccagaaaggttaaataacttgctaggg<br>tcacacaagtcataactgacaaagcctgattcaaacccaggtct<br>ccctaacctttaaggtttctatgacgccagctctcctagggagt<br>ttgtcttcagatgtcttggctctaggtgtcaaaaaaagacttgg<br>tgtcaggcaggcataggttcaagtcccaactctgtcacttacca<br>actgtgactaggtgattgaactgaccatggaacctggtcacatg<br>caggagcaggatggtgaagggttcttgaaggcacttaggcagga<br>catttaggcaggagagaaaacctggaaacagaagagctgtctcc<br>aaaaatacccactggggaagcaggttgtcatgtgggccatgaat<br>gggacctgttctggtaaccaagcattgcttatgtgtccattaca<br>tttcataacacttccatcctactttacagggaacaaccaagact<br>ggggttaaatctcacagcctgcaagtggaagagaagaacttgaa<br>cccaggtccaacttttgcgccacagcaggctgcctcttggtcct<br>gacaggaagtcacaacttgggtctgagtactgatccctggctat<br>tttttggctgtgttaccttggacaagtcacttattcctcctccc<br>gtttcctcctatgtaaaatggaaataataatgttgaccctgggt<br>ctgagagagtggatttgaaagtacttagtgcatcacaaagcaca<br>gaacacacttccagtctcgtgattatgtacttatgtaactggtc<br>atcacccatcttgagaatgaatgcattggggaaagggccatcca<br>ctaggctgcgaagtttctgagggactccttcgggctggagaagg<br>atggccacaggagggaggagagattgccttatcctgcagtgatc<br>atgtcattgagaacagagccagattctttttttcctggcagggc<br>caacttgttttaacatctaaggactgagctatttgtgtctgtgc<br>cctttgtccaagcagtgtttcccaaagtgtagcccaagaaccat<br>ctccctcagagccaccaggaagtgctttaaattgcaggttccta<br>ggccacagcctgcacctgcagagtcagaatcatggaggttggga<br>cccaggcacctgcgtttctaacaaatgcctcgggtgattctgat<br>gcaattgaaagtttgagatccacagttctgagacaataacagaa<br>tggtttttctaacccctgcagccctgacttcctatcctagggaa<br>ggggccggctggagaggccaggacagagaaagcagatcccttct<br>ttttccaaggactctgtgtcttccataggcaac |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:)AND SEQUENCE |
|---|---|
| HUMAN RPE65 PROMOTER | 11<br>tacgtaatatttattgaagtttaatattgtgtttgtgatacaga<br>agtatttgctttaattctaaataaaaattttatgcttttattgc<br>tggtttaagaagatttggattatccttgtactttgaggagaagt<br>ttcttatttgaaatattttggaaacaggtcttttaatgtggaaa<br>gatagatattaatctcctcttctattactctccaagatccaaca<br>aaagtgattatacccccaaaatatgatggtagtatcttatact<br>accatcattttataggcatagggctcttagctgcaaataatgga<br>actaactctaataaagcagaacgcaaatattgtaaatattagag<br>agctaacaatctctgggatggctaaaggatggagcttggaggct<br>acccagccagtaacaatattccgggctccactgttgaatggaga<br>cactacaactgccttggatgggcagagatattatggatgctaag<br>ccccaggtgctaccattaggacttctaccactgtccctaacggg<br>tggagcccatcacatgcctatgccctcactgtaaggaaatgaag<br>ctactgttgtatatcttgggaagcacttggattaattgttatac<br>agttttgttgaagaagacccctagggtaagtagccataactgca<br>cactaaatttaaaattgttaatgagtttctcaaaaaaaatgtta<br>aggttgttagctggtatagtatatatcttgcctgttttccaagg<br>acttctttgggcagtaccttgtctgtgctggcaagcaactgaga<br>cttaatgaaagagtattggagatatgaatgaattgatgctgtat<br>actctcagagtgccaaacatataccaatggacaagaaggtgagg<br>cagagagcagacaggcattagtgacaagcaaagatatgcagaat<br>ttcattctcagcaaatcaaaagtcctcaacctggttggaagaat<br>attggcactgaatggtatcaataaggttgctagagagggttaga<br>ggtgcacaatgtgcttccataacattttatacttctccaatctt<br>agcactaatcaaacatggttgaatactttgtttactataactct<br>tacagagttataagatctgtgaagacagggacagggacaatacc<br>catctctgtctggttcataggtggtatgtaatagatatttttaa<br>aaataagtgagttaatgaatgagggtgagaatgaaggcacagag<br>gtattagggggaggtgggccccagagaatggtgccaaggtccag<br>tggggtgactgggatcagctcaggcctgacgctggccactccca<br>cctagctcctttctttctaatctgttctcattctccttgggaag<br>gattgaggtctctggaaaacagccaaacaactgttatgggaaca<br>gcaagcccaaataaagccaagcatcaggggggatctgagagctga<br>aagcaacttctgttcccccctccctcagctgaaggggtggggaag<br>ggctcccaaagccataactccttttaagggatttagaaggcata<br>aaaaggcccctggctgagaacttccttcttcattctgcagttgg<br>t |
| HUMAN VMD2 PROMOTER | 12<br>tacgtaattctgtcattttactagggtgatgaaattcccaagca<br>acaccatccttttcagataagggcactgaggctgagagaggagc<br>tgaaacctacccggcgtcaccacacacaggtggcaaggctggga<br>ccagaaaccaggactgttgactgcagcccggtattcattctttc<br>catagcccacagggctgtcaaagaccccagggcctagtcagagg<br>ctcctccttcctggagagttcctggcacagaagttgaagctcag<br>cacagccccctaacccccaactctctctgcaaggcctcaggggt<br>cagaacactggtggagcagatcctttagcctctggattttaggg<br>ccatggtagaggggggtgttgccctaaattccagccctggtctca<br>gcccaacaccctccaagaagaaattagaggggccatggccaggc<br>tgtgctagccgttgcttctgagcagattacaagaagggactaag<br>acaaggactcctttgtggaggtcctggcttagggagtcaagtga<br>cggcggctcagcactcacgtgggcagtgccagcctctaagagtg<br>ggcaggggcactggccacagagtcccagggagtcccaccagcct<br>agtcgccagacc |
| SYNUCLEIN INTRONIC SEQUENCE AS STUFFER SEQUENCE | 13<br>gggccccggtgttatctcattctttttctcctctgtaagttga<br>catgtgatgtgggaacaaaggggataaagtcattattttgtgct<br>aaaatcgtaattggagaggacctcctgttagctgggctttcttc<br>tatttattgtggtggttactggagttccttcttctagttttagg<br>atatatatatatatttttttttttttctttccctgaagatataat<br>aatatatatacttctgaagattgagatttttaaattagttgtat<br>tgaaaactagctaatcagcaatttaaggctagcttgagacttat<br>gtcttgaatttgtttttgtaggctccaaaaccaaggagggagtg<br>gtgcatggtgtggcaacaggtaagctccattgtgcttatatcca<br>aagatgatatttaaagtatctagtgattagtgtggcccagtatt<br>caagattcctatgaaattgtaaaacaatcactgagcattctaag<br>aacatatcagtcttattgaaactgaattctttataaagtatttt<br>taaaaaggtaaatattgattataaataaaaaatatacttgccaa<br>gaataatgagggctttgaattgataagctatgtttaatttatag<br>taagtgggcatttaaatattctgaccaaaaatgtattgacaaac<br>tgctgacaaaaataaaatgtgaatattgccataattttaaaaaa<br>agagtaaaatttctgttgattacagtaaaatattttgaccttaa |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:)AND SEQUENCE |
|---|---|
| | attatgttgattacaatattcctttgataattcagagtgcattt<br>caggaaacacccttggacagtcagtaaattgtttattgtattta<br>tctttgtattgttatggtatagctatttgtacaaatattattgt<br>gcaattattacatttctgattatattattcatttggcctaaatt<br>taccaagaatttgaacaagtcaattaggtttacaatcaagaaat<br>atcaaaaatgatgaaaaggatgataatcatcatcagatgttgag<br>gaagatgacgatgagagtgccagaaatagagaaatcaaaggaga<br>accaaaatttaacaaattaaaagcccacagacttgctgtaatta<br>agttttctgttgtaagtactccacgtttcctggcagatgtggtg<br>aagcaaaagatataatcagaaatataatttatatgatcggaaag<br>cattaaacacaatagtgcctatacaaataaaatgttcctatcac<br>tgacttctaaaatggaaatgaggacaatgatatgggaatcttaa<br>tacagtgttgtggataggactaaaaacacaggagtcagatcttc<br>ttggttcaacttcctgcttactccttaccagctgtgtgtttttt<br>gcaaggttcttcacctctatgtgatttagcttcctcatctataa<br>aataattcagtgaattaatgtacacaaaacatctggaaaacaaa<br>agcaaacaatatgtattttataagtgttacttatagttttatag<br>tgaactttcttgtgcaacatttttacaactagtggagaaaaata<br>tttctttaaatgaatacttttgatttaaaaatcagagtgtaaaa<br>ataaaacagactcctttgaaactagttctgttagaagttaattg<br>tgcacctttaatgggctctgttgcaatccaacagagaagtagtt<br>aagtaagtggactatgatggcttctagggacctcctataaatat<br>gatattgtgaagcatgattataataagaactagataacagacag<br>gtggagactccactatctgaagagggtcaacctagatgaatggt<br>gttccatttagtagttgaggaagaacccatgaggtttagaaagc<br>agacaagcatgtggcaagttctggagtcagtggtaaaaattaaa<br>gaacccaactattactgtcacctaatgatctaatggagactgtg<br>gagatgggctgcatttttttaatcttctccagaatgccaaaatg<br>taaacacatatctgtgtgtgtgtgtgtgtgtgtgtgtgtgtgtg<br>agagagagagagagagagagagagagactgaagtttgtacaattag<br>acattttataaaatgttttctgaaggacagtggctcacaatctt<br>aagtttctaacattgtacaatgttgggagactttgtatacttta<br>ttttctctttagcatattaaggaatctgagatgtcctacagtaa<br>agaaatttgcattacatagttaaaatcagggttattcaaacttt<br>ttgattattgaaacctttcttcattagttactagggttgaatga<br>aactagtgttccacagaaaactatgggaaatgttgctaggcagt<br>aaggacatggtgatttcagcatgtgcaatatttacagcgattgc<br>acccatggaccaccctggcagtagtgaaataaccaaaaatgctg<br>tcataactagtatggctatgagaaacacattggg |
| RLBP1 INTRONIC SEQUENCE AS STUFFER SEQUENCE (NT 010274.17) | 14<br>ATTCTCCAGGTTGAGCCAGACCAATTTGATGGTAGATTTAGCAA<br>ATAAAAATACAGGACACCCAGTTAAATGTGAATTTCCGATGAAC<br>AGCAAATACTTTTTTAGTATTAAAAAAGTTCACATTTAGGCTCA<br>CGCCTGTAATCCCAGCACTTTGGGAGGCCGAGGCAGGCAGATCA<br>CCTGAGGTCAGGAGTTCGAGACCAGCCTGGCCAACATGGTGAAA<br>CCCCATCTCCACTAAAAATACCAAAAATTAGCCAGGCGTGCTGG<br>TGGGCACCTGTAGTTCCAGCTACTCAGGAGGCTAAGGCAGGAGA<br>ATTGCTTGAACCTGGGAGGCAGAGGTTGCAGTGAGCTGAGATCG<br>CACCATTGCACTCTAGCCTGGGCGACAAGAACAAAACTCCATCT<br>CAAAAAAAAAAAAAAAAAAAAAAGTTCACATTTAACTGGGCATTC<br>TGTATTTAATTGGTAATCTGAGATGGCAGGGAACAGCATCAGCA<br>TGGTGTGAGGGATAGGCATTTTTTCATTGTGTACAGCTTGTAAA<br>TCAGTATTTTTAAAACTCAAAGTTAATGGCTTGGGCATATTTAG<br>AAAAGAGTTGCCGCACGGACTTGAACCCTGTATTCCTAAAATCT<br>AGGATCTTGTTCTGATGGTCTGCACAACTGGCTGGGGGTGTCCA<br>GCCACTGTCCCTCTTGCCTGGGCTCCCCAGGGCAGTTCTGTCAG<br>CCTCTCCATTTCCATTCCTGTTCCAGCAAAACCCAACTGATAGC<br>ACAGCAGCATTTCAGCCTGTCTACCTCTGTGCCCACATACCTGG<br>ATGTCTACCAGCCAGAAAGGTGGCTTAGATTTGGTTCCTGTGGG<br>TGGATTATGGCCCCCAGAACTTCCCTGTGCTTGCTGGGGGTGTG<br>GAGTGGAAAGAGCAGGAAATGGGGGACCCTCCGATACTCTATGG<br>GGGTCCTCCAAGTCTCTTTGTGCAAGTTAGGGTAATAATCAATA<br>TGGAGCTAAGAAAGAGAAGGGGAACTATGCTTTAGAACAGGACA<br>CTGTGCCAGGAGCATTGCAGAAATTATATGGTTTTCACGACAGT<br>TCTTTTTGGTAGGTACTGTTATTATCCTCAGTTTGCAGATGAGG<br>AAACTGAGACCCAGAAAGGTTAAATAACTTGCTAGGGTCACACA<br>AGTCATAACTGACAAAGCCTGATTCAAACCCAGGTCTCCCTAAC<br>CTTTAAGGTTTCTATGACGCCAGCTCTCCTAGGGAGTTTGTCTT<br>CAGATGTCTTGGCTCTAGGTGTCAAAAAAAGACTTGGTGTCAGG<br>CAGGCATAGGTTCAAGTCCCAACTCTGTCACTTACCAACTGTGA<br>CTAGGTGATTGAACTGACCATGGAACCTGGTCACATGCAGGAGC<br>AGGATGGTGAAGGGTTCTTGAAGGCACTTAGGCAGGACATTTAG<br>GCAGGAGAGAAAACCTGGAAACAGAAGAGCTGTCTCCAAAAATA |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:)AND SEQUENCE |
|---|---|
| | CCCACTGGGGAAGCAGGTTGTCATGTGGGCCATGAATGGGACCT GTTCTGG |
| AMP BACTERIAL BACKBONE | 15<br>ctgcctgcaggggcgcctgatgcggtattttctccttacgcatc tgtgcggtatttcacaccgcatacgtcaaagcaaccatagtacg cgccctgtagcggcgcattaagcgcggcgggtgtggtggttacg cgcagcgtgaccgctacacttgccagcgccttagcgcccgctcc tttcgctttcttcccttcctttctcgccacgttcgccggctttc cccgtcaagctctaaatcgggggctccctttagggttccgattt agtgctttacggcacctcgaccccaaaaaacttgatttgggtga tggttcacgtagtgggccatcgccctgatagacggtttttcgcc ctttgacgttggagtccacgttctttaatagtggactcttgttc caaactggaacaacactcaactctatctcgggctattcttttga tttataagggattttgccgatttcggtctattggttaaaaaatg agctgatttaacaaaaatttaacgcgaattttaacaaaatatta acgtttacaattttatggtgcactctcagtacaatctgctctga tgccgcatagttaagccagccccgacacccgccaacacccgctg acgcgccctgacgggcttgtctgctcccggcatccgcttacaga caagctgtgaccgtctccgggagctgcatgtgtcagaggttttc accgtcatcaccgaaacgcgcgagacgaaagggcctcgtgatac gcctatttttataggttaatgtcatgataataatggtttcttag acgtcaggtggcacttttcggggaaatgtgcgcggaacccctat ttgtttatttttctaaatacattcaaatatgtatccgctcatga gacaataaccctgataaatgcttcaataatattgaaaaaggaag agtatgagtattcaacatttccgtgtcgcccttattcccttttt tgcggcattttgccttcctgtttttgctcacccagaaacgctgg tgaaagtaaaagatgctgaagatcagttgggtgcacgagtgggt tacatcgaactggatctcaacagcggtaagatccttgagagttt tcgccccgaagaacgttttccaatgatgagcacttttaaagttc tgctatgtggcgcggtattatcccgtattgacgccgggcaagag caactcggtcgccgcatacactattctcagaatgacttggttga gtactcaccagtcacagaaaagcatcttacggatggcatgacag taagagaattatgcagtgctgccataaccatgagtgataacact gcggccaacttacttctgacaacgatcggaggaccgaaggagct aaccgcttttttgcacaacatgggggatcatgtaactcgccttg atcgttgggaaccggagctgaatgaagccataccaaacgacgag cgtgacaccacgatgcctgtagcaatggcaacaacgttgcgcaa actattaactggcgaactacttactctagcttcccggcaacaat taatagactggatggaggcggataaagttgcaggaccacttctg cgctcggcccttccggctggctggtttattgctgataaatctgg agccggtgagcgtgggtctcgcggtatcattgcagcactggggc cagatggtaagccctcccgtatcgtagttatctacacgacgggg agtcaggcaactatggatgaacgaaatagacagatcgctgagat aggtgcctcactgattaagcattggtaactgtcagaccaagttt actcatatatactttagattgatttaaaacttcatttttaattt aaaaggatctaggtgaagatcctttttgataatctcatgaccaa aatcccttaacgtgagttttcgttccactgagcgtcagaccccg tagaaaagatcaaaggatcttcttgaaatcctttttttctgcgc gtaatctgctgcttgcaaacaaaaaaaccaccgctaccagcggt ggtttgtttgccggatcaagagctaccaactctttttccgaagg taactggcttcagcagagcgcagataccaaatactgttcttcta gtgtagccgtagttaggccaccacttcaagaactctgtagcacc gcctacatacctcgctctgctaatcctgttaccagtggctgctg ccagtggcgataagtcgtgtcttaccgggttggactcaagacga tagttaccggataaggcgcagcggtcgggctgaacggggggttc gtgcacacagcccagcttggagcgaacgacctacaccgaactga gatacctacagcgtgagctatgagaaagcgccacgcttcccgaa gggagaaaggcggacaggtatccggtaagcggcagggtcggaac aggagagcgcacgagggagcttccagggggaaacgcctggtatc tttatagtcctgtcgggtttcgccacctctgacttgagcgtcga tttttgtgatgctcgtcaggggggcggagcctatggaaaaacgc cagcaacgcggcctttttacggttcctggccttttgctggcctt ttgctcacatgtcctgcaggcag |
| 5' ITR - STRATAGENE | 16<br>Ctgcgcgctcgctcgctcactgaggccgcccgggcaaagcccgg gcgtcgggcgacctttggtcgcccggcctcagtgagcgagcgag cgcgcagagagggagtggccaactccatcactaggggttcct |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:)AND SEQUENCE |
|---|---|
| 5' ITR - NCBI (AF043303) | 17<br>Ttggccactccctctctgcgcgctcgctcgctcactgaggccgg<br>gcgaccaaaggtcgcccgacgcccgggctttgcccgggcggcct<br>cagtgagcgagcgagcgcgcagagagggagtggccaactccatc<br>actaggggttcct |
| AAV2 CAPSID CODING SEQUENCE | 18<br>atggctgccgatggttatcttccagattggctcgaggacactct<br>ctctgaaggaataagacagtggtggaagctcaaacctggcccac<br>caccaccaaagcccgcagagcggcataaggacgacagcaggggt<br>cttgtgcttcctgggtacaagtacctcggacccttcaacggact<br>cgacaagggagagccggtcaacgaggcagacgccgcggccctcg<br>agcacgacaaagcctacgaccggcagctcgacagcggagacaac<br>ccgtacctcaagtacaaccacgccgacgcggagtttcaggagcg<br>ccttaaagaagatacgtcttttgggggcaacctcggacgagcag<br>tcttccaggcgaaaaagagggttcttgaacctctgggcctggtt<br>gaggaacctgttaagacggctccgggaaaaaagaggccggtaga<br>gcactctcctgtggagccagactcctcctcgggaaccggaaagg<br>cgggccagcagcctgcaagaaaaagattgaattttggtcagact<br>ggagacgcagactcagtacctgacccccagcctctcggacagcc<br>accagcagccccctctggtctgggaactaatacgatggctacag<br>gcagtggcgcaccaatggcagacaataacgagggcgccgacgga<br>gtgggtaattcctcgggaaattggcattgcgattccacatggat<br>gggcgacagagtcatcaccaccagcacccgaacctgggccctgc<br>ccacctacaacaaccacctctacaaacaaatttccagccaatca<br>ggagcctcgaacgacaatcactactttggctacagcaccccttg<br>ggggtattttgacttcaacagattccactgccacttttcaccac<br>gtgactggcaaagactcatcaacaacaactggggattccgaccc<br>aagagactcaacttcaagctctttaacattcaagtcaaagaggt<br>cacgcagaatgacggtacgacgacgattgccaataaccttacca<br>gcacggttcaggtgtttactgactcggagtaccagctcccgtac<br>gtcctcggctcggcgcatcaaggatgcctcccgccgttcccagc<br>agacgtcttcatggtgccacagtatggatacctcaccctgaaca<br>acgggagtcaggcagtaggacgctcttcattttactgcctggag<br>tactttccttctcagatgctgcgtaccggaaacaactttacctt<br>cagctacacttttgaggacgttcctttccacagcagctacgctc<br>acagccagagtctggaccgtctcatgaatcctctcatcgaccag<br>tacctgtattacttgagcagaacaaacactccaagtggaaccac<br>cacgcagtcaaggcttcagttttctcaggccggagcgagtgaca<br>ttcgggaccagtctaggaactggcttcctggaccctgttaccgc<br>cagcagcgagtatcaaagacatctgcggataacaacaacagtga<br>atactcgtggactggagctaccaagtaccacctcaatggcagag<br>actctctggtgaatccgggcccggccatggcaagccacaaggac<br>gatgaagaaaagtttttcctcagagcggggttctcatctttgg<br>gaagcaaggctcagagaaaacaaatgtggacattgaaaaggtca<br>tgattacagacgaagaggaaatcaggacaaccaatcccgtggct<br>acggagcagtatggttctgtatctaccaacctccagagaggcaa<br>cagacaagcagctaccgcagatgtcaacacacaaggcgttcttc<br>caggcatggtctggcaggacagagatgtgtaccttcaggggccc<br>atctgggcaaagattccacacacggacggacattttcacccctc<br>tcccctcatgggtggattcggacttaaacaccctcctccacaga<br>ttctcatcaagaacaccccggtacctgcgaatccttcgaccacc<br>ttcagtgcggcaaagtttgcttccttcatcacacagtactccac<br>gggacaggtcagcgtggagatcgagtgggagctgcagaaggaaa<br>acagcaaacgctggaatcccgaaattcagtacacttccaactac<br>aacaagtctgttaatgtggactttactgtggacactaatggcgt<br>gtattcagagcctcgccccattggcaccagatacctgactcgta<br>atctgtaa |
| AAV2 CAPSID SEQUENCE (VP1) | 19<br>maadgylpdwledtlsegirqwwklkpgppppkpaerhkddsrg<br>lvlpgykylgpfngldkgepvneadaaalehdkaydrqldsgdn<br>pylkynhadaefqerlkedtsfggnlgravfqakkrvleplglv<br>eepvktapgkkrpvehspvepdsssgtgkagqqparkrlnfgqt<br>gdadsvpdpqplgqppaapsglgtntmatgsgapmadnnegadg<br>vgnssgnwhcdstwmgdrvittstrtwalptynnhlykqissqs<br>gasndnhyfgystpwgyfdfnrfhchfsprdwqrlinnnwgfrp<br>krlnfklfniqvkevtqndgtttiannltstvqvftdseyqlpy<br>vlgsahqgclppfpadvfmvpqygyltlnngsqavgrssfycle<br>yfpsqmlrtgnnftfsytfedvpfhssyahsqsldrlmnplidq<br>ylyylsrtntpsgtttqsrlqfsqagasdirdqsrnwlpgpcyr<br>qqrvsktsadnnnseyswtgatkyhlngrdslvnpgpamashkd<br>deekffpqsgvlifgkqgsektnvdiekvmitdeeeirttnpva |

TABLE 1-continued

| Sequence of viral vector and plasmid elements AMINO ACID SEQUENCE OR POLYNUCLEOTIDE (PN) | |
|---|---|
| SEQUENCE ELEMENTS | SEQUENCE IDENTIFIER (SEQ. ID. NO:)AND SEQUENCE |
| | teqygsvstnlqrgnrqaatadvntqgvlpgmvwqdrdvylqgp iwakiphtdghfhpsplmggfglkhpppqilikntpvpanpstt fsaakfasfitqystgqvsveiewelqkenskrwnpeiqytsny nksvnvdftvdtngvyseprpigtryltrnl |
| AAV2 CAPSID SEQUENCE (VP2) | 68 mapgkkrpvehspvepdsssgtgkagqqparkrlnfgqtgdads vpdpqplgqppaapsglgtntmatgsgapmadnnegadgvgnss gnwhcdstwmgdrvittstrtwalptynnhlykqissqsgasnd nhyfgystpwgyfdfnrfhchfsprdwqrlinnnwgfrpkrlnf klfniqvkevtqndgtttiannltstvqvftdseyqlpyvlgsa hqgclppfpadvfmvpqygyltlnngsqavgrssfycleyfpsq mlrtgnnftfsytfedvpfhssyahsqsldrlmnplidqylyyl srtntpsgtttqsrlqfsqagasdirdqsrnwlpgpcyrqqrvs ktsadnnnseyswtgatkyhlngrdslvnpgpamashkddeekf fpqsgvlifgkqgsektnvdiekvmitdeeeirttnpvateqyg systnlqrgnrqaatadvntqgvlpgmvwqdrdvylqgpiwaki phtdghfhpsplmggfglkhpppqilikntpvpanpsttfsaak fasfitqystgqvsveiewelqkenskrwnpeiqytsnynksvn vdftvdtngvyseprpigtryltrnl |
| AAV2 CAPSID SEQUENCE (VP3) | 69 matgsgapmadnnegadgvgnssgnwhcdstwmgdrvittstrt walptynnhlykqissqsgasndnhyfgystpwgyfdfnrfhch fsprdwqrlinnnwgfrpkrlnfklfniqvkevtqndgtttian nltstvqvftdseyqlpyvlgsahqgclppfpadvfmvpqygyl tlnngsqavgrssfycleyfpsqmlrtgnnftfsytfedvpfhs syahsqsldrlmnplidqylyylsrtntpsgtttqsrlqfsqag asdirdqsrnwlpgpcyrqqrvsktsadnnnseyswtgatkyhl ngrdslvnpgpamashkddeekffpqsgvlifgkqgsektnvdi ekvmitdeeeirttnpvateqygsvstnlqrgnrqaatadvntq gvlpgmvwqdrdvylqgpiwakiphtdghfhpsplmggfglkhp ppqilikntpvpanpsttfsaakfasfitqystgqvsveiewel qkenskrwnpeiqytsnynksvnvdftvdtngvyseprpigtry ltrnl |
| AAV8 CAPSID CODING SEQUENCE | 20 atggctgccgatggttatcttccagattggctcgaggacaacct ctctgagggcattcgcgagtggtgggcgctgaaacctggagccc cgaagcccaaagccaaccagcaaaagcaggacgacggccggggt ctggtgcttcctggctacaagtacctcggacccttcaacggact cgacaagggggagcccgtcaacgcggcggacgcagcggccctcg agcacgacaaggcctacgaccagcagctgcaggcgggtgacaat ccgtacctgcggtataaccacgccgacgccgagtttcaggagcg tctgcaagaagatacgtcttttgggggcaacctcgggcgagcag tcttccaggccaagaagcgggttctcgaacctctcggtctggtt gaggaaggcgctaagacggctcctggaaagaagagaccggtaga gccatcaccccagcgttctccagactcctctacgggcatcggca agaaaggccaacagcccgccagaaaaagactcaattttggtcag actggcgactcagagtcagttccagaccctcaacctctcggaga acctccagcagcgccctctggtgtgggacctaatacaatggctg caggcggtggcgcaccaatggcagacaataacgaaggcgccgac ggagtgggtagttcctcgggaaattggcattgcgattccacatg gctgggcgacagagtcatcaccaccagcacccgaacctgggccc tgcccacctacaacaaccacctctacaagcaaatctccaacggg acatcgggaggagccaccaacgacaacacctacttcggctacag cacccccctgggggtattttgactttaacagattccactgccact tttcaccacgtgactggcagcgactcatcaacaacaactgggga ttccggcccaagagactcagcttcaagctcttcaacatccaggt caaggaggtcacgcagaatgaaggcaccaagaccatcgccaata acctcaccagcaccatccaggtgtttacggactcggagtaccag ctgccgtacgttctcggctctgcccaccagggctgcctgcctcc gttcccggcggacgtgttcatgattccccagtacggctacctaa cactcaacaacggtagtcaggccgtgggacgctcctccttctac tgcctggaatactttccttcgcagatgctgagaaccggcaacaa cttccagtttacttacaccttcgaggacgtgcctttccacagca gctacgcccacagccagagcttggaccggctgatgaatcctctg attgaccagtacctgtactacttgtctcggactcaaacaacagg aggcacggcaaatacgcagactctgggcttcagccaaggtgggc ctaatacaatggccaatcaggcaaagaactggctgccaggaccc tgttaccgccaacaacgcgtctcaacgacaaccgggcaaaacaa caatagcaactttgcctggactgctgggaccaaataccatctga atggaagaaattcattggctaatcctggcatcgctatggcaaca cacaaagacgacgaggagcgtttttttcccagtaacgggatcct |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:) AND SEQUENCE |
|---|---|
| | gatttttggcaaacaaaatgctgccagagacaatgcggattaca gcgatgtcatgctcaccagcgaggaagaaatcaaaaccactaac cctgtggctacagaggaatacggtatcgtggcagataacttgca gcagcaaaacacggctcctcaaattggaactgtcaacagccagg gggccttacccggtatggtctggcagaaccgggacgtgtacctg cagggtcccatctgggccaagattcctcacacggacggcaactt ccacccgtctccgctgatgggcggctttggcctgaaacatcctc cgcctcagatcctgatcaagaacacgcctgtacctgcggatcct ccgaccaccttcaaccagtcaaagctgaactctttcatcacgca atacagcaccggacaggtcagcgtggaaattgaatgggagctgc agaaggaaaacagcaagcgctggaaccccgagatccagtacacc tccaactactacaaatctacaagtgtggactttgctgttaatac agaaggcgtgtactctgaaccccgccccattggcacccgttacc tcacccgtaatctgtaa |
| AAV8 CAPSID SEQUENCE (VP1) | 21<br>maadgylpdwlednlsegirewwalkpgapkpkanqqkqddgrg lvlpgykylgpfngldkgepvnaadaaalehdkaydqqlqagdn pylrynhadaefqerlqedtsfggnlgravfqakkrvleplglv eegaktapgkkrpvepspqrspdsstgigkkgqqparkrlnfgq tgdsesvpdpqplgeppaapsgvgpntmaagggapmadnnegad gvgsssgnwhcdstwlgdrvittstrtwalptynnhlykqisng tsggatndntyfgystpwgyfdfnrfhchfsprdwqrlinnnwg frpkrlsfklfniqvkevtqnegtktiannltstiqvftdseyq lpyvlgsahqgclppfpadvfmipqygyltlnngsqavgrssfy cleyfpsqmlrtgnnfqftytfedvpfhssyahsqsldrlmnpl idqylyylsrtqttggtantqtlgfsqggpntmanqaknwlpgp cyrqqrvstttgqnnnsnfawtagtkyhlngrnslanpgiamat hkddeerffpsngilifgkqnaardnadysdvmltseeeikttn pvateeygivadnlqqqntapqigtvnsqgalpgmvwqnrdvyl qgpiwakiphtdgnfhpsplmggfglkhpppqilikntpvpadp pttfnqsklnsfitqystgqvsveiewelqkenskrwnpeiqyt snyykstsvdfavntegvyseprpigtryltrnl |
| AAV8 CAPSID SEQUENCE (VP2) | 70<br>mapgkkrpvepspqrspdsstgigkkgqqparkrlnfgqtgdse svpdpqplgeppaapsgvgpntmaagggapmadnnegadgvgss sgnwhcdstwlgdrvittstrtwalptynnhlykqisngtsgga tndntyfgystpwgyfdfnrfhchfsprdwqrlinnnwgfrpkr lsfklfniqvkevtqnegtktiannltstiqvftdseyqlpyvl gsahqgclppfpadvfmipqygyltlnngsqavgrssfycleyf psqmlrtgnnfqftytfedvpfhssyahsqsldrlmnplidqyl yylsrtqttggtantqtlgfsqggpntmanqaknwlpgpcyrqq rvstttgqnnnsnfawtagtkyhlngrnslanpgiamathkdde erffpsngilifgkqnaardnadysdvmltseeeikttnpvate eygivadnlqqqntapqigtvnsqgalpgmvwqnrdvylqgpiw akiphtdgnfhpsplmggfglkhpppqilikntpvpadpttfn qsklnsfitqystgqvsveiewelqkenskrwnpeiqytsnyyk stsvdfavntegvyseprpigtryltrnl |
| AAV8 CAPSID SEQUENCE (VP3) | 71<br>maagggapmadnnegadgvgsssgnwhcdstwlgdrvittstrt walptynnhlykqisngtsggatndntyfgystpwgyfdfnrfh chfsprdwqrlinnnwgfrpkrlsfklfniqvkevtqnegtkti annltstiqvftdseyqlpyvlgsahqgclppfpadvfmipqyg yltlnngsqavgrssfycleyfpsqmlrtgnnfqftytfedvpf hssyahsqsldrlmnplidqylyylsrtqttggtantqtlgfsq ggpntmanqaknwlpgpcyrqqrvstttgqnnnsnfawtagtky hlngrnslanpgiamathkddeerffpsngilifgkqnaardna dysdvmltseeeikttnpvateeygivadnlqqqntapqigtvn sqgalpgmvwqnrdvylqgpiwakiphtdgnfhpsplmggfglk hpppqilikntpvpadpttfnqsklnsfitqystgqvsveiew elqkenskrwnpeiqytsnyykstsvdfavntegvyseprpigt ryltrnl |
| CVM ENHANCER AND CBA PROMOTER (GENBANK ACCESSION DD215332 FROM BP 1-BP 1616) | 22<br>ACTAGTTATTAATAGTAATCAATTACGGGGTCATTAGTTCATAG CCCATATATGGAGTTCCGCGTTACATAACTTACGGTAAATGGCC CGCCTGGCTGACCGCCCAACGACCCCCGCCCATTGACGTCAATA ATGACGTATGTTCCCATAGTAACGCCAATAGGGACTTTCCATTG ACGTCAATGGGTGGAGTATTTACGGTAAACTGCCCACTTGGCAG TACATCAAGTGTATCATATGCCAAGTACGCCCCCTATTGACGTC AATGACGGTAAATGGCCCGCCTGGCATTATGCCCAGTACATGAC CTTATGGGACTTTCCTACTTGGCAGTACATCTACGTATTAGTCA |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:)AND SEQUENCE |
|---|---|
| | TCGCTATTACCATGGTCGAGGTGAGCCCCACGTTCTGCTTCACT<br>CTCCCCATCTCCCCCCCCTCCCCACCCCCAATTTTGTATTTATT<br>TATTTTTTAATTATTTTGTGCAGCGATGGGGGCGGGGGGGGGGG<br>GGGGGCGCGCGCCAGGCGGGGCGGGGCGGGGCGAGGGGCGGGGC<br>GGGGCGAGGCGGAGAGGTGCGGCGGCAGCCAATCAGAGCGGCGC<br>GCTCCGAAAGTTTCCTTTTATGGCGAGGCGGCGGCGGCGGCGGC<br>CCTATAAAAAGCGAAGCGCGCGGCGGGCGGGGAGTCGCTGCGAC<br>GCTGCCTTCGCCCCGTGCCCCGCTCCGCCGCCGCCTCGCGCCGC<br>CCGCCCCGGCTCTGACTGACCGCGTTACTCCCACAGGTGAGCGG<br>GCGGGACGGCCCTTCTCCTCCGGGCTGTAATTAGCGCTTGGTTT<br>AATGACGGCTTGTTTCTTTTCTGTGGCTGCGTGAAAGCCTTGAG<br>GGGCTCCGGGAGGGCCCTTTGTGCGGGGGGAGCGGCTCGGGGGG<br>TGCGTGCGTGTGTGTGTGCGTGGGGAGCGCCGCGTGCGGCTCCG<br>CGCTGCCCGGCGGCTGTGAGCGCTGCGGGCGCGGCGCGGGGCTT<br>TGTGCGCTCCGCAGTGTGCGCGAGGGGAGCGCGGCCGGGGGCGG<br>TGCCCCGCGGTGCGGGGGGGGCTGCGAGGGGAACAAAGGCTGCG<br>TGCGGGGTGTGTGCGTGGGGGGGTGAGCAGGGGGTGTGGGCGCG<br>TCGGTCGGGCTGCAACCCCCCCTGCACCCCCCTCCCCGAGTTGC<br>TGAGCACGGCCCGGCTTCGGGTGCGGGGCTCCGTACGGGGCGTG<br>GCGCGGGGCTCGCCGTGCCGGGCGGGGGGTGGCGGCAGGTGGGG<br>GTGCCGGGCGGGGCGGGGCCGCCTCGGGCCGGGGAGGGCTCGGG<br>GGAGGGGCGCGGCGGCCCCCGGAGCGCCGGCGGCTGTCGAGGCG<br>CGGCGAGCCGCAGCCATTGCCTTTTATGGTAATCGTGCGAGAGG<br>GCGCAGGGACTTCCTTTGTCCCAAATCTGTGCGGAGCCGAAATC<br>TGGGAGGCGCCGCCGCACCCCCTCTAGCGGGCGCGGGGCGAAGC<br>GGTGCGGCGCCGGCAGGAAGGAAATGGGCGGGGAGGGCCTTCGT<br>GCGTCGCCGCGCCGCCGTCCCCTTCTCCCTCTCCAGCCTCGGGG<br>CTGTCCGCGGGGGGACGGCTGCCTTCGGGGGGGACGGGGCAGGG<br>CGGGGTTCGGCTTCTGGCGTGTGACCGGCGGC |
| REVERSE COMPLEMENT OF RLBP1 INTRONIC SEQUENCE AS STUFFER SEQUENCE (NT 010274.17) | 23<br>CCAGAACAGGTCCCATTCATGGCCCACATGACAACCTGCTTCCC<br>CAGTGGGTATTTTTGGAGACAGCTCTTCTGTTTCCAGGTTTTCT<br>CTCCTGCCTAAATGTCCTGCCTAAGTGCCTTCAAGAACCCTTCA<br>CCATCCTGCTCCTGCATGTGACCAGGTTCCATGGTCAGTTCAAT<br>CACCTAGTCACAGTTGGTAAGTGACAGAGTTGGGACTTGAACCT<br>ATGCCTGCCTGACACCAAGTCTTTTTTTGACACCTAGAGCCAAG<br>ACATCTGAAGACAAACTCCCTAGGAGAGCTGGCGTCATAGAAAC<br>CTTAAAGGTTAGGGAGACCTGGGTTTGAATCAGGCTTTGTCAGT<br>TATGACTTGTGTGACCCTAGCAAGTTATTTAACCTTTCTGGGTC<br>TCAGTTTCCTCATCTGCAAACTGAGGATAATAACAGTACCTACC<br>AAAAAGAACTGTCGTGAAAACCATATAATTTCTGCAATGCTCCT<br>GGCACAGTGTCCTGTTCTAAAGCATAGTTCCCCTTCTCTTTCTT<br>AGCTCCATATTGATTATTACCCTAACTTGCACAAAGAGACTTGG<br>AGGACCCCCATAGAGTATCGGAGGGTCCCCCATTTCCTGCTCTT<br>TCCACTCCACACCCCCAGCAAGCACAGGGAAGTTCTGGGGGCCA<br>TAATCCACCCACAGGAACCAAATCTAAGCCACCTTTCTGGCTGG<br>TAGACATCCAGGTATGTGGGCACAGAGGTAGACAGGCTGAAATG<br>CTGCTGTGCTATCAGTTGGGTTTTGCTGGAACAGGAATGGAAAT<br>GGAGAGGCTGACAGAACTGCCCTGGGGAGCCCAGGCAAGAGGGA<br>CAGTGGCTGGACACCCCCAGCCAGTTGTGCAGACCATCAGAACA<br>AGATCCTAGATTTTAGGAATACAGGGTTCAAGTCCGTGCGGCAA<br>CTCTTTTCTAAATATGCCCAAGCCATTAACTTTGAGTTTTAAAA<br>ATACTGATTTACAAGCTGTACACAATGAAAAAATGCCTATCCCT<br>CACACCATGCTGATGCTGTTCCCTGCCATCTCAGATTACCAATT<br>AAATACAGAATGCCCAGTTAAATGTGAACTTTTTTTTTTTTTTT<br>TTTTTTGAGATGGAGTTTTGTTCTTGTCGCCCAGGCTAGAGTGC<br>AATGGTGCGATCTCAGCTCACTGCAACCTCTGCCTCCCAGGTTC<br>AAGCAATTCTCCTGCCTTAGCCTCCTGAGTAGCTGGAACTACAG<br>GTGCCCACCAGCACGCCTGGCTAATTTTTGGTATTTTTAGTGGA<br>GATGGGGTTTCACCATGTTGGCCAGGCTGGTCTCGAACTCCTGA<br>CCTCAGGTGATCTGCCTGCCTCGGCCTCCCAAAGTGCTGGGATT<br>ACAGGCGTGAGCCTAAATGTGAACTTTTTTAATACTAAAAAAGT<br>ATTTGCTGTTCATCGGAAATTCACATTTAACTGGGTGTCCTGTA<br>TTTTTATTTGCTAAATCTACCATCAAATTGGTCTGGCTCAACCT<br>GGAGAAT |
| EGFP SEQUENCE | 24<br>ATGGTGAGCAAGGGCGAGGAGCTGTTCACCGGGGTGGTGCCCAT<br>CCTGGTCGAGCTGGACGGCGACGTAAACGGCCACAAGTTCAGCG<br>TGTCCGGCGAGGGCGAGGGCGATGCCACCTACGGCAAGCTGACC<br>CTGAAGTTCATCTGCACCACCGGCAAGCTGCCCGTGCCCTGGCC<br>CACCCTCGTGACCACCCTGACCTACGGCGTGCAGTGCTTCAGCC<br>GCTACCCCGACCACATGAAGCAGCACGACTTCTTCAAGTCCGCC |

TABLE 1-continued

| Sequence of viral vector and plasmid elements AMINO ACID SEQUENCE OR POLYNUCLEOTIDE (PN) | |
|---|---|
| SEQUENCE ELEMENTS | SEQUENCE IDENTIFIER (SEQ. ID. NO:)AND SEQUENCE |
| | ATGCCCGAAGGCTACGTCCAGGAGCGCACCATCTTCTTCAAGGA CGACGGCAACTACAAGACCCGCGCCGAGGTGAAGTTCGAGGGCG ACACCCTGGTGAACCGCATCGAGCTGAAGGGCATCGACTTCAAG GAGGACGGCAACATCCTGGGGCACAAGCTGGAGTACAACTACAA CAGCCACAACGTCTATATCATGGCCGACAAGCAGAAGAACGGCA TCAAGGTGAACTTCAAGATCCGCCACAACATCGAGGACGGCAGC GTGCAGCTCGCCGACCACTACCAGCAGAACACCCCCATCGGCGA CGGCCCCGTGCTGCTGCCCGACAACCACTACCTGAGCACCCAGT CCGCCCTGAGCAAAGACCCCAACGAGAAGCGCGATCACATGGTC CTGCTGGAGTTCGTGACCGCCGCCGGGATCACTCTCGGCATGGA CGAGCTGTACAAGTAA |
| GFP AMINO ACID SEQUENCE | 25 MVSKGEELFTGVVPILVELDGDVNGHKFSVSGEGEGDATYGKLT LKFICT TGKLPVPWPTLVTTLTYGVQCFSRYPDHMKQHDFFKSAMPEGYV QERTIF FKDDGNYKTRAEVKFEGDTLVNRIELKGIDFKEDGNILGHKLEY NYNSHN VYIMADKQKNGIKVNFKIRHNIEDGSVQLADHYQQNTPIGDGPV LLPDNH YLSTQSALSKDPNEKRDHMVLLEFVTAAGITLGMDELYK |
| SC5'ITR | 36 CTGCGCGCTCGCTCGCTCACTGAGGCCGCCCGGGCAAAGCCCGG GCGTCGGGCGACCTTTGGTCGCCCGGCCTCAGTGAGCGAGCGAG CGCGCAGAGAGGGAGTGGCCAACTCCATCACTAGGGGTTCCT |
| *MACACA MULATTA* (RHESUS MONKEY) RLBP1 CDS XM_001091538 | 37 ATGTCAGAAGGGGTGGGCACGTTCCGCATGGTACCTGAAGAGGA ACAGGAGCTCCGTGCCCAACTGGAGCAGCTCACAACCAAGGACC ATGGACCTGTCTTTGGCCCGTGCAGCCAGCTGCCCCGCCACACC TTGCAGAAGGCCAAAGATGAGCTGAATGAGAGAGAGGAGACCCG GGAGGAGGCAGTGCGAGAGCTGCAGGAGATGGTGCAGGCGCAGG CGGCCTCGGGGGAGGAGCTGGCCGTGGCCGTGGCGGAGAGGGTG CAAGAGAAGGACAGCGGCTTCTTCCTGCGCTTCATCCGCGCGCG AAAGTTCAACGTGGGCCGTGCCTATGAGCTGCTCAGAGGCTATG TGAATTTCCGGCTGCAGTACCCTGAGCTCTTTGACAGCCTGTCC CCAGAGGCTGTCCGCTGTACCATTGAAGCTGGCTACCCTGGTGT CCTCTCTAGTCGGGACAAGTATGGCCGAGTGGTCATGCTCTTCA ACATTGAGAACTGGCAAAGTCAAGAAATCACCTTCGATGAGATC TTGCAGGCATATTGCTTCATCCTGGAGAAGCTGCTGGAGAATGA GGAAACTCAAATTAATGGATTCTGCATCATTGAGAACTTCAAGG GCTTTACCATGCAGCAGGCTGCTAGTCTCCGCACTTCAGATCTC AGGAAGATGGTGGACATGCTCCAGGATTCCTTCCCAGCCCGGTT CAAAGCCATCCACTTCATCCACCAGCCATGGTACTTCACCACGA CCTACAATGTGGTCAAGCCCTTCTTGAAGAGCAAGCTGCTTGAG AGGGTCTTTGTCCACGGGGAGGACCTCTCTGGTTTCTACCAGGA GATTGATGAGAACATCCTGCCCTCTGACTTTGGGGGCACGCTGC CCAAGTATGATGGCAAAGCTGTTGCTGAGCAGCTCTTTGGCCCC CGGGCCCAAGCTGAGAACACAGCCTTCTGA |
| *MACACA MULATTA* (RHESUS MONKEY) RLBP1 GENE PRODUCT (CELLULAR RETINALDEHYDE BINDING PROTEIN - CRALBP) | 38 MSEGVGTFRMVPEEEQELRAQLEQLTTKDHGPVFGPCSQLPRHT LQKAKDELNEREETREEAVRELQEMVQAQAASGEELAVAVAERV QEKDSGFFLRFIRARKFNVGRAYELLRGYVNFRLQYPELFDSLS PEAVRCTIEAGYPGVLSSRDKYGRVVMLFNIENWQSQEITFDEI LQAYCFILEKLLENEETQINGFCIIENFKGFTMQQAASLRTSDL RKMVDMLQDSFPARFKAIHFIHQPWYFTTTYNVVKPFLKSKLLE RVFVHGEDLSGFYQEIDENILPSDFGGTLPKYDGKAVAEQLFGP RAQAENTAF |
| *BOS TAURUS* RLBP1 CDS NM_174451 | 39 ATGTCAGAGGGGGCGGGCACGTTCCGCATGGTCCCTGAAGAGGA ACAGGAGCTCCGTGCCCAACTGGAGAGGCTTACGACCAAAGACC ATGGACCTGTCTTTGGCCCGTGCAGCCAGCTGCCCCGCCACACC TTGCAGAAGGCCAAGGACGAGCTGAATGAAAAGGAAGAGACCCG GGAAGAGGCAGTGCGGGAGCTACAGGAGCTGGTGCAGGCGGAGG CCGCCTCGGGGCAGGAGCTGGCCGTGGCCGTGGCGGAGAGGGTG CAGGGAAAAGACAGTGCCTTCTTCCTGCGCTTCATCCGCGCGCG CAAGTTCCACGTGGGGCGCGCCTACGAGCTGCTCAGAGGCTACG TGAACTTCCGGCTGCAGTACCCAGAGCTCTTCGACAGCCTGTCC CCAGAGGCTGTCCGCTGCACCGTTGAGGCTGGCTACCCTGGTGT CCTCTCCACGCGGGACAAGTATGGCCGAGTGGTCATGCTCTTCA |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:)AND SEQUENCE |
|---|---|
| | ATATTGAGAACTGGGACTCTGAAGAAATCACCTTTGATGAGATC |
| | TTGCAGGCATACTGCGTCATCCTGGAGAAGCTACTGGAGAATGA |
| | GGAGACTCAAATTAATGGCTTTTGCATCATTGAGAACTTCAAGG |
| | GCTTCACCATGCAGCAGGCTGCCGGACTTCGGCCTTCCGATC |
| | TCAGAAAGATGGTGGACATGCTCCAGGATTCCTTCCCAGCTCGG |
| | TTCAAAGCCATCCACTTCATCTACCAGCCCTGGTACTTCACCAC |
| | CACCTACAACGTGGTCAAGCCCTTCTTGAAGAGCAAATTGCTCC |
| | AGAGGGTATTTGTCCATGGAGAAGACCTCTCCAGCTTCTACCAG |
| | GAGTTTGACGAGGACATCCTGCCCTCCGACTTTGGGGGTACACT |
| | GCCCAAGTATGATGGCAAGGCCGTTGCTGAGCAGCTCTTTGGTC |
| | CTCGGGACCAAACTGAGAACACAGCCTTCTGA |
| *BOS TAURUS* | 40 |
| RLBP1 GENE | MSEGAGTFRMVPEEEQELRAQLERLTTKDHGPVFGPCSQLPRHT |
| PRODUCT | LQKAKDELNEKEETREEAVRELQELVQAEAASGQELAVAVAERV |
| (CELLULAR | QGKDSAFFLRFIRARKFHVGRAYELLRGYVNFRLQYPELFDSLS |
| RETINALDEHYDE | PEAVRCTVEAGYPGVLSTRDKYGRVVMLFNIENWDSEEITFDEI |
| BINDING PROTEIN - | LQAYCVILEKLLENEETQINGFCIIENFKGFTMQQAAGLRPSDL |
| CRALBP) | RKMVDMLQDSFPARFKAIHFIYQPWYFTTTYNVVKPFLKSKLLQ |
| | RVFVHGEDLSSFYQEFDEDILPSDFGGTLPKYDGKAVAEQLFGP |
| | RDQTENTAF |
| *CANIS LUPUS* | 41 |
| *FAMILIARIS* | ATGTCAGAAGGCGTGGGCACATTCCGTGTGGTCCCTGAAGAGGA |
| RLBP1 CDS | ACAGGAGCTCCGTGCCCAGCTGGAGCGGCTTACAACCAAGGACC |
| XM_549634 | ATGGGCCTGTCTTTGGCCCTTGCAGCCAGCTCCCTCGTCATACC |
| | TTACAGAAGGCCAAGGACGAGCTGAACGAGAGGGAGGAGACCCG |
| | GGAGGAGGTGGTGCGAGAGCTGCAGGAGCTGGTGCAGGCACAGG |
| | CTGCCACCGGGCAGGAGCTGGCCAGGGCGGTGGCTGAGAGGGTG |
| | CAGGGAAGGGACAGTGCCTTCTTCCTGCGCTTCATCCGCGCGCG |
| | GAAGTTCCATGTGGGGCGTGCCTACGAGCTGCTTCGAGGCTACG |
| | TGAACTTCCGGCTGCAGTACCCAGAGCTCTTCGACAGCCTGTCC |
| | CTGGAGGCTGTCCGTTGCACCGTCGAGGCCGGCTATCCTGGGGT |
| | CCTCCCCAGTCGGGACAAGTATGGCCGAGTGGTCATGCTCTTCA |
| | ACATCGAGAACTGGGACTCCGAAGAAATCACCTTCGATGAGATC |
| | TTGCAGGCATATTGTTTCATCCTGGAGAAGCTACTAGAGAATGA |
| | GGAAACTCAAATTAATGGCTTCTGCATTATTGAGAACTTTAAGG |
| | GCTTTACCATGCAGCAGGCTGCTGGACTTCGGGCTTCCGATCTC |
| | AGGAAGATGGTGGACATGCTCCAGGATTCCTTCCCAGCGCGGTT |
| | CAAAGCCATCCACTTCATTCACCAACCATGGTACTTCACCACCA |
| | CCTACAACATGGTCAAGCCCCTCCTGAAGAACAAGCTGCTCCAA |
| | AGAGTCTTTGTCCATGGAGATGACCTCTCTGGCTTCTTCCAGGA |
| | GATTGATGAAGACATACTGCCCGCTGACTTTGGGGGCACACTGC |
| | CCAAGTATGATGGCAAGGTGGTTGCTGAGCAGCTCTTTGGCCCC |
| | CGGGCCCAAGCTGAGAACACAGCCTTCTGA |
| *CANIS LUPUS* | 42 |
| *FAMILIARIS* | MSEGVGTFRVVPEEEQELRAQLERLTTKDHGPVFGPCSQLPRHT |
| RLBP1 GENE | LQKAKDELNEREETREEVVRELQELVQAQAATGQELARAVAERV |
| PRODUCT | QGRDSAFFLRFIRARKFHVGRAYELLRGYVNFRLQYPELFDSLS |
| (CELLULAR | LEAVRCTVEAGYPGVLPSRDKYGRVVMLFNIENWDSEEITFDEI |
| RETINALDEHYDE | LQAYCFILEKLLENEETQINGFCIIENFKGFTMQQAAGLRASDL |
| BINDING PROTEIN - | RKMVDMLQDSFPARFKAIHFIHQPWYFTTTYNMVKPLLKNKLLQ |
| CRALBP) | RVFVHGDDLSGFFQEIDEDILPADFGGTLPKYDGKVVAEQLFGP |
| | RAQAENTAF |
| *RATTUS* | 43 |
| *NORVEGICUS* | ATGTCAGAGGGGGTGGGCACATTCCGAATGGTCCCTGAAGAGGA |
| RLBP1 CDS | GCAGGAGCTCCGGGCACAGCTAGAACAGCTCACAACCAAGGATC |
| NM_001106274.1 | ATGGTCCTGTCTTTGGCCCATGCAGCCAGCTGCCCCGCCACACT |
| | TTGCAGAAGGCTAAGGATGAGCTGAATGAAAGGGAGGAAACCCG |
| | GGATGAGGCGGTGAGGGAGCTACAGGAGCTGGTCCAGGCACAGG |
| | CAGCTTCTGGGGAAGAGTTGGCCGTGGCAGTGGCTGAGAGGGTG |
| | CAGGCAAGAGACAGCGCCTTCCTCCTGCGCTTCATCCGTGCCCG |
| | AAAGTTTGATGTGGGCCGGGCTTATGAGCTGCTCAAAGGCTATG |
| | TGAACTTCCGGCTCCAGTACCCTGAACTCTTCGATAGCCTATC |
| | TATGGAGGCTCTCCGCTGCACTATCGAGGCCGGTTACCCTGGTG |
| | TCCTTTCCAGTCGGGACAAGTATGGTCGAGTGGTTATGCTCTTC |
| | AACATTGAAAACTGGCACTGTGAAGAAGTCACCTTTGATGAGAT |
| | CTTACAGGCATATTGTTTCATTCTGGAGAAACTGCTGGAGAACG |
| | AGGAAACCCAAATCAACGGCTTCTGTATTGTGGAGAACTTCAAG |
| | GGCTTCACCATGCAGCAGGCCGCGGGACTCCGCCCCTCCGATCT |
| | CAAGAAGATGGTGGACATGCTCCAGGATTCATTCCCAGCCAGGT |
| | TCAAAGCTATCCACTTCATCCACCAACCATGGTACTTCACCACC |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:)AND SEQUENCE |
|---|---|
| | ACTTACAATGTGGTCAAGCCCTTCTTGAAGAACAAGTTGCTACA<br>GAGGGTCTTCGTTCATGGAGATGACCTGGACGGCTTCTTCCAGG<br>AGATTGATGAGAATATCTTGCCTGCTGACTTTGGGGGTACACTG<br>CCCAAGTATGACGGCAAAGTTGTCGCTGAGCAGCTCTTCGGTCC<br>CCGGGTTGAGGTTGAGAACACAGCCTTGTGA |
| *RATTUS NORVEGICUS* RLBP1 GENE PRODUCT (CELLULAR RETINALDEHYDE BINDING PROTEIN - CRALBP) | 44<br>MSEGVGTFRMVPEEEQELRAQLEQLTTKDHGPVFGPCSQLPRHT<br>LQKAKDELNEREETRDEAVRELQELVQAQAASGEELAVAVAERV<br>QARDSAFLLRFIRARKFDVGRAYELLKGYVNFRLQYPELFDSLS<br>MEALRCTIEAGYPGVLSSRDKYGRVVMLFNIENWHCEEVTFDEI<br>LQAYCFILEKLLENEETQINGFCIVENFKGFTMQQAAGLRPS<br>DLKKMVDMLQDSFPARFKAIHFIHQPWYFTTTYNVVKPFLKNKL<br>LQRVFVHGDDLDGFFQEIDENILPADFGGTLPKYDGKVVAEQLF<br>GPRVEVENTAL |
| *MUS MUSCULUS* RLBP1 CDS NM_020599.2 | 45<br>ATGTCAGACGGGGTGGGCACTTTCCGCATGGTTCCTGAAGAGGA<br>GCAGGAGCTCCGAGCACAACTGGAGCAGCTCACAACCAAGGATC<br>ATGGTCCTGTCTTTGGCCCATGCAGCCAGCTGCCCCGCCACACT<br>TTGCAGAAGGCCAAGGATGAGCTGAATGAAAAGGAGGAGACCCG<br>GGAGGAAGCGGTGAGGGAGCTACAGGAGCTGGTACAGGCACAGG<br>CAGCTTCTGGCGAGGAATTGGCCCTGGCAGTGGCTGAGAGGGTG<br>CAGGCAAGAGACAGCGCCTTCCTCCTGCGCTTCATCCGTGCCCG<br>CAAGTTCGATGTGGGTCGTGCTTATGAGCTGCTCAAAGGCTATG<br>TGAACTTCCGCCTCCAGTACCCTGAACTCTTCGATAGTCTCTCC<br>ATGGAGGCTCTCCGCTGCACTATCGAGGCCGGATACCCTGGTGT<br>CCTTTCCAGTCGGGACAAGTATGGTCGAGTGGTTATGCTCTTCA<br>ACATCGAAAACTGGCACTGTGAAGAAGTGACCTTTGATGAGATC<br>TTACAGGCATATTGTTTCATTTTGGAGAAACTGCTGGAAAATGA<br>GGAAACCCAAATCAACGGCTTCTGTATTGTTGAGAACTTCAAGG<br>GCTTCACCATGCAGCAGGCAGCAGGGCTCCGCCCCTCGGATCTC<br>AAGAAGATGGTGGACATGCTCCAGGATTCATTCCCAGCCAGGTT<br>CAAAGCTATCCACTTCATCCACCAGCCATGGTACTTCACCACCA<br>CCTATAATGTGGTCAAGCCCTTCTTGAAGAACAAGCTGCTACAG<br>AGGGTCTTTGTTCACGGAGATGACCTGGATGGCTTCTTCCAGGA<br>GATTGATGAGAACATCCTGCCTGCTGACTTTGGGGGTACACTGC<br>CCAAGTACGACGGCAAAGTTGTTGCTGAGCAGCTCTTTGGTCCC<br>CGGGCTGAAGTTGAGAACACAGCCTTATGA |
| *MUS MUSCULUS* RLBP1 GENE PRODUCT (CELLULAR RETINALDEHYDE BINDING PROTEIN - CRALBP) | 46<br>MSDGVGTFRMVPEEEQELRAQLEQLTTKDHGPVFGPCSQLPRHT<br>LQKAKDELNEKEETREEAVRELQELVQAQAASGEELALAVAERV<br>QARDSAFLLRFIRARKFDVGRAYELLKGYVNFRLQYPELFDSLS<br>MEALRCTIEAGYPGVLSSRDKYGRVVMLFNIENWHCEEVTFDEI<br>LQAYCFILEKLLENEETQINGFCIVENFKGFTMQQAAGLRPSDL<br>KKMVDMLQDSFPARFKAIHFIHQPWYFTTTYNVVKPFLKNKLLQ<br>RVFVHGDDLDGFFQEIDENILPADFGGTLPKYDGKVVAEQLFGP<br>RAEVENTAL |
| *GALLUS GALLUS* RLBP1 CDS NM_001024694.1 | 47<br>ATGTCTGCTGTTACGGGCACCTTCCGCATTGTCTCGGAAGAGGA<br>GCAGGCGCTGCGCACCAAACTGGAGCGCCTCACCACCAAGGACC<br>ACGGCCCTGTTTTTGGGAGGTGCCAGCAGATCCCCCCTCACACC<br>CTGCAGAAGGCAAAAGATGAGCTGAATGAGACGGAGGAGCAGAG<br>GGAGGCAGCGGTCAAAGCGCTGCGGGAGCTGGTGCAGGAGCGGG<br>CCGGCAGCGAGGATGTCTGCAAGGCAGTGGCAGAGAAGATGCAG<br>GGGAAGGACGATTCCTTCTTCCTCCGCTTCATCCGTGCCCGCAA<br>GTTTGACGTGCACAGGGCCTACGACCTGCTGAAAGGCTATGTGA<br>ACTTTCGCCAGCAATACCCTGAACTCTTTGACAACCTGACCCCC<br>GAGGCCGTGCGCAGCACCATCGAGGCGGGCTACCCCGGCATCCT<br>GGCCAGCAGGGACAAATACGGGCGGGTAGTGATGCTCTTCAACA<br>TCGAGAACTGGGACTACGAGGAGATCACCTTTGATGAGATCCTT<br>CGTGCCTACTGCGTTATCTTGGAGAAGCTGCTGGAAAACGAAGA<br>GACCCAGATCAATGGGTTCTGCATCATTGAGAACTTCAAGGGCT<br>TCACCATGCAGCAGGCATCAGGGATCAAACCCTCCGAGCTCAAG<br>AAGATGGTGGACATGCTACAGGACTCCTTCCCAGCGCGGTTCAA<br>AGCTGTCCACTTCATCCACCAGCCCTGGTACTTCACCACTACCT<br>ACAACGTGGTCAAACCGTTCCTGAAGAGCAAGCTGCTGGAGAGG<br>GTGTTTGTGCACGGCGAGGAGCTGGAGTCCTTCTACCAGGAG<br>ATCGATGCTGACATACTGCCAGCAGACTTCGGTGGCAACCTGCC<br>CAAGTACGACGGCAAAGCAACTGCAGAGCAGCTCTTTGGGCCCC<br>GCATTGAGGCTGAAGACACGGCACTTTAA |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:)AND SEQUENCE |
|---|---|
| *GALLUS GALLUS* RLBP1 GENE PRODUCT (CELLULAR RETINALDEHYDE BINDING PROTEIN - CRALBP) NP_001019865.1 | 48<br>MSAVTGTFRIVSEEEQALRTKLERLTTKDHGPVFGRCQQIPPHT<br>LQKAKDELNETEEQREAAVKALRELVQERAGSEDVCKAVAEKMQ<br>GKDDSFFLRFIRARKFDVHRAYDLLKGYVNFRQQYPELFDNLTP<br>EAVRSTIEAGYPGILASRDKYGRVVMLFNIENWDYEEITFDEIL<br>RAYCVILEKLLENEETQINGFCIIENFKGFTMQQASGIKPSELK<br>KMVDMLQDSFPARFKAVHFIHQPWYFTTTYNVVKPFLKSKLLER<br>VFVHGEELESFYQEIDADILPADFGGNLPKYDGKATAEQLFGPR<br>IEAEDTAL |
| KAN-R BACTERIAL BACKBONE | 49<br>CTGCCTGCAGGGTTCCATCCCAATGGCGCGTCAATTCACTGGCC<br>GTCGTTTTACAACGTCGTGACTGGGAAAACCCTGGCGTTACCCA<br>ACTTAATCGCCTTGCAGCACATCCCCCTTTCGCCAGCTGGCGTA<br>ATAGCGAAGAGGCCCGCACCGATCGCCCTTCCCAACAGTTGCGC<br>AGCCTGAATGGCGAATGGCGCCTGATGCGGTATTTTCTCCTTAC<br>GCATCTGTGCGGTATTTCACACCGCATATGGTGCACTCTCAGTA<br>CAATCTGCTCTGATGCCGCATAGTTAAGCCAGCCCCGACACCCG<br>CCAACACCCGCTGACGCGCCCTGACGGGCTTGTCTGCTCCCGGC<br>ATCCGCTTACAGACAAGCTGTGACCGTCTCCGGGAGCTGCATGT<br>GTCAGAGGTTTTCACCGTCATCACCGAAACGCGCGAGACGAAAG<br>GGCCTCGTGATACGCCTATTTTTATAGGTTAATGTCATGATAAT<br>AATGGTTTCTTAGACGTCAGGTGGCACTTTTCGGGGAAATGTGC<br>GCGGAACCCCTATTTGTTTATTTTTCTAAATACATTCAAATATG<br>TATCCGCTCATGAGACAATAACCCTGATAAATGCTTCAATAATA<br>TTGAAAAAGGAAGAGTATGAGCCATATTCAACGGGAAACGTCTT<br>GCTCTAGGCCGCGATTAAATTCCAACATGGATGCTGATTTATAT<br>GGGTATAAATGGGCTCGCGATAATGTCGGGCAATCAGGTGCGAC<br>AATCTATCGATTGTATGGGAAGCCCGATGCGCCAGAGTTGTTTC<br>TGAAACATGGCAAAGGTAGCGTTGCCAATGATGTTACAGATGAG<br>ATGGTCAGACTAAACTGGCTGACGGAATTTATGCCTCTTCCGAC<br>CATCAAGCATTTTATCCGTACTCCTGATGATGCATGGTTACTCA<br>CCACTGCGATCCCTGGGAAAACAGCATTCCAGGTATTAGAAGAA<br>TATCCTGATTCAGGTGAAAATATTGTTGATGCGCTGGCAGTGTT<br>CCTGCGCCGGTTGCATTCGATTCCTGTTTGTAATTGTCCTTTTA<br>ACAGCGATCGCGTATTTCGTCTCGCTCAGGCGCAATCACGAATG<br>AATAACGGTTTGGTTGATGCGAGTGATTTTGATGACGAGCGTAA<br>TGGCTGGCCTGTTGAACAAGTCTGGAAAGAAATGCATAAACTTT<br>TGCCATTCTCACCGGATTCAGTCGTCACTCATGGTGATTTCTCA<br>CTTGATAACCTTATTTTTGACGAGGGGAAATTAATAGGTTGTAT<br>TGATGTTGGACGAGTCGGAATCGCAGACCGATACCAGGATCTTG<br>CCATCCTATGGAACTGCCTCGGTGAGTTTTCTCCTTCATTACAG<br>AAACGGCTTTTTCAAAAATATGGTATTGATAATCCTGATATGAA<br>TAAATTGCAGTTTCATTTGATGCTCGATGAGTTTTTCTAACTGT<br>CAGACCAAGTTTACTCATATATACTTTAGATTGATTTAAAACTT<br>CATTTTTAATTTAAAAGGATCTAGGTGAAGATCCTTTTTGATAA<br>TCTCATGACCAAAATCCCTTAACGTGAGTTTTCGTTCCACTGAG<br>CGTCAGACCCCGTAGAAAAGATCAAAGGATCTTCTTGAGATCCT<br>TTTTTTCTGCGCGTAATCTGCTGCTTGCAAACAAAAAAACCACC<br>GCTACCAGCGGTGGTTTGTTTGCCGGATCAAGAGCTACCAACTC<br>TTTTTCCGAAGGTAACTGGCTTCAGCAGAGCGCAGATACCAAAT<br>ACTGTTCTTCTAGTGTAGCCGTAGTTAGGCCACCACTTCAAGAA<br>CTCTGTAGCACCGCCTACATACCTCGCTCTGCTAATCCTGTTAC<br>CAGTGGCTGCTGCCAGTGGCGATAAGTCGTGTCTTACCGGGTTG<br>GACTCAAGACGATAGTTACCGGATAAGGCGCAGCGGTCGGGCTG<br>AACGGGGGGTTCGTGCACACAGCCCAGCTTGGAGCGAACGACCT<br>ACACCGAACTGAGATACCTACAGCGTGAGCTATGAGAAAGCGCC<br>ACGCTTCCCGAAGGGAGAAAGGCGGACAGGTATCCGGTAAGCGG<br>CAGGGTCGGAACAGGAGAGCGCACGAGGGAGCTTCCAGGGGGAA<br>ACGCCTGGTATCTTTATAGTCCTGTCGGGTTTCGCCACCTCTGA<br>CTTGAGCGTCGATTTTTGTGATGCTCGTCAGGGGGGCGGAGCCT<br>ATGGAAAAACGCCAGCAACGCGGCCTTTTTACGGTTCCTGGCCT<br>TTTGCTGGCCTTTTGCTCACATGTTCTTTCCTGCGTTATCCCCT<br>GATTCTGTGGATAACCGTATTACCGCCTTTGAGTGAGCTGATAC<br>CGCTCGCCGCAGCCGAACGACCGAGCGCAGCGAGTCAGTGAGCG<br>AGGAAGCGGAAGAGCGCCCAATACGCAAACCGCCTCTCCCCGCG<br>CGTTGGCCGATTCATTAATGCAGCTGGCACGACAGGTTTCCCGA<br>CTGGAAAGCGGGCAGTGAGCGCAACGCAATTAATGTGAGTTAGC<br>TCACTCATTAGGCACCCCAGGCTTTACACTTTATGCTTCCGGCT<br>CGTATGTTGTGTGGAATTGTGAGCGGATAACAATTTCACACAGG<br>AAACAGCTATGACCATGATTACGCCAAGCTCGGCGCGCCATTGG<br>GATGGAACCCTGCAGGCAG |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:)AND SEQUENCE |
|---|---|
| Reverse Complementary sequence of SV40polyA (SEQ ID NO: 8) | 62<br>AGACATGATAAGATACATTGATGAGTTTGGACAAACCACAACTA<br>GAATGCAGTGAAAAAAATGCTTTATTTGTGAAATTTGTGATGCT<br>ATTGCTTTATTTGTAACCATTATAAGCTGCAATAAACAAGTTAA<br>CAACAACAATTGCATTCATTTTATGTTTCAGGTTCAGGGGGAGG<br>TGTGGGAGGTTTTTTAAAGCAAGTAAAACCTCTACAAATGTGGT<br>ATGGCTGATTATGATC |
| Reverse Complementary sequence of HUMAN RLBP1 GENE CDS (SEQ ID NO: 7) | 63<br>TCAGAAGGCTGTGTTCTCAGCTTGGGCCTGGGGGCCAAAGAGCT<br>GCTCAGCAACGGCCTTGCCATCATACTTGGGCAGCGTGCCCCCG<br>AAGTCAGAGGGCAGGATGTTCTCATCGATCTCCTGGTAGAAACC<br>AGAAAGGTCATCCCCGTGGACAAAGACCCTCTCAAGCAGCTTGC<br>TCTTCAAGAAGGGCTTGACCACATTGTAGGTCGTGGTGAAGTAC<br>CATGGCTGGTGGATGAAGTGGATGGCTTTGAACCGGGCTGGGAA<br>GGAATCCTGGAGCATGTCCACCATCTTCCTGAGATCTGAAGTCC<br>GGAGACTAGCAGCCTGCTGCATGGTAAAGCCCTTGAAGTTCTCA<br>ATGATGCAGAAGCCATTGATTTGAGTTTCCTCATTCTCCAGCAG<br>CTTCTCCAGGATGAAGCAATATGCCTGCAAGATCTCATCAAAGG<br>TGATTTCTTGACTTTGCCAGTTCTCAATGTTGAAGAGCATGACC<br>ACTCGGCCATACTTGTCCCGACTAGAGAGGACACCAGGGTAGCC<br>AGCTTCAATGGTGCAGCGGACAGCCTCTGGGGACAGGCTGTCAA<br>AGAGCTCAGGGTACTGCAGCCGGAAATTCACATAGCCTCTGAGC<br>AGCTCATAGGCACGGCCCACGTTGAACTTCCGTGCGCGGATGAA<br>GCGCAGGAAGAAGCCGCTGTCCTTCTCTTGCACCCTCTCCGCCA<br>CGGCCACCGCCAGCTCCTCCCCCGAGGCCGCCTGCGCCTGCACC<br>ATCTCCTGCAGCTCTCGCACTGCCTCCTCCCGGGTCTCCTCTCT<br>CTCGTTCAGCTCATCCTTGGCCTTCTGCAAGGTGTGGCGGGGCA<br>GCTGGCTGCACGGGCCAAAGACAGGTCCATGGTCCTTGGTTGTG<br>AGCTGCTCCAGTTGGGCACGGAGCTCCTGTTCCTCTTCAGGTAC<br>CATGCGGAACGTGCCCACCCCTTCTGACAT |
| Reverse Complementary sequence of Added KOZAK (SEQ ID NO: 5) | 64<br>GGTGGC |
| Reverse Complementary sequence of Modified SV40INTRON (SEQ ID NO: 4) | 65<br>GGATCCCGGGGCGGGTACAATTCCGCAGCTTTTAGAGCAGAAGT<br>AACACTTCCGTACAGGCCTAGAAGTAAAGGCAACATCCACTGAG<br>GAGCAGTTCTTTGATTTGCACCACCACCGGATCCGGGACCTGAA<br>ATAAAAGACAAAAAGACTAAACTTACCAGTTAACTTTCTGGTTT<br>TTCAGTT |
| Reverse Complementary sequence of Human RLBP1 PROMOTER (short) (SEQ ID NO: 3) | 66<br>TCGGCAGCTCCTCCTTGGGGCTACCTGGTACCTGAATGTCCTGG<br>AGCTCTAGAGGTTCCCTCCGCTGGAGGCGTGGTCCGGTCAGCAG<br>GTTGGGATTAGTGTGTCATAAGGAACTTCTCACCGCCCACAGTT<br>TCCGTTAAATCGGGCTCACAGGAGGCCCTCAGTGGGGCAAAGGA<br>AGACCCAGAGAGAAAGGGGAGAGGGGAGAGGCCTGGGCCTGGCT<br>GGAGGCGCATCAAAGCCCTCCTTTGTGTGCTCCTGCTCTGGAGT<br>TCCTGCTCGGCCATGTGGAAGCCCGGCTGTGGGGCTGGGATCTG<br>GGCCAGTCCCATTCCCTCTTTTCTCTGCCCTCTTTCTCCTCAAG<br>ATCCCGGGGTGGGGTTGCTGAGAGAGCACCCCCCCCCCCCCACC<br>ACCACCACCAGGGTAATAAGAGGTGAAGGGAAATCGTAAATATG<br>ACTACATCTACAGTGGCAGCTCTGGCAAATCCAGGCCTATTGCC<br>CACCCCTCCCCCAGCCAGCAGGACCTGGCATGGTAGTTTTCACC<br>TCTGCAGTGAGTGGGGTCAGTTGAGAAATGTGGCTGGTTAAGGC<br>CAAGCAGGGAGAGGACAA |
| Reverse Complementary sequence of eGFP (SEQ ID NO: 24) | 67<br>TTACTTGTACAGCTCGTCCATGCCGAGAGTGATCCCGGCGGCGG<br>TCACGAACTCCAGCAGGACCATGTGATCGCGCTTCTCGTTGGGG<br>TCTTTGCTCAGGGCGGACTGGGTGCTCAGGTAGTGGTTGTCGGG<br>CAGCAGCACGGGGCCGTCGCCGATGGGGGTGTTCTGCTGGTAGT<br>GGTCGGCGAGCTGCACGCTGCCGTCCTCGATGTTGTGGCGGATC<br>TTGAAGTTCACCTTGATGCCGTTCTTCTGCTTGTCGGCCATGAT<br>ATAGACGTTGTGGCTGTTGTAGTTGTACTCCAGCTTGTGCCCCA<br>GGATGTTGCCGTCCTCCTTGAAGTCGATGCCCTTCAGCTCGATG<br>CGGTTCACCAGGGTGTCGCCCTCGAACTTCACCTCGGCGCGGGT<br>CTTGTAGTTGCCGTCGTCCTTGAAGAAGATGGTGCGCTCCTGGA<br>CGTAGCCTTCGGGCATGGCGGACTTGAAGAAGTCGTGCTGCTTC |

TABLE 1-continued

| Sequence of viral vector and plasmid elements AMINO ACID SEQUENCE OR POLYNUCLEOTIDE (PN) | |
|---|---|
| SEQUENCE ELEMENTS | SEQUENCE IDENTIFIER (SEQ. ID. NO:)AND SEQUENCE |
| | ATGTGGTCGGGGTAGCGGCTGAAGCACTGCACGCCGTAGGTCAG<br>GGTGGTCACGAGGGTGGGCCAGGGCACGGGCAGCTTGCCGGTGG<br>TGCAGATGAACTTCAGGGTCAGCTTGCCGTAGGTGGCATCGCCC<br>TCGCCCTCGCCGGACACGCTGAACTTGTGGCCGTTTACGTCGCC<br>GTCCAGCTCGACCAGGATGGGCACCACCCCGGTGAACAGCTCCT<br>CGCCCTTGCTCACCAT |

TABLE 2

| Plasmid Composition<br>Plasmid Composition | |
|---|---|
| Elements | SEQUENCE IDENTIFIER (SEQ. ID. NO:)AND SEQUENCE INFORMATION |
| | Plasmid TM017 Composition |
| ΔITR | 1<br>occurs at bp 4 through bp 106 of SEQ ID NO: 26 |
| Human RLBP1 Promoter(short) | 3<br>Occurs at bp 119 through bp 708 of SEQ ID NO: 26 |
| MODIFIED SV40INTRON | 4<br>occurs at bp 723 through bp 905 of SEQ ID NO: 26 |
| Added Kozak | 5<br>occurs at bp 919 through bp 924 of SEQ ID NO: 26 |
| HUMAN RLBP1 GENE CDS | 6<br>occurs at bp 925 through bp 1878 of SEQ ID NO: 26 |
| SV40 POLYA | 8<br>occurs at bp 1937 through bp 2172 of SEQ ID NO: 26 |
| 3' ITR | 9<br>occurs at bp 2201 through bp 2330 of SEQ ID NO: 26 |
| AMP BACTERIAL BACKBONE | 15<br>occurs at bp 2331 through bp 4949 of SEQ ID NO: 26 |
| TM017 PLASMID SEQUENCE | 26<br>ctgcgcgctcgctcgctcactgaggccgcccgggcaaagccc<br>gggcgtcgggcgacctttggtcgcccggcctcagtgagcgag<br>cgagcgcgcagagagggagtggggtaccacgcgtttgtcctc<br>tccctgcttggccttaaccagccacatttctcaactgacccc<br>actcactgcagaggtgaaaactaccatgccaggtcctgctgg<br>ctgggggaggggtgggcaataggcctggatttgccagagctg<br>ccactgtagatgtagtcatatttacgatttcccttcacctct<br>tattaccctggtggtggtggtgggggggggggtgctctct<br>cagcaaccccaccccgggatcttgaggagaaagagggcagag<br>aaaagagggaatgggactggcccagatcccagccccacagcc<br>gggcttccacatggccgagcaggaactccagagcaggagcac<br>acaaaggagggctttgatgcgcctccagccaggcccaggcct<br>ctcccctctcccctttctctctgggtcttcctttgccccact<br>gagggcctcctgtgagcccgatttaacggaaactgtgggcgg<br>tgagaagttccttatgacacactaatcccaacctgctgaccg<br>gaccacgcctccagcggagggaacctctagagctccaggaca<br>ttcaggtaccaggtagccccaaggaggagctgccgaatcgat<br>ggatcgggaactgaaaaaccagaaagttaactggtaagttta<br>gtctttttgtcttttatttcaggtcccggatccggtggtggt<br>gcaaatcaaagaactgctcctcagtggatgttgcctttactt<br>ctaggcctgtacggaagtgttacttctgctctaaaagctgcg<br>gaattgtacccgccccgggatccatcgattgaattcgccacc<br>atgtcagaaggggtgggcacgttccgcatggtacctgaagag<br>gaacaggagctccgtgcccaactggagcagctcacaaccaag<br>gaccatggacctgtctttggcccgtgcagccagctgccccgc<br>cacaccttgcagaaggccaaggatgagctgaacgagagagag<br>gagacccgggaggaggcagtgcgagagctgcaggagatggtg<br>caggcgcaggcggcctcgggggaggagctggcggtggccgtg<br>gcggagagggtgcaagagaaggacagcggcttcttcctgcgc |

TABLE 2-continued

Plasmid Composition
Plasmid Composition

| Elements | SEQUENCE IDENTIFIER (SEQ. ID. NO:)AND SEQUENCE INFORMATION |
|---|---|
| | ttcatccgcgcacggaagttcaacgtgggccgtgcctatgag |
| | ctgctcagaggctatgtgaatttccggctgcagtaccctgag |
| | ctctttgacagcctgtccccagaggctgtccgctgcaccatt |
| | gaagctggctaccctggtgtcctctctagtcgggacaagtat |
| | ggccgagtggtcatgctcttcaacattgagaactggcaaagt |
| | caagaaatcacctttgatgagatcttgcaggcatattgcttc |
| | atcctggagagaagctgctggagaatgaggaaactcaaatcaat |
| | ggcttctgcatcattgagaacttcaagggctttaccatgcag |
| | caggctgctagtctccggacttcagatctcaggaagatggtg |
| | gacatgctccaggattccttcccagcccggttcaaagccatc |
| | cacttcatccaccagccatggtacttcaccacgacctacaat |
| | gtggtcaagcccttcttgaagagcaagctgcttgagagggtc |
| | tttgtccacggggatgacctttctggtttctaccaggagatc |
| | gatgagaacatcctgccctctgacttcgggggcacgctgccc |
| | aagtatgatggcaaggccgttgctgagcagctctttggcccc |
| | caggcccaagctgagaacacagccttctgaggatcgtaccgg |
| | tcgacctgcagaagcttgcctcgagcagcgctgctcgagaga |
| | tctggatcataatcagccataccacatttgtagaggttttac |
| | ttgctttaaaaaacctcccacacctccccctgaacctgaaac |
| | ataaaatgaatgcaattgttgttgttaacttgtttattgcag |
| | cttataatggttacaaataaagcaatagcatcacaaatttca |
| | caaataaagcatttttttcactgcattctagttgtggtttgt |
| | ccaaactcatcaatgtatcttatcatgtctggtaaccacgtg |
| | cggaccgagcggccgcaggaacccctagtgatggagttggcc |
| | actccctctctgcgcgctcgctcgctcactgaggccgggcga |
| | ccaaaggtcgcccgacgcccgggctttgcccgggcggcctca |
| | gtgagcgagcgagcgcgcagctgcctgcaggggcgcctgatg |
| | cggtattttctccttacgcatctgtgcggtatttcacaccgc |
| | atacgtcaaagcaaccatagtacgcgccctgtagcggcgcat |
| | taagcgcggcgggtgtggtggttacgcgcagcgtgaccgcta |
| | cacttgccagcgccttagcgcccgctcctttcgctttcttcc |
| | cttcctttctcgccacgttcgccggctttccccgtcaagctc |
| | taaatcgggggctccctttagggttccgatttagtgctttac |
| | ggcacctcgaccccaaaaaacttgatttgggtgatggttcac |
| | gtagtgggccatcgccctgatagacggtttttcgccctttga |
| | cgttggagtccacgttctttaatagtggactcttgttccaaa |
| | ctggaacaacactcaactctatctcgggctattcttttgatt |
| | tataagggattttgccgatttcggtctattggttaaaaaatg |
| | agctgatttaacaaaaatttaacgcgaattttaacaaaatat |
| | taacgtttacaattttatggtgcactctcagtacaatctgct |
| | ctgatgccgcatagttaagccagccccgacacccgccaacac |
| | ccgctgacgcgccctgacgggcttgtctgctcccggcatccg |
| | cttacagacaagctgtgaccgtctccgggagctgcatgtgtc |
| | agaggttttcaccgtcatcaccgaaacgcgcgagacgaaagg |
| | gcctcgtgatacgcctatttttataggttaatgtcatgataa |
| | taatggtttcttagacgtcaggtggcacttttcggggaaatg |
| | tgcgcggaacccctatttgtttatttttctaaatacattcaa |
| | atatgtatccgctcatgagacaataaccctgataaatgcttc |
| | aataatattgaaaaaggaagagtatgagtattcaacatttcc |
| | gtgtcgcccttattcccttttttgcggcattttgccttcctg |
| | tttttgctcacccagaaacgctggtgaaagtaaaagatgctg |
| | aagatcagttgggtgcacgagtgggttacatcgaactggatc |
| | tcaacagcggtaagatccttgagagttttcgccccgaagaac |
| | gttttccaatgatgagcacttttaaagttctgctatgtggcg |
| | cggtattatcccgtattgacgccgggcaagagcaactcggtc |
| | gccgcatacactattctcagaatgacttggttgagtactcac |
| | cagtcacagaaaagcatcttacggatggcatgacagtaagag |
| | aattatgcagtgctgccataaccatgagtgataacactgcgg |
| | ccaacttacttctgacaacgatcggaggaccgaaggagctaa |
| | ccgcttttttgcacaacatgggggatcatgtaactcgccttg |
| | atcgttgggaaccggagctgaatgaagccataccaaacgacg |
| | agcgtgacaccacgatgcctgtagcaatggcaacaacgttgc |
| | gcaaactattaactggcgaactacttactctagcttcccggc |
| | aacaattaatagactggatggaggcggataaagttgcaggac |
| | cacttctgcgctcggcccttccggctggctggtttattgctg |
| | ataaatctggagccggtgagcgtgggtctcgcggtatcattg |
| | cagcactggggccagatggtaagccctcccgtatcgtagtta |
| | tctacacgacggggagtcaggcaactatggatgaacgaaata |
| | gacagatcgctgagataggtgcctcactgattaagcattggt |
| | aactgtcagaccaagtttactcatatatactttagattgatt |
| | taaaacttcatttttaatttaaaaggatctaggtgaagatcc |
| | tttttgataatctcatgaccaaaatcccttaacgtgagtttt |
| | cgttccactgagcgtcagaccccgtagaaaagatcaaaggat |
| | cttcttgaaatcctttttttctgcgcgtaatctgctgcttgc |

TABLE 2-continued

Plasmid Composition
Plasmid Composition

| Elements | SEQUENCE IDENTIFIER (SEQ. ID. NO:) AND SEQUENCE INFORMATION |
|---|---|
| | aaacaaaaaaaccaccgctaccagcggtggtttgtttgccgg<br>atcaagagctaccaactctttttccgaaggtaactggcttca<br>gcagagcgcagataccaaatactgttcttctagtgtagccgt<br>agttaggccaccacttcaagaactctgtagcaccgcctacat<br>acctcgctctgctaatcctgttaccagtggctgctgccagtg<br>gcgataagtcgtgtcttaccgggttggactcaagacgatagt<br>taccggataaggcgcagcggtcgggctgaacggggggttcgt<br>gcacacagcccagcttggagcgaacgacctacaccgaactga<br>gatacctacagcgtgagctatgagaaagcgccacgcttcccg<br>aagggagaaaggcggacaggtatccggtaagcggcagggtcg<br>gaacaggagagcgcacgagggagcttccagggggaaacgcct<br>ggtatctttatagtcctgtcgggtttcgccacctctgacttg<br>agcgtcgatttttgtgatgctcgtcaggggggcggagcctat<br>ggaaaaacgccagcaacgcggcctttttacggttcctggcct<br>tttgctggccttttgctcacatgtcctgcaggcag |
| GENE CASSETTE OF PLASMID TM017 OCCURS AT BP 4 THROUGH 2330 OF SEQ ID NO: 26 | 51<br>cgcgctcgctcgctcactgaggccgcccgggcaaagcccggg<br>cgtcgggcgacctttggtcgcccggcctcagtgagcgagcga<br>gcgcgcagagagggagtggggtaccacgcgtttgtcctctcc<br>ctgcttggccttaaccagccacatttctcaactgaccccact<br>cactgcagaggtgaaaactaccatgccaggtcctgctggctg<br>ggggaggggtgggcaataggcctggatttgccagagctgcca<br>ctgtagatgtagtcatatttacgatttcccttcacctcttat<br>taccctggtggtggtggtgggggggggggggtgctctctcag<br>caaccccaccccgggatcttgaggagaaagagggcagagaaa<br>agagggaatgggactggcccagatcccagccccacagccggg<br>cttccacatggccgagcaggaactccagagcaggagcacaca<br>aaggagggctttgatgcgcctccagccaggcccaggcctctc<br>ccctctcccctttctctctgggtcttcctttgccccactgag<br>ggcctcctgtgagcccgatttaacggaaactgtgggcggtga<br>gaagttccttatgacacactaatcccaacctgctgaccggac<br>cacgcctccagcggagggaacctctagagctccaggacattc<br>aggtaccaggtagccccaaggaggagctgccgaatcgatgga<br>tcgggaactgaaaaaccagaaagttaactggtaagtttagtc<br>tttttgtcttttatttcaggtcccggatccggtggtggtgca<br>aatcaaagaactgctcctcagtggatgttgcctttacttcta<br>ggcctgtacggaagtgttacttctgctctaaaagctgcggaa<br>ttgtacccgccccgggatccatcgattgaattcgccaccatg<br>tcagaaggggtgggcacgttccgcatggtacctgaagaggaa<br>caggagctccgtgcccaactggagcagctcacaaccaaggac<br>catggacctgtctttggcccgtgcagccagctgccccgccac<br>accttgcagaaggccaaggatgagctgaacgagagagaggag<br>acccgggaggaggcagtgcgagagctgcaggagatggtgcag<br>gcgcaggcggcctcgggggaggagctggcggtggccgtggcg<br>gagagggtgcaagagaaggacagcggcttcttcctgcgcttc<br>atccgcgcacggaagttcaacgtgggccgtgcctatgagctg<br>ctcagaggctatgtgaatttccggctgcagtaccctgagctc<br>tttgacagcctgtccccagaggctgtccgctgcaccattgaa<br>gctggctaccctggtgtcctctctagtcgggacaagtatggc<br>cgagtggtcatgctcttcaacattgagaactggcaaagtcaa<br>gaaatcacctttgatgagatcttgcaggcatattgcttcatc<br>ctggagaagctgctggagaatgaggaaactcaaatcaatggc<br>ttctgcatcattgagaacttcaagggctttaccatgcagcag<br>gctgctagtctccggacttcagatctcaggaagatggtggac<br>atgctccaggattccttcccagcccggttcaaagccatccac<br>ttcatccaccagccatggtacttcaccacgacctacaatgtg<br>gtcaagcccttcttgaagagcaagctgcttgagagggtcttt<br>gtccacggggatgacctttctggtttctaccaggagatcgat<br>gagaacatcctgccctctgacttcgggggcacgctgcccaag<br>tatgatggcaaggccgttgctgagcagctctttggcccccag<br>gcccaagctgagaacacagccttctgaggatcgtaccggtcg<br>acctgcagaagcttgcctcgagcagcgctgctcgagagatct<br>ggatcataatcagccataccacatttgtagaggttttacttg<br>ctttaaaaaacctcccacacctccccctgaacctgaaacata<br>aaatgaatgcaattgttgttgttaacttgtttattgcagctt<br>ataatggttacaaataaagcaatagcatcacaaatttcacaa<br>ataaagcatttttttcactgcattctagttgtggtttgtcca<br>aactcatcaatgtatcttatcatgtctggtaaccacgtgcgg<br>accgagcggccgcaggaacccctagtgatggagttggccact<br>ccctctctgcgcgctcgctcgctcactgaggccgggcgacca<br>aaggtcgcccgacgcccgggctttgcccgggcggcctcagtg<br>agcgagcgagcgcgcag |

TABLE 2-continued

| Plasmid Composition | |
|---|---|
| Plasmid Composition | |
| Elements | SEQUENCE IDENTIFIER (SEQ. ID. NO:) AND SEQUENCE INFORMATION |
| Plasmid TM037 Composition | |
| 5' ITR | 2<br>occurs @ bp 1 through bp 119 of SEQ ID NO: 27 |
| Human RLBP1 Promoter (long) | 10<br>occurs @ bp 137 through bp 3293 of SEQ ID NO: 27 |
| Added Kozak | 5<br>occurs at bp 3300 through bp 3305 of SEQ ID NO: 27 |
| HUMAN RLBP1 GENE CDS | 6<br>occurs at bp 3306 through bp 4259 of SEQ ID NO: 27 |
| SV40 POLYA | 8<br>occurs at bp 4318 through bp 4553 of SEQ ID NO: 27 |
| 3' ITR | 9<br>occurs at bp 4582 through bp 4711 of SEQ ID NO: 27 |
| AMP BACTERIAL BACKBONE | 15<br>occurs at bp 4712 through bp 7330 of SEQ ID NO: 27 |
| Plasmid TM037 sequence | 27<br>CTGCGCGCTCGCTCGCTCACTGAGGCCGCCCGGGCGTCGGGC<br>GACCTTTGGTCGCCCGGCCTCAGTGAGCGAGCGAGCGCGCAG<br>AGAGGGAGTGGCCAACTCCATCACTAGGGGTTCCTGCGGCCG<br>CACGCAGCTTTTGTCCTCTCCCTGCTTGGCCTTAACCAGCCA<br>CATTTCTCAACTGACCCCACTCACTGCAGAGGTGAAAACTAC<br>CATGCCAGGTCCTGCTGGCTGGGGGAGGGGTGGGCAATAGGC<br>CTGGATTTGCCAGAGCTGCCACTGTAGATGTAGTCATATTTA<br>CGATTTCCCTTCACCTCTTATTACCCTGGTGGTGGTGGTGGG<br>GGGGGGGGGGTGCTCTCTCAGCAACCCCACCCCGGGATCTTG<br>AGGAGAAAGAGGGCAGAGAAAAGAGGGAATGGGACTGGCCCA<br>GATCCCAGCCCCACAGCCGGGCTTCCACATGGCCGAGCAGGA<br>ACTCCAGAGCAGGAGCACACAAAGGAGGGCTTTGATGCGCCT<br>CCAGCCAGGCCCAGGCCTCTCCCCTCTCCCCTTTCTCTCTGG<br>GTCTTCCTTTGCCCCACTGAGGGCCTCCTGTGAGCCCGATTT<br>AACGGAAACTGTGGGCGGTGAGAAGTTCCTTATGACACACTA<br>ATCCCAACCTGCTGACCGGACCACGCCTCCAGCGGAGGGAAC<br>CTCTAGAGCTCCAGGACATTCAGGTACCAGGTAGCCCCAAGG<br>AGGAGCTGCCGACCTGGCAGGTAAGTCAATACCTGGGGCTTG<br>CCTGGGCCAGGGAGCCCAGGACTGGGGTGAGGACTCAGGGGA<br>GCAGGGAGACCACGTCCCAAGATGCCTGTAAAACTGAAACCA<br>CCTGGCCATTCTCCAGGTTGAGCCAGACCAATTTGATGGCAG<br>ATTTAGCAAATAAAAATACAGGACACCCAGTTAAATGTGAAT<br>TTCAGATGAACAGCAAATACTTTTTTAGTATTAAAAAAGTTC<br>ACATTTAGGCTCACGCCTGTAATCCCAGCACTTTGGGAGGCC<br>GAGGCAGGCAGATCACCTGAGGTCAGGAGTTCGAGACCAGCC<br>TGGCCAACATGGTGAAACCCCATCTCCACTAAAAATACCAAA<br>AATTAGCCAGGCGTGCTGGTGGGCACCTGTAGTTCCAGCTAC<br>TCAGGAGGCTAAGGCAGGAGAATTGCTTGAACCTGGGAGGCA<br>GAGGTTGCAGTGAGCTGAGATCGCACCATTGCACTCTAGCCT<br>GGGCGACAAGAACAAAACTCCATCTCAAAAAAAAAAAAAAAA<br>AAAAAGTTCACATTTAACTGGGCATTCTGTATTTAATTGGTA<br>ATCTGAGATGGCAGGGAACAGCATCAGCATGGTGTGAGGGAT<br>AGGCATTTTTTCATTGTGTACAGCTTGTAAATCAGTATTTTT<br>AAAACTCAAAGTTAATGGCTTGGGCATATTTAGAAAAGAGTT<br>GCCGCACGGACTTGAACCCTGTATTCCTAAAATCTAGGATCT<br>TGTTCTGATGGTCTGCACAACTGGCTGGGGGTGTCCAGCCAC<br>TGTCCCTCTTGCCTGGGCTCCCCAGGGCAGTTCTGTCAGCCT<br>CTCCATTTCCATTCCTGTTCCAGCAAAACCCAACTGATAGCA<br>CAGCAGCATTTCAGCCTGTCTACCTCTGTGCCCACATACCTG<br>GATGTCTACCAGCCAGAAAGGTGGCTTAGATTTGGTTCCTGT<br>GGGTGGATTATGGCCCCCAGAACTTCCCTGTGCTTGCTGGGG<br>GTGTGGAGTGGAAAGAGCAGGAAATGGGGGACCCTCCGATAC<br>TCTATGGGGGTCCTCCAAGTCTCTTTGTGCAAGTTAGGGTAA<br>TAATCAATATGGAGCTAAGAAAGAGAAGGGGAACTATGCTTT<br>AGAACAGGACACTGTGCCAGGAGCATTGCAGAAATTATATGG<br>TTTTCACGACAGTTCTTTTTGGTAGGTACTGTTATTATCCTC<br>AGTTTGCAGATGAGGAAACTGAGACCCAGAAAGGTTAAATAA<br>CTTGCTAGGGTCACACAAGTCATAACTGACAAAGCCTGATTC<br>AAACCCAGGTCTCCCTAACCTTTAAGGTTTCTATGACGCCAG |

TABLE 2-continued

Plasmid Composition
Plasmid Composition

| Elements | SEQUENCE IDENTIFIER (SEQ. ID. NO:)AND SEQUENCE INFORMATION |
|---|---|
| | CTCTCCTAGGGAGTTTGTCTTCAGATGTCTTGGCTCTAGGTG |
| | TCAAAAAAAGACTTGGTGTCAGGCAGGCATAGGTTCAAGTCC |
| | CAACTCTGTCACTTACCAACTGTGACTAGGTGATTGAACTGA |
| | CCATGGAACCTGGTCACATGCAGGAGCAGGATGGTGAAGGGT |
| | TCTTGAAGGCACTTAGGCAGGACATTTAGGCAGGAGAGAAAA |
| | CCTGGAAACAGAAGAGCTGTCTCCAAAAATACCCACTGGGGA |
| | AGCAGGTTGTCATGTGGGCCATGAATGGGACCTGTTCTGGTA |
| | ACCAAGCATTGCTTATGTGTCCATTACATTTCATAACACTTC |
| | CATCCTACTTTACAGGGAACAACCAAGACTGGGGTTAAATCT |
| | CACAGCCTGCAAGTGGAAGAGAAGAACTTGAACCCAGGTCCA |
| | ACTTTTGCGCCACAGCAGGCTGCCTCTTGGTCCTGACAGGAA |
| | GTCACAACTTGGGTCTGAGTACTGATCCCTGGCTATTTTTTG |
| | GCTGTGTTACCTTGGACAAGTCACTTATTCCTCCTCCCGTTT |
| | CCTCCTATGTAAAATGGAAATAATAATGTTGACCCTGGGTCT |
| | GAGAGAGTGGATTTGAAAGTACTTAGTGCATCACAAAGCACA |
| | GAACACACTTCCAGTCTCGTGATTATGTACTTATGTAACTGG |
| | TCATCACCCATCTTGAGAATGAATGCATTGGGGAAAGGGCCA |
| | TCCACTAGGCTGCGAAGTTTCTGAGGGACTCCTTCGGGCTGG |
| | AGAAGGATGGCCACAGGAGGGAGGAGAGATTGCCTTATCCTG |
| | CAGTGATCATGTCATTGAGAACAGAGCCAGATTCTTTTTTTC |
| | CTGGCAGGGCCAACTTGTTTTAACATCTAAGGACTGAGCTAT |
| | TTGTGTCTGTGCCCTTTGTCCAAGCAGTGTTTCCCAAAGTGT |
| | AGCCCAAGAACCATCTCCCTCAGAGCCACCAGGAAGTGCTTT |
| | AAATTGCAGGTTCCTAGGCCACAGCCTGCACCTGCAGAGTCA |
| | GAATCATGGAGGTTGGGACCCAGGCACCTGCGTTTCTAACAA |
| | ATGCCTCGGGTGATTCTGATGCAATTGAAAGTTTGAGATCCA |
| | CAGTTCTGAGACAATAACAGAATGGTTTTTCTAACCCCTGCA |
| | GCCCTGACTTCCTATCCTAGGGAAGGGGCCGGCTGGAGAGGC |
| | CAGGACAGAGAAAGCAGATCCCTTCTTTTTCCAAGGACTCTG |
| | TGTCTTCCATAGGCAACGAATTCGCCACCATGTCAGAAGGGG |
| | TGGGCACGTTCCGCATGGTACCTGAAGAGGAACAGGAGCTCC |
| | GTGCCCAACTGGAGCAGCTCACAACCAAGGACCATGGACCTG |
| | TCTTTGGCCCGTGCAGCCAGCTGCCCCGCCACACCTTGCAGA |
| | AGGCCAAGGATGAGCTGAACGAGAGAGAGGAGACCCGGGAGG |
| | AGGCAGTGCGAGAGCTGCAGGAGATGGTGCAGGCGCAGGCGG |
| | CCTCGGGGGAGGAGCTGGCGGTGGCCGTGGCGGAGAGGGTGC |
| | AAGAGAAGGACAGCGGCTTCTTCCTGCGCTTCATCCGCGCAC |
| | GGAAGTTCAACGTGGGCCGTGCCTATGAGCTGCTCAGAGGCT |
| | ATGTGAATTTCCGGCTGCAGTACCCTGAGCTCTTTGACAGCC |
| | TGTCCCCAGAGGCTGTCCGCTGCACCATTGAAGCTGGCTACC |
| | CTGGTGTCCTCTCTAGTCGGGACAAGTATGGCCGAGTGGTCA |
| | TGCTCTTCAACATTGAGAACTGGCAAAGTCAAGAAATCACCT |
| | TTGATGAGATCTTGCAGGCATATTGCTTCATCCTGGAGAAGC |
| | TGCTGGAGAATGAGGAAACTCAAATCAATGGCTTCTGCATCA |
| | TTGAGAACTTCAAGGGCTTTACCATGCAGCAGGCTGCTAGTC |
| | TCCGGACTTCAGATCTCAGGAAGATGGTGGACATGCTCCAGG |
| | ATTCCTTCCCAGCCCGGTTCAAAGCCATCCACTTCATCCACC |
| | AGCCATGGTACTTCACCACGACCTACAATGTGGTCAAGCCCT |
| | TCTTGAAGAGCAAGCTGCTTGAGAGGGTCTTTGTCCACGGGG |
| | ATGACCTTTCTGGTTTCTACCAGGAGATCGATGAGAACATCC |
| | TGCCCTCTGACTTCGGGGGCACGCTGCCCAAGTATGATGGCA |
| | AGGCCGTTGCTGAGCAGCTCTTTGGCCCCCAGGCCCAAGCTG |
| | AGAACACAGCCTTCTGAGGATCGTACCGGTCGACCTGCAGAA |
| | GCTTGCCTCGAGCAGCGCTGCTCGAGAGATCTGGATCATAAT |
| | CAGCCATACCACATTTGTAGAGGTTTTACTTGCTTTAAAAAA |
| | CCTCCCACACCTCCCCCTGAACCTGAAACATAAAATGAATGC |
| | AATTGTTGTTGTTAACTTGTTTATTGCAGCTTATAATGGTTA |
| | CAAATAAAGCAATAGCATCACAAATTTCACAAATAAAGCATT |
| | TTTTTCACTGCATTCTAGTTGTGGTTTGTCCAAACTCATCAA |
| | TGTATCTTATCATGTCTGGTAACCACGTGCGGACCGAGCGGC |
| | CGCAGGAACCCCTAGTGATGGAGTTGGCCACTCCCTCTCTGC |
| | GCGCTCGCTCGCTCACTGAGGCCGGGCGACCAAAGGTCGCCC |
| | GACGCCCGGGCTTTGCCCGGGCGGCCTCAGTGAGCGAGCGAG |
| | CGCGCAGCTGCCTGCAGGGGCGCCTGATGCGGTATTTTCTCC |
| | TTACGCATCTGTGCGGTATTTCACACCGCATACGTCAAAGCA |
| | ACCATAGTACGCGCCCTGTAGCGGCGCATTAAGCGCGGCGGG |
| | TGTGGTGGTTACGCGCAGCGTGACCGCTACACTTGCCAGCGC |
| | CTTAGCGCCCGCTCCTTTCGCTTTCTTCCCTTCCTTTCTCGC |
| | CACGTTCGCCGGCTTTCCCCGTCAAGCTCTAAATCGGGGGCT |
| | CCCTTTAGGGTTCCGATTTAGTGCTTTACGGCACCTCGACCC |
| | CAAAAAACTTGATTTGGGTGATGGTTCACGTAGTGGGCCATC |
| | GCCCTGATAGACGGTTTTTCGCCCTTTGACGTTGGAGTCCAC |
| | GTTCTTTAATAGTGGACTCTTGTTCCAAACTGGAACAACACT |
| | CAACTCTATCTCGGGCTATTCTTTTGATTTATAAGGGATTTT |

TABLE 2-continued

Plasmid Composition
Plasmid Composition

| Elements | SEQUENCE IDENTIFIER (SEQ. ID. NO:) AND SEQUENCE INFORMATION |
|---|---|
| | GCCGATTTCGGTCTATTGGTTAAAAAATGAGCTGATTTAACA AAAATTTAACGCGAATTTTAACAAAATATTAACGTTTACAAT TTTATGGTGCACTCTCAGTACAATCTGCTCTGATGCCGCATA GTTAAGCCAGCCCCGACACCCGCCAACACCCGCTGACGCGCC CTGACGGGCTTGTCTGCTCCCGGCATCCGCTTACAGACAAGC TGTGACCGTCTCCGGGAGCTGCATGTGTCAGAGGTTTTCACC GTCATCACCGAAACGCGCGAGACGAAAGGGCCTCGTGATACG CCTATTTTTATAGGTTAATGTCATGATAATAATGGTTTCTTA GACGTCAGGTGGCACTTTTCGGGGAAATGTGCGCGGAACCCC TATTTGTTTATTTTTCTAAATACATTCAAATATGTATCCGCT CATGAGACAATAACCCTGATAAATGCTTCAATAATATTGAAA AAGGAAGAGTATGAGTATTCAACATTTCCGTGTCGCCCTTAT TCCCTTTTTTGCGGCATTTTGCCTTCCTGTTTTTGCTCACCC AGAAACGCTGGTGAAAGTAAAAGATGCTGAAGATCAGTTGGG TGCACGAGTGGGTTACATCGAACTGGATCTCAACAGCGGTAA GATCCTTGAGAGTTTTCGCCCCGAAGAACGTTTTCCAATGAT GAGCACTTTTAAAGTTCTGCTATGTGGCGCGGTATTATCCCG TATTGACGCCGGGCAAGAGCAACTCGGTCGCCGCATACACTA TTCTCAGAATGACTTGGTTGAGTACTCACCAGTCACAGAAAA GCATCTTACGGATGGCATGACAGTAAGAGAATTATGCAGTGC TGCCATAACCATGAGTGATAACACTGCGGCCAACTTACTTCT GACAACGATCGGAGGACCGAAGGAGCTAACCGCTTTTTTGCA CAACATGGGGGATCATGTAACTCGCCTTGATCGTTGGGAACC GGAGCTGAATGAAGCCATACCAAACGACGAGCGTGACACCAC GATGCCTGTAGCAATGGCAACAACGTTGCGCAAACTATTAAC TGGCGAACTACTTACTCTAGCTTCCCGGCAACAATTAATAGA CTGGATGGAGGCGGATAAAGTTGCAGGACCACTTCTGCGCTC GGCCCTTCCGGCTGGCTGGTTTATTGCTGATAAATCTGGAGC CGGTGAGCGTGGGTCTCGCGGTATCATTGCAGCACTGGGGCC AGATGGTAAGCCCTCCCGTATCGTAGTTATCTACACGACGGG GAGTCAGGCAACTATGGATGAACGAAATAGACAGATCGCTGA GATAGGTGCCTCACTGATTAAGCATTGGTAACTGTCAGACCA AGTTTACTCATATATACTTTAGATTGATTTAAAACTTCATTT TTAATTTAAAAGGATCTAGGTGAAGATCCTTTTTGATAATCT CATGACCAAAATCCCTTAACGTGAGTTTTCGTTCCACTGAGC GTCAGACCCCGTAGAAAAGATCAAAGGATCTTCTTGAAATCC TTTTTTTCTGCGCGTAATCTGCTGCTTGCAAACAAAAAAACC ACCGCTACCAGCGGTGGTTTGTTTGCCGGATCAAGAGCTACC AACTCTTTTTCCGAAGGTAACTGGCTTCAGCAGAGCGCAGAT ACCAAATACTGTTCTTCTAGTGTAGCCGTAGTTAGGCCACCA CTTCAAGAACTCTGTAGCACCGCCTACATACCTCGCTCTGCT AATCCTGTTACCAGTGGCTGCTGCCAGTGGCGATAAGTCGTG TCTTACCGGGTTGGACTCAAGACGATAGTTACCGGATAAGGC GCAGCGGTCGGGCTGAACGGGGGGTTCGTGCACACAGCCCAG CTTGGAGCGAACGACCTACACCGAACTGAGATACCTACAGCG TGAGCTATGAGAAAGCGCCACGCTTCCCGAAGGGAGAAAGGC GGACAGGTATCCGGTAAGCGGCAGGGTCGGAACAGGAGAGCG CACGAGGGAGCTTCCAGGGGGAAACGCCTGGTATCTTTATAG TCCTGTCGGGTTTCGCCACCTCTGACTTGAGCGTCGATTTTT GTGATGCTCGTCAGGGGGGCGGAGCCTATGGAAAAACGCCAG CAACGCGGCCTTTTTACGGTTCCTGGCCTTTTGCTGGCCTTT TGCTCACATGTCCTGCAGGCAG |
| GENE CASSETTE OF PLASMID TM037 OCCURS AT BP 1 THROUGH 4711 OF SEQ ID NO: 27 | 52 ctgcgcgctcgctcgctcactgaggccgcccgggcgtcgggc gacctttggtcgcccggcctcagtgagcgagcgagcgcgcag agagggagtggccaactccatcactaggggttcctgcggccg cacgcagcttttgtcctctccctgcttggccttaaccagcca catttctcaactgaccccactcactgcagaggtgaaaactac catgccaggtcctgctggctgggggaggggtgggcaataggc ctggacttgccagagctgccactgtagatgtagtcatattta cgatttcccttcacctcttattaccctggtggtggtggtggg gggggggggtgctctctcagcaaccccaccccgggatcttg aggagaaagagggcagagaaaagagggaatgggactggccca gatcccagccccacagccgggcttccacatggccgagcagga actccagagcaggagcacacaaaggagggctttgatgcgcct ccagccaggcccaggcctctcccctctcccctttctctctgg gtcttcctttgccccactgagggcctcctgtgagcccgattt aacggaaactgtgggcggtgagaagttccttatgacacacta atcccaacctgctgaccggaccacgcctccagcggagggaac ctctagagctccaggacattcaggtaccaggtagccccaagg aggagctgccgacctggcaggtaagtcaatacctggggcttg cctgggccagggagcccaggactggggtgaggactcaggga gcagggagaccacgtcccaagatgcctgtaaaactgaaacca cctggccattctccaggttgagccagaccaatttgatggcag |

TABLE 2-continued

Plasmid Composition

Plasmid Composition

| Elements | SEQUENCE IDENTIFIER (SEQ. ID. NO:)AND SEQUENCE INFORMATION |
|---|---|
| | atttagcaaataaaaatacaggacacccagttaaatgtgaat<br>ttcagatgaacagcaaatactttttcagtattaaaaagttc<br>acatttaggctcacgcctgtaatcccagcactttgggaggcc<br>gaggcaggcagatcacctgaggtcaggagttcgagaccagcc<br>tggccaacatggtgaaaccccatctccactaaaaataccaaa<br>aattagccaggcgtgctggtgggcacctgtagttccagctac<br>tcaggaggctaaggcaggagaattgcttgaacctgggaggca<br>gaggttgcagtgagctgagatcgcaccattgcactctagcct<br>gggcgacaagaacaaaactccatctcaaaaaaaaaaaaaaaa<br>aaaaagttcacatttaactgggcattctgtatttaattggta<br>atctgagatggcagggaacagcatcagcatggtgtgagggat<br>aggcatttttcattgtgtacagcttgtaaatcagtattttt<br>aaaactcaaagttaatggcttgggcatatttagaaaagagtt<br>gccgcacggacttgaaccctgtattcctaaaatctaggatct<br>tgttctgatggtctgcacaactggctgggggtgtccagccac<br>tgtccctcttgcctgggctccccagggcagttctgtcagcct<br>ctccatttccattcctgttccagcaaaacccaactgatagca<br>cagcagcatttcagcctgtctacctctgtgcccacatacctg<br>gatgtctaccagccagaaaggtggcttagatttggttcctgt<br>gggtggattatggcccccagaacttccctgtgcttgctgggg<br>gtgtggagtggaaagagcaggaaatgggggaccctccgatac<br>tctatggggggtcctccaagtctctttgtgcaagttagggtaa<br>taatcaatatggagctaagaaagagaaggggaactatgcttt<br>agaacaggacactgtgccaggagcattgcagaaattatatgg<br>ttttcacgacagttctttttggtaggtactgttattatcctc<br>agtttgcagatgaggaaactgagacccagaaaggttaaataa<br>cttgctagggtcacacaagtcataactgacaaagcctgattc<br>aaacccaggtctccctaacctttaaggtttctatgacgccag<br>ctctcctagggagtttgtcttcagatgtcttggctctaggtg<br>tcaaaaaaagacttggtgtcaggcaggcataggttcaagtcc<br>caactctgtcacttaccaactgtgactaggtgattgaactga<br>ccatggaacctggtcacatgcaggagcaggatggtgaagggt<br>tcttgaaggcacttaggcaggacatttaggcaggagagaaaa<br>cctggaaacagaagagctgtctccaaaaatacccactgggga<br>agcaggttgtcatgtgggccatgaatgggacctgttctggta<br>accaagcattgcttatgtgtccattacatttcataacacttc<br>catcctactttacagggaacaaccaagactggggttaaatct<br>cacagcctgcaagtggaagagaagaacttgaacccaggtcca<br>acttttgcgccacagcaggctgcctcttggtcctgacaggaa<br>gtcacaacttgggtctgagtactgatccctggctatttttg<br>gctgtgttaccttggacaagtcacttattcctcctcccgttt<br>cctcctatgtaaaatggaaataataatgttgaccctgggtct<br>gagagagtggatttgaaagtacttagtgcatcacaaagcaca<br>gaacacacttccagtctcgtgattatgtacttatgtaactgg<br>tcatcacccatcttgagaatgaatgcattggggaaagggcca<br>tccactaggctgcgaagtttctgagggactccttcgggctgg<br>agaaggatggccacaggagggaggagagattgccttatcctg<br>cagtgatcatgtcattgagaacagagccagattcttttttc<br>ctggcagggccaacttgttttaacatctaaggactgagctat<br>ttgtgtctgtgccctttgtccaagcagtgtttcccaaagtgt<br>agcccaagaaccatctccctcagagccaccaggaagtgcttt<br>aaattgcaggttcctaggccacagcctgcacctgcagagtca<br>gaatcatggaggttgggacccaggcacctgcgtttctaacaa<br>atgcctcgggtgattctgatgcaattgaaagtttgagatcca<br>cagttctgagacaataacagaatggtttttctaacccctgca<br>gccctgacttcctatcctagggaaggggccggctggagaggc<br>caggacagagaaagcagatcccttctttttccaaggactctg<br>tgtcttccataggcaacgaattcgccaccatgtcagaagggg<br>tgggcacgttccgcatggtacctgaagaggaacaggagctcc<br>gtgcccaactggagcagctcacaaccaaggaccatggacctg<br>tctttggcccgtgcagccagctgccccgccacaccttgcaga<br>aggccaaggatgagctgaacgagagagaggagacccgggagg<br>aggcagtgcgagagctgcaggagatggtgcaggcgcaggcgg<br>cctcgggggaggagctggcggtggccgtggcggagagggtgc<br>aagagaaggacagcggcttcttcctgcgcttcatccgcgcac<br>ggaagttcaacgtgggccgtgcctatgagctgctcagaggct<br>atgtgaatttccggctgcagtaccctgagctctttgacagcc<br>tgtccccagaggctgtccgctgcaccattgaagctggctacc<br>ctggtgtcctctctagtcgggacaagtatggccgagtggtca<br>tgctcttcaacattgagaactggcaaagtcaagaaatcacct<br>ttgatgagatcttgcaggcatattgcttcatcctggagaagc<br>tgctggagaatgaggaaactcaaatcaatggcttctgcatca<br>ttgagaacttcaagggctttaccatgcagcaggctgctagtc<br>tccggacttcagatctcaggaagatggtggacatgctccagg |

TABLE 2-continued

Plasmid Composition
Plasmid Composition

| Elements | SEQUENCE IDENTIFIER (SEQ. ID. NO:) AND SEQUENCE INFORMATION |
|---|---|
| | attccttcccagcccggttcaaagccatccacttcatccacc<br>agccatggtacttcaccacgacctacaatgtggtcaagccct<br>tcttgaagagcaagctgcttgagagggtctttgtccacgggg<br>atgacctttctggtttctaccaggagatcgatgagaacatcc<br>tgccctctgacttcgggggcacgctgcccaagtatgatggca<br>aggccgttgctgagcagctctttggcccccaggcccaagctg<br>agaacacagccttctgaggatcgtaccggtcgacctgcagaa<br>gcttgcctcgagcagcgctgctcgagagatctggatcataat<br>cagccataccacatttgtagaggttttacttgctttaaaaaa<br>cctcccacacctccccctgaacctgaaacataaaatgaatgc<br>aattgttgttgttaacttgtttattgcagcttataatggtta<br>caaataaagcaatagcatcacaaatttcacaaataaagcatt<br>tttttcactgcattctagttgtggtttgtccaaactcatcaa<br>tgtatcttatcatgtctggtaaccacgtgcggaccgagcggc<br>cgcaggaacccctagtgatggagttggccactccctctctgc<br>gcgctcgctcgctcactgaggccgggcgaccaaaggtcgccc<br>gacgcccgggctttgcccgggcggcctcagtgagcgagcgag<br>cgcgcag |
| | **Plasmid AG007 Composition** |
| 5' ITR | 2<br>occurs @ bp 1 through bp 119 of SEQ ID NO: 28 |
| Human RPE65 Promoter | 11<br>occurs @ bp 134 through bp 1718 of SEQ ID NO: 28 |
| ADDED-KOZAK | 5<br>occurs @ bp 1725 through bp 1730 of SEQ ID NO: 28 |
| HUMAN RLBP1 GENE CDS | 6<br>occurs at bp 1731 through bp 2684 of SEQ ID NO: 28 |
| SV40 POLYA | 8<br>occurs at bp 2742 through bp 2977 of SEQ ID NO: 28 |
| RLBP1 INTRONIC SEQUENCE AS STUFFER SEQUENCE | 14<br>occurs at bp 2985 through bp 4487 of SEQ ID NO: 28 |
| 3' ITR | 9<br>occurs at bp 4516 through bp 4645 of SEQ ID NO: 28 |
| AMP BACTERIAL BACKBONE | 15<br>occurs at bp 4646 through bp 7264 of SEQ ID NO: 28 |
| AG007 Plasmid Sequence | 28<br>ctgcgcgctcgctcgctcactgaggccgcccgggcgtcgggc<br>gacctttggtcgcccggcctcagtgagcgagcgagcgcgcag<br>agagggagtggccaactccatcactaggggttcctgcggccg<br>cacgcgttacgtaatatttattgaagtttaatattgtgtttg<br>tgatacagaagtatttgctttaattctaaataaaaattttat<br>gcttttattgctggtttaagaagatttggattatccttgtac<br>tttgaggagaagtttcttatttgaaatattttggaaacaggt<br>cttttaatgtggaaagatagatattaatctcctcttctatta<br>ctctccaagatccaacaaaagtgattataccccccaaaatat<br>gatggtagtatcttatactaccatcattttataggcataggg<br>ctcttagctgcaaataatggaactaactctaataaagcagaa<br>cgcaaatattgtaaatattagagagctaacaatctctgggat<br>ggctaaaggatggagcttggaggctacccagccagtaacaat<br>attccgggctccactgttgaatggagacactacaactgcctt<br>ggatgggcagagatattatggatgctaagccccaggtgctac<br>cattaggacttctaccactgtccctaacgggtggagcccatc<br>acatgcctatgccctcactgtaaggaaatgaagctactgttg<br>tatatcttgggaagcacttggattaattgttatacagttttg<br>ttgaagaagacccctagggtaagtagccataactgcacacta<br>aatttaaaattgttaatgagtttctcaaaaaaaatgttaagg<br>ttgttagctggtatagtatatatcttgcctgttttccaagga<br>cttctttgggcagtaccttgtctgtgctggcaagcaactgag<br>acttaatgaaagagtattggagatatgaatgaattgatgctg<br>tatactctcagagtgccaaacatataccaatggacaagaagg<br>tgaggcagagagcagacaggcattagtgacaagcaaagatat<br>gcagaatttcattctcagcaaatcaaaagtcctcaacctggt<br>tggaagaatattggcactgaatggtatcaataaggttgctag |

TABLE 2-continued

Plasmid Composition
Plasmid Composition

| Elements | SEQUENCE IDENTIFIER (SEQ. ID. NO:) AND SEQUENCE INFORMATION |
|---|---|
| | agagggttagaggtgcacaatgtgcttccataacattttata |
| | cttctccaatcttagcactaatcaaacatggttgaatacttt |
| | gtttactataactcttacagagttataagatctgtgaagaca |
| | gggacagggacaatacccatctctgtctggttcataggtggt |
| | atgtaatagatatttttaaaaataagtgagttaatgaatgag |
| | ggtgagaatgaaggcacagaggtattaggggaggtgggccc |
| | cagagaatggtgccaaggtccagtggggtgactgggatcagc |
| | tcaggcctgacgctggccactcccacctagctcctttctttc |
| | taatctgttctcattctccttgggaaggattgaggtctctgg |
| | aaaacagccaaacaactgttatgggaacagcaagcccaaata |
| | aagccaagcatcagggggatctgagagctgaaagcaacttct |
| | gttcccccctccctcagctgaaggggtggggaagggctcccaa |
| | agccataactccttttaagggatttagaaggcataaaaaggc |
| | ccctggctgagaacttccttcttcattctgcagttggtgaat |
| | tcgccaccatgtcagaaggggtgggcacgttccgcatggtac |
| | ctgaagaggaacaggagctccgtgcccaactggagcagctca |
| | caaccaaggaccatggacctgtctttggcccgtgcagccagc |
| | tgccccgccacaccttgcagaaggccaaggatgagctgaacg |
| | agagagaggagacccgggaggaggcagtgcgagagctgcagg |
| | agatggtgcaggcgcaggcggcctcgggggaggagctggcgg |
| | tggccgtggcggagagggtgcaagagaaggacagcggcttct |
| | tcctgcgcttcatccgcgcacggaagttcaacgtgggccgtg |
| | cctatgagctgctcagaggctatgtgaatttccggctgcagt |
| | accctgagctctttgacagcctgtccccagaggctgtccgct |
| | gcaccattgaagctggctaccctggtgtcctctctagtcggg |
| | acaagtatggccgagtggtcatgctcttcaacattgagaact |
| | ggcaaagtcaagaaatcacctttgatgagatcttgcaggcat |
| | attgcttcatcctggagaagctgctggagaatgaggaaactc |
| | aaatcaatggcttctgcatcattgagaacttcaagggcttta |
| | ccatgcagcaggctgctagtctccggacttcagatctcagga |
| | agatggtggacatgctccaggattccttcccagcccggttca |
| | aagccatccacttcatccaccagccatggtacttcaccacga |
| | cctacaatgtggtcaagcccttcttgaagagcaagctgcttg |
| | agagggtctttgtccacggggatgacctttctggtttctacc |
| | aggagatcgatgagaacatcctgccctctgacttcgggggca |
| | cgctgcccaagtatgatggcaaggccgttgctgagcagctct |
| | ttggcccccaggcccaagctgagaacacagccttctgaggat |
| | ctaccggtcgacctgcagaagcttgcctcgagcagcgctgct |
| | cgagagatctggatcataatcagccataccacatttgtagag |
| | gttttacttgctttaaaaaacctcccacacctccccctgaac |
| | ctgaaacataaaatgaatgcaattgttgttgttaacttgttt |
| | attgcagcttataatggttacaaataaagcaatagcatcaca |
| | aatttcacaaataaagcatttttttcactgcattctagttgt |
| | ggtttgtccaaactcatcaatgtatcttatcatgtctggtaa |
| | ccattctccaggttgagccagaccaatttgatggtagattta |
| | gcaaataaaaatacaggacacccagttaaatgtgaatttccg |
| | atgaacagcaaatactttttttagtattaaaaaagttcacatt |
| | taggctcacgcctgtaatcccagcactttgggaggccgaggc |
| | aggcagatcacctgaggtcaggagttcgagaccagcctggcc |
| | aacatggtgaaaccccatctccactaaaaataccaaaaatta |
| | gccaggcgtgctggtgggcacctgtagttccagctactcagg |
| | aggctaaggcaggagaattgcttgaacctgggaggcagaggt |
| | tgcagtgagctgagatcgcaccattgcactctagcctgggcg |
| | acaagaacaaaactccatctcaaaaaaaaaaaaaaaaaaaaa |
| | gttcacatttaactgggcattctgtatttaattggtaatctg |
| | agatggcagggaacagcatcagcatggtgtgagggataggca |
| | tttttttcattgtgtacagcttgtaaatcagtatttttaaaac |
| | tcaaagttaatggcttgggcatatttagaaaagagttgccgc |
| | acggacttgaaccctgtattcctaaaatctaggatcttgttc |
| | tgatggtctgcacaactggctggggggtgtccagccactgtcc |
| | ctcttgcctgggctccccagggcagttctgtcagcctctcca |
| | tttccattcctgttccagcaaaacccaactgatagcacagca |
| | gcatttcagcctgtctacctctgtgcccacatacctggatgt |
| | ctaccagccagaaaggtggcttagatttggttcctgtgggtg |
| | gattatggcccccagaacttccctgtgcttgctgggggtgtg |
| | gagtggaaagagcaggaaatgggggaccctccgatactctat |
| | gggggtcctccaagtctctttgtgcaagttagggtaataatc |
| | aatatggagctaagaaagagaaggggaactatgctttagaac |
| | aggacactgtgccaggagcattgcagaaattatatggttttc |
| | acgacagttctttttggtaggtactgttattatcctcagttt |
| | gcagatgaggaaactgagacccagaaaggttaaataacttgc |
| | tagggtcacacaagtcataactgacaaagcctgattcaaacc |
| | caggtctccctaacctttaaggtttctatgacgccagctctc |
| | ctagggagtttgtcttcagatgtcttggctctaggtgtcaaa |

TABLE 2-continued

Plasmid Composition
Plasmid Composition

| Elements | SEQUENCE IDENTIFIER (SEQ. ID. NO:) AND SEQUENCE INFORMATION |
|---|---|
| | aaaagacttggtgtcaggcaggcataggttcaagtcccaact |
| | ctgtcacttaccaactgtgactaggtgattgaactgaccatg |
| | gaacctggtcacatgcaggagcaggatggtgaagggttcttg |
| | aaggcacttaggcaggacatttaggcaggagagaaaacctgg |
| | aaacagaagagctgtctccaaaaatacccactggggaagcag |
| | gttgtcatgtgggccatgaatgggacctgttctggggtaacc |
| | acgtgcggaccgagcggccgcaggaacccctagtgatggagt |
| | tggccactccctctctgcgcgctcgctcgctcactgaggccg |
| | ggcgaccaaaggtcgcccgacgcccgggctttgcccgggcgg |
| | cctcagtgagcgagcgagcgcgcagctgcctgcaggggcgcc |
| | tgatgcggtattttctccttacgcatctgtgcggtatttcac |
| | accgcatacgtcaaagcaaccatagtacgcgccctgtagcgg |
| | cgcattaagcgcggcgggtgtggtggttacgcgcagcgtgac |
| | cgctacacttgccagcgccttagcgcccgctcctttcgcttt |
| | cttcccttcctttctcgccacgttcgccggctttccccgtca |
| | agctctaaatcgggggctccctttagggttccgatttagtgc |
| | tttacggcacctcgaccccaaaaaacttgatttgggtgatgg |
| | ttcacgtagtgggccatcgccctgatagacggtttttcgccc |
| | tttgacgttggagtccacgttctttaatagtggactcttgtt |
| | ccaaactggaacaacactcaactctatctcgggctattcttt |
| | tgatttataagggattttgccgatttcggtctattggttaaa |
| | aaatgagctgatttaacaaaaatttaacgcgaattttaacaa |
| | aatattaacgtttacaattttatggtgcactctcagtacaat |
| | ctgctctgatgccgcatagttaagccagccccgacacccgcc |
| | aacacccgctgacgcgccctgacgggcttgtctgctcccggc |
| | atccgcttacagacaagctgtgaccgtctccgggagctgcat |
| | gtgtcagaggttttcaccgtcatcaccgaaacgcgcgagacg |
| | aaagggcctcgtgatacgcctatttttataggttaatgtcat |
| | gataataatggtttcttagacgtcaggtggcacttttcgggg |
| | aaatgtgcgcggaacccctatttgtttatttttctaaataca |
| | ttcaaatatgtatccgctcatgagacaataaccctgataaat |
| | gcttcaataatattgaaaaaggaagagtatgagtattcaaca |
| | tttccgtgtcgcccttattcccttttttgcggcattttgcct |
| | tcctgtttttgctcacccagaaacgctggtgaaagtaaaaga |
| | tgctgaagatcagttgggtgcacgagtgggttacatcgaact |
| | ggatctcaacagcggtaagatccttgagagttttcgccccga |
| | agaacgttttccaatgatgagcacttttaaagttctgctatg |
| | tggcgcggtattatcccgtattgacgccgggcaagagcaact |
| | cggtcgccgcatacactattctcagaatgacttggttgagta |
| | ctcaccagtcacagaaaagcatcttacggatggcatgacagt |
| | aagagaattatgcagtgctgccataaccatgagtgataacac |
| | tgcggccaacttacttctgacaacgatcggaggaccgaagga |
| | gctaaccgcttttttgcacaacatgggggatcatgtaactcg |
| | ccttgatcgttgggaaccggagctgaatgaagccataccaaa |
| | cgacgagcgtgacaccacgatgcctgtagcaatggcaacaac |
| | gttgcgcaaactattaactggcgaactacttactctagcttc |
| | ccggcaacaattaatagactggatggaggcggataaagttgc |
| | aggaccacttctgcgctcggcccttccggctggctggtttat |
| | tgctgataaatctggagccggtgagcgtgggtctcgcggtat |
| | cattgcagcactggggccagatggtaagccctcccgtatcgt |
| | agttatctacacgacggggagtcaggcaactatggatgaacg |
| | aaatagacagatcgctgagataggtgcctcactgattaagca |
| | ttggtaactgtcagaccaagtttactcatatatactttagat |
| | tgatttaaaacttcatttttaatttaaaaggatctaggtgaa |
| | gatcctttttgataatctcatgaccaaaatcccttaacgtga |
| | gttttcgttccactgagcgtcagaccccgtagaaaagatcaa |
| | aggatcttcttgaatcctttttttctgcgcgtaatctgctg |
| | cttgcaaacaaaaaaaccaccgctaccagcggtggtttgttt |
| | gccggatcaagagctaccaactctttttccgaaggtaactgg |
| | cttcagcagagcgcagataccaaatactgttcttctagtgta |
| | gccgtagttaggccaccacttcaagaactctgtagcaccgcc |
| | tacatacctcgctctgctaatcctgttaccagtggctgctgc |
| | cagtggcgataagtcgtgtcttaccgggttggactcaagacg |
| | atagttaccggataaggcgcagcggtcgggctgaacgggggg |
| | ttcgtgcacacagcccagcttggagcgaacgacctacaccga |
| | actgagatacctacagcgtgagctatgagaaagcgccacgct |
| | tcccgaagggagaaaggcggacaggtatccggtaagcggcag |
| | ggtcggaacaggagagcgcacgagggagcttccagggggaaa |
| | cgcctggtatctttatagtcctgtcgggtttcgccacctctg |
| | acttgagcgtcgatttttgtgatgctcgtcaggggggcggag |
| | cctatggaaaaacgccagcaacgcggcctttttacggttcct |
| | ggccttttgctggccttttgctcacatgtcctgcaggcag |

TABLE 2-continued

Plasmid Composition
Plasmid Composition

| Elements | SEQUENCE IDENTIFIER (SEQ. ID. NO:) AND SEQUENCE INFORMATION |
|---|---|
| GENE CASSETTE OF PLASMID AG007 OCCURS AT BP 1 THROUGH 4645 OF SEQ ID NO: 28 | 53<br>ctgcgcgctcgctcgctcactgaggccgcccgggcgtcgggc<br>gacctttggtcgcccggcctcagtgagcgagcgagcgcgcag<br>agagggagtggccaactccatcactaggggttcctgcggccg<br>cacgcgttacgtaatatttattgaagtttaatattgtgtttg<br>tgatacagaagtatttgctttaattctaaataaaaattttat<br>gcttttattgctggtttaagaagatttggattatccttgtac<br>tttgaggagaagtttcttatttgaaatattttggaaacaggt<br>cttttaatgtggaaagatagatattaatctcctcttctatta<br>ctctccaagatccaacaaaagtgattataccccccaaaatat<br>gatggtagtatcttatactaccatcattttataggcataggg<br>ctcttagctgcaaataatggaactaactctaataaagcagaa<br>cgcaaatattgtaaatattagagagctaacaatctctgggat<br>ggctaaaggatggagcttggaggctacccagccagtaacaat<br>attccgggctccactgttgaatggagacactacaactgcctt<br>ggatgggcagagatattatggatgctaagccccaggtgctac<br>cattaggacttctaccactgtccctaacgggtggagcccatc<br>acatgcctatgccctcactgtaaggaaatgaagctactgttg<br>tatatcttgggaagcacttggattaattgttatacagttttg<br>ttgaagaagacccctagggtaagtagccataactgcacacta<br>aatttaaaattgttaatgagtttctcaaaaaaaatgttaagg<br>ttgttagctggtatagtatatatcttgcctgttttccaagga<br>cttctttgggcagtaccttgtctgtgctggcaagcaactgag<br>acttaatgaaagagtattggagatatgaatgaattgatgctg<br>tatactctcagagtgccaaacatataccaatggacaagaagg<br>tgaggcagagagcagacaggcattagtgacaagcaaagatat<br>gcagaatttcattctcagcaaatcaaaagtcctcaacctggt<br>tggaagaatattggcactgaatggtatcaataaggttgctag<br>agagggttagaggtgcacaatgtgcttccataacattttata<br>cttctccaatcttagcactaatcaaacatggttgaatacttt<br>gtttactataactcttacagagttataagatctgtgaagaca<br>gggacagggacaatacccatctctgtctggttcataggtggt<br>atgtaatagatatttttaaaaataagtgagttaatgaatgag<br>ggtgagaatgaaggcacagaggtattagggggaggtgggccc<br>cagagaatggtgccaaggtccagtggggtgactgggatcagc<br>tcaggcctgacgctggccactcccacctagctcctttctttc<br>taatctgttctcattctccttgggaaggattgaggtctctgg<br>aaaacagccaaacaactgttatgggaacagcaagcccaaata<br>aagccaagcatcaggggggatctgagagctgaaagcaacttct<br>gttcccccctccctcagctgaaggggtggggaagggctcccaa<br>agccataactccttttaagggatttagaaggcataaaaaggc<br>ccctggctgagaacttccttcttcattctgcagttggtgaat<br>tcgccaccatgtcagaaggggtgggcacgttccgcatggtac<br>ctgaagaggaacaggagctccgtgcccaactggagcagctca<br>caaccaaggaccatggacctgtctttggcccgtgcagccagc<br>tgccccgccacaccttgcagaaggccaaggatgagctgaacg<br>agagagaggagacccgggaggaggcagtgcgagagctgcagg<br>agatggtgcaggcgcaggcggcctcgggggaggagctggcgg<br>tggccgtggcggagagggtgcaagagaaggacagcggcttct<br>tcctgcgcttcatccgcgcacggaagttcaacgtgggccgtg<br>cctatgagctgctcagaggctatgtgaatttccggctgcagt<br>accctgagctctttgacagcctgtccccagaggctgtccgct<br>gcaccattgaagctggctaccctggtgtcctctctagtcggg<br>acaagtatggccgagtggtcatgctcttcaacattgagaact<br>ggcaaagtcaagaaatcacctttgatgagatcttgcaggcat<br>attgcttcatcctggagaagctgctggagaatgaggaaactc<br>aaatcaatggcttctgcatcattgagaacttcaagggcttta<br>ccatgcagcaggctgctagtctccggacttcagatctcagga<br>agatggtggacatgctccaggattccttcccagcccggttca<br>aagccatccacttcatccaccagccatggtacttcaccacga<br>cctacaatgtggtcaagcccttcttgaagagcaagctgcttg<br>agagggtctttgtccacggggatgacctttctggtttctacc<br>aggagatcgatgagaacatcctgccctctgacttcgggggca<br>cgctgcccaagtatgatggcaaggccgttgctgagcagctct<br>ttggcccccaggcccaagctgagaacacagccttctgaggat<br>ctaccggtcgacctgcagaagcttgcctcgagcagcgctgct<br>cgagagatctggatcataatcagccataccacatttgtagag<br>gttttacttgctttaaaaaacctcccacacctccccctgaac<br>ctgaaacataaaatgaatgcaattgttgttgttaacttgttt<br>attgcagcttataatggttacaaataaagcaatagcatcaca<br>aatttcacaaataaagcatttttttcactgcattctagttgt<br>ggtttgtccaaactcatcaatgtatcttatcatgtctggtaa<br>ccattctccaggttgagccagaccaatttgatggtagattta<br>gcaaataaaaatacaggacacccagttaaatgtgaatttccg |

TABLE 2-continued

Plasmid Composition

Plasmid Composition

| Elements | SEQUENCE IDENTIFIER (SEQ. ID. NO:)AND SEQUENCE INFORMATION |
|---|---|
| | atgaacagcaaatactttttttagtattaaaaaagttcacatt<br>taggctcacgcctgtaatcccagcactttgggaggccgaggc<br>aggcagatcacctgaggtcaggagttcgagaccagcctggcc<br>aacatggtgaaaccccatctccactaaaaataccaaaaatta<br>gccaggcgtgctggtgggcacctgtagttccagctactcagg<br>aggctaaggcaggagaattgcttgaacctgggaggcagaggt<br>tgcagtgagctgagatcgcaccattgcactctagcctgggcg<br>acaagaacaaaactccatctcaaaaaaaaaaaaaaaaaaaaa<br>gttcacatttaactgggcattctgtatttaattggtaatctg<br>agatggcagggaacagcatcagcatggtgtgagggataggca<br>tttttcattgtgtacagcttgtaaatcagtatttttaaaac<br>tcaaagttaatggcttgggcatatttagaaaagagttgccgc<br>acggacttgaaccctgtattcctaaaatctaggatcttgttc<br>tgatggtctgcacaactggctgggggtgtccagccactgtcc<br>ctcttgcctgggctccccagggcagttctgtcagcctctcca<br>tttccattcctgttccagcaaaacccaactgatagcacagca<br>gcatttcagcctgtctacctctgtgcccacatacctggatgt<br>ctaccagccagaaaggtggcttagatttggttcctgtgggtg<br>gattatggcccccagaacttccctgtgcttgctgggggtgtg<br>gagtggaaagagcaggaaatgggggaccctccgatactctat<br>gggggtcctccaagtctctttgtgcaagttagggtaataatc<br>aatatggagctaagaaagagaaggggaactatgctttagaac<br>aggacactgtgccaggagcattgcagaaattatatggttttc<br>acgacagttctttttggtaggtactgttattatcctcagttt<br>gcagatgaggaaactgagacccagaaaggttaaataacttgc<br>tagggtcacacaagtcataactgacaaagcctgattcaaacc<br>caggtctccctaacctttaaggtttctatgacgccagctctc<br>ctagggagtttgtcttcagatgtcttggctctaggtgtcaaa<br>aaaagacttggtgtcaggcaggcataggttcaagtcccaact<br>ctgtcacttaccaactgtgactaggtgattgaactgaccatg<br>gaacctggtcacatgcaggagcaggatggtgaagggttcttg<br>aaggcacttaggcaggacatttaggcaggagagaaaacctgg<br>aaacagaagagctgtctccaaaaatacccactggggaagcag<br>gttgtcatgtgggccatgaatgggacctgttctggggtaacc<br>acgtgcggaccgagcggccgcaggaacccctagtgatggagt<br>tggccactccctctctgcgcgctcgctcgctcactgaggccg<br>ggcgaccaaaggtcgcccgacgcccgggctttgcccgggcgg<br>cctcagtgagcgagcgagcgcgcag |

Plasmid TM039 Composition

| | |
|---|---|
| 5' ITR | 2<br>occurs at bp 1 through bp 119 of SEQ ID NO: 29 |
| CVM ENHANCER AND CBA PROMOTER GENBANK ACCESSION DD215332 FROM BP 1-BP 1616) | 22<br>occurs at bp 134 through bp 1749 of SEQ ID NO: 29 |
| Added Kozak | 5<br>occurs at bp 1763 through bp 1768 of SEQ ID NO: 29 |
| HUMAN RLBP1 GENE CDS | 6<br>occurs at bp 1769 through bp 2722 of SEQ ID NO: 29 |
| SV40 POLYA | 8<br>occurs at bp 2781 through bp 3016 of SEQ ID NO: 29 |
| REVERSE COMPLEMENT OF RLBP1 INTRONIC SEQUENCE AS STUFFER SEQUENCE (NT 010274.17) | 23<br>occurs at bp 3032 through bp 4534 of SEQ ID NO: 29 |
| 3' ITR | 9<br>occurs at bp 4573 through bp 4702 of SEQ ID NO: 29 |
| AMP BACTERIAL BACKBONE | 15<br>occurs at bp 4703 through bp 7321 of SEQ ID NO: 29 |

TABLE 2-continued

Plasmid Composition
Plasmid Composition

| Elements | SEQUENCE IDENTIFIER (SEQ. ID. NO:)AND SEQUENCE INFORMATION |
|---|---|
| PLASMID TM039 SEQUENCE | 29<br>ctgcgcgctcgctcgctcactgaggccgcccgggcgtcgggc<br>gacctttggtcgcccggcctcagtgagcgagcgagcgcgcag<br>agagggagtggccaactccatcactaggggttcctgcggccg<br>cacgcgtactagttattaatagtaatcaattacggggtcatt<br>agttcatagcccatatatggagttccgcgttacataacttac<br>ggtaaatggcccgcctggctgaccgcccaacgacccccgccc<br>attgacgtcaataatgacgtatgttcccatagtaacgccaat<br>agggactttccattgacgtcaatgggtggagtatttacggta<br>aactgcccacttggcagtacatcaagtgtatcatatgccaag<br>tacgccccctattgacgtcaatgacggtaaatggcccgcctg<br>gcattatgcccagtacatgaccttatgggactttcctacttg<br>gcagtacatctacgtattagtcatcgctattaccatggtcga<br>ggtgagccccacgttctgcttcactctccccatctcccccc<br>ctccccacccccaattttgtatttatttattttttaattatt<br>ttgtgcagcgatgggggcgggggggggggggggcgcgcgcc<br>aggcggggcggggcggggcgaggggcggggcggggcgaggcg<br>gagaggtgcggcggcagccaatcagagcggcgcgctccgaaa<br>gtttccttttatggcgaggcggcggcggcggcggccctataa<br>aaagcgaagcgcgcggcgggcggggagtcgctgcgacgctgc<br>cttcgccccgtgccccgctccgccgccgcctcgcgccgcccg<br>ccccggctctgactgaccgcgttactcccacaggtgagcggg<br>cgggacggcccttctcctccgggctgtaattagcgcttggtt<br>taatgacggcttgtttcttttctgtggctgcgtgaaagcctt<br>gaggggctccgggagggccctttgtgcggggggagcggctcg<br>gggggtgcgtgcgtgtgtgtgtgcgtggggagcgccgcgtgc<br>ggctccgcgctgcccggcggctgtgagcgctgcgggcgcggc<br>gcggggctttgtgcgctccgcagtgtgcgcgaggggagcgcg<br>gccgggggcggtgccccgcggtgcggggggggctgcgagggg<br>aacaaaggctgcgtgcggggtgtgtgcgtgggggggtgagca<br>gggggtgtgggcgcgtcggtcgggctgcaaccccccctgcac<br>ccccctccccgagttgctgagcacggcccggcttcgggtgcg<br>gggctccgtacggggcgtggcgcggggctcgccgtgccgggc<br>ggggggtggcggcaggtgggggtgccgggcggggcggggccg<br>cctcgggccggggagggctcgggggaggggcgcggcggcccc<br>cggagcgccggcggctgtcgaggcgcggcgagccgcagccat<br>tgccttttatggtaatcgtgcgagagggcgcagggacttcct<br>ttgtcccaaatctgtgcggagccgaaatctgggaggcgccgc<br>cgcaccccctctagcgggcgcggggcgaagcggtgcggcgcc<br>ggcaggaaggaaatgggcggggagggccttcgtgcgtcgccg<br>cgccgccgtccccttctccctctccagcctcggggctgtccg<br>cggggggacggctgccttcgggggggacggggcagggcgggg<br>ttcggcttctggcgtgtgaccggcggcatcgattgaattcgc<br>caccatgtcagaaggggtgggcacgttccgcatggtacctga<br>agaggaacaggagctccgtgcccaactggagcagctcacaac<br>caaggaccatggacctgtctttggcccgtgcagccagctgcc<br>ccgccacaccttgcagaaggccaaggatgagctgaacgagag<br>agaggagacccgggaggaggcagtgcgagagctgcaggagat<br>ggtgcaggcgcaggcggcctcgggggaggagctggcggtggc<br>cgtggcggagagggtgcaagagaaggacagcggcttcttcct<br>gcgcttcatccgcgcacggaagttcaacgtgggccgtgccta<br>tgagctgctcagaggctatgtgaatttccggctgcagtaccc<br>tgagctctttgacagcctgtccccagaggctgtccgctgcac<br>cattgaagctggctaccctggtgtcctctctagtcgggacaa<br>gtatggccgagtggtcatgctcttcaacattgagaactggca<br>aagtcaagaaatcacctttgatgagatcttgcaggcatattg<br>cttcatcctggagaagctgctggagaatgaggaaactcaaat<br>caatggcttctgcatcattgagaacttcaagggctttaccat<br>gcagcaggctgctagtctccggacttcagatctcaggaagat<br>ggtggacatgctccaggattccttcccagcccggttcaaagc<br>catccacttcatccaccagccatggtacttcaccacgaccta<br>caatgtggtcaagcccttcttgaagagcaagctgcttgagag<br>ggtctttgtccacggggatgacctttctggtttctaccagga<br>gatcgatgagaacatcctgccctctgacttcgggggcacgct<br>gcccaagtatgatggcaaggccgttgctgagcagctctttgg<br>cccccaggcccaagctgagaacacagccttctgaggatcgta<br>ccggtcgacctgcagaagcttgcctcgagcagcgctgctcga<br>gagatctggatcataatcagccataccacatttgtagaggtt<br>ttacttgctttaaaaaacctcccacacctccccctgaacctg<br>aaacataaaatgaatgcaattgttgttgttaacttgtttatt<br>gcagcttataatggttacaaataaagcaatagcatcacaaat<br>ttcacaaataaagcatttttttcactgcattctagttgtggt<br>ttgtccaaactcatcaatgtatcttatcatgtctggtactag<br>ggttaccccagaacaggtcccattcatggcccacatgacaac |

TABLE 2-continued

| Plasmid Composition | |
|---|---|
| Plasmid Composition | |
| Elements | SEQUENCE IDENTIFIER (SEQ. ID. NO:)AND SEQUENCE INFORMATION |
| | ctgcttccccagtgggtatttttggagacagctcttctgttt<br>ccaggttttctctcctgcctaaatgtcctgcctaagtgcctt<br>caagaacccttcaccatcctgctcctgcatgtgaccaggttc<br>catggtcagttcaatcacctagtcacagttggtaagtgacag<br>agttgggacttgaacctatgcctgcctgacaccaagtctttt<br>tttgacacctagagccaagacatctgaagacaaactccctag<br>gagagctggcgtcatagaaaccttaaaggttagggagacctg<br>ggtttgaatcaggctttgtcagttatgacttgtgtgacccta<br>gcaagttatttaacctttctgggtctcagtttcctcatctgc<br>aaactgaggataataacagtacctaccaaaaagaactgtcgt<br>gaaaaccatataatttctgcaatgctcctggcacagtgtcct<br>gttctaaagcatagttcccttctctttcttagctccatatt<br>gattattaccctaacttgcacaaagagacttggaggaccccc<br>atagagtatcggagggtcccccatttcctgctctttccactc<br>cacacccccagcaagcacagggaagttctgggggccataatc<br>cacccacaggaaccaaatctaagccacctttctggctggtag<br>acatccaggtatgtgggcacagaggtagacaggctgaaatgc<br>tgctgtgctatcagttgggttttgctggaacaggaatggaaa<br>tggagaggctgacagaactgccctggggagcccaggcaagag<br>ggacagtggctggacacccccagccagttgtgcagaccatca<br>gaacaagatcctagattttaggaatacagggttcaagtccgt<br>gcggcaactcttttctaaatatgcccaagccattaactttga<br>gttttaaaaatactgatttacaagctgtacacaatgaaaaaa<br>tgcctatccctcacaccatgctgatgctgttccctgccatct<br>cagattaccaattaaatacagaatgcccagttaaatgtgaac<br>tttttttttttttttttttgagatggagttttgttcttgt<br>cgcccaggctagagtgcaatggtgcgatctcagctcactgca<br>acctctgcctcccaggttcaagcaattctcctgccttagcct<br>cctgagtagctggaactacaggtgcccaccagcacgcctggc<br>taatttttggtatttttagtggagatggggtttcaccatgtt<br>ggccaggctggtctcgaactcctgacctcaggtgatctgcct<br>gcctcggcctcccaaagtgctgggattacaggcgtgagccta<br>aatgtgaactttttttaatactaaaaaagtatttgctgttcat<br>cggaaattcacatttaactgggtgtcctgtatttttatttgc<br>taaatctaccatcaaattggtctggctcaacctggagaatgg<br>ttaccctaggtaaccacgtgcggaccgagcggccgcaggaac<br>ccctagtgatggagttggccactccctctctgcgcgctcgct<br>cgctcactgaggccgggcgaccaaaggtcgcccgacgcccgg<br>gctttgcccgggcggcctcagtgagcgagcgagcgcgcagct<br>gcctgcaggggcgcctgatgcggtattttctccttacgcatc<br>tgtgcggtatttcacaccgcatacgtcaaagcaaccatagta<br>cgcgccctgtagcggcgcattaagcgcggcgggtgtggtggt<br>tacgcgcagcgtgaccgctacacttgccagcgccttagcgcc<br>cgctcctttcgctttcttcccttcctttctcgccacgttcgc<br>cggctttccccgtcaagctctaaatcgggggctccctttagg<br>gttccgatttagtgctttacggcacctcgaccccaaaaaact<br>tgatttgggtgatggttcacgtagtgggccatcgccctgata<br>gacggtttttcgccctttgacgttggagtccacgttctttaa<br>tagtggactcttgttccaaactggaacaacactcaactctat<br>ctcgggctattcttttgatttataagggattttgccgatttc<br>ggtctattggttaaaaaatgagctgatttaacaaaaatttaa<br>cgcgaattttaacaaaatattaacgtttacaattttatggtg<br>cactctcagtacaatctgctctgatgccgcatagttaagcca<br>gccccgacacccgccaacacccgctgacgcgccctgacgggc<br>ttgtctgctcccggcatccgcttacagacaagctgtgaccgt<br>ctccgggagctgcatgtgtcagaggttttcaccgtcatcacc<br>gaaacgcgcgagacgaaagggcctcgtgatacgcctattttt<br>ataggttaatgtcatgataataatggtttcttagacgtcagg<br>tggcacttttcggggaaatgtgcgcggaacccctatttgttt<br>atttttctaaatacattcaaatatgtatccgctcatgagaca<br>ataaccctgataaatgcttcaataatattgaaaaaggaagag<br>tatgagtattcaacatttccgtgtcgcccttattcccttttt<br>tgcggcattttgccttcctgtttttgctcacccagaaacgct<br>ggtgaaagtaaaagatgctgaagatcagttgggtgcacgagt<br>gggttacatcgaactggatctcaacagcggtaagatccttga<br>gagttttcgccccgaagaacgttttccaatgatgagcacttt<br>taaagttctgctatgtggcgcggtattatcccgtattgacgc<br>cgggcaagagcaactcggtcgccgcatacactattctcagaa<br>tgacttggttgagtactcaccagtcacagaaaagcatcttac<br>ggatggcatgacagtaagagaattatgcagtgctgccataac<br>catgagtgataacactgcggccaacttacttctgacaacgat<br>cggaggaccgaaggagctaaccgcttttttgcacaacatggg<br>ggatcatgtaactcgccttgatcgttgggaaccggagctgaa<br>tgaagccataccaaacgacgagcgtgacaccacgatgcctgt |

TABLE 2-continued

Plasmid Composition
Plasmid Composition

| Elements | SEQUENCE IDENTIFIER (SEQ. ID. NO:) AND SEQUENCE INFORMATION |
|---|---|
| | agcaatggcaacaacgttgcgcaaactattaactggcgaact acttactctagcttcccggcaacaattaatagactggatgga ggcggataaagttgcaggaccacttctgcgctcggcccttcc ggctggctggtttattgctgataaatctggagccggtgagcg tgggtctcgcggtatcattgcagcactggggccagatggtaa gccctcccgtatcgtagttatctacacgacggggagtcaggc aactatggatgaacgaaatagacagatcgctgagataggtgc ctcactgattaagcattggtaactgtcagaccaagtttactc atatatactttagattgatttaaaacttcatttttaatttaa aaggatctaggtgaagatcctttttgataatctcatgaccaa aatcccttaacgtgagttttcgttccactgagcgtcagaccc cgtagaaaagatcaaaggatcttcttgaaatcctttttttct gcgcgtaatctgctgcttgcaaacaaaaaaaccaccgctacc agcggtggtttgtttgccggatcaagagctaccaactctttt tccgaaggtaactggcttcagcagagcgcagataccaaatac tgttcttctagtgtagccgtagttaggccaccacttcaagaa ctctgtagcaccgcctacatacctcgctctgctaatcctgtt accagtggctgctgccagtggcgataagtcgtgtcttaccgg gttggactcaagacgatagttaccggataaggcgcagcggtc gggctgaacggggggttcgtgcacacagcccagcttggagcg aacgacctacaccgaactgagatacctacagcgtgagctatg agaaagcgccacgcttcccgaagggagaaaggcggacaggta tccggtaagcggcagggtcggaacaggagagcgcacgaggga gcttccagggggaaacgcctggtatctttatagtcctgtcgg gtttcgccacctctgacttgagcgtcgatttttgtgatgctc gtcaggggggcggagcctatggaaaaacgccagcaacgcggc ctttttacggttcctggccttttgctggccttttgctcacat gtcctgcaggcag |
| GENE CASSETTE OF PLASMID TM039 OCCURS AT BP 1 THROUGH 4702 OF SEQ ID NO: 29 | 54 ctgcgcgctcgctcgctcactgaggccgcccgggcgtcgggc gacctttggtcgcccggcctcagtgagcgagcgagcgcgcag agagggagtggccaactccatcactaggggttcctgcggccg cacgcgtactagttattaatagtaatcaattacggggtcatt agttcatagcccatatatggagttccgcgttacataacttac ggtaaatggcccgcctggctgaccgcccaacgacccccgccc attgacgtcaataatgacgtatgttcccatagtaacgccaat agggactttccattgacgtcaatgggtggagtatttacggta aactgcccacttggcagtacatcaagtgtatcatatgccaag tacgccccctattgacgtcaatgacggtaaatggcccgcctg gcattatgcccagtacatgaccttatgggactttcctacttg gcagtacatctacgtattagtcatcgctattaccatggtcga ggtgagccccacgttctgcttcactctccccatctcccccc ctccccacccccaattttgtatttatttattttttaattatt ttgtgcagcgatgggggcgggggggggggggggcgcgcgcc aggcggggcggggcggggcgaggggcggggcggggcgaggcg gagaggtgcggcggcagccaatcagagcggcgcgctccgaaa gtttccttttatggcgaggcggcggcggcggcggccctataa aaagcgaagcgcgcggcgggcggggagtcgctgcgacgctgc cttcgccccgtgccccgctccgccgccgcctcgcgccgcccg ccccggctctgactgaccgcgttactcccacaggtgagcggg cgggacggcccttctcctccgggctgtaattagcgcttggtt taatgacggcttgtttcttttctgtggctgcgtgaaagcctt gaggggctccgggagggccctttgtgcggggggagcggctcg gggggtgcgtgcgtgtgtgtgtgcgtggggagcgccgcgtgc ggctccgcgctgcccggcggctgtgagcgctgcgggcgcggc gcggggctttgtgcgctccgcagtgtgcgcgaggggagcgcg gccgggggcggtgccccgcggtgcgggggggggctgcgagggg aacaaaggctgcgtgcggggtgtgtgcgtgggggggtgagca gggggtgtgggcgcgtcggtcgggctgcaacccccccctgcac ccccctccccgagttgctgagcacggcccggcttcgggtgcg gggctccgtacggggcgtggcgcggggctcgccgtgccgggc ggggggtggcggcaggtgggggtgccgggcggggcggggccg cctcgggccggggagggctcgggggaggggcgcggcggcccc cggagcgccggcggctgtcgaggcgcggcgagccgcagccat tgccttttatggtaatcgtgcgagagggcgcagggacttcct ttgtcccaaatctgtgcggagccgaaatctgggaggcgccgc cgcaccccctctagcgggcgcggggcgaagcggtgcggcgcc ggcaggaaggaaatgggcggggagggccttcgtgcgtcgccg cgccgccgtccccttctccctctccagcctcggggctgtccg cggggggacggctgccttcgggggggacggggcagggcgggg ttcggcttctggcgtgtgaccggcggcatcgattgaattcgc caccatgtcagaaggggtgggcacgttccgcatggtacctga agaggaacaggagctccgtgcccaactggagcagctcacaac caaggaccatggacctgtctttggcccgtgcagccagctgcc |

TABLE 2-continued

Plasmid Composition
Plasmid Composition

| Elements | SEQUENCE IDENTIFIER (SEQ. ID. NO:) AND SEQUENCE INFORMATION |
|---|---|
| | ccgccacaccttgcagaaggccaaggatgagctgaacgagag<br>agaggagacccgggaggaggcagtgcgagagctgcaggagat<br>ggtgcaggcgcaggcggcctcgggggaggagctggcggtggc<br>cgtggcggagagggtgcaagagaaggacagcggcttcttcct<br>gcgcttcatccgcgcacggaagttcaacgtgggccgtgccta<br>tgagctgctcagaggctatgtgaatttccggctgcagtaccc<br>tgagctctttgacagcctgtccccagaggctgtccgctgcac<br>cattgaagctggctaccctggtgtcctctctagtcgggacaa<br>gtatggccgagtggtcatgctcttcaacattgagaactggca<br>aagtcaagaaatcacctttgatgagatcttgcaggcatattg<br>cttcatcctggagaagctgctggagaatgaggaaactcaaat<br>caatggcttctgcatcattgagaacttcaagggctttaccat<br>gcagcaggctgctagtctccggacttcagatctcaggaagat<br>ggtggacatgctccaggattccttcccagcccggttcaaagc<br>catccacttcatccaccagccatggtacttcaccacgaccta<br>caatgtggtcaagcccttcttgaagagcaagctgcttgagag<br>ggtctttgtccacggggatgacctttctggtttctaccagga<br>gatcgatgagaacatcctgccctctgacttcgggggcacgct<br>gcccaagtatgatggcaaggccgttgctgagcagctctttgg<br>cccccaggcccaagctgagaacacagccttctgaggatcgta<br>ccggtcgacctgcagaagcttgcctcgagcagcgctgctcga<br>gagatctggatcataatcagccataccacatttgtagaggtt<br>ttacttgctttaaaaaacctcccacacctccccctgaacctg<br>aaacataaaatgaatgcaattgttgttgttaacttgtttatt<br>gcagcttataatggttacaaataaagcaatagcatcacaaat<br>ttcacaaataaagcatttttttcactgcattctagttgtggt<br>ttgtccaaactcatcaatgtatcttatcatgtctggtactag<br>ggttaccccagaacaggtcccattcatggcccacatgacaac<br>ctgcttccccagtgggtatttttggagacagctcttctgttt<br>ccaggttttctctcctgcctaaatgtcctgcctaagtgcctt<br>caagaacccttcaccatcctgctcctgcatgtgaccaggttc<br>catggtcagttcaatcacctagtcacagttggtaagtgacag<br>agttgggacttgaacctatgcctgcctgacaccaagtctttt<br>tttgacacctagagccaagacatctgaagacaaactccctag<br>gagagctggcgtcatagaaaccttaaaggttagggagacctg<br>ggtttgaatcaggctttgtcagttatgacttgtgtgacccta<br>gcaagttatttaacctttctgggtctcagtttcctcatctgc<br>aaactgaggataataacagtacctaccaaaaagaactgtcgt<br>gaaaaccatataatttctgcaatgctcctggcacagtgtcct<br>gttctaaagcatagttccccttctctttcttagctccatatt<br>gattattaccctaacttgcacaaagagacttggaggaccccc<br>atagagtatcggagggtcccccatttcctgctctttccactc<br>cacacccccagcaagcacagggaagttctgggggccataatc<br>cacccacaggaaccaaatctaagccacctttctggctggtag<br>acatccaggtatgtgggcacagaggtagacaggctgaaatgc<br>tgctgtgctatcagttgggttttgctggaacaggaatggaaa<br>tggagaggctgacagaactgccctggggagcccaggcaagag<br>ggacagtggctggacacccccagccagttgtgcagaccatca<br>gaacaagatcctagattttaggaatacagggttcaagtccgt<br>gcggcaactcttttctaaatatgcccaagccattaactttga<br>gttttaaaaatactgatttacaagctgtacacaatgaaaaaa<br>tgcctatccctcacaccatgctgatgctgttccctgccatct<br>cagattaccaattaaatacagaatgcccagttaaatgtgaac<br>tttttttttttttttttttttgagatggagttttgttcttgt<br>cgcccaggctagagtgcaatggtgcgatctcagctcactgca<br>acctctgcctcccaggttcaagcaattctcctgccttagcct<br>cctgagtagctggaactacaggtgcccaccagcacgcctggc<br>taatttttggtatttttagtggagatggggtttcaccatgtt<br>ggccaggctggtctcgaactcctgacctcaggtgatctgcct<br>gcctcggcctcccaaagtgctgggattacaggcgtgagccta<br>aatgtgaactttttttaatactaaaaaagtatttgctgttcat<br>cggaaattcacatttaactgggtgtcctgtatttttatttgc<br>taaatctaccatcaaattggtctggctcaacctggagaatgg<br>ttaccctaggtaaccacgtgcggaccgagcggccgcaggaac<br>ccctagtgatggagttggccactccctctctgcgcgctcgct<br>cgctcactgaggccgggcgaccaaaggtcgcccgacgcccgg<br>gctttgcccgggcggcctcagtgagcgagcgagcgcgcag |

TABLE 2-continued

| Plasmid Composition | |
|---|---|
| Plasmid Composition | |
| Elements | SEQUENCE IDENTIFIER (SEQ. ID. NO:) AND SEQUENCE INFORMATION |
| Plasmid TM040 Composition | |
| 5' ITR | 2<br>occurs at bp 1 through bp 119 of SEQ ID NO: 30 |
| Human RLBP1 Promoter(short) | 3<br>occurs at bp 134 through bp 723 of SEQ ID NO: 30 |
| Modified SV40 intron | 4<br>occurs at bp 738 through bp 920 of SEQ ID NO: 30 |
| Added Kozak | 5<br>occurs at bp 934 through bp 939 of SEQ ID NO: 30 |
| HUMAN RLBP1 GENE CDS | 6<br>occurs at bp 940 through bp 1893 of SEQ ID NO: 30 |
| SV40 POLYA | 8<br>occurs at bp 1952 through bp 2187 of SEQ ID NO: 30 |
| REVERSE COMPLEMENT OF RLBP1 INTRONIC SEQUENCE AS STUFFER SEQUENCE (NT 010274.17) | 23<br>occurs at bp 2203 through bp 3705 of SEQ ID NO: 30 |
| 3' ITR | 9<br>occurs at bp 3744 through bp 3873 of SEQ ID NO: 30 |
| AMP BACTERIAL BACKBONE | 15<br>occurs at bp 3874 through bp 6492 of SEQ ID NO: 30 |
| TM040 plasmid sequence | 30<br>ctgcgcgctcgctcgctcactgaggccgcccgggcgtcgggc<br>gacctttggtcgcccggcctcagtgagcgagcgagcgcgcag<br>agagggagtggccaactccatcactaggggttcctgcggccg<br>cacgcgtttgtcctctccctgcttggccttaaccagccacat<br>ttctcaactgaccccactcactgcagaggtgaaaactaccat<br>gccaggtcctgctggctgggggaggggtgggcaataggcctg<br>gatttgccagagctgccactgtagatgtagtcatatttacga<br>tttcccttcacctcttattaccctggtggtggtggtgggggg<br>ggggggtgctctctcagcaaccccaccccgggatcttgagg<br>agaaagagggcagagaaaagagggaatgggactggcccagat<br>cccagccccacagccgggcttccacatggccgagcaggaact<br>ccagagcaggagcacacaaaggagggctttgatgcgcctcca<br>gccaggcccaggcctctcccctctcccctttctctctgggtc<br>ttcctttgccccactgagggcctcctgtgagcccgatttaac<br>ggaaactgtgggcggtgagaagttccttatgacacactaatc<br>ccaacctgctgaccggaccacgcctccagcggagggaacctc<br>tagagctccaggacattcaggtaccaggtagccccaaggagg<br>agctgccgaatcgatggatcgggaactgaaaaaccagaaagt<br>taactggtaagtttagtctttttgtcttttatttcaggtccc<br>ggatccggtggtggtgcaaatcaaagaactgctcctcagtgg<br>atgttgcctttacttctaggcctgtacggaagtgttacttct<br>gctctaaaagctgcggaattgtacccgccccgggatccatcg<br>attgaattcgccaccatgtcagaaggggtgggcacgttccgc<br>atggtacctgaagaggaacaggagctccgtgcccaactggag<br>cagctcacaaccaaggaccatggacctgtctttggcccgtgc<br>agccagctgccccgccacaccttgcagaaggccaaggatgag<br>ctgaacgagagagaggagacccgggaggaggcagtgcgagag<br>ctgcaggagatggtgcaggcgcaggcggcctcgggggaggag<br>ctggcggtggccgtggcggagagggtgcaagagaaggacagc<br>ggcttcttcctgcgcttcatccgcgcacggaagttcaacgtg<br>ggccgtgcctatgagctgctcagaggctatgtgaatttccgg<br>ctgcagtaccctgagctctttgacagcctgtccccagaggct<br>gtccgctgcaccattgaagctggctaccctggtgtcctctct<br>agtcgggacaagtatggccgagtggtcatgctcttcaacatt<br>gagaactggcaaagtcaagaaatcacctttgatgagatcttg<br>caggcatattgcttcatcctggagaagctgctggagaatgag<br>gaaactcaaatcaatggcttctgcatcattgagaacttcaag<br>ggcttcaccatgcagcaggctgctagtctccggacttcagat<br>ctcaggaagatggtggacatgctccaggattccttcccagcc |

TABLE 2-continued

Plasmid Composition
Plasmid Composition

| Elements | SEQUENCE IDENTIFIER (SEQ. ID. NO:)AND SEQUENCE INFORMATION |
| --- | --- |
| | cggttcaaagccatccacttcatccaccagccatggtacttc |
| | accacgacctacaatgtggtcaagcccttcttgaagagcaag |
| | ctgcttgagagggtctttgtccacggggatgacctttctggt |
| | ttctaccaggagatcgatgagaacatcctgccctctgacttc |
| | gggggcacgctgcccaagtatgatggcaaggccgttgctgag |
| | cagctctttggcccccaggcccaagctgagaacacagccttc |
| | tgaggatcgtaccggtcgacctgcagaagcttgcctcgagca |
| | gcgctgctcgagagatctggatcataatcagccataccacat |
| | ttgtagaggttttacttgctttaaaaaacctcccacacctcc |
| | ccctgaacctgaaacataaaatgaatgcaattgttgttgtta |
| | acttgtttattgcagcttataatggttacaaataaagcaata |
| | gcatcacaaatttcacaaataaagcatttttttcactgcatt |
| | ctagttgtggtttgtccaaactcatcaatgtatcttatcatg |
| | tctggtactagggttaccccagaacaggtcccattcatggcc |
| | cacatgacaacctgcttccccagtgggtattttttggagacag |
| | ctcttctgtttccaggttttctctcctgcctaaatgtcctgc |
| | ctaagtgccttcaagaacccttcaccatcctgctcctgcatg |
| | tgaccaggttccatggtcagttcaatcacctagtcacagttg |
| | gtaagtgacagagttgggacttgaacctatgcctgcctgaca |
| | ccaagtctttttttgacacctagagccaagacatctgaagac |
| | aaactccctaggagagctggcgtcatagaaaccttaaaggtt |
| | agggagacctgggtttgaatcaggctttgtcagttatgactt |
| | gtgtgaccctagcaagttatttaacctttctgggtctcagtt |
| | tcctcatctgcaaactgaggataataacagtacctaccaaaa |
| | agaactgtcgtgaaaaccatataatttctgcaatgctcctgg |
| | cacagtgtcctgttctaaagcatagttccccttctctttctt |
| | agctccatattgattattaccctaacttgcacaaagagactt |
| | ggaggacccccatagagtatcggagggtcccccatttcctgc |
| | tctttccactccacacccccagcaagcacagggaagttctgg |
| | gggccataatccacccacaggaaccaaatctaagccaccttt |
| | ctggctggtagacatccaggtatgtgggcacagaggtagaca |
| | ggctgaaatgctgctgtgctatcagttgggttttgctggaac |
| | aggaatggaaatggagaggctgacagaactgccctggggagc |
| | ccaggcaagagggacagtggctggacacccccagccagttgt |
| | gcagaccatcagaacaagatcctagattttaggaatacaggg |
| | ttcaagtccgtgcggcaactcttttctaaatatgcccaagcc |
| | attaactttgagttttaaaaatactgatttacaagctgtaca |
| | caatgaaaaaatgcctatccctcacaccatgctgatgctgtt |
| | ccctgccatctcagattaccaattaaatacagaatgcccagt |
| | taaatgtgaacttttttttttttttttttttgagatggagt |
| | tttgttcttgtcgcccaggctagagtgcaatggtgcgatctc |
| | agctcactgcaacctctgcctcccaggttcaagcaattctcc |
| | tgccttagcctcctgagtagctggaactacaggtgcccacca |
| | gcacgcctggctaattttttggtatttttagtggagatggggt |
| | ttcaccatgttggccaggctggtctcgaactcctgacctcag |
| | gtgatctgcctgcctcggcctcccaaagtgctgggattacag |
| | gcgtgagcctaaatgtgaactttttttaatactaaaaaagtat |
| | ttgctgttcatcggaaattcacatttaactgggtgtcctgta |
| | tttttatttgctaaatctaccatcaaattggtctggctcaac |
| | ctggagaatggttaccctaggtaaccacgtgcggaccgagcg |
| | gccgcaggaacccctagtgatggagttggccactccctctct |
| | gcgcgctcgctcgctcactgaggccgggcgaccaaaggtcgc |
| | ccgacgcccgggctttgcccgggcggcctcagtgagcgagcg |
| | agcgcgcagctgcctgcaggggcgcctgatgcggtattttct |
| | ccttacgcatctgtgcggtatttcacaccgcatacgtcaaag |
| | caaccatagtacgcgccctgtagcggcgcattaagcgcggcg |
| | ggtgtggtggttacgcgcagcgtgaccgctacacttgccagc |
| | gccttagcgcccgctcctttcgctttcttcccttcctttctc |
| | gccacgttcgccggctttccccgtcaagctctaaatcggggg |
| | ctccctttagggttccgatttagtgctttacggcacctcgac |
| | cccaaaaaacttgatttgggtgatggttcacgtagtgggcca |
| | tcgccctgatagacggtttttcgccctttgacgttggagtcc |
| | acgttctttaatagtggactcttgttccaaactggaacaaca |
| | ctcaactctatctcgggctattcttttgatttataagggatt |
| | ttgccgatttcggtctattggttaaaaaatgagctgatttaa |
| | caaaaatttaacgcgaattttaacaaaatattaacgtttaca |
| | attttatggtgcactctcagtacaatctgctctgatgccgca |
| | tagttaagccagccccgacacccgccaacacccgctgacgcg |
| | ccctgacgggcttgtctgctcccggcatccgcttacagacaa |
| | gctgtgaccgtctccgggagctgcatgtgtcagaggttttca |
| | ccgtcatcaccgaaacgcgcgagacgaaagggcctcgtgata |
| | cgcctatttttataggttaatgtcatgataataatggtttct |
| | tagacgtcaggtggcacttttcggggaaatgtgcgcggaacc |
| | cctatttgtttatttttctaaatacattcaaatatgtatccg |

TABLE 2-continued

Plasmid Composition
Plasmid Composition

| Elements | SEQUENCE IDENTIFIER (SEQ. ID. NO:)AND SEQUENCE INFORMATION |
|---|---|
| | ctcatgagacaataaccctgataaatgcttcaataatattga<br>aaaaggaagagtatgagtattcaacatttccgtgtcgccctt<br>attcccttttttgcggcattttgccttcctgtttttgctcac<br>ccagaaacgctggtgaaagtaaaagatgctgaagatcagttg<br>ggtgcacgagtgggttacatcgaactggatctcaacagcggt<br>aagatccttgagagttttcgccccgaagaacgttttccaatg<br>atgagcacttttaaagttctgctatgtggcgcggtattatcc<br>cgtattgacgccgggcaagagcaactcggtcgccgcatacac<br>tattctcagaatgacttggttgagtactcaccagtcacagaa<br>aagcatcttacggatggcatgacagtaagagaattatgcagt<br>gctgccataaccatgagtgataacactgcggccaacttactt<br>ctgacaacgatcggaggaccgaaggagctaaccgcttttttg<br>cacaacatgggggatcatgtaactcgccttgatcgttgggaa<br>ccggagctgaatgaagccataccaaacgacgagcgtgacacc<br>acgatgcctgtagcaatggcaacaacgttgcgcaaactatta<br>actggcgaactacttactctagcttcccggcaacaattaata<br>gactggatggaggcggataaagttgcaggaccacttctgcgc<br>tcggcccttccggctggctggtttattgctgataaatctgga<br>gccggtgagcgtgggtctcgcggtatcattgcagcactgggg<br>ccagatggtaagccctcccgtatcgtagttatctacacgacg<br>gggagtcaggcaactatggatgaacgaaatagacagatcgct<br>gagataggtgcctcactgattaagcattggtaactgtcagac<br>caagtttactcatatatactttagattgatttaaaacttcat<br>ttttaatttaaaaggatctaggtgaagatcctttttgataat<br>ctcatgaccaaaatcccttaacgtgagttttcgttccactga<br>gcgtcagaccccgtagaaaagatcaaaggatcttcttgaaat<br>cctttttttctgcgcgtaatctgctgcttgcaaacaaaaaaa<br>ccaccgctaccagcggtggtttgtttgccggatcaagagcta<br>ccaactctttttccgaaggtaactggcttcagcagagcgcag<br>ataccaaatactgttcttctagtgtagccgtagttaggccac<br>cacttcaagaactctgtagcaccgcctacatacctcgctctg<br>ctaatcctgttaccagtggctgctgccagtggcgataagtcg<br>tgtcttaccgggttggactcaagacgatagttaccggataag<br>gcgcagcggtcgggctgaacggggggttcgtgcacacagccc<br>agcttggagcgaacgacctacaccgaactgagatacctacag<br>cgtgagctatgagaaagcgccacgcttcccgaagggagaaag<br>gcggacaggtatccggtaagcggcagggtcggaacaggagag<br>cgcacgagggagcttccagggggaaacgcctggtatctttat<br>agtcctgtcgggtttcgccacctctgacttgagcgtcgattt<br>ttgtgatgctcgtcaggggggcggagcctatggaaaaacgcc<br>agcaacgcggcctttttacggttcctggccttttgctggcct<br>tttgctcacatgtcctgcaggcag |
| GENE CASSETTE OF PLASMID TM040 OCCURS AT BP 1 THROUGH 3873 OF SEQ ID NO: 30 | 55<br>ctgcgcgctcgctcgctcactgaggccgcccgggcgtcgggc<br>gacctttggtcgcccggcctcagtgagcgagcgagcgcgcag<br>agagggagtggccaactccatcactaggggttcctgcggccg<br>cacgcgtttgtcctctccctgcttggccttaaccagccacat<br>ttctcaactgaccccactcactgcagaggtgaaaactaccat<br>gccaggtcctgctggctgggggaggggtgggcaataggcctg<br>gatttgccagagctgccactgtagatgtagtcatatttacga<br>tttcccttcacctcttattaccctggtggtggtggtgggggg<br>gggggggtgctctctcagcaaccccaccccgggatcttgagg<br>agaaagagggcagagaaaagagggaatgggactggcccagat<br>cccagccccacagccgggcttccacatggccgagcaggaact<br>ccagagcaggagcacacaaaggagggctttgatgcgcctcca<br>gccaggcccaggcctctcccctctcccctttctctctgggtc<br>ttcctttgccccactgagggcctcctgtgagcccgatttaac<br>ggaaactgtgggcggtgagaagttccttatgacacactaatc<br>ccaacctgctgaccggaccacgcctccagcggagggaacctc<br>tagagctccaggacattcaggtaccaggtagccccaaggagg<br>agctgccgaatcgatggatcgggaactgaaaaaccagaaagt<br>taactggtaagtttagtctttttgtcttttatttcaggtccc<br>ggatccggtggtggtgcaaatcaaagaactgctcctcagtgg<br>atgttgcctttacttctaggcctgtacggaagtgttacttct<br>gctctaaaagctgcggaattgtacccgccccgggatccatcg<br>attgaattcgccaccatgtcagaaggggtgggcacgttccgc<br>atggtacctgaagaggaacaggagctccgtgcccaactggag<br>cagctcacaaccaaggaccatggacctgtctttggcccgtgc<br>agccagctgccccgccacaccttgcagaaggccaaggatgag<br>ctgaacgagagagaggagacccgggaggaggcagtgcgagag<br>ctgcaggagatggtgcaggcgcaggcggcctcgggggaggag<br>ctggcggtggccgtggcggagagggtgcaagagaaggacagc<br>ggcttcttcctgcgcttcatccgcgcacggaagttcaacgtg<br>ggccgtgcctatgagctgctcagaggctatgtgaatttccgg |

TABLE 2-continued

Plasmid Composition
Plasmid Composition

| Elements | SEQUENCE IDENTIFIER (SEQ. ID. NO:)AND SEQUENCE INFORMATION |
|---|---|
| | ctgcagtaccctgagctctttgacagcctgtccccagaggct |
| | gtccgctgcaccattgaagctggctaccctggtgtcctctct |
| | agtcgggacaagtatggccgagtggtcatgctcttcaacatt |
| | gagaactggcaaagtcaagaaatcacctttgatgagatcttg |
| | caggcatattgcttcatcctggagaagctgctggagaatgag |
| | gaaactcaaatcaatggcttctgcatcattgagaacttcaag |
| | ggctttaccatgcagcaggctgctagtctccggacttcagat |
| | ctcaggaagatggtggacatgctccaggattccttcccagcc |
| | cggttcaaagccatccacttcatccaccagccatggtacttc |
| | accacgacctacaatgtggtcaagcccttcttgaagagcaag |
| | ctgcttgagagggtctttgtccacggggatgacctttctggt |
| | ttctaccaggagatcgatgagaacatcctgccctctgacttc |
| | gggggcacgctgcccaagtatgatggcaaggccgttgctgag |
| | cagctctttggcccccaggcccaagctgagaacacagccttc |
| | tgaggatcgtaccggtcgacctgcagaagcttgcctcgagca |
| | gcgctgctcgagagatctggatcataatcagccataccacat |
| | ttgtagaggttttacttgctttaaaaaacctcccacacctcc |
| | ccctgaacctgaaacataaaatgaatgcaattgttgttgtta |
| | acttgtttattgcagcttataatggttacaaataaagcaata |
| | gcatcacaaatttcacaaataaagcatttttttcactgcatt |
| | ctagttgtggtttgtccaaactcatcaatgtatcttatcatg |
| | tctggtactagggttaccccagaacaggtcccattcatggcc |
| | cacatgacaacctgcttccccagtgggtatttttggagacag |
| | ctcttctgtttccaggttttctctcctgcctaaatgtcctgc |
| | ctaagtgccttcaagaacccttcaccatcctgctcctgcatg |
| | tgaccaggttccatggtcagttcaatcacctagtcacagttg |
| | gtaagtgacagagttgggacttgaacctatgcctgcctgaca |
| | ccaagtctttttttgacacctagagccaagacatctgaagac |
| | aaactccctaggagagctggcgtcatagaaaccttaaaggtt |
| | agggagacctgggtttgaatcaggctttgtcagttatgactt |
| | gtgtgaccctagcaagttatttaacctttctgggtctcagtt |
| | tcctcatctgcaaactgaggataataacagtacctaccaaaa |
| | agaactgtcgtgaaaaccatataatttctgcaatgctcctgg |
| | cacagtgtcctgttctaaagcatagttccccttctctttctt |
| | agctccatattgattattaccctaacttgcacaaagagactt |
| | ggaggacccccatagagtatcggagggtcccccatttcctgc |
| | tctttccactccacacccccagcaagcacagggaagttctgg |
| | gggccataatccacccacaggaaccaaatctaagccaccttt |
| | ctggctggtagacatccaggtatgtgggcacagaggtagaca |
| | ggctgaaatgctgctgtgctatcagttgggttttgctggaac |
| | aggaatggaaatggagaggctgacagaactgccctggggagc |
| | ccaggcaagagggacagtggctggacacccccagccagttgt |
| | gcagaccatcagaacaagatcctagattttaggaatacaggg |
| | ttcaagtccgtgcggcaactcttttctaaatatgcccaagcc |
| | attaactttgagttttaaaaatactgatttacaagctgtaca |
| | caatgaaaaaatgcctatccctcacaccatgctgatgctgtt |
| | ccctgccatctcagattaccaattaaatacagaatgcccagt |
| | taaatgtgaactttttttttttttttttttgagatggagt |
| | tttgttcttgtcgcccaggctagagtgcaatggtgcgatctc |
| | agctcactgcaacctctgcctcccaggttcaagcaattctcc |
| | tgccttagcctcctgagtagctggaactacaggtgcccacca |
| | gcacgcctggctaatttttggtatttttagtggagatggggt |
| | ttcaccatgttggccaggctggtctcgaactcctgacctcag |
| | gtgatctgcctgcctcggcctcccaaagtgctgggattacag |
| | gcgtgagcctaaatgtgaactttttaatactaaaaaagtat |
| | ttgctgttcatcggaaattcacatttaactgggtgtcctgta |
| | tttttatttgctaaatctaccatcaaattggtctggctcaac |
| | ctggagaatggttaccctaggtaaccacgtgcggaccgagcg |
| | gccgcaggaacccctagtgatggagttggccactccctctct |
| | gcgcgctcgctcgctcactgaggccgggcgaccaaaggtcgc |
| | ccgacgcccgggctttgcccgggcggcctcagtgagcgagcg |
| | agcgcgcag |

Plasmid TM016 Composition

| | |
|---|---|
| Δ5' ITR | 1<br>occurs at bp 1 through bp 103 of SEQ ID NO: 31 |
| Human RLBP1 Promoter(short) | 3<br>occurs at bp 116 through bp 705 of SEQ ID NO: 31 |
| Modified SV40 intron | 4<br>occurs at bp 720 through bp 902 of SEQ ID NO: 31 |

TABLE 2-continued

Plasmid Composition
Plasmid Composition

| Elements | SEQUENCE IDENTIFIER (SEQ. ID. NO:) AND SEQUENCE INFORMATION |
|---|---|
| Added Kozak | 5<br>occurs at bp 943 through bp 948 of SEQ ID NO: 31 |
| E_GFP | 24<br>occurs at bp 949 through bp 1668 of SEQ ID NO: 31 |
| SV40 POLYA | 8<br>occurs at bp 1726 through bp 1961 of SEQ ID NO: 31 |
| 3' ITR | 9<br>occurs at bp 1990 through bp 2119 of SEQ ID NO: 31 |
| AMP BACTERIAL BACKBONE | 15<br>occurs at bp 2120 through bp 4738 of SEQ ID NO: 31 |
| Sequence of TM016 Plasmid | 31<br>cgcgctcgctcgctcactgaggccgcccgggcaaagcccggg<br>cgtcgggcgacctttggtcgcccggcctcagtgagcgagcga<br>gcgcgcagagagggagtggggtaccacgcgtttgtcctctcc<br>ctgctcggcctcaaccagccacatttctcaactgaccccact<br>cactgcagaggtgaaaactaccatgccaggtcctgctggctg<br>gggagggggtgggcaataggcctggatttgccagagctgcca<br>ctgtagatgtagtcatatttacgatttcccttcacctcttat<br>taccctggtggtggtggtgggggggggggggtgctctctcag<br>caaccccaccccgggatcttgaggagaaagagggcagagaaa<br>agagggaatgggactggcccagatcccagccccacagccggg<br>cttccacatggccgagcaggaactccagagcaggagcacaca<br>aaggagggctttgatgcgcctccagccaggcccaggcctctc<br>ccctctcccctttctctctgggtcttcctttgccccactgag<br>ggcctcctgtgagcccgatttaacggaaactgtgggcggtga<br>gaagttccttatgacacactaatcccaacctgctgaccggac<br>cacgcctccagcggagggaacctctagagctccaggacattc<br>aggtaccaggtagccccaaggaggagctgccgaatcgatgga<br>tcgggaactgaaaaaccagaaagttaactggtaagtttagtc<br>tttttgtcttttatttcaggtcccggatccggtggtggtgca<br>aatcaaagaactgctcctcagtggatgttgcctttacttcta<br>ggcctgtacggaagtgttacttctgctctaaaagctgcggaa<br>ttgtacccgccccgggatccatcgattgaattccccggggat<br>cctctagagtcgaaattcgccaccatggtgagcaagggcgag<br>gagctgttcaccggggtggtgcccatcctggtcgagctggac<br>ggcgacgtaaacggccacaagttcagcgtgtccggcgagggc<br>gagggcgatgccacctacggcaagctgaccctgaagttcatc<br>tgcaccaccggcaagctgcccgtgccctggcccaccctcgtg<br>accaccctgacctacggcgtgcagtgcttcagccgctacccc<br>gaccacatgaagcagcacgacttcttcaagtccgccatgccc<br>gaaggctacgtccaggagcgcaccatcttcttcaaggacgac<br>ggcaactacaagacccgcgccgaggtgaagttcgagggcgac<br>accctggtgaaccgcatcgagctgaagggcatcgacttcaag<br>gaggacggcaacatcctggggcacaagctggagtacaactac<br>aacagccacaacgtctatatcatggccgacaagcagaagaac<br>ggcatcaaggtgaacttcaagatccgccacaacatcgaggac<br>ggcagcgtgcagctcgccgaccactaccagcagaacaccccc<br>atcggcgacggccccgtgctgctgcccgacaaccactacctg<br>agcacccagtccgccctgagcaaagaccccaacgagaagcgc<br>gatcacatggtcctgctggagttcgtgaccgccgccgggatc<br>actctcggcatggacgagctgtacaagtaatagggtaccggt<br>cgacctgcagaagcttgcctcgagcagcgctgctcgagagat<br>ctggatcataatcagccataccacatttgtagaggttttact<br>tgctttaaaaaacctcccacacctccccctgaacctgaaaca<br>taaaatgaatgcaattgttgttgttaacttgtttattgcagc<br>ttataatggttacaaataaagcaatagcatcacaaatttcac<br>aaataaagcatttttttcactgcattctagttgtggtttgtc<br>caaactcatcaatgtatcttatcatgtctggtaaccacgtgc<br>ggaccgagcggccgcaggaacccctagtgatggagttggcca<br>ctccctctctgcgcgctcgctcgctcactgaggccgggcgac<br>caaaggtcgcccgacgcccgggctttgcccgggcggcctcag<br>tgagcgagcgagcgcgcagctgcctgcaggggcgcctgatgc<br>ggtattttctccttacgcatctgtgcggtatttcacaccgca<br>tacgtcaaagcaaccatagtacgcgccctgtagcggcgcatt<br>aagcgcggcgggtgtggtggttacgcgcagcgtgaccgctac<br>acttgccagcgccttagcgcccgctcctttcgctttcttccc<br>ttcctttctcgccacgttcgccggctttccccgtcaagctct<br>aaatcgggggctccctttagggttccgatttagtgctttacg<br>gcacctcgaccccaaaaaacttgatttgggtgatggttcacg |

TABLE 2-continued

Plasmid Composition

Plasmid Composition

| Elements | SEQUENCE IDENTIFIER (SEQ. ID. NO:)AND SEQUENCE INFORMATION |
|---|---|
| | tagtgggccatcgccctgatagacggtttttcgccctttgac<br>gttggagtccacgttctttaatagtggactcttgttccaaac<br>tggaacaacactcaactctatctcgggctattcttttgattt<br>ataagggattttgccgatttcggtctattggttaaaaaatga<br>gctgatttaacaaaaatttaacgcgaattttaacaaaatatt<br>aacgtttacaattttatggtgcactctcagtacaatctgctc<br>tgatgccgcatagttaagccagccccgacacccgccaacacc<br>cgctgacgcgccctgacgggcttgtctgctcccggcatccgc<br>ttacagacaagctgtgaccgtctccgggagctgcatgtgtca<br>gaggttttcaccgtcatcaccgaaacgcgcgagacgaaaggg<br>cctcgtgatacgcctatttttataggttaatgtcatgataat<br>aatggtttcttagacgtcaggtggcacttttcggggaaatgt<br>gcgcggaacccctatttgtttatttttctaaatacattcaaa<br>tatgtatccgctcatgagacaataaccctgataaatgcttca<br>ataatattgaaaaaggaagagtatgagtattcaacatttccg<br>tgtcgcccttattcccttttttgcggcattttgccttcctgt<br>ttttgctcacccagaaacgctggtgaaagtaaaagatgctga<br>agatcagttgggtgcacgagtgggttacatcgaactggatct<br>caacagcggtaagatccttgagagttttcgccccgaagaacg<br>ttttccaatgatgagcacttttaaagttctgctatgtggcgc<br>ggtattatcccgtattgacgccgggcaagagcaactcggtcg<br>ccgcatacactattctcagaatgacttggttgagtactcacc<br>agtcacagaaaagcatcttacggatggcatgacagtaagaga<br>attatgcagtgctgccataaccatgagtgataacactgcggc<br>caacttacttctgacaacgatcggaggaccgaaggagctaac<br>cgcttttttgcacaacatgggggatcatgtaactcgccttga<br>tcgttgggaaccggagctgaatgaagccataccaaacgacga<br>gcgtgacaccacgatgcctgtagcaatggcaacaacgttgcg<br>caaactattaactggcgaactacttactctagcttcccggca<br>acaattaatagactggatggaggcggataaagttgcaggacc<br>acttctgcgctcggcccttccggctggctggtttattgctga<br>taaatctggagccggtgagcgtgggtctcgcggtatcattgc<br>agcactggggccagatggtaagccctcccgtatcgtagttat<br>ctacacgacggggagtcaggcaactatggatgaacgaaatag<br>acagatcgctgagataggtgcctcactgattaagcattggta<br>actgtcagaccaagtttactcatatatactttagattgattt<br>aaaacttcatttttaatttaaaaggatctaggtgaagatcct<br>ttttgataatctcatgaccaaaatcccttaacgtgagttttc<br>gttccactgagcgtcagaccccgtagaaaagatcaaaggatc<br>ttcttgaaatcctttttttctgcgcgtaatctgctgcttgca<br>aacaaaaaaaccaccgctaccagcggtggtttgtttgccgga<br>tcaagagctaccaactctttttccgaaggtaactggcttcag<br>cagagcgcagataccaaatactgttcttctagtgtagccgta<br>gttaggccaccacttcaagaactctgtagcaccgcctacata<br>cctcgctctgctaatcctgttaccagtggctgctgccagtgg<br>cgataagtcgtgtcttaccgggttggactcaagacgatagtt<br>accggataaggcgcagcggtcgggctgaacggggggttcgtg<br>cacacagcccagcttggagcgaacgacctacaccgaactgag<br>atacctacagcgtgagctatgagaaagcgccacgcttcccga<br>agggagaaaggcggacaggtatccggtaagcggcagggtcgg<br>aacaggagagcgcacgagggagcttccagggggaaacgcctg<br>gtatctttatagtcctgtcgggtttcgccacctctgacttga<br>gcgtcgatttttgtgatgctcgtcaggggggcggagcctatg<br>gaaaaacgccagcaacgcggcctttttacggttcctggcctt<br>ttgctggccttttgctcacatgtcctgcaggcagctg |
| GENE CASSETTE OF PLASMID TM016 OCCURS AT BP 1 THROUGH 2119 OF SEQ ID NO: 31 | 56<br>cgcgctcgctcgctcactgaggccgcccgggcaaagcccggg<br>cgtcgggcgacctttggtcgcccggcctcagtgagcgagcga<br>gcgcgcagagagggagtggggtaccacgcgtttgtcctctcc<br>ctgctcggccttaaccagccacatttctcaactgaccccact<br>cactgcagaggtgaaaactaccatgccaggtcctgctggctg<br>gggagggggtgggcaataggcctggatttgccagagctgcca<br>ctgtagatgtagtcatatttacgatttcccttcacctcttat<br>taccctggtggtggtggtgggggggggggggtgctctctcag<br>caaccccaccccgggatcttgaggagaaagagggcagagaaa<br>agagggaatgggactggcccagatcccagccccacagccggg<br>cttccacatggccgagcaggaactccagagcaggagcacaca<br>aaggagggctttgatgcgcctccagccaggcccaggcctctc<br>ccctctcccctttctctctgggtcttcctttgccccactgag<br>ggcctcctgtgagcccgatttaacggaaactgtgggcggtga<br>gaagttccttatgacacactaatcccaacctgctgaccggac<br>cacgcctccagcggagggaacctctagagctccaggacattc<br>aggtaccaggtagccccaaggaggagctgccgaatcgatgga<br>tcgggaactgaaaaaccagaaagttaactggtaagtttagtc |

TABLE 2-continued

Plasmid Composition
Plasmid Composition

| Elements | SEQUENCE IDENTIFIER (SEQ. ID. NO:) AND SEQUENCE INFORMATION |
|---|---|
| | tttttgtcttttatttcaggtcccggatccggtggtggtgca |
| | aatcaaagaactgctcctcagtggatgttgcctttacttcta |
| | ggcctgtacggaagtgttacttctgctctaaaagctgcggaa |
| | ttgtacccgccccgggatccatcgattgaattccccggggat |
| | cctctagagtcgaaattcgccaccatggtgagcaagggcgag |
| | gagctgttcaccggggtggtgcccatcctggtcgagctggac |
| | ggcgacgtaaacggccacaagttcagcgtgtccggcgagggc |
| | gagggcgatgccacctacggcaagctgaccctgaagttcatc |
| | tgcaccaccggcaagctgcccgtgccctggcccaccctcgtg |
| | accaccctgacctacggcgtgcagtgcttcagccgctacccc |
| | gaccacatgaagcagcacgacttcttcaagtccgccatgccc |
| | gaaggctacgtccaggagcgcaccatcttcttcaaggacgac |
| | ggcaactacaagacccgcgccgaggtgaagttcgagggcgac |
| | accctggtgaaccgcatcgagctgaagggcatcgacttcaag |
| | gaggacggcaacatcctggggcacaagctggagtacaactac |
| | aacagccacaacgtctatatcatggccgacaagcagaagaac |
| | ggcatcaaggtgaacttcaagatccgccacaacatcgaggac |
| | ggcagcgtgcagctcgccgaccactaccagcagaacacccccc |
| | atcggcgacggccccgtgctgctgcccgacaaccactacctg |
| | agcacccagtccgccctgagcaaagaccccaacgagaagcgc |
| | gatcacatggtcctgctggagttcgtgaccgccgccgggatc |
| | actctcggcatggacgagctgtacaagtaatagggtaccggt |
| | cgacctgcagaagcttgcctcgagcagcgctgctcgagagat |
| | ctggatcataatcagccataccacatttgtagaggttttact |
| | tgctttaaaaaacctcccacacctccccctgaacctgaaaca |
| | taaaatgaatgcaattgttgttgttaacttgtttattgcagc |
| | ttataatggttacaaataaagcaatagcatcacaaatttcac |
| | aaataaagcatttttttcactgcattctagttgtggtttgtc |
| | caaactcatcaatgtatcttatcatgtctggtaaccacgtgc |
| | ggaccgagcggccgcaggaacccctagtgatggagttggcca |
| | ctccctctctgcgcgctcgctcgctcactgaggccgggcgac |
| | caaaggtcgcccgacgcccgggctttgcccgggcggcctcag |
| | tgagcgagcgagcgcgcag |

Plasmid TM035 Composition

| Elements | SEQUENCE IDENTIFIER (SEQ. ID. NO:) AND SEQUENCE INFORMATION |
|---|---|
| 5' ITR | 2 |
| | occurs at bp 1 through bp 119 of SEQ ID NO: 32 |
| Human RLBP1 | 10 |
| Promoter(long) | occurs at bp 137 through bp 3293 of SEQ ID NO: 32 |
| Added Kozak | 5 |
| | occurs at bp 3327 through bp 3332 of SEQ ID NO: 32 |
| E_GFP | 24 |
| | occurs at bp 3333 through bp 4052 of SEQ ID NO: 32 |
| SV40 POLYA | 8 |
| | occurs at bp 4110 through bp 4345 of SEQ ID NO: 32 |
| 3' ITR | 9 |
| | occurs at bp 4374 through bp 4503 of SEQ ID NO: 32 |
| AMP BACTERIAL | 15 |
| BACKBONE | occurs at bp 4504 through bp 7122 of SEQ ID NO: 32 |
| Sequence of | 32 |
| TM035 Plasmid | ctgcgcgctcgctcgctcactgaggccgcccgggcgtcgggc |
| | gacctttggtcgcccggcctcagtgagcgagcgagcgcgcag |
| | agagggagtggccaactccatcactaggggttcctgcggccg |
| | cacgcagcttttgtcctctccctgcttggccttaaccagcca |
| | catttctcaactgaccccactcactgcagaggtgaaaactac |
| | catgccaggtcctgctggctgggggaggggtgggcaataggc |
| | ctggatttgccagagctgccactgtagatgtagtcatattta |
| | cgatttcccttcacctcttattaccctggtggtggtggtggg |
| | ggggggggggtgctctctcagcaaccccaccccgggatcttg |
| | aggagaaagagggcagagaaaagagggaatgggactggccca |
| | gatcccagccccacagccgggcttccacatggccgagcagga |
| | actccagagcaggagcacacaaaggagggctttgatgcgcct |
| | ccagccaggcccaggcctctcccctctcccctttctctctgg |
| | gtcttcctttgccccactgagggcctcctgtgagcccgattt |
| | aacggaaactgtgggcggtgagaagttccttatgacacacta |
| | atcccaacctgctgaccggaccacgcctccagcggagggaac |

TABLE 2-continued

Plasmid Composition
Plasmid Composition

| Elements | SEQUENCE IDENTIFIER (SEQ. ID. NO:)AND SEQUENCE INFORMATION |
|---|---|
| | ctctagagctccaggacattcaggtaccaggtagccccaagg |
| | aggagctgccgacctggcaggtaagtcaatacctggggcttg |
| | cctgggccagggagcccaggactggggtgaggactcagggga |
| | gcagggagaccacgtcccaagatgcctgtaaaactgaaacca |
| | cctggccattctccaggttgagccagaccaatttgatggcag |
| | atttagcaaataaaaatacaggacacccagttaaatgtgaat |
| | ttcagatgaacagcaaatactttttttagtattaaaaaagttc |
| | acatttaggctcacgcctgtaatcccagcactttgggaggcc |
| | gaggcaggcagatcacctgaggtcaggagttcgagaccagcc |
| | tggccaacatggtgaaaccccatctccactaaaaataccaaa |
| | aattagccaggcgtgctggtgggcacctgtagttccagctac |
| | tcaggaggctaaggcaggagaattgcttgaacctgggaggca |
| | gaggttgcagtgagctgagatcgcaccattgcactctagcct |
| | gggcgacaagaacaaaactccatctcaaaaaaaaaaaaaaaa |
| | aaaaagttcacatttaactgggcattctgtatttaattggta |
| | atctgagatggcagggaacagcatcagcatggtgtgagggat |
| | aggcatttttttcattgtgtacagcttgtaaatcagtattttt |
| | aaaactcaaagttaatggcttgggcatatttagaaaagagtt |
| | gccgcacggacttgaaccctgtattcctaaaatctaggatct |
| | tgttctgatggtctgcacaactggctgggggtgtccagccac |
| | tgtccctcttgcctgggctccccagggcagttctgtcagcct |
| | ctccatttccattcctgttccagcaaaacccaactgatagca |
| | cagcagcatttcagcctgtctacctctgtgcccacatacctg |
| | gatgtctaccagccagaaaggtggcttagatttggttcctgt |
| | gggtggattatggcccccagaacttccctgtgcttgctgggg |
| | gtgtggagtggaaagagcaggaaatgggggaccctccgatac |
| | tctatgggggtcctccaagtctctttgtgcaagttagggtaa |
| | taatcaatatggagctaagaaagagaaggggaactatgcttt |
| | agaacaggacactgtgccaggagcattgcagaaattatatgg |
| | ttttcacgacagttctttttggtaggtactgttattatcctc |
| | agtttgcagatgaggaaactgagacccagaaaggttaaataa |
| | cttgctagggtcacacaagtcataactgacaaagcctgattc |
| | aaacccaggtctccctaacctttaaggtttctatgacgccag |
| | ctctcctagggagtttgtcttcagatgtcttggctctaggtg |
| | tcaaaaaaagacttggtgtcaggcaggcataggttcaagtcc |
| | caactctgtcacttaccaactgtgactaggtgattgaactga |
| | ccatggaacctggtcacatgcaggagcaggatggtgaagggt |
| | tcttgaaggcacttaggcaggacatttaggcaggagagaaaa |
| | cctggaaacagaagagctgtctccaaaaatacccactgggga |
| | agcaggttgtcatgtgggccatgaatgggacctgttctggta |
| | accaagcattgcttatgtgtccattacatttcataacacttc |
| | catcctactttacagggaacaaccaagactggggttaaatct |
| | cacagcctgcaagtggaagagaagaacttgaacccaggtcca |
| | acttttgcgccacagcaggctgcctcttggtcctgacaggaa |
| | gtcacaacttgggtctgagtactgatccctggctatttttttg |
| | gctgtgttaccttggacaagtcacttattcctcctcccgttt |
| | cctcctatgtaaaatggaaataataatgttgaccctgggtct |
| | gagagagtggatttgaaagtacttagtgcatcacaaagcaca |
| | gaacacacttccagtctcgtgattatgtacttatgtaactgg |
| | tcatcacccatcttgagaatgaatgcattggggaaagggcca |
| | tccactaggctgcgaagtttctgagggactccttcgggctgg |
| | agaaggatggccacaggagggaggagagattgccttatcctg |
| | cagtgatcatgtcattgagaacagagccagattcttttttttc |
| | ctggcagggccaacttgttttaacatctaaggactgagctat |
| | ttgtgtctgtgccctttgtccaagcagtgtttcccaaagtgt |
| | agcccaagaaccatctccctcagagccaccaggaagtgcttt |
| | aaattgcaggttcctaggccacagcctgcacctgcagagtca |
| | gaatcatggaggttgggacccaggcacctgcgtttctaacaa |
| | atgcctcgggtgattctgatgcaattgaaagtttgagatcca |
| | cagttctgagacaataacagaatggtttttctaacccctgca |
| | gccctgacttcctatcctagggaaggggccggctggagaggc |
| | caggacagagaaagcagatcccttctttttccaaggactctg |
| | tgtcttccataggcaacgaattccccggggatcctctagagt |
| | cgaaattcgccaccatggtgagcaagggcgaggagctgttca |
| | ccggggtggtgcccatcctggtcgagctggacggcgacgtaa |
| | acggccacaagttcagcgtgtccggcgagggcgagggcgatg |
| | ccacctacggcaagctgaccctgaagttcatctgcaccaccg |
| | gcaagctgcccgtgccctggcccaccctcgtgaccaccctga |
| | cctacggcgtgcagtgcttcagccgctaccccgaccacatga |
| | agcagcacgacttcttcaagtccgccatgcccgaaggctacg |
| | tccaggagcgcaccatcttcttcaaggacgacggcaactaca |
| | agacccgcgccgaggtgaagttcgagggcgacaccctggtga |
| | accgcatcgagctgaagggcatcgacttcaaggaggacggca |
| | acatcctggggcacaagctggagtacaactacaacagccaca |

TABLE 2-continued

Plasmid Composition
Plasmid Composition

| Elements | SEQUENCE IDENTIFIER (SEQ. ID. NO:) AND SEQUENCE INFORMATION |
|---|---|
| | acgtctatatcatggccgacaagcagaagaacggcatcaagg |
| | tgaacttcaagatccgccacaacatcgaggacggcagcgtgc |
| | agctcgccgaccactaccagcagaacacccccatcggcgacg |
| | gccccgtgctgctgcccgacaaccactacctgagcacccagt |
| | ccgccctgagcaaagaccccaacgagaagcgcgatcacatgg |
| | tcctgctggagttcgtgaccgccgccgggatcactctcggca |
| | tggacgagctgtacaagtaatagggtaccggtcgacctgcag |
| | aagcttgcctcgagcagcgctgctcgagagatctggatcata |
| | atcagccataccacatttgtagaggttttacttgctttaaaa |
| | aacctcccacacctccccctgaacctgaaacataaaatgaat |
| | gcaattgttgttgttaacttgtttattgcagcttataatggt |
| | tacaaataaagcaatagcatcacaaatttcacaaataaagca |
| | tttttttcactgcattctagttgtggtttgtccaaactcatc |
| | aatgtatcttatcatgtctggtaaccacgtgcggaccgagcg |
| | gccgcaggaacccctagtgatggagttggccactccctctct |
| | gcgcgctcgctcgctcactgaggccgggcgaccaaaggtcgc |
| | ccgacgcccgggctttgcccgggcggcctcagtgagcgagcg |
| | agcgcgcagctgcctgcaggggcgcctgatgcggtattttct |
| | ccttacgcatctgtgcggtatttcacaccgcatacgtcaaag |
| | caaccatagtacgcgccctgtagcggcgcattaagcgcggcg |
| | ggtgtggtggttacgcgcagcgtgaccgctacacttgccagc |
| | gccttagcgcccgctcctttcgctttcttcccttcctttctc |
| | gccacgttcgccggctttccccgtcaagctctaaatcggggg |
| | ctccctttagggttccgatttagtgctttacggcacctcgac |
| | cccaaaaaacttgatttgggtgatggttcacgtagtgggcca |
| | tcgccctgatagacggtttttcgccctttgacgttggagtcc |
| | acgttctttaatagtggactcttgttccaaactggaacaaca |
| | ctcaactctatctcgggctattcttttgatttataagggatt |
| | ttgccgatttcggtctattggttaaaaaatgagctgatttaa |
| | caaaaatttaacgcgaattttaacaaaatattaacgtttaca |
| | attttatggtgcactctcagtacaatctgctctgatgccgca |
| | tagttaagccagccccgacacccgccaacacccgctgacgcg |
| | ccctgacgggcttgtctgctcccggcatccgcttacagacaa |
| | gctgtgaccgtctccgggagctgcatgtgtcagaggttttca |
| | ccgtcatcaccgaaacgcgcgagacgaaagggcctcgtgata |
| | cgcctatttttataggttaatgtcatgataataatggtttct |
| | tagacgtcaggtggcacttttcggggaaatgtgcgcggaacc |
| | cctatttgtttatttttctaaatacattcaaatatgtatccg |
| | ctcatgagacaataaccctgataaatgcttcaataatattga |
| | aaaaggaagagtatgagtattcaacatttccgtgtcgccctt |
| | attccctttttttgcggcattttgccttcctgtttttgctcac |
| | ccagaaacgctggtgaaagtaaaagatgctgaagatcagttg |
| | ggtgcacgagtgggttacatcgaactggatctcaacagcggt |
| | aagatccttgagagttttcgccccgaagaacgttttccaatg |
| | atgagcacttttaaagttctgctatgtggcgcggtattatcc |
| | cgtattgacgccgggcaagagcaactcggtcgccgcatacac |
| | tattctcagaatgacttggttgagtactcaccagtcacagaa |
| | aagcatcttacggatggcatgacagtaagagaattatgcagt |
| | gctgccataaccatgagtgataacactgcggccaacttactt |
| | ctgacaacgatcggaggaccgaaggagctaaccgcttttttg |
| | cacaacatgggggatcatgtaactcgccttgatcgttgggaa |
| | ccggagctgaatgaagccataccaaacgacgagcgtgacacc |
| | acgatgcctgtagcaatggcaacaacgttgcgcaaactatta |
| | actggcgaactacttactctagcttcccggcaacaattaata |
| | gactggatggaggcggataaagttgcaggaccacttctgcgc |
| | tcggcccttccggctggctggtttattgctgataaatctgga |
| | gccggtgagcgtgggtctcgcggtatcattgcagcactgggg |
| | ccagatggtaagccctcccgtatcgtagttatctacacgacg |
| | gggagtcaggcaactatggatgaacgaaatagacagatcgct |
| | gagataggtgcctcactgattaagcattggtaactgtcagac |
| | caagtttactcatatatactttagattgatttaaaacttcat |
| | ttttaatttaaaaggatctaggtgaagatcctttttgataat |
| | ctcatgaccaaaatcccttaacgtgagttttcgttccactga |
| | gcgtcagaccccgtagaaaagatcaaaggatcttcttgaaat |
| | cctttttttctgcgcgtaatctgctgcttgcaaacaaaaaaa |
| | ccaccgctaccagcggtggtttgtttgccggatcaagagcta |
| | ccaactctttttccgaaggtaactggcttcagcagagcgcag |
| | ataccaaatactgttcttctagtgtagccgtagttaggccac |
| | cacttcaagaactctgtagcaccgcctacatacctcgctctg |
| | ctaatcctgttaccagtggctgctgccagtggcgataagtcg |
| | tgtcttaccgggttggactcaagacgatagttaccggataag |
| | gcgcagcggtcgggctgaacggggggttcgtgcacacagccc |
| | agcttggagcgaacgacctacaccgaactgagatacctacag |
| | cgtgagctatgagaaagcgccacgcttcccgaagggagaaag |

TABLE 2-continued

Plasmid Composition
Plasmid Composition

| Elements | SEQUENCE IDENTIFIER (SEQ. ID. NO:) AND SEQUENCE INFORMATION |
|---|---|
| | gcggacaggtatccggtaagcggcagggtcggaacaggagag |
| | cgcacgagggagcttccagggggaaacgcctggtatctttat |
| | agtcctgtcgggtttcgccacctctgacttgagcgtcgattt |
| | ttgtgatgctcgtcaggggggcggagcctatggaaaaacgcc |
| | agcaacgcggcctttttacggttcctggccttttgctggcct |
| | tttgctcacatgtcctgcaggcag |
| GENE CASSETTE | 57 |
| OF PLASMID | ctgcgcgctcgctcgctcactgaggccgcccgggcgtcgggc |
| TM035 OCCURS AT | gacctttggtcgcccggcctcagtgagcgagcgagcgcgcag |
| BP 1 THROUGH | agagggagtggccaactccatcactaggggttcctgcggccg |
| 4503 OF SEQ ID | cacgcagcttttgtcctctccctgcttggccttaaccagcca |
| NO: 32 | catttctcaactgaccccactcactgcagaggtgaaaactac |
| | catgccaggtcctgctggctgggggagggggtgggcaataggc |
| | ctggatttgccagagctgccactgtagatgtagtcatattta |
| | cgatttcccttcacctcttattaccctggtggtggtggtggg |
| | gggggggggggtgctctctcagcaaccccaccccgggatcttg |
| | aggagaaagagggcagagaaaagagggaatgggactggccca |
| | gatcccagccccacagccgggcttccacatggccgagcagga |
| | actccagagcaggagcacacaaaggagggctttgatgcgcct |
| | ccagccaggcccaggcctctcccctctcccctttctctctgg |
| | gtcttcctttgccccactgagggcctcctgtgagcccgattt |
| | aacggaaactgtgggcggtgagaagttccttatgacacacta |
| | atcccaacctgctgaccggaccacgcctccagcggagggaac |
| | ctctagagctccaggacattcaggtaccaggtagccccaagg |
| | aggagctgccgacctggcaggtaagtcaatacctggggcttg |
| | cctgggccagggagcccaggactggggtgaggactcagggga |
| | gcagggagaccacgtcccaagatgcctgtaaaactgaaacca |
| | cctggccattctccaggttgagccagaccaatttgatggcag |
| | atttagcaaataaaaatacaggacacccagttaaatgtgaat |
| | ttcagatgaacagcaaatactttttttagtattaaaaaagttc |
| | acatttaggctcacgcctgtaatcccagcactttgggaggcc |
| | gaggcaggcagatcacctgaggtcaggagttcgagaccagcc |
| | tggccaacatggtgaaaccccatctccactaaaaataccaaa |
| | aattagccaggcgtgctggtgggcacctgtagttccagctac |
| | tcaggaggctaaggcaggagaattgcttgaacctgggaggca |
| | gaggttgcagtgagctgagatcgcaccattgcactctagcct |
| | gggcgacaagaacaaaactccatctcaaaaaaaaaaaaaaaa |
| | aaaaagttcacatttaactgggcattctgtatttaattggta |
| | atctgagatggcagggaacagcatcagcatggtgtgagggat |
| | aggcatttttttcattgtgtacagcttgtaaatcagtatttt |
| | aaaactcaaagttaatggcttgggcatatttagaaaagagtt |
| | gccgcacggacttgaaccctgtattcctaaaatctaggatct |
| | tgttctgatggtctgcacaactggctggggggtgtccagccac |
| | tgtccctcttgcctgggctccccagggcagttctgtcagcct |
| | ctccatttccattcctgttccagcaaaacccaactgatagca |
| | cagcagcatttcagcctgtctacctctgtgcccacatacctg |
| | gatgtctaccagccagaaaggtggcttagatttggttcctgt |
| | gggtggattatggcccccagaacttccctgtgcttgctgggg |
| | gtgtggagtggaaagagcaggaaatgggggaccctccgatac |
| | tctatggggggtcctccaagtctctttgtgcaagttagggtaa |
| | taatcaatatggagctaagaaagagaaggggaactatgcttt |
| | agaacaggacactgtgccaggagcattgcagaaattatatgg |
| | ttttcacgacagttctttttggtaggtactgttattatcctc |
| | agtttgcagatgaggaaactgagacccagaaaggttaaataa |
| | cttgctagggtcacacaagtcataactgacaaagcctgattc |
| | aaacccaggtctccctaacctttaaggtttctatgacgccag |
| | ctctcctagggagtttgtcttcagatgtcttggctctaggtg |
| | tcaaaaaaagacttggtgtcaggcaggcataggttcaagtcc |
| | caactctgtcacttaccaactgtgactaggtgattgaactga |
| | ccatggaacctggtcacatgcaggagcaggatggtgaagggt |
| | tcttgaaggcacttaggcaggacatttaggcaggagagaaaa |
| | cctggaaacagaagagctgtctccaaaaatacccactgggga |
| | agcaggttgtcatgtgggccatgaatgggacctgttctggta |
| | accaagcattgcttatgtgtccattacatttcataacacttc |
| | catcctactttacagggaacaaccaagactggggttaaatct |
| | cacagcctgcaagtggaagagaagaacttgaacccaggtcca |
| | acttttgcgccacagcaggctgcctcttggtcctgacaggaa |
| | gtcacaacttgggtctgagtactgatccctggctattttttg |
| | gctgtgttaccttggacaagtcacttattcctcctcccgttt |
| | cctcctatgtaaaatggaaataataatgttgaccctgggtct |
| | gagagagtggatttgaaagtacttagtgcatcacaaagcaca |
| | gaacacacttccagtctcgtgattatgtacttatgtaactgg |
| | tcatcacccatcttgagaatgaatgcattggggaaagggcca |
| | tccactaggctgcgaagtttctgagggactccttcgggctgg |

TABLE 2-continued

| | |
|---|---|
| | Plasmid Composition |
| | Plasmid Composition |
| Elements | SEQUENCE IDENTIFIER (SEQ. ID. NO:)AND SEQUENCE INFORMATION |
| | agaaggatggccacaggagggaggagagattgccttatcctg cagtgatcatgtcattgagaacagagccagattcttttttc ctggcagggccaacttgttttaacatctaaggactgagctat ttgtgtctgtgccctttgtccaagcagtgtttcccaaagtgt agcccaagaaccatctccctcagagccaccaggaagtgcttt aaattgcaggttcctaggccacagcctgcacctgcagagtca gaatcatggaggttgggacccaggcacctgcgtttctaacaa atgcctcgggtgattctgatgcaattgaaagtttgagatcca cagttctgagacaataacagaatggtttttctaacccctgca gccctgacttcctatcctagggaaggggccggctggagaggc caggacagagaaagcagatcccttctttttccaaggactctg tgtcttccataggcaacgaattccccggggatcctctagagt cgaaattcgccaccatggtgagcaagggcgaggagctgttca ccggggtggtgcccatcctggtcgagctggacggcgacgtaa acggccacaagttcagcgtgtccggcgagggcgagggcgatg ccacctacggcaagctgaccctgaagttcatctgcaccaccg gcaagctgcccgtgccctggcccaccctcgtgaccaccctga cctacggcgtgcagtgcttcagccgctaccccgaccacatga agcagcacgacttcttcaagtccgccatgcccgaaggctacg tccaggagcgcaccatcttcttcaaggacgacggcaactaca agacccgcgccgaggtgaagttcgagggcgacaccctggtga accgcatcgagctgaagggcatcgacttcaaggaggacggca acatcctggggcacaagctggagtacaactacaacagccaca acgtctatatcatggccgacaagcagaagaacggcatcaagg tgaacttcaagatccgccacaacatcgaggacggcagcgtgc agctcgccgaccactaccagcagaacacccccatcggcgacg gccccgtgctgctgcccgacaaccactacctgagcacccagt ccgccctgagcaaagaccccaacgagaagcgcgatcacatgg tcctgctggagttcgtgaccgccgccgggatcactctcggca tggacgagctgtacaagtaatagggtaccggtcgacctgcag aagcttgcctcgagcagcgctgctcgagagatctggatcata atcagccataccacatttgtagaggttttacttgctttaaaa aacctcccacacctccccctgaacctgaaacataaaatgaat gcaattgttgttgttaacttgtttattgcagcttataatggt tacaaataaagcaatagcatcacaaatttcacaaataaagca tttttttcactgcattctagttgtggtttgtccaaactcatc aatgtatcttatcatgtctggtaaccacgtgcggaccgagcg gccgcaggaacccctagtgatggagttggccactccctctct gcgcgctcgctcgctcactgaggccgggcgaccaaaggtcgc ccgacgcccgggctttgcccgggcggcctcagtgagcgagcg agcgcgcag |
| | Plasmid AG012 Composition |
| 5' ITR | 2 occurs @ bp 1 through bp 119 of SEQ ID NO: 33 |
| SYNUCLEIN INTRONIC SEQUENCE AS STUFFER SEQUENCE | 13 occurs @ bp 148 through bp 2601 of SEQ ID NO: 33 |
| SV40 POLYA | 8 occurs @ bp 2640 through bp 2875 of SEQ ID NO: 33 |
| RLBP1 INTRONIC SEQUENCE AS STUFFER SEQUENCE | 14 occurs at bp 2883 through bp 4385 of SEQ ID NO: 33 |
| 3' ITR | 9 occurs at bp 4414 through bp 4543 of SEQ ID NO: 33 |
| AMP BACTERIAL BACKBONE | 15 occurs at bp 4544 through bp 7162 of SEQ ID NO: 33 |
| Sequence of AG012 Plasmid | 33 ctgcgcgctcgctcgctcactgaggccgcccgggcgtcgggc gacctttggtcgcccggcctcagtgagcgagcgagcgcgcag agagggagtggccaactccatcactaggggttcctgcggccg cacgcgtgacgtcgtttaaacgggccccggtgttatctcatt ctttttctcctctgtaagttgacatgtgatgtgggaacaaa ggggataaagtcattattttgtgctaaaatcgtaattggaga ggacctcctgttagctgggctttcttctatttattgtggtgg ttactggagttccttcttctagttttaggatatatatatata |

TABLE 2-continued

Plasmid Composition
Plasmid Composition

| Elements | SEQUENCE IDENTIFIER (SEQ. ID. NO:) AND SEQUENCE INFORMATION |
|---|---|
| | ttttttttttttctttccctgaagatataataatatatatac |
| | ttctgaagattgagattttaaattagttgtattgaaaacta |
| | gctaatcagcaatttaaggctagcttgagacttatgtcttga |
| | atttgtttttgtaggctccaaaaccaaggagggagtggtgca |
| | tggtgtggcaacaggtaagctccattgtgcttatatccaaag |
| | atgatatttaaagtatctagtgattagtgtggcccagtattc |
| | aagattcctatgaaattgtaaaacaatcactgagcattctaa |
| | gaacatatcagtcttattgaaactgaattctttataaagtat |
| | ttttaaaaaggtaaatattgattataaataaaaaatatactt |
| | gccaagaataatgagggctttgaattgataagctatgtttaa |
| | tttatagtaagtgggcatttaaatattctgaccaaaaatgta |
| | ttgacaaactgctgacaaaaataaaatgtgaatattgccata |
| | attttaaaaaaagagtaaaatttctgttgattacagtaaaat |
| | attttgaccttaaattatgttgattacaatattcctttgata |
| | attcagagtgcatttcaggaaacacccttggacagtcagtaa |
| | attgtttattgtatttatctttgtattgttatggtatagcta |
| | tttgtacaaatattattgtgcaattattacatttctgattat |
| | attattcatttggcctaaatttaccaagaatttgaacaagtc |
| | aattaggtttacaatcaagaaatatcaaaaatgatgaaaagg |
| | atgataatcatcatcagatgttgaggaagatgacgatgagag |
| | tgccagaaatagagaaatcaaaggagaaccaaaatttaacaa |
| | attaaaagcccacagacttgctgtaattaagttttctgttgt |
| | aagtactccacgtttcctggcagatgtggtgaagcaaaagat |
| | ataatcagaaatataatttatatgatcggaaagcattaaaca |
| | caatagtgcctatacaaataaaatgttcctatcactgacttc |
| | taaaatggaaatgaggacaatgatatgggaatcttaatacag |
| | tgttgtggataggactaaaaacacaggagtcagatcttcttg |
| | gttcaacttcctgcttactccttaccagctgtgtgtttttttg |
| | caaggttcttcacctctatgtgatttagcttcctcatctata |
| | aaataattcagtgaattaatgtacacaaaacatctggaaaac |
| | aaaagcaaacaatatgtattttataagtgttacttatagttt |
| | tatagtgaactttcttgtgcaacatttttacaactagtggag |
| | aaaaatatttctttaaatgaatacttttgatttaaaaatcag |
| | agtgtaaaaataaaacagactcctttgaaactagttctgtta |
| | gaagttaattgtgcacctttaatgggctctgttgcaatccaa |
| | cagagaagtagttaagtaagtggactatgatggcttctaggg |
| | acctcctataaatatgatattgtgaagcatgattataataag |
| | aactagataacagacaggtggagactccactatctgaagagg |
| | gtcaacctagatgaatggtgttccatttagtagttgaggaag |
| | aacccatgaggtttagaaagcagacaagcatgtggcaagttc |
| | tggagtcagtggtaaaaattaaagaacccaactattactgtc |
| | acctaatgatctaatggagactgtggagatgggctgcatttt |
| | tttaatcttctccagaatgccaaaatgtaaacacatatctgt |
| | gtgtgtgtgtgtgtgtgtgtgtgtgtgtgagagagagagaga |
| | gagagagagagactgaagtttgtacaattagacattttataa |
| | aatgttttctgaaggacagtggctcacaatcttaagtttcta |
| | acattgtacaatgttgggagactttgtatactttattttctc |
| | tttagcatattaaggaatctgagatgtcctacagtaaagaaa |
| | tttgcattacatagttaaaatcagggtattcaaactttttg |
| | attattgaaacctttcttcattagttactagggttgaatgaa |
| | actagtgttccacagaaaactatgggaaatgttgctaggcag |
| | taaggacatggtgatttcagcatgtgcaatatttacagcgat |
| | tgcacccatggaccaccctggcagtagtgaaataaccaaaaa |
| | tgctgtcataactagtatggctatgagaaacacattgggcag |
| | aagcttgcctcgagcagcgctgctcgagagatctggatcata |
| | atcagccataccacatttgtagaggttttacttgctttaaaa |
| | aacctcccacacctccccctgaacctgaaacataaaatgaat |
| | gcaattgttgttgttaacttgtttattgcagcttataatggt |
| | tacaaataaagcaatagcatcacaaatttcacaaataaagca |
| | tttttttcactgcattctagttgtggtttgtccaaactcatc |
| | aatgtatcttatcatgtctggtaaccattctccaggttgagc |
| | cagaccaatttgatggtagatttagcaaataaaaatacagga |
| | cacccagttaaatgtgaatttccgatgaacagcaaatacttt |
| | tttagtattaaaaaagttcacatttaggctcacgcctgtaat |
| | cccagcactttgggaggccgaggcaggcagatcacctgaggt |
| | caggagttcgagaccagcctggccaacatggtgaaaccccat |
| | ctccactaaaaataccaaaaattagccaggcgtgctggtggg |
| | cacctgtagttccagctactcaggaggctaaggcaggagaat |
| | tgcttgaacctgggaggcagaggttgcagtgagctgagatcg |
| | caccattgcactctagcctgggcgacaagaacaaaactccat |
| | ctcaaaaaaaaaaaaaaaaaaaaaaagttcacatttaactgggc |
| | attctgtatttaattggtaatctgagatggcagggaacagca |
| | tcagcatggtgtgagggataggcatttttttcattgtgtacag |
| | cttgtaaatcagtatttttaaaactcaaagttaatggcttgg |

TABLE 2-continued

Plasmid Composition
Plasmid Composition

| Elements | SEQUENCE IDENTIFIER (SEQ. ID. NO:) AND SEQUENCE INFORMATION |
|---|---|
| | gcatatttagaaaagagttgccgcacggacttgaaccctgta |
| | ttcctaaaatctaggatcttgttctgatggtctgcacaactg |
| | gctgggggtgtccagccactgtccctcttgcctgggctcccc |
| | agggcagttctgtcagcctctccatttccattcctgttccag |
| | caaaacccaactgatagcacagcagcatttcagcctgtctac |
| | ctctgtgcccacatacctggatgtctaccagccagaaaggtg |
| | gcttagatttggttcctgtgggtggattatggcccccagaac |
| | ttccctgtgcttgctgggggtgtggagtggaaagagcaggaa |
| | atgggggaccctccgatactctatgggggtcctccaagtctc |
| | tttgtgcaagttagggtaataatcaatatggagctaagaaag |
| | agaaggggaactatgctttagaacaggacactgtgccaggag |
| | cattgcagaaattatatggttttcacgacagttctttttggt |
| | aggtactgttattatcctcagtttgcagatgaggaaactgag |
| | acccagaaaggttaaataacttgctagggtcacacaagtcat |
| | aactgacaaagcctgattcaaacccaggtctccctaacccttt |
| | aaggtttctatgacgccagctctcctagggagtttgtcttca |
| | gatgtcttggctctaggtgtcaaaaaaagacttggtgtcagg |
| | caggcataggttcaagtcccaactctgtcacttaccaactgt |
| | gactaggtgattgaactgaccatggaacctggtcacatgcag |
| | gagcaggatggtgaagggttcttgaaggcacttaggcaggac |
| | atttaggcaggagagaaaacctggaaacagaagagctgtctc |
| | caaaaatacccactggggaagcaggttgtcatgtgggccatg |
| | aatgggacctgttctggggtaaccacgtgcggaccgagcggc |
| | cgcaggaacccctagtgatggagttggccactccctctctgc |
| | gcgctcgctcgctcactgaggccgggcgaccaaaggtcgccc |
| | gacgcccgggctttgcccgggcggcctcagtgagcgagcgag |
| | cgcgcagctgcctgcaggggcgcctgatgcggtattttctcc |
| | ttacgcatctgtgcggtatttcacaccgcatacgtcaaagca |
| | accatagtacgcgccctgtagcggcgcattaagcgcggcggg |
| | tgtggtggttacgcgcagcgtgaccgctacacttgccagcgc |
| | cttagcgcccgctcctttcgctttcttcccttcctttctcgc |
| | cacgttcgccggctttccccgtcaagctctaaatcgggggct |
| | ccctttagggttccgatttagtgctttacggcacctcgaccc |
| | caaaaaacttgatttgggtgatggttcacgtagtgggccatc |
| | gccctgatagacggtttttcgccctttgacgttggagtccac |
| | gttctttaatagtggactcttgttccaaactggaacaacact |
| | caactctatctcgggctattcttttgatttataagggatttt |
| | gccgatttcggtctattggttaaaaaatgagctgatttaaca |
| | aaaatttaacgcgaattttaacaaaatattaacgtttacaat |
| | tttatggtgcactctcagtacaatctgctctgatgccgcata |
| | gttaagccagccccgacacccgccaacacccgctgacgcgcc |
| | ctgacgggcttgtctgctcccggcatccgcttacagacaagc |
| | tgtgaccgtctccgggagctgcatgtgtcagaggttttcacc |
| | gtcatcaccgaaacgcgcgagacgaaagggcctcgtgatacg |
| | cctatttttataggttaatgtcatgataataatggtttctta |
| | gacgtcaggtggcacttttcggggaaatgtgcgcggaacccc |
| | tatttgtttatttttctaaatacattcaaatatgtatccgct |
| | catgagacaataaccctgataaatgcttcaataatattgaaa |
| | aaggaagagtatgagtattcaacatttccgtgtcgcccttat |
| | tcccttttttgcggcattttgccttcctgtttttgctcaccc |
| | agaaacgctggtgaaagtaaaagatgctgaagatcagttggg |
| | tgcacgagtgggttacatcgaactggatctcaacagcggtaa |
| | gatccttgagagttttcgccccgaagaacgttttccaatgat |
| | gagcacttttaaagttctgctatgtggcgcggtattatcccg |
| | tattgacgccgggcaagagcaactcggtcgccgcatacacta |
| | ttctcagaatgacttggttgagtactcaccagtcacagaaaa |
| | gcatcttacggatggcatgacagtaagagaattatgcagtgc |
| | tgccataaccatgagtgataacactgcggccaacttacttct |
| | gacaacgatcggaggaccgaaggagctaaccgcttttttgca |
| | caacatgggggatcatgtaactcgccttgatcgttgggaacc |
| | ggagctgaatgaagccataccaaacgacgagcgtgacaccac |
| | gatgcctgtagcaatggcaacaacgttgcgcaaactattaac |
| | tggcgaactacttactctagcttcccggcaacaattaataga |
| | ctggatggaggcggataaagttgcaggaccacttctgcgctc |
| | ggcccttccggctggctggtttattgctgataaatctggagc |
| | cggtgagcgtgggtctcgcggtatcattgcagcactggggcc |
| | agatggtaagccctcccgtatcgtagttatctacacgacggg |
| | gagtcaggcaactatggatgaacgaaatagacagatcgctga |
| | gataggtgcctcactgattaagcattggtaactgtcagacca |
| | agtttactcatatatactttagattgatttaaaacttcattt |
| | ttaatttaaaaggatctaggtgaagatcctttttgataatct |
| | catgaccaaaatcccttaacgtgagttttcgttccactgagc |
| | gtcagaccccgtagaaaagatcaaaggatcttcttgaaatcc |
| | tttttttctgcgcgtaatctgctgcttgcaaacaaaaaaacc |

TABLE 2-continued

Plasmid Composition
Plasmid Composition

| Elements | SEQUENCE IDENTIFIER (SEQ. ID. NO:)AND SEQUENCE INFORMATION |
|---|---|
| | accgctaccagcggtggtttgtttgccggatcaagagctacc<br>aactctttttccgaaggtaactggcttcagcagagcgcagat<br>accaaatactgttcttctagtgtagccgtagttaggccacca<br>cttcaagaactctgtagcaccgcctacatacctcgctctgct<br>aatcctgttaccagtggctgctgccagtggcgataagtcgtg<br>tcttaccgggttggactcaagacgatagttaccggataaggc<br>gcagcggtcgggctgaacggggggttcgtgcacacagcccag<br>cttggagcgaacgacctacaccgaactgagatacctacagcg<br>tgagctatgagaaagcgccacgcttcccgaagggagaaaggc<br>ggacaggtatccggtaagcggcagggtcggaacaggagagcg<br>cacgagggagcttccagggggaaacgcctggtatctttatag<br>tcctgtcgggtttcgccacctctgacttgagcgtcgattttt<br>gtgatgctcgtcaggggggcggagcctatggaaaaacgccag<br>caacgcggcctttttacggttcctggccttttgctggccttt<br>tgctcacatgtcctgcaggcag |
| INSERT OF PLASMID AG012 OCCURS AT BP 1 THROUGH 4543 OF SEQ ID NO: 33 (USED AS NEGATIVE CONTROL FOR GENE CASSETTE) | 58<br>ctgcgcgctcgctcgctcactgaggccgcccgggcgtcgggc<br>gacctttggtcgcccggcctcagtgagcgagcgagcgcgcag<br>agagggagtggccaactccatcactaggggttcctgcggccg<br>cacgcgtgacgtcgtttaaacgggcccccggtgttatctcatt<br>ctttttctcctctgtaagttgacatgtgatgtgggaacaaa<br>ggggataaagtcattattttgtgctaaaatcgtaattggaga<br>ggacctcctgttagctgggctttcttctatttattgtggtgg<br>ttactggagttccttcttctagttttaggatatatatatata<br>ttttttttttttctttccctgaagatataataatatatatac<br>ttctgaagattgagattttaaattagttgtattgaaaacta<br>gctaatcagcaatttaaggctagcttgagacttatgtcttga<br>atttgtttttgtaggctccaaaaccaaggagggagtggtgca<br>tggtgtggcaacaggtaagctccattgtgcttatatccaaag<br>atgatatttaaagtatctagtgattagtgtggcccagtattc<br>aagattcctatgaaattgtaaaacaatcactgagcattctaa<br>gaacatatcagtcttattgaaactgaattctttataaagtat<br>ttttaaaaaggtaaatattgattataaataaaaaatatactt<br>gccaagaataatgagggctttgaattgataagctatgtttaa<br>tttatagtaagtgggcatttaaatattctgaccaaaaatgta<br>ttgacaaactgctgacaaaaataaaatgtgaatattgccata<br>attttaaaaaaagagtaaaatttctgttgattacagtaaaat<br>attttgaccttaaattatgttgattacaatattcctttgata<br>attcagagtgcatttcaggaaacacccttggacagtcagtaa<br>attgtttattgtatttatctttgtattgttatggtatagcta<br>tttgtacaaatattattgtgcaattattacatttctgattat<br>attattcatttggcctaaatttaccaagaatttgaacaagtc<br>aattaggtttacaatcaagaaatatcaaaaatgatgaaaagg<br>atgataatcatcatcagatgttgaggaagatgacgatgagag<br>tgccagaaatagagaaatcaaaggagaaccaaaatttaacaa<br>attaaaagcccacagacttgctgtaattaagttttctgttgt<br>aagtactccacgtttcctggcagatgtggtgaagcaaaagat<br>ataatcagaaatataatttatatgatcggaaagcattaaaca<br>caatagtgcctatacaaataaaatgttcctatcactgacttc<br>taaaatggaaatgaggacaatgatatgggaatcttaatacag<br>tgttgtggataggactaaaaacacaggagtcagatcttcttg<br>gttcaacttcctgcttactccttaccagctgtgtgtttttttg<br>caaggttcttcacctctatgtgatttagcttcctcatctata<br>aaataattcagtgaattaatgtacacaaaacatctggaaaac<br>aaaagcaaacaatatgtattttataagtgttacttatagttt<br>tatagtgaactttcttgtgcaacatttttacaactagtggag<br>aaaaatatttctttaaatgaatacttttgatttaaaaatcag<br>agtgtaaaaataaaacagactcctttgaaactagttctgtta<br>gaagttaattgtgcacctttaatgggctctgttgcaatccaa<br>cagagaagtagttaagtaagtggactatgatggcttctaggg<br>acctcctataaatatgatattgtgaagcatgattataataag<br>aactagataacagacaggtggagactccactatctgaagagg<br>gtcaacctagatgaatggtgttccatttagtagttgaggaag<br>aacccatgaggtttagaaagcagacaagcatgtggcaagttc<br>tggagtcagtggtaaaaattaaagaacccaactattactgtc<br>acctaatgatctaatggagactgtggagatgggctgcatttt<br>tttaatcttctccagaatgccaaaatgtaaacacatatctgt<br>gtgtgtgtgtgtgtgtgtgtgtgtgtgtgagagagagagaga<br>gagagagagagactgaagtttgtacaattagacattttataa<br>aatgttttctgaaggacagtggctcacaatcttaagtttcta<br>acattgtacaatgttgggagactttgtatactttattttctc<br>tttagcatattaaggaatctgagatgtcctacagtaaagaaa<br>tttgcattacatagttaaaatcagggttattcaaacttttttg<br>attattgaaacctttcttcattagttactagggttgaatgaa |

TABLE 2-continued

Plasmid Composition
Plasmid Composition

| Elements | SEQUENCE IDENTIFIER (SEQ. ID. NO:)AND SEQUENCE INFORMATION |
|---|---|
| | actagtgttccacagaaaactatgggaaatgttgctaggcag<br>taaggacatggtgatttcagcatgtgcaatatttacagcgat<br>tgcacccatggaccaccctggcagtagtgaaataaccaaaaa<br>tgctgtcataactagtatggctatgagaaacacattgggcag<br>aagcttgcctcgagcagcgctgctcgagagatctggatcata<br>atcagccataccacatttgtagaggttttacttgctttaaaa<br>aacctcccacacctccccctgaacctgaaacataaaatgaat<br>gcaattgttgttgttaacttgtttattgcagcttataatggt<br>tacaaataaagcaatagcatcacaaatttcacaaataaagca<br>tttttttcactgcattctagttgtggtttgtccaaactcatc<br>aatgtatcttatcatgtctggtaaccattctccaggttgagc<br>cagaccaatttgatggtagatttagcaaataaaaatacagga<br>cacccagttaaatgtgaatttccgatgaacagcaaatacttt<br>tttagtattaaaaaagttcacatttaggctcacgcctgtaat<br>cccagcactttgggaggccgaggcaggcagatcacctgaggt<br>caggagttcgagaccagcctggccaacatggtgaaaccccat<br>ctccactaaaaataccaaaaattagccaggcgtgctggtggg<br>cacctgtagttccagctactcaggaggctaaggcaggagaat<br>tgcttgaacctgggaggcagaggttgcagtgagctgagatcg<br>caccattgcactctagcctgggcgacaagaacaaaactccat<br>ctcaaaaaaaaaaaaaaaaaaaagttcacatttaactgggc<br>attctgtatttaattggtaatctgagatggcagggaacagca<br>tcagcatggtgtgagggataggcatttttttcattgtgtacag<br>cttgtaaatcagtatttttaaaactcaaagttaatggcttgg<br>gcatatttagaaaagagttgccgcacggacttgaaccctgta<br>ttcctaaaatctaggatcttgttctgatggtctgcacaactg<br>gctgggggtgtccagccactgtccctcttgcctgggctcccc<br>agggcagttctgtcagcctctccatttccattcctgttccag<br>caaaacccaactgatagcacagcagcatttcagcctgtctac<br>ctctgtgcccacatacctggatgtctaccagccagaaaggtg<br>gcttagatttggttcctgtgggtggattatggcccccagaac<br>ttccctgtgcttgctgggggtgtggagtggaaagagcaggaa<br>atgggggaccctccgatactctatgggggtcctccaagtctc<br>tttgtgcaagttagggtaataatcaatatggagctaagaaag<br>agaaggggaactatgctttagaacaggacactgtgccaggag<br>cattgcagaaattatatggttttcacgacagttctttttggt<br>aggtactgttattatcctcagtttgcagatgaggaaactgag<br>acccagaaaggttaaataacttgctagggtcacacaagtcat<br>aactgacaaagcctgattcaaacccaggtctccctaacttt<br>aaggtttctatgacgccagctctcctagggagtttgtcttca<br>gatgtcttggctctaggtgtcaaaaaaagacttggtgtcagg<br>caggcataggttcaagtcccaactctgtcacttaccaactgt<br>gactaggtgattgaactgaccatggaacctggtcacatgcag<br>gagcaggatggtgaagggttcttgaaggcacttaggcaggac<br>atttaggcaggagagaaaacctggaaacagaagagctgtctc<br>caaaaatacccactggggaagcaggttgtcatgtgggccatg<br>aatgggacctgttctggggtaaccacgtgcggaccgagcggc<br>cgcaggaacccctagtgatggagttggccactccctctctgc<br>gcgctcgctcgctcactgaggccgggcgaccaaaggtcgccc<br>gacgcccgggctttgcccgggcggcctcagtgagcgagcgag<br>cgcgcag |

Plasmid AG004 Composition

| | |
|---|---|
| 5' ITR | 2<br>occurs @ bp 1 through bp 119 of SEQ ID NO: 34 |
| Human RPE65 Promoter | 11<br>occurs @ bp 134 through bp 1718 of SEQ ID NO: 34 |
| Added Kozak | 5<br>occurs @ bp 1752 through 1757 of of SEQ ID NO: 34 |
| E-GFP | 24<br>occurs @ bp 1758 through bp 2477 of SEQ ID NO: 34 |
| SV40 POLYA | 8<br>occurs at bp 2535 through bp 2770 of SEQ ID NO: 34 |
| RLBP1 INTRONIC SEQUENCE AS STUFFER SEQUENCE | 14<br>occurs at bp 2778 through bp 4280 of SEQ ID NO: 34 |

TABLE 2-continued

Plasmid Composition
Plasmid Composition

| Elements | SEQUENCE IDENTIFIER (SEQ. ID. NO:) AND SEQUENCE INFORMATION |
|---|---|
| 3' ITR | 9<br>occurs at bp 4309 through bp 4438 of SEQ ID NO: 34 |
| AMP BACTERIAL BACKBONE | 15<br>occurs at bp 4439 through bp 7057 of SEQ ID NO: 34 |
| Sequence of plasmid AG004 | 34<br>ctgcgcgctcgctcgctcactgaggccgcccgggcgtcgggc<br>gacctttggtcgcccggcctcagtgagcgagcgagcgcgcag<br>agagggagtggccaactccatcactaggggttcctgcggccg<br>cacgcgttacgtaatatttattgaagtttaatattgtgtttg<br>tgatacagaagtatttgctttaattctaaataaaaattttat<br>gcttttattgctggtttaagaagatttggattatccttgtac<br>tttgaggagaagtttcttatttgaaatattttggaaacaggt<br>cttttaatgtggaaagatagatattaatctcctcttctatta<br>ctctccaagatccaacaaaagtgattataccccccaaaatat<br>gatggtagtatcttatactaccatcattttataggcataggg<br>ctcttagctgcaaataatggaactaactctaataaagcagaa<br>cgcaaatattgtaaatattagagagctaacaatctctgggat<br>ggctaaaggatggagcttggaggctacccagccagtaacaat<br>attccgggctccactgttgaatggagacactacaactgcctt<br>ggatgggcagagatattatggatgctaagccccaggtgctac<br>cattaggacttctaccactgtccctaacgggtggagcccatc<br>acatgcctatgccctcactgtaaggaaatgaagctactgttg<br>tatatcttgggaagcacttggattaattgttatacagttttg<br>ttgaagaagacccctagggtaagtagccataactgcacacta<br>aatttaaaattgttaatgagtttctcaaaaaaaatgttaagg<br>ttgttagctggtatagtatatatcttgcctgttttccaagga<br>cttctttgggcagtaccttgtctgtgctggcaagcaactgag<br>acttaatgaaagagtattggagatatgaatgaattgatgctg<br>tatactctcagagtgccaaacatataccaatggacaagaagg<br>tgaggcagagagcagacaggcattagtgacaagcaaagatat<br>gcagaatttcattctcagcaaatcaaaagtcctcaacctggt<br>tggaagaatattggcactgaatggtatcaataaggttgctag<br>agagggttagaggtgcacaatgtgcttccataacattttata<br>cttctccaatcttagcactaatcaaacatggttgaatacttt<br>gtttactataactcttacagagttataagatctgtgaagaca<br>gggacagggacaatacccatctctgtctggttcataggtggt<br>atgtaatagatattttttaaaaataagtgagttaatgaatgag<br>ggtgagaatgaaggcacagaggtattaggggggaggtgggccc<br>cagagaatggtgccaaggtccagtggggtgactgggatcagc<br>tcaggcctgacgctggccactcccacctagctcctttctttc<br>taatctgttctcattctccttgggaaggattgaggtctctgg<br>aaaacagccaaacaactgttatgggaacagcaagcccaaata<br>aagccaagcatcaggggggatctgagagctgaaagcaacttct<br>gttcccccctccctcagctgaaggggtggggaagggctcccaa<br>agccataactccttttaagggatttagaaggcataaaaaggc<br>ccctggctgagaacttccttcttcattctgcagttggtgaat<br>tccccggggatcctctagagtcgaaattcgccaccatggtga<br>gcaagggcgaggagctgttcaccggggtggtgcccatcctgg<br>tcgagctggacggcgacgtaaacggccacaagttcagcgtgt<br>ccggcgagggcgagggcgatgccacctacggcaagctgaccc<br>tgaagttcatctgcaccaccggcaagctgcccgtgccctggc<br>ccaccctcgtgaccaccctgacctacggcgtgcagtgcttca<br>gccgctaccccgaccacatgaagcagcacgacttcttcaagt<br>ccgccatgcccgaaggctacgtccaggagcgcaccatcttct<br>tcaaggacgacggcaactacaagacccgcgccgaggtgaagt<br>tcgagggcgacaccctggtgaaccgcatcgagctgaagggca<br>tcgacttcaaggaggacggcaacatcctggggcacaagctgg<br>agtacaactacaacagccacaacgtctatatcatggccgaca<br>agcagaagaacggcatcaaggtgaacttcaagatccgccaca<br>acatcgaggacggcagcgtgcagctcgccgaccactaccagc<br>agaacacccccatcggcgacggccccgtgctgctgcccgaca<br>accactacctgagcacccagtccgccctgagcaaagacccca<br>acgagaagcgcgatcacatggtcctgctggagttcgtgaccg<br>ccgccgggatcactctcggcatggacgagctgtacaagtaat<br>agggtaccggtcgacctgcagaagcttgcctcgagcagcgct<br>gctcgagagatctggatcataatcagccataccacatttgta<br>gaggttttacttgctttaaaaaacctcccacacctccccctg<br>aacctgaaacataaaatgaatgcaattgttgttgttaacttg<br>tttattgcagcttataatggttacaaataaagcaatagcatc<br>acaaatttcacaaataaagcatttttttcactgcattctagt<br>tgtggtttgtccaaactcatcaatgtatcttatcatgtctgg<br>taaccattctccaggttgagccagaccaatttgatggtagat |

TABLE 2-continued

Plasmid Composition
Plasmid Composition

| Elements | SEQUENCE IDENTIFIER (SEQ. ID. NO:)AND SEQUENCE INFORMATION |
|---|---|
| | ttagcaaataaaaatacaggacacccagttaaatgtgaattt |
| | ccgatgaacagcaaatactttttagtattaaaaagttcac |
| | atttaggctcacgcctgtaatcccagcactttgggaggccga |
| | ggcaggcagatcacctgaggtcaggagttcgagaccagcctg |
| | gccaacatggtgaaaccccatctccactaaaaataccaaaaa |
| | ttagccaggcgtgctggtgggcacctgtagttccagctactc |
| | aggaggctaaggcaggagaattgcttgaacctgggaggcaga |
| | ggttgcagtgagctgagatcgcaccattgcactctagcctgg |
| | gcgacaagaacaaaactccatctcaaaaaaaaaaaaaaaaaa |
| | aaagttcacatttaactgggcattctgtatttaattggtaat |
| | ctgagatggcagggaacagcatcagcatggtgtgagggatag |
| | gcatttttcattgtgtacagcttgtaaatcagtattttaa |
| | aactcaaagttaatggcttgggcatatttagaaaagagttgc |
| | cgcacggacttgaaccctgtattcctaaaatctaggatcttg |
| | ttctgatggtctgcacaactggctgggggtgtccagccactg |
| | tccctcttgcctgggctccccagggcagttctgtcagcctct |
| | ccatttccattcctgttccagcaaaacccaactgatagcaca |
| | gcagcatttcagcctgtctacctctgtgcccacatacctgga |
| | tgtctaccagccagaaaggtggcttagatttggttcctgtgg |
| | gtggattatggcccccagaacttccctgtgcttgctgggggt |
| | gtggagtggaaagagcaggaaatgggggaccctccgatactc |
| | tatgggggtcctccaagtctctttgtgcaagttagggtaata |
| | atcaatatggagctaagaaagagaaggggaactatgctttag |
| | aacaggacactgtgccaggagcattgcagaaattatatggtt |
| | ttcacgacagttctttttggtaggtactgttattatcctcag |
| | tttgcagatgaggaaactgagacccagaaaggttaaataact |
| | tgctagggtcacacaagtcataactgacaaagcctgattcaa |
| | acccaggtctccctaacctttaaggtttctatgacgccagct |
| | ctcctagggagtttgtcttcagatgtcttggctctaggtgtc |
| | aaaaaaagacttggtgtcaggcaggcataggttcaagtccca |
| | actctgtcacttaccaactgtgactaggtgattgaactgacc |
| | atggaacctggtcacatgcaggagcaggatggtgaagggttc |
| | ttgaaggcacttaggcaggacatttaggcaggagagaaaacc |
| | tggaaacagaagagctgtctccaaaaatacccactggggaag |
| | caggttgtcatgtgggccatgaatgggacctgttctggggta |
| | accacgtgcggaccgagcggccgcaggaacccctagtgatgg |
| | agttggccactccctctctgcgcgctcgctcgctcactgagg |
| | ccgggcgaccaaaggtcgcccgacgcccgggctttgcccggg |
| | cggcctcagtgagcgagcgagcgcgcagctgcctgcaggggc |
| | gcctgatgcggtattttctccttacgcatctgtgcggtattt |
| | cacaccgcatacgtcaaagcaaccatagtacgcgccctgtag |
| | cggcgcattaagcgcggcgggtgtggtggttacgcgcagcgt |
| | gaccgctacacttgccagcgccttagcgcccgctcctttcgc |
| | tttcttcccttcctttctcgccacgttcgccggctttccccg |
| | tcaagctctaaatcgggggctccctttagggttccgatttag |
| | tgctttacggcacctcgaccccaaaaaacttgatttgggtga |
| | tggttcacgtagtgggccatcgccctgatagacggtttttcg |
| | ccctttgacgttggagtccacgttctttaatagtggactctt |
| | gttccaaactggaacaacactcaactctatctcggctattc |
| | ttttgatttataagggattttgccgatttcggtctattggtt |
| | aaaaaatgagctgatttaacaaaaatttaacgcgaattttaa |
| | caaaatattaacgtttacaattttatggtgcactctcagtac |
| | aatctgctctgatgccgcatagttaagccagccccgacaccc |
| | gccaacacccgctgacgcgccctgacgggcttgtctgctccc |
| | ggcatccgcttacagacaagctgtgaccgtctccgggagctg |
| | catgtgtcagaggttttcaccgtcatcaccgaaacgcgcgag |
| | acgaaagggcctcgtgatacgcctatttttataggttaatgt |
| | catgataataatggtttcttagacgtcaggtggcacttttcg |
| | gggaaatgtgcgcggaacccctatttgtttatttttctaaat |
| | acattcaaatatgtatccgctcatgagacaataaccctgata |
| | aatgcttcaataatattgaaaaaggaagagtatgagtattca |
| | acatttccgtgtcgcccttattcccttttttgcggcattttg |
| | ccttcctgtttttgctcacccagaaacgctggtgaaagtaaa |
| | agatgctgaagatcagttgggtgcacgagtgggttacatcga |
| | actggatctcaacagcggtaagatccttgagagttttcgccc |
| | cgaagaacgttttccaatgatgagcacttttaaagttctgct |
| | atgtggcgcggtattatcccgtattgacgccgggcaagagca |
| | actcggtcgccgcatacactattctcagaatgacttggttga |
| | gtactcaccagtcacagaaaagcatcttacggatggcatgac |
| | agtaagagaattatgcagtgctgccataaccatgagtgataa |
| | cactgcggccaacttacttctgacaacgatcggaggaccgaa |
| | ggagctaaccgcttttttgcacaacatgggggatcatgtaac |
| | tcgccttgatcgttgggaaccggagctgaatgaagccatacc |
| | aaacgacgagcgtgacaccacgatgcctgtagcaatggcaac |

TABLE 2-continued

Plasmid Composition
Plasmid Composition

| Elements | SEQUENCE IDENTIFIER (SEQ. ID. NO:) AND SEQUENCE INFORMATION |
|---|---|
| | aacgttgcgcaaactattaactggcgaactacttactctagc ttcccggcaacaattaatagactggatggaggcggataaagt tgcaggaccacttctgcgctcggcccttccggctggctggtt tattgctgataaatctggagccggtgagcgtgggtctcgcgg tatcattgcagcactggggccagatggtaagccctcccgtat cgtagttatctacacgacggggagtcaggcaactatggatga acgaaatagacagatcgctgagataggtgcctcactgattaa gcattggtaactgtcagaccaagtttactcatatatacttta gattgatttaaaacttcatttttaatttaaaaggatctaggt gaagatcctttttgataatctcatgaccaaaatcccttaacg tgagttttcgttccactgagcgtcagaccccgtagaaaagat caaaggatcttcttgaaatcctttttttctgcgcgtaatctg ctgcttgcaaacaaaaaaaccaccgctaccagcggtggtttg tttgccggatcaagagctaccaactctttttccgaaggtaac tggcttcagcagagcgcagataccaaatactgttcttctagt gtagccgtagttaggccaccacttcaagaactctgtagcacc gcctacatacctcgctctgctaatcctgttaccagtggctgc tgccagtggcgataagtcgtgtcttaccgggttggactcaag acgatagttaccggataaggcgcagcggtcgggctgaacggg gggttcgtgcacacagcccagcttggagcgaacgacctacac cgaactgagatacctacagcgtgagctatgagaaagcgccac gcttcccgaagggagaaaggcggacaggtatccggtaagcgg cagggtcggaacaggagagcgcacgagggagcttccaggggg aaacgcctggtatctttatagtcctgtcgggtttcgccacct ctgacttgagcgtcgatttttgtgatgctcgtcaggggggcg gagcctatggaaaaacgccagcaacgcggcctttttacggtt cctggccttttgctggccttttgctcacatgtcctgcaggca g |
| GENE CASSETTE AG004 OCCURS AT BP 1 THROUGH 4438 OF SEQ ID NO: 34 | 59<br>ctgcgcgctcgctcgctcactgaggccgcccgggcgtcgggc gacctttggtcgcccggcctcagtgagcgagcgagcgcgcag agagggagtggccaactccatcactaggggttcctgcggccg cacgcgttacgtaatatttattgaagtttaatattgtgtttg tgatacagaagtatttgctttaattctaaataaaaattttat gcttttattgctggtttaagaagatttggattatccttgtac tttgaggagaagtttcttatttgaaatattttggaaacaggt cttttaatgtggaaagatagatattaatctcctcttctatta ctctccaagatccaacaaaagtgattataccccccaaaatat gatggtagtatcttatactaccatcattttataggcataggg ctcttagctgcaaataatggaactaactctaataaagcagaa cgcaaatattgtaaatattagagagctaacaatctctgggat ggctaaaggatggagcttggaggctacccagccagtaacaat attccgggctccactgttgaatggagacactacaactgcctt ggatgggcagagatattatggatgctaagccccaggtgctac cattaggacttctaccactgtccctaacgggtggagcccatc acatgcctatgccctcactgtaaggaaatgaagctactgttg tatatcttgggaagcacttggattaattgttatacagttttg ttgaagaagacccctagggtaagtagccataactgcacacta aatttaaaattgttaatgagtttctcaaaaaaaatgttaagg ttgttagctggtatagtatatatcttgcctgttttccaagga cttctttgggcagtaccttgtctgtgctggcaagcaactgag acttaatgaaagagtattggagatatgaatgaattgatgctg tatactctcagagtgccaaacatataccaatggacaagaagg tgaggcagagagcagacaggcattagtgacaagcaaagatat gcagaatttcattctcagcaaatcaaaagtcctcaacctggt tggaagaatattggcactgaatggtatcaataaggttgctag agagggttagaggtgcacaatgtgcttccataacattttata cttctccaatcttagcactaatcaaacatggttgaatacttt gtttactataactcttacagagttataagatctgtgaagaca gggacagggacaatacccatctctgtctggttcataggtggt atgtaatagatatttttaaaaataagtgagttaatgaatgag ggtgagaatgaaggcacagaggtattaggggggaggtgggccc cagagaatggtgccaaggtccagtggggtgactgggatcagc tcaggcctgacgctggccactcccacctagctcctttctttc taatctgttctcattctccttgggaaggattgaggtctctgg aaaacagccaaacaactgttatgggaacagcaagcccaaata aagccaagcatcaggggggatctgagagctgaaagcaacttct gttcccccctccctcagctgaaggggtggggaagggctcccaa agccataactccttttaagggatttagaaggcataaaaaggc ccctggctgagaacttccttcttcattctgcagttggtgaat tccccggggatcctctagagtcgaaattcgccaccatggtga gcaagggcgaggagctgttcaccggggtggtgcccatcctgg tcgagctggacggcgacgtaaacggccacaagttcagcgtgt ccggcgagggcgagggcgatgccacctacggcaagctgaccc |

TABLE 2-continued

Plasmid Composition
Plasmid Composition

| Elements | SEQUENCE IDENTIFIER (SEQ. ID. NO:)AND SEQUENCE INFORMATION |
|---|---|
| | tgaagttcatctgcaccaccggcaagctgcccgtgccctggc<br>ccaccctcgtgaccaccctgacctacggcgtgcagtgcttca<br>gccgctaccccgaccacatgaagcagcacgacttcttcaagt<br>ccgccatgcccgaaggctacgtccaggagcgcaccatcttct<br>tcaaggacgacggcaactacaagacccgcgccgaggtgaagt<br>tcgagggcgacaccctggtgaaccgcatcgagctgaagggca<br>tcgacttcaaggaggacggcaacatcctggggcacaagctgg<br>agtacaactacaacagccacaacgtctatatcatggccgaca<br>agcagaagaacggcatcaaggtgaacttcaagatccgccaca<br>acatcgaggacggcagcgtgcagctcgccgaccactaccagc<br>agaacacccccatcggcgacggccccgtgctgctgcccgaca<br>accactacctgagcacccagtccgccctgagcaaagacccca<br>acgagaagcgcgatcacatggtcctgctggagttcgtgaccg<br>ccgccgggatcactctcggcatggacgagctgtacaagtaat<br>agggtaccggtcgacctgcagaagcttgcctcgagcagcgct<br>gctcgagagatctggatcataatcagccataccacatttgta<br>gaggttttacttgctttaaaaaacctcccacacctccccctg<br>aacctgaaacataaaatgaatgcaattgttgttgttaacttg<br>tttattgcagcttataatggttacaaataaagcaatagcatc<br>acaaatttcacaaataaagcatttttttcactgcattctagt<br>tgtggtttgtccaaactcatcaatgtatcttatcatgtctgg<br>taaccattctccaggttgagccagaccaatttgatggtagat<br>ttagcaaataaaaatacaggacacccagttaaatgtgaattt<br>ccgatgaacagcaaatactttttttagtattaaaaaagttcac<br>atttaggctcacgcctgtaatcccagcactttgggaggccga<br>ggcaggcagatcacctgaggtcaggagttcgagaccagcctg<br>gccaacatggtgaaaccccatctccactaaaaataccaaaaa<br>ttagccaggcgtgctggtgggcacctgtagttccagctactc<br>aggaggctaaggcaggagaattgcttgaacctgggaggcaga<br>ggttgcagtgagctgagatcgcaccattgcactctagcctgg<br>gcgacaagaacaaaactccatctcaaaaaaaaaaaaaaaaaa<br>aaagttcacatttaactgggcattctgtatttaattggtaat<br>ctgagatggcagggaacagcatcagcatggtgtgagggatag<br>gcatttttttcattgtgtacagcttgtaaatcagtatttttaa<br>aactcaaagttaatggcttgggcatatttagaaaagagttgc<br>cgcacggacttgaaccctgtattcctaaaatctaggatcttg<br>ttctgatggtctgcacaactggctgggggtgtccagccactg<br>tccctcttgcctgggctccccagggcagttctgtcagcctct<br>ccatttccattcctgttccagcaaaacccaactgatagcaca<br>gcagcatttcagcctgtctacctctgtgcccacatacctgga<br>tgtctaccagccagaaaggtggcttagatttggttcctgtgg<br>gtggattatggcccccagaacttccctgtgcttgctgggggt<br>gtggagtggaaagagcaggaaatgggggaccctccgatactc<br>tatgggggtcctccaagtctctttgtgcaagttagggtaata<br>atcaatatggagctaagaaagagaaggggaactatgctttag<br>aacaggacactgtgccaggagcattgcagaaattatatggtt<br>ttcacgacagttctttttggtaggtactgttattatcctcag<br>tttgcagatgaggaaactgagacccagaaaggttaaataact<br>tgctagggtcacacaagtcataactgacaaagcctgattcaa<br>acccaggtctccctaacctttaaggtttctatgacgccagct<br>ctcctagggagtttgtcttcagatgtcttggctctaggtgtc<br>aaaaaaagacttggtgtcaggcaggcataggttcaagtccca<br>actctgtcacttaccaactgtgactaggtgattgaactgacc<br>atggaacctggtcacatgcaggagcaggatggtgaagggttc<br>ttgaaggcacttaggcaggacatttaggcaggagagaaaacc<br>tggaaacagaagagctgtctccaaaaatacccactggggaag<br>caggttgtcatgtgggccatgaatgggacctgttctggggta<br>accacgtgcggaccgagcggccgcaggaacccctagtgatgg<br>agttggccactccctctctgcgcgctcgctcgctcactgagg<br>ccgggcgaccaaaggtcgcccgacgcccgggctttgcccggg<br>cggcctcagtgagcgagcgagcgcgcag |

Plasmid AG006 Composition

| | |
|---|---|
| 5' ITR | 2<br>occurs @ bp 1 through bp 119 of SEQ ID NO: 35 |
| Human VMD2 Promoter | 12<br>occurs @ bp 134 through bp 761 of SEQ ID NO: 35 |
| Added Kozak | 5<br>occurs @ bp 795 through 800 of SEQ ID NO: 34 |

TABLE 2-continued

Plasmid Composition
Plasmid Composition

| Elements | SEQUENCE IDENTIFIER (SEQ. ID. NO:) AND SEQUENCE INFORMATION |
|---|---|
| E-GFP | 24<br>occurs @ bp 801 through bp 1520 of SEQ ID NO: 35 |
| SV40 POLYA | 8<br>occurs at bp 1578 through bp 1813 of SEQ ID NO: 35 |
| RLBP1 INTRONIC SEQUENCE AS STUFFER SEQUENCE | 14<br>occurs at bp 1821 through bp 3323 of SEQ ID NO: 35 |
| 3' ITR | 9<br>occurs at bp 3352 through bp 3481 of SEQ ID NO: 35 |
| AMP BACTERIAL BACKBONE | 15<br>occurs at bp 3482 through bp 6100 of SEQ ID NO: 35 |
| Sequence of plasmid AG006 | 35<br>ctgcgcgctcgctcgctcactgaggccgcccgggcgtcgggc<br>gacctttggtcgcccggcctcagtgagcgagcgagcgcgcag<br>agagggagtggccaactccatcactaggggttcctgcggccg<br>cacgcgttacgtaattctgtcattttactagggtgatgaaat<br>tcccaagcaacaccatccttttcagataagggcactgaggct<br>gagagaggagctgaaacctacccggcgtcaccacacacaggt<br>ggcaaggctgggaccagaaaccaggactgttgactgcagccc<br>ggtattcattctttccatagcccacagggctgtcaaagaccc<br>cagggcctagtcagaggctcctccttcctggagagttcctgg<br>cacagaagttgaagctcagcacagccccctaacccccaactc<br>tctctgcaaggcctcaggggtcagaacactggtggagcagat<br>cctttagcctctggattttagggccatggtagagggggtgtt<br>gccctaaattccagccctggtctcagcccaacaccctccaag<br>aagaaattagaggggccatggccaggctgtgctagccgttgc<br>ttctgagcagattacaagaagggactaagacaaggactcctt<br>tgtggaggtcctggcttagggagtcaagtgacggcggctcag<br>cactcacgtgggcagtgccagcctctaagagtgggcaggggc<br>actggccacagagtcccagggagtcccaccagcctagtcgcc<br>agaccgaattccccggggatcctctagagtcgaaattcgcca<br>ccatggtgagcaagggcgaggagctgttcaccggggtggtgc<br>ccatcctggtcgagctggacggcgacgtaaacggccacaagt<br>tcagcgtgtccggcgagggcgagggcgatgccacctacggca<br>agctgaccctgaagttcatctgcaccaccggcaagctgcccg<br>tgccctggcccaccctcgtgaccaccctgacctacggcgtgc<br>agtgcttcagccgctaccccgaccacatgaagcagcacgact<br>tcttcaagtccgccatgcccgaaggctacgtccaggagcgca<br>ccatcttcttcaaggacgacggcaactacaagacccgcgccg<br>aggtgaagttcgagggcgacaccctggtgaaccgcatcgagc<br>tgaagggcatcgacttcaaggaggacggcaacatcctggggc<br>acaagctggagtacaactacaacagccacaacgtctatatca<br>tggccgacaagcagaagaacggcatcaaggtgaacttcaaga<br>tccgccacaacatcgaggacggcagcgtgcagctcgccgacc<br>actaccagcagaacacccccatcggcgacggccccgtgctgc<br>tgcccgacaaccactacctgagcacccagtccgccctgagca<br>aagaccccaacgagaagcgcgatcacatggtcctgctggagt<br>tcgtgaccgccgccgggatcactctcggcatggacgagctgt<br>acaagtaatagggtaccggtcgacctgcagaagcttgcctcg<br>agcagcgctgctcgagagatctggatcataatcagccatacc<br>acatttgtagaggttttacttgctttaaaaaacctcccacac<br>ctccccctgaacctgaaacataaaatgaatgcaattgttgtt<br>gttaacttgtttattgcagcttataatggttacaaataaagc<br>aatagcatcacaaatttcacaaataaagcatttttttcactg<br>cattctagttgtggtttgtccaaactcatcaatgtatcttat<br>catgtctggtaaccattctccaggttgagccagaccaatttg<br>atggtagatttagcaaataaaaatacaggacacccagttaaa<br>tgtgaatttccgatgaacagcaaatactttttttagtattaaa<br>aaagttcacatttaggctcacgcctgtaatcccagcactttg<br>ggaggccgaggcaggcagatcacctgaggtcaggagttcgag<br>accagcctggccaacatggtgaaaccccatctccactaaaaa<br>taccaaaaattagccaggcgtgctggtgggcacctgtagttc<br>cagctactcaggaggctaaggcaggagaattgcttgaacctg<br>ggaggcagaggttgcagtgagctgagatcgcaccattgcact<br>ctagcctgggcgacaagaacaaaactccatctcaaaaaaaaa<br>aaaaaaaaaaaagttcacatttaactgggcattctgtattta<br>attggtaatctgagatggcagggaacagcatcagcatggtgt<br>gagggataggcatttttttcattgtgtacagcttgtaaatcag<br>tatttttaaaactcaaagttaatggcttgggcatatttagaa |

TABLE 2-continued

| Plasmid Composition | |
|---|---|
| Plasmid Composition | |
| Elements | SEQUENCE IDENTIFIER (SEQ. ID. NO:) AND SEQUENCE INFORMATION |
| | aagagttgccgcacggacttgaaccctgtattcctaaaatct<br>aggatcttgttctgatggtctgcacaactggctgggggtgtc<br>cagccactgtccctcttgcctgggctccccagggcagttctg<br>tcagcctctccatttccattcctgttccagcaaaacccaact<br>gatagcacagcagcatttcagcctgtctacctctgtgcccac<br>atacctggatgtctaccagccagaaaggtggcttagatttgg<br>ttcctgtgggtggattatggcccccagaacttccctgtgctt<br>gctggggggtgtggagtggaaagagcaggaaatgggggaccct<br>ccgatactctatgggggtcctccaagtctctttgtgcaagtt<br>agggtaataatcaatatggagctaagaaagagaaggggaact<br>atgctttagaacaggacactgtgccaggagcattgcagaaat<br>tatatggttttcacgacagttctttttggtaggtactgttat<br>tatcctcagtttgcagatgaggaaactgagacccagaaaggt<br>taaataacttgctagggtcacacaagtcataactgacaaagc<br>ctgattcaaacccaggtctccctaacctttaaggtttctatg<br>acgccagctctcctagggagtttgtcttcagatgtcttggct<br>ctaggtgtcaaaaaaagacttggtgtcaggcaggcataggtt<br>caagtcccaactctgtcacttaccaactgtgactaggtgatt<br>gaactgaccatggaacctggtcacatgcaggagcaggatggt<br>gaagggttcttgaaggcacttaggcaggacatttaggcagga<br>gagaaaacctggaaacagaagagctgtctccaaaaataccca<br>ctggggaagcaggttgtcatgtgggccatgaatgggacctgt<br>tctggggtaaccacgtgcggaccgagcggccgcaggaacccc<br>tagtgatggagttggccactccctctctgcgcgctcgctcgc<br>tcactgaggccgggcgaccaaaggtcgcccgacgcccgggct<br>ttgcccgggcggcctcagtgagcgagcgagcgcgcagctgcc<br>tgcaggggcgcctgatgcggtattttctccttacgcatctgt<br>gcggtatttcacaccgcatacgtcaaagcaaccatagtacgc<br>gccctgtagcggcgcattaagcgcggcgggtgtggtggttac<br>gcgcagcgtgaccgctacacttgccagcgccttagcgcccgc<br>tcctttcgctttcttcccttcctttctcgccacgttcgccgg<br>ctttccccgtcaagctctaaatcgggggctccctttagggtt<br>ccgatttagtgctttacggcacctcgaccccaaaaaacttga<br>tttgggtgatggttcacgtagtgggccatcgccctgatagac<br>ggtttttcgccctttgacgttggagtccacgttctttaatag<br>tggactcttgttccaaactggaacaacactcaactctatctc<br>gggctattcttttgatttataagggattttgccgatttcggt<br>ctattggttaaaaaatgagctgatttaacaaaaatttaacgc<br>gaattttaacaaaatattaacgtttacaattttatggtgcac<br>tctcagtacaatctgctctgatgccgcatagttaagccagcc<br>ccgacacccgccaacacccgctgacgcgccctgacgggcttg<br>tctgctcccggcatccgcttacagacaagctgtgaccgtctc<br>cgggagctgcatgtgtcagaggttttcaccgtcatcaccgaa<br>acgcgcgagacgaaagggcctcgtgatacgcctatttttata<br>ggttaatgtcatgataataatggtttcttagacgtcaggtgg<br>cacttttcggggaaatgtgcgcggaacccctatttgtttatt<br>tttctaaatacattcaaatatgtatccgctcatgagacaata<br>accctgataaatgcttcaataatattgaaaaaggaagagtat<br>gagtattcaacatttccgtgtcgcccttattcccttttttgc<br>ggcattttgccttcctgtttttgctcacccagaaacgctggt<br>gaaagtaaaagatgctgaagatcagttgggtgcacgagtggg<br>ttacatcgaactggatctcaacagcggtaagatccttgagag<br>ttttcgccccgaagaacgttttccaatgatgagcacttttaa<br>agttctgctatgtggcgcggtattatcccgtattgacgccgg<br>gcaagagcaactcggtcgccgcatacactattctcagaatga<br>cttggttgagtactcaccagtcacagaaaagcatcttacgga<br>tggcatgacagtaagagaattatgcagtgctgccataaccat<br>gagtgataacactgcggccaacttacttctgacaacgatcgg<br>aggaccgaaggagctaaccgcttttttgcacaacatgggga<br>tcatgtaactcgccttgatcgttgggaaccggagctgaatga<br>agccataccaaacgacgagcgtgacaccacgatgcctgtagc<br>aatggcaacaacgttgcgcaaactattaactggcgaactact<br>tactctagcttcccggcaacaattaatagactggatggaggc<br>ggataaagttgcaggaccacttctgcgctcggcccttccggc<br>tggctggtttattgctgataaatctggagccggtgagcgtgg<br>gtctcgcggtatcattgcagcactggggccagatggtaagcc<br>ctcccgtatcgtagttatctacacgacggggagtcaggcaac<br>tatggatgaacgaaatagacagatcgctgagataggtgcctc<br>actgattaagcattggtaactgtcagaccaagtttactcata<br>tatactttagattgatttaaaacttcatttttaatttaaaag<br>gatctaggtgaagatcctttttgataatctcatgaccaaaat<br>cccttaacgtgagttttcgttccactgagcgtcagaccccgt<br>agaaaagatcaaaggatcttcttgaaatcctttttttctgcg<br>cgtaatctgctgcttgcaaacaaaaaaaccaccgctaccagc |

TABLE 2-continued

Plasmid Composition
Plasmid Composition

| Elements | SEQUENCE IDENTIFIER (SEQ. ID. NO:) AND SEQUENCE INFORMATION |
|---|---|
| | ggtggtttgtttgccggatcaagagctaccaactctttttcc<br>gaaggtaactggcttcagcagagcgcagataccaaatactgt<br>tcttctagtgtagccgtagttaggccaccacttcaagaactc<br>tgtagcaccgcctacatacctcgctctgctaatcctgttacc<br>agtggctgctgccagtggcgataagtcgtgtcttaccgggtt<br>ggactcaagacgatagttaccggataaggcgcagcggtcggg<br>ctgaacggggggttcgtgcacacagcccagcttggagcgaac<br>gacctacaccgaactgagatacctacagcgtgagctatgaga<br>aagcgccacgcttcccgaagggagaaaggcggacaggtatcc<br>ggtaagcggcagggtcggaacaggagagcgcacgagggagct<br>tccagggggaaacgcctggtatctttatagtcctgtcgggtt<br>tcgccacctctgacttgagcgtcgatttttgtgatgctcgtc<br>aggggggcggagcctatggaaaaacgccagcaacgcggcctt<br>tttacggttcctggccttttgctggcctcttgctcacatgtc<br>ctgcaggcag |
| GENE CASSETTE OF PLASMID AG006 OCCURS AT BP 1 THROUGH 3481 OF SEQ ID NO: 35 | 60<br>ctgcgcgctcgctcgctcactgaggccgcccgggcgtcgggc<br>gacctttggtcgcccggcctcagtgagcgagcgagcgcgcag<br>agagggagtggccaactccatcactaggggttcctgcggccg<br>cacgcgttacgtaattctgtcattttactagggtgatgaaat<br>tcccaagcaacaccatccttttcagataagggcactgaggct<br>gagagaggagctgaaacctacccggcgtcaccacacacaggt<br>ggcaaggctgggaccagaaaccaggactgttgactgcagccc<br>ggtattcattctttccatagcccacagggctgtcaaagaccc<br>cagggcctagtcagaggctcctccttcctggagagttcctgg<br>cacagaagttgaagctcagcacagccccctaaccccaactc<br>tctctgcaaggcctcaggggtcagaacactggtggagcagat<br>cctctagcctctggattttagggccatggtagaggggtgtt<br>gccctaaattccagccctggtctcagcccaacaccctccaag<br>aagaaattagaggggccatggccaggctgtgctagccgttgc<br>ttctgagcagattacaagaagggactaagacaaggactcctt<br>tgtggaggtcctggcttagggagtcaagtgacggcggctcag<br>cactcacgtgggcagtgccagcctctaagagtgggcaggggc<br>actggccacagagtcccagggagtcccaccagcctagtcgcc<br>agaccgaattccccggggatcctctagagtcgaaattcgcca<br>ccatggtgagcaagggcgaggagctgttcaccggggtggtgc<br>ccatcctggtcgagctggacggcgacgtaaacggccacaagt<br>tcagcgtgtccggcgagggcgagggcgatgccacctacggca<br>agctgaccctgaagttcatctgcaccaccggcaagctgcccg<br>tgccctggcccaccctcgtgaccaccctgacctacggcgtgc<br>agtgcttcagccgctaccccgaccacatgaagcagcacgact<br>tcttcaagtccgccatgcccgaaggctacgtccaggagcgca<br>ccatcttcttcaaggacgacggcaactacaagacccgcgccg<br>aggtgaagttcgagggcgacaccctggtgaaccgcatcgagc<br>tgaagggcatcgacttcaaggaggacggcaacatcctggggc<br>acaagctggagtacaactacaacagccacaacgtctatatca<br>tggccgacaagcagaagaacggcatcaaggtgaacttcaaga<br>tccgccacaacatcgaggacggcagcgtgcagctcgccgacc<br>actaccagcagaacacccccatcggcgacggccccgtgctgc<br>tgcccgacaaccactacctgagcacccagtccgccctgagca<br>aagaccccaacgagaagcgcgatcacatggtcctgctggagt<br>tcgtgaccgccgccgggatcactctcggcatggacgagctgt<br>acaagtaatagggtaccggtcgacctgcagaagcttgcctcg<br>agcagcgctgctcgagagatctggatcataatcagccatacc<br>acatttgtagaggttttacttgctttaaaaaacctcccacac<br>ctccccctgaacctgaaacataaaatgaatgcaattgttgtt<br>gttaacttgtttattgcagcttataatggttacaaataaagc<br>aatagcatcacaaatttcacaaataaagcatttttttcactg<br>cattctagttgtggtttgtccaaactcatcaatgtatcttat<br>catgtctggtaaccattctccaggttgagccagaccaatttg<br>atggtagatttagcaaataaaaatacaggacacccagttaaa<br>tgtgaatttccgatgaacagcaaatactttttttagtattaaa<br>aaagttcacatttaggctcacgcctgtaatcccagcactttg<br>ggaggccgaggcaggcagatcacctgaggtcaggagttcgag<br>accagcctggccaacatggtgaaaccccatctccactaaaaa<br>taccaaaaattagccaggcgtgctggtgggcacctgtagttc<br>cagctactcaggaggctaaggcaggagaattgcttgaacctg<br>ggaggcagaggttgcagtgagctgagatcgcaccattgcact<br>ctagcctgggcgacaagaacaaaactccatctcaaaaaaaaa<br>aaaaaaaaaaaagttcacatttaactgggcattctgtattta<br>attggtaatctgagatggcagggaacagcatcagcatggtgt<br>gagggataggcatttttttcattgtgtacagcttgtaaatcag<br>tatttttaaaactcaaagttaatggcttgggcatatttagaa<br>aagagttgccgcacggacttgaaccctgtattcctaaaatct |

TABLE 2-continued

Plasmid Composition

Plasmid Composition

| Elements | SEQUENCE IDENTIFIER (SEQ. ID. NO:)AND SEQUENCE INFORMATION |
|---|---|
| | aggatcttgttctgatggtctgcacaactggctgggggtgtc<br>cagccactgtccctcttgcctgggctccccagggcagttctg<br>tcagcctctccatttccattcctgttccagcaaaacccaact<br>gatagcacagcagcatttcagcctgtctacctctgtgcccac<br>atacctggatgtctaccagccagaaaggtggcttagatttgg<br>ttcctgtgggtggattatggcccccagaacttccctgtgctt<br>gctgggggtgtggagtggaaagagcaggaaatgggggaccct<br>ccgatactctatgggggtcctccaagtctctttgtgcaagtt<br>agggtaataatcaatatggagctaagaaagagaaggggaact<br>atgctttagaacaggacactgtgccaggagcattgcagaaat<br>tatatggttttcacgacagttctttttggtaggtactgttat<br>tatcctcagtttgcagatgaggaaactgagacccagaaaggt<br>taaataacttgctagggtcacacaagtcataactgacaaagc<br>ctgattcaaacccaggtctccctaacctttaaggtttctatg<br>acgccagctctcctagggagtttgtcttcagatgtcttggct<br>ctaggtgtcaaaaaaagacttggtgtcaggcaggcataggtt<br>caagtcccaactctgtcacttaccaactgtgactaggtgatt<br>gaactgaccatggaacctggtcacatgcaggagcaggatggt<br>gaagggttcttgaaggcacttaggcaggacatttaggcagga<br>gagaaaacctggaaacagaagagctgtctccaaaaataccca<br>ctggggaagcaggttgtcatgtgggccatgaatgggacctgt<br>tctggggtaaccacgtgcggaccgagcggccgcaggaacccc<br>tagtgatggagttggccactccctctctgcgcgctcgctcgc<br>tcactgaggccgggcgaccaaaggtcgcccgacgcccgggct<br>ttgcccgggcggcctcagtgagcgagcgagcgcgcag |

Plasmid TM042 Composition

| | |
|---|---|
| ΔITR | 1<br>occurs at bp 4 through bp 106 of SEQ ID NO: 50 |
| Human RLBP1 Promoter(short) | 3<br>Occurs at bp 119 through bp 708 of SEQ ID NO: 50 |
| MODIFIED SV40INTRON | 4<br>occurs at bp 723 through bp 905 of SEQ ID NO: 50 |
| Added Kozak | 5<br>occurs at bp 919 through bp 924 of SEQ ID NO: 50 |
| HUMAN RLBP1 GENE CDS | 6<br>occurs at bp 925 through bp 1878 of SEQ ID NO: 50 |
| SV40 POLYA | 8<br>occurs at bp 1937 through bp 2172 of SEQ ID NO: 50 |
| 3' ITR | 9<br>occurs at bp 2201 through bp 2330 of SEQ ID NO: 50 |
| KAN-R BACTERIAL BACKBONE | 49<br>occurs at bp 2331 through bp 4989 of SEQ ID NO: 50 |
| Sequence of plasmid TM042 | 50<br>ctgcgcgctcgctcgctcactgaggccgcccgggcaaagccc<br>gggcgtcgggcgacctttggtcgcccggcctcagtgagcgag<br>cgagcgcgcagagagggagtggggtaccacgcgtttgtcctc<br>tccctgcttggccttaaccagccacatttctcaactgacccc<br>actcactgcagaggtgaaaactaccatgccaggtcctgctgg<br>ctgggggaggggtgggcaataggcctggatttgccagagctg<br>ccactgtagatgtagtcatatttacgatttcccttcacctct<br>tattaccctggtggtggtggtgggggggggggggtgctctct<br>cagcaaccccaccccgggatcttgaggagaaagagggcagag<br>aaaagagggaatgggactggcccagatcccagccccacagcc<br>gggcttccacatggccgagcaggaactccagagcaggagcac<br>acaaaggagggctttgatgcgcctccagccaggcccaggcct<br>ctcccctctcccctttctctctgggtcttcctttgccccact<br>gagggcctcctgtgagcccgatttaacggaaactgtgggcgg<br>tgagaagttccttatgacacactaatcccaacctgctgaccg<br>gaccacgcctccagcggagggaacctctagagctccaggaca<br>ttcaggtaccaggtagccccaaggaggagctgccgaatcgat<br>ggatcgggaactgaaaaaccagaaagttaactggtaagttta<br>gtctttttgtcttttatttcaggtcccggatccggtggtggt<br>gcaaatcaaagaactgctcctcagtggatgttgcctttactt<br>ctaggcctgtacggaagtgttacttctgctctaaaagctgcg |

TABLE 2-continued

Plasmid Composition
Plasmid Composition

| Elements | SEQUENCE IDENTIFIER (SEQ. ID. NO:) AND SEQUENCE INFORMATION |
|---|---|
| | gaattgtacccgccccgggatccatcgattgaattcgccacc |
| | atgtcagaaggggtgggcacgttccgcatggtacctgaagag |
| | gaacaggagctccgtgcccaactggagcagctcacaaccaag |
| | gaccatggacctgtctttggcccgtgcagccagctgccccgc |
| | cacaccttgcagaaggccaaggatgagctgaacgagagagag |
| | gagacccgggaggaggcagtgcgagagctgcaggagatggtg |
| | caggcgcaggcggcctcgggggaggagctggcggtggccgtg |
| | gcggagagggtgcaagagaaggacagcggcttcttcctgcgc |
| | ttcatccgcgcacggaagttcaacgtgggccgtgcctatgag |
| | ctgctcagaggctatgtgaatttccggctgcagtaccctgag |
| | ctctttgacagcctgtccccagaggctgtccgctgcaccatt |
| | gaagctggctaccctggtgtcctctctagtcgggacaagtat |
| | ggccgagtggtcatgctcttcaacattgagaactggcaaagt |
| | caagaaatcacctttgatgagatcttgcaggcatattgcttc |
| | atcctggagaagctgctggagaatgaggaaactcaaatcaat |
| | ggcttctgcatcattgagaacttcaagggctttaccatgcag |
| | caggctgctagtctccggacttcagatctcaggaagatggtg |
| | gacatgctccaggattccttcccagcccggttcaaagccatc |
| | cacttcatccaccagccatggtacttcaccacgacctacaat |
| | gtggtcaagcccttcttgaagagcaagctgcttgagagggtc |
| | tttgtccacggggatgacctttctggtttctaccaggagatc |
| | gatgagaacatcctgccctctgacttcgggggcacgctgccc |
| | aagtatgatggcaaggccgttgctgagcagctctttggcccc |
| | caggcccaagctgagaacacagccttctgaggatcgtaccgg |
| | tcgacctgcagaagcttgcctcgagcagcgctgctcgagaga |
| | tctggatcataatcagccataccacatttgtagaggttttac |
| | ttgctttaaaaaacctcccacacctccccctgaacctgaaac |
| | ataaaatgaatgcaattgttgttgttaacttgtttattgcag |
| | cttataatggttacaaataaagcaatagcatcacaaatttca |
| | caaataaagcatttttttcactgcattctagttgtggtttgt |
| | ccaaactcatcaatgtatcttatcatgtctggtaaccacgtg |
| | cggaccgagcggccgcaggaacccctagtgatggagttggcc |
| | actccctctctgcgcgctcgctcgctcactgaggccgggcga |
| | ccaaaggtcgcccgacgcccgggctttgcccgggcggcctca |
| | gtgagcgagcgagcgcgcagctgcctgcagggttccatccca |
| | atggcgcgtcaattcactggccgtcgttttacaacgtcgtga |
| | ctgggaaaaccctggcgttacccaacttaatcgccttgcagc |
| | acatccccctttcgccagctggcgtaatagcgaagaggcccg |
| | caccgatcgcccttcccaacagttgcgcagcctgaatggcga |
| | atggcgcctgatgcggtattttctccttacgcatctgtgcgg |
| | tatttcacaccgcatatggtgcactctcagtacaatctgctc |
| | tgatgccgcatagttaagccagccccgacacccgccaacacc |
| | cgctgacgcgccctgacgggcttgtctgctcccggcatccgc |
| | ttacagacaagctgtgaccgtctccgggagctgcatgtgtca |
| | gaggttttcaccgtcatcaccgaaacgcgcgagacgaaaggg |
| | cctcgtgatacgcctatttttataggttaatgtcatgataat |
| | aatggtttcttagacgtcaggtggcacttttcggggaaatgt |
| | gcgcggaacccctatttgtttatttttctaaatacattcaaa |
| | tatgtatccgctcatgagacaataaccctgataaatgcttca |
| | ataatattgaaaaaggaagagtatgagccatattcaacggga |
| | aacgtcttgctctaggccgcgattaaattccaacatggatgc |
| | tgatttatatgggtataaatgggctcgcgataatgtcgggca |
| | atcaggtgcgacaatctatcgattgtatgggaagcccgatgc |
| | gccagagttgtttctgaaacatggcaaaggtagcgttgccaa |
| | tgatgttacagatgagatggtcagactaaactggctgacgga |
| | atttatgcctcttccgaccatcaagcattttatccgtactcc |
| | tgatgatgcatggttactcaccactgcgatccctgggaaaac |
| | agcattccaggtattagaagaatatcctgattcaggtgaaaa |
| | tattgttgatgcgctggcagtgttcctgcgccggttgcattc |
| | gattcctgtttgtaattgtccttttaacagcgatcgcgtatt |
| | tcgtctcgctcaggcgcaatcacgaatgaataacggtttggt |
| | tgatgcgagtgattttgatgacgagcgtaatggctggcctgt |
| | tgaacaagtctggaaagaaatgcataaacttttgccattctc |
| | accggattcagtcgtcactcatggtgatttctcacttgataa |
| | ccttatttttgacgaggggaaattaataggttgtattgatgt |
| | tggacgagtcggaatcgcagaccgataccaggatcttgccat |
| | cctatggaactgcctcggtgagttttctccttcattacagaa |
| | acggctttttcaaaaatatggtattgataatcctgatatgaa |
| | taaattgcagtttcatttgatgctcgatgagtttttctaact |
| | gtcagaccaagtttactcatatatactttagattgatttaaa |
| | acttcatttttaatttaaaaggatctaggtgaagatcctttt |
| | tgataatctcatgaccaaaatcccttaacgtgagttttcgtt |
| | ccactgagcgtcagaccccgtagaaaagatcaaaggatcttc |
| | ttgagatcctttttttctgcgcgtaatctgctgcttgcaaac |

TABLE 2-continued

Plasmid Composition
Plasmid Composition

| Elements | SEQUENCE IDENTIFIER (SEQ. ID. NO:)AND SEQUENCE INFORMATION |
|---|---|
| | aaaaaaaccaccgctaccagcggtggtttgtttgccggatca agagctaccaactctttttccgaaggtaactggcttcagcag agcgcagataccaaatactgttcttctagtgtagccgtagtt aggccaccacttcaagaactctgtagcaccgcctacatacct cgctctgctaatcctgttaccagtggctgctgccagtggcga taagtcgtgtcttaccgggttggactcaagacgatagttacc ggataaggcgcagcggtcgggctgaacggggggttcgtgcac acagcccagcttggagcgaacgacctacaccgaactgagata cctacagcgtgagctatgagaaagcgccacgcttcccgaagg gagaaaggcggacaggtatccggtaagcggcagggtcggaac aggagagcgcacgagggagcttccagggggaaacgcctggta tctttatagtcctgtcgggtttcgccacctctgacttgagcg tcgatttttgtgatgctcgtcaggggggcggagcctatggaa aaacgccagcaacgcggcctttttacggttcctggccttttg ctggccttttgctcacatgttctttcctgcgttatcccctga ttctgtggataaccgtattaccgcctttgagtgagctgatac cgctcgccgcagccgaacgaccgagcgcagcgagtcagtgag cgaggaagcggaagagcgcccaatacgcaaaccgcctctccc cgcgcgttggccgattcattaatgcagctggcacgacaggtt tcccgactggaaagcgggcagtgagcgcaacgcaattaatgt gagttagctcactcattaggcaccccaggctttacactttat gcttccggctcgtatgttgtgtggaattgtgagcggataaca atttcacacaggaaacagctatgaccatgattacgccaagct cggcgcgccattgggatggaaccctgcaggcag |
| GENE CASSETTE TM042 OCCURS AT BP 4 THROUGH 2330 OF SEQ ID NO: 50 | 61 cgcgctcgctcgctcactgaggccgcccgggcaaagcccggg cgtcgggcgacctttggtcgcccggcctcagtgagcgagcga gcgcgcagagagggagtggggtaccacgcgtttgtcctctcc ctgcttggccttaaccagccacatttctcaactgaccccact cactgcagaggtgaaaactaccatgccaggtcctgctggctg gggaggggtgggcaataggcctggatttgccagagctgcca ctgtagatgtagtcatatttacgatttcccttcacctcttat taccctggtggtggtggtggggggggggggggtgctctctcag caaccccaccccgggatcttgaggagaaagagggcagagaaa agagggaatgggactggcccagatcccagccccacagccggg cttccacatggccgagcaggaactccagagcaggagcacaca aaggagggctttgatgcgcctccagccaggcccaggcctctc ccctctccccctttctctctgggtcttcctttgccccactgag ggcctcctgtgagcccgatttaacggaaactgtgggcggtga gaagttccttatgacacactaatcccaacctgctgaccggac cacgcctccagcggagggaacctctagagctccaggacattc aggtaccaggtagccccaaggaggagctgccgaatcgatgga tcgggaactgaaaaaccagaaagttaactggtaagtttagtc tttttgtcttttatttcaggtcccggatccggtggtggtgca aatcaaagaactgctcctcagtggatgttgcctttacttcta ggcctgtacggaagtgttacttctgctctaaaagctgcggaa ttgtacccgccccgggatccatcgattgaattcgccaccatg tcagaaggggtgggcacgttccgcatggtacctgaagaggaa caggagctccgtgcccaactggagcagctcacaaccaaggac catggacctgtctttggcccgtgcagccagctgccccgccac accttgcagaaggccaaggatgagctgaacgagagagaggag acccgggaggaggcagtgcgagagctgcaggagatggtgcag gcgcaggcggcctcggggggaggagctggcggtggccgtggcg gagagggtgcaagagaaggacagcggcttcttcctgcgcttc atccgcgcacggaagttcaacgtgggccgtgcctatgagctg ctcagaggctatgtgaatttccggctgcagtaccctgagctc tttgacagcctgtccccagaggctgtccgctgcaccattgaa gctggctaccctggtgtcctctctagtcgggacaagtatggc cgagtggtcatgctcttcaacattgagaactggcaaagtcaa gaaatcacctttgatgagatcttgcaggcatattgcttcatc ctggagaagctgctggagaatgaggaaactcaaatcaatggc ttctgcatcattgagaacttcaagggctttaccatgcagcag gctgctagtctccggacttcagatctcaggaagatggtggac atgctccaggattccttcccagcccggttcaaagccatccac ttcatccaccagccatggtacttcaccacgacctacaatgtg gtcaagcccttcttgaagagcaagctgcttgagagggtcttt gtccacggggatgacctttctggtttctaccaggagatcgat gagaacatcctgccctctgacttcgggggcacgctgcccaag tatgatggcaaggccgttgctgagcagctctttggcccccag gcccaagctgagaacacagccttctgaggatcgtaccggtcg acctgcagaagcttgcctcgagcagcgctgctcgagagatct ggatcataatcagccataccacatttgtagaggttttacttg ctttaaaaaacctcccacacctccccctgaacctgaaacata aaatgaatgcaattgttgttgttaacttgtttattgcagctt |

TABLE 2-continued

| Plasmid Composition | |
|---|---|
| Plasmid Composition | |
| Elements | SEQUENCE IDENTIFIER (SEQ. ID. NO:) AND SEQUENCE INFORMATION |
| | ataatggttacaaataaagcaatagcatcacaaatttcacaa ataaagcatttttttcactgcattctagttgtggtttgtcca aactcatcaatgtatcttatcatgtctggtaaccacgtgcgg accgagcggccgcaggaacccctagtgatggagttggccact ccctctctgcgcgctcgctcgctcactgaggccgggcgacca aaggtcgcccgacgcccgggctttgcccgggcggcctcagtg agcgagcgagcgcgcag |

TABLE 3

| SEQUENCE IDENTIFIER (SEQ. ID. NO:) | Construction summary |
|---|---|
| **Plasmid TM017** | |
| 1 ΔITR | PvuII/MluI restriction fragment of Δ5' ITR element cloned into PvuII/MluI restriction fragment of plasmid backbone |
| 3 Human RLBP1 Promoter(short) | Blunted BamHI/MluI restriction fragment of human RLBP1 promoter (short) was cloned into blunted SacII/MluI restriction fragment of plasmid backbone |
| 4 MODIFIED SV40INTRON | MluI/ClaI restriction fragment a clone containing an hCMV promoter and modified SV40 intron was cloned into MluI/ClaI restriction fragment of plasmid backbone. The hCMV promoter was removed during subsequent cloning to insert human RLBP1 promoter (short) |
| 5, 6 Added Kozak AND HUMAN RLBP1 GENE CDS | EcoRI/AgeI restriction fragment containing Kozak and human RLBP1 gene CDS was cloned into EcoRI/AgeI restriction fragment of plasmid backbone |
| 8 SV40 POLYA | BglII/BstEII restriction fragment of SV40 polyA was cloned into BglII/BsteII restriction fragment of the plasmid backbone |
| 9 3' ITR | Present in original Amp resistant backbone, AAV-MCS (Stratagene) |
| **Plasmid TM037 construction summary** | |
| 2 5' ITR | Present in original Amp resistant backbone, AAV-MCS (Stratagene) |
| 10 Human RLBP1 Promoter(long) | Blunted HindIII/EcoRI restriction fragment of human RLBP1 promoter (long) was cloned into blunted MluI/EcoRI restriction fragment of plasmid backbone |
| 5, 6 Added Kozak AND HUMAN RLBP1 GENE CDS | EcoRI/AgeI restriction fragment containing Kozak and human RLBP1 gene CDS cloned into EcoRI/AgeI restriction fragment of plasmid backbone |
| 8 SV40 POLYA | BglII/BstEII restriction fragment containing SV40 polyA was cloned into BglII/BsteII restriction fragment of the plasmid backbone |
| 9 3' ITR | Present in original Amp resistant backbone, AAV-MCS (Stratagene) |
| **Plasmid AG007 construction summary** | |
| 2 5' ITR | Present in original Amp resistant backbone, pAAV-MCS (Stratagene) |
| 11 Human RPE65 Promoter | MluI/EcoRI restriction fragment containing human RPE65 promoter cloned into MluI/EcoRI restriction fragment of the plasmid backbone |

TABLE 3-continued

| SEQUENCE IDENTIFIER (SEQ. ID. NO:) | Construction summary |
|---|---|
| 5, 6 ADDED-KOZAK and HUMAN RLBP1 GENE CDS | EcoRI/AgeI restriction fragment containing Kozak and human RLBP1 gene CDS cloned into EcoRI/AgeI restriction fragment of plasmid backbone |
| 8 SV40 POLYA | BglII/BstEII restriction fragment containing SV40 polyA was cloned into BglII/BsteII restriction fragment of the plasmid backbone |
| 14 RLBP1 INTRONIC SEQUENCE AS STUFFER SEQUENCE | BstEII restriction fragment containing RLBP1 intron1 stuffer sequence was cloned into BstEII restriction fragment of the plasmid backbone |
| 9 3' ITR | Present in original Amp resistant backbone, pAAV-MCS (Stratagene) |
| **Plasmid TM039 construction summary** | |
| 2 5' ITR | Present in original Amp resistant backbone, AAV-MCS purchased from Stratagene |
| 22 CMV-enhancer with CBA promoter | EcoRI/MluI restriction fragment containing CMV-enhancer with CBA promoter was cloned into EcoRI/MluI restriction fragment of plasmid backbone |
| 5, 6 Added Kozak AND HUMAN RLBP1 GENE CDS | EcoRI/SalI restriction fragment containing Kozak and human RLBP1 gene CDS was cloned into EcoRI/SalI restriction fragment of plasmid backbone |
| 8 SV40 POLYA | BglII/BstEII restriction fragment containing SV40 polyA was cloned into BglII/BsteII restriction fragment of the plasmid backbone |
| 23 REVERSE COMPLEMENT OF RLBP1 INTRON STUFFER | Plasmid backbone was cut with BstEII then blunted. The stuffer was PCR amplified from human cell line (HEK293 or ARPE19) genomic DNA, the product was phosphorylated and ligated into backbone. |
| 9 3' ITR | Present in original Amp resistant backbone, AAV-MCS (Stratagene) |
| **Plasmid TM040 construction summary** | |
| 2 5' ITR | Present in original Amp resistant backbone, AAV-MCS (Stratagene) |
| 3 Human RLBP1 promoter (short) | Blunted BamHI/MluI restriction fragment of human RLBP1 promoter (short) was cloned into blunted SacII/MluI restriction fragment of plasmid backbone |
| 4 MODIFIED SV40INTRON | MluI/ClaI restriction fragment containing an hCMV promoter and modified SV40 intron was cloned into MluI/ClaI restriction fragment of plasmid backbone. The hCMV promoter was removed during subsequent cloning to insert human RLBP1 promoter (short) |

TABLE 3-continued

Plasmid Construction

| SEQUENCE IDENTIFIER (SEQ. ID. NO:) | Construction summary |
| --- | --- |
| 5, 6 Added Kozak AND HUMAN RLBP1 GENE CDS | EcoRI/SalI restriction fragment containing Kozak and human RLBP1 gene CDS cloned into EcoRI/SalI restriction fragment of plasmid backbone |
| 8 SV40 POLYA | BglII/BstEII restriction fragment containing SV40 polyA was cloned into BglII/BsteII restriction fragment of the plasmid backbone |
| 23 REVERSE COMPLEMENT OF RLBP1 INTRON STUFFER | Plasmid backbone was cut with BstEII then blunted. The stuffer was PCR amplified from human cell line (HEK293 or ARPE19) genomic DNA, the product was phosphorylated and ligated into backbone. |
| 9 3' ITR | Present in original Amp resistant backbone, AAV-MCS purchased from Stratagene |
| Plasmid TM016 construction summary | |
| 1 Δ5' ITR | PvuII/MluI restriction of Δ5' ITR element cloned into PvuII/MluI restriction fragment of plasmid backbone |
| 3 Human RLBP1 promoter (short) | Blunted BamHI/MluI restriction fragment of human RLBP1 promoter (short) was cloned into blunted SacII/MluI restriction fragment of plasmid backbone |
| 4 MODIFIED SV40INTRON | MluI/ClaI restriction fragment of containing an hCMV promoter and modified SV40 intron was cloned into MluI/ClaI restriction fragment of plasmid backbone. The hCMV promoter was removed during subsequent cloning to insert human RLBP1 promoter (short) |
| 24 E__GFP | EcoRI/Age fragment containing GFP was blunted then cloned into the SalI digested and blunted backbone |
| 8 SV40 POLYA | BglII/BstEII restriction fragment containing SV40 polyA was cloned into BglII/BsteII restriction fragment of the plasmid backbone |
| 9 3' ITR | Present in original Amp resistant backbone, AAV-MCS purchased from Stratagene |
| Plasmid TM035 construction summary | |
| 2 5' ITR | Present in original Amp resistant backbone, AAV-MCS purchased from Stratagene |
| 10 Human RLBP1 promoter (long) | Blunted HindIII/EcoRI restriction fragment of human RLBP1 promoter (long) was cloned into blunted MluI/EcoRI restriction fragment of plasmid backbone |
| 24 E__GFP | EcoRI/Age I digested fragment containing GFP was blunted then cloned into the SalI digested and blunted backbone |
| 8 SV40 POLYA | BglII/BstEII restriction fragment containing SV40 polyA was cloned into BglII/BstEII restriction fragment of the plasmid backbone |
| 9 3' ITR | Present in original Amp resistant backbone, AAV-MCS purchased from Stratagene |
| Plasmid AG012 construction summary | |
| 2 5' ITR | Present in original Amp resistant backbone, AAV-MCS purchased from Stratagene |
| 13 SYNUCLEIN INTRONIC SEQUENCE AS STUFFER SEQUENCE | The plasmid backbone was digested with MluI/AgeI. The synuclein stuffer was PCR amplified from plasmid pBV5, the product was digested with MluI/AgeI, phosphorylated and ligated into the plasmid backbone. |

TABLE 3-continued

Plasmid Construction

| SEQUENCE IDENTIFIER (SEQ. ID. NO:) | Construction summary |
| --- | --- |
| 8 SV40 POLYA | BglII/BstEII restriction fragment from GeneArt synthesized clone containing SV40 polyA was cloned into BglII/BstEII restriction fragment of the plasmid backbone |
| 14 RLBP1 INTRONIC SEQUENCE AS STUFFER SEQUENCE | BstEII restriction fragment from intermediary clone containing RLBP1 intron1 stuffer sequence cloned into BstEII restriction fragment of the plasmid backbone |
| 9 3' ITR | Present in original Amp resistant backbone, AAV-MCS purchased from Stratagene |
| Plasmid AG004 construction summary | |
| 2 5' ITR | Present in original Amp resistant backbone, AAV-MCS purchased from Stratagene |
| 11 Human RPE65 Promoter | MluI/EcoRI restriction fragment from GeneArt synthesized clone containing human RPE65 promoter cloned into MluI/EcoRI restriction fragment of the plasmid backbone |
| 24 E__GFP | An EcoRI/AgeI digested fragment from an intermediary clone was blunted then cloned into the SalI digested and blunted backbone |
| 8 SV40 POLYA | BglII/BstEII restriction fragment from GeneArt synthesized clone containing SV40 polyA was cloned into BglII/BstEII restriction fragment of the plasmid backbone |
| 14 RLBP1 INTRONIC SEQUENCE AS STUFFER SEQUENCE | BstEII restriction fragment from intermediary clone containing RLBP1 intron1 stuffer sequence cloned into BstEII restriction fragment of the plasmid backbone |
| 9 3' ITR | Present in original Amp resistant backbone, AAV-MCS purchased from Stratagene |
| Plasmid AG006 construction summary | |
| 2 5' ITR | Present in original Amp resistant backbone, AAV-MCS purchased from Stratagene |
| 12 HUMAN VMD2 PROMOTER | MluI/EcoRI restriction fragment from GeneArt synthesized clone containing human VMD2 promoter cloned into MluI/EcoRI restriction fragment of the plasmid backbone |
| 24 E__GFP | An EcoRI/AgeI digested fragment from an intermediary clone was blunted then cloned into the SalI digested and blunted backbone |
| 8 SV40 POLYA | BglII/BstEII restriction fragment from GeneArt synthesized clone containing SV40 polyA was cloned into BglII/BstEII restriction fragment of the plasmid backbone |
| 14 RLBP1 INTRONIC SEQUENCE AS STUFFER SEQUENCE | BstEII restriction fragment from intermediary clone containing RLBP1 intron1 stuffer sequence cloned into BstEII restriction fragment of the plasmid backbone |
| 9 3' ITR | Present in original Amp resistant backbone, AAV-MCS purchased from Stratagene |

TABLE 3-continued

| Plasmid Construction | |
|---|---|
| SEQUENCE IDENTIFIER (SEQ. ID. NO:) | Construction summary |
| Plasmid TM042 Construction Summary | |
| 1—ΔITR, 3—Human RLBP1 Promoter(short), 4—MODIFIED SV40INTRON, 5,6—Added Kozak AND HUMAN RLBP1 GENE, 8—SV40 POLYA, and 9—3'ITR | SbfI restriction fragment of Plamsid pTM017 was cloned into a SbfI restriction fragment of Puc57 with kanamycin resistance gene backbone. |

TABLE 4

| Viral Vector Composition: Vector Genome and Caspid | |
|---|---|
| SEQUENCE ELEMENTS | SEQUENCE IDENTIFIER (SEQ. ID. NO:) |
| Viral Vector NVS1 (Generated from plasmid TM017 or TM042, and AAVRep2/Cap2 plasmid) The viral vector contains a self complementary genome with the following genomic elements in the 5' to 3' direction packaged in the viral capsid AAV2. | |
| SC5'ITR | 36 |
| Reverse Complementary sequence of SV40polyA | 62 |
| Reverse Complementary sequence of HUMAN RLBP1 GENE CDS | 63 |
| Reverse Complementary sequence of Added KOZAK | 64 |
| Reverse Complementary sequence of Modified SV40INTRON | 65 |
| Reverse Complementary sequence of Human RLBP1 PROMOTER (short) | 66 |
| ΔITR | 1 |
| Human RLBP1 PROMOTER (short) | 3 |
| Modified SV40INTRON | 4 |
| Added Kozak | 5 |
| HUMAN RLBP1 GENE CDS | 6 |
| SV40 POLYA | 8 |
| 3' ITR | 9 |

TABLE 4-continued

| Viral Vector Composition: Vector Genome and Caspid | |
|---|---|
| SEQUENCE ELEMENTS | SEQUENCE IDENTIFIER (SEQ. ID. NO:) |
| CAPSID PROTEIN SEQUENCE OF NVS1 | |
| AAV2 CAPSID SEQUENCE | 19, 68 and 69 (Encoded by 18) |
| Viral Vector NVS2 (Generated from plasmid TM017 or TM042, and AAVRep2/Cap8 plasmid) The viral vector contains a self complementary genome with the following genomic elements in the 5' to 3' direction packaged in the viral capsid AAV8. | |
| SC5'ITR | 36 |
| Reverse Complementary sequence of SV40polyA | 62 |
| Reverse Complementary sequence of HUMAN RLBP1 GENE CDS | 63 |
| Reverse Complementary sequence of Added KOZAK | 64 |
| Reverse Complementary sequence of Modified SV40INTRON | 65 |
| Reverse Complementary sequence of Human RLBP1 PROMOTER (short) | 66 |
| ΔITR | 1 |
| Human RLBP1 PROMOTER (short) | 3 |
| Modified SV40INTRON | 4 |
| Added Kozak | 5 |
| HUMAN RLBP1 GENE CDS | 6 |
| SV40 POLYA | 8 |
| 3' ITR | 9 |
| CAPSID PROTEIN SEQUENCE OF NVS2 | |
| AAV8 CAPSID SEQUENCE | 21, 70, and 71 (Encoded by 20) |
| Viral Vector NVS3 (Generated from plasmid TM037 and AAVRep2/Cap2 plasmid) The viral vector genome contains the following genomic elements in the 5' to 3' direction | |
| 5' ITR | 2 |
| HUMAN RLBP1 PROMOTER (long) | 10 |
| ADDED KOZAK | 5 |
| HUMAN RLBP1 GENE CDS | 6 |
| SV40 POLYA | 8 |
| 3' ITR | 9 |
| CAPSID PROTEIN SEQUENCE OF NVS3 | |
| AAV2 CAPSID SEQUENCE | 19, 68 and 69 (Encoded by 18) |
| Viral Vector NVS4 (Generated from plasmid TM037 and AAVRep2/Cap8 plasmid) The viral vector genome contains the following genomic elements in the 5' to 3' direction | |
| 5' ITR | 2 |
| HUMAN RLBP1 PROMOTER (long) | 10 |
| ADDED KOZAK | 5 |
| HUMAN RLBP1 | 6 |

TABLE 4-continued

Viral Vector Composition: Vector Genome and Caspid

| SEQUENCE ELEMENTS | SEQUENCE IDENTIFIER (SEQ. ID. NO:) |
|---|---|
| GENE CDS | |
| SV40 POLYA | 8 |
| 3' ITR | 9 |
| CAPSID PROTEIN SEQUENCE OF NVS4 | |
| AAV8 CAPSID SEQUENCE | 21, 70, and 71 (Encoded by 20) |
| Viral Vector NVS5 (Generated from plasmid AG007 and AAVRep2/Cap2 plasmid) The viral vector genome contains the following genomic elements in the 5' to 3' direction | |
| 5' ITR | 2 |
| HUMAN RPE65 PROMOTER | 11 |
| ADDED-KOZAK | 5 |
| HUMAN RLBP1 GENE CDS | 6 |
| SV40 POLYA | 8 |
| RLBP1 INTRONIC SEQUENCE AS STUFFER SEQUENCE | 14 |
| 3' ITR | 9 |
| CAPSID PROTEIN SEQUENCE OF NVS5 | |
| AAV2 CAPSID SEQUENCE | 19, 68 and 69 (Encoded by 18) |
| Viral Vector NVS6 (Generated from plasmid AG007 and AAVRep2/Cap8 plasmid) The viral vector genome contains the following genomic elements in the 5' to 3' direction | |
| 5' ITR | 2 |
| HUMAN RPE65 PROMOTER | 11 |
| ADDED-KOZAK | 5 |
| HUMAN RLBP1 GENE CDS | 6 |
| SV40 POLYA | 8 |
| RLBP1 INTRONIC SEQUENCE AS STUFFER SEQUENCE | 14 |
| 3' ITR | 9 |
| CAPSID PROTEIN SEQUENCE OF NVS6 | |
| AAV8 CAPSID SEQUENCE | 21, 70, and 71 (Encoded by 20) |
| Viral Vector NVS7 (Generated from plasmid TM039 and AAVRep2/Cap2 plasmid) The viral vector genome contains the following genomic elements in the 5' to 3' direction | |
| 5' ITR | 2 |
| CMV Enhancer and CBA PROMOTER (GENEBANK ACCESSION DD215332 FROM BP 1 to BP 161) | 22 |
| ADDED KOZAK | 5 |
| HUMAN RLBP1 GENE CDS | 6 |
| SV40 POLYA | 8 |
| REVERSE COMPLEMENT OF RLBP1 INTRONIC SEQUENCE AS STUFFER SEQUENCE (NT 010274.17) | 23 |
| 3' ITR | 9 |

TABLE 4-continued

Viral Vector Composition: Vector Genome and Caspid

| SEQUENCE ELEMENTS | SEQUENCE IDENTIFIER (SEQ. ID. NO:) |
|---|---|
| CAPSID PROTEIN SEQUENCE OF NVS7 | |
| AAV2 CAPSID SEQUENCE | 19, 68 and 69 (Encoded by 18) |
| Viral Vector NVS8 (Generated from plasmid TM039 and AAVRep2/Cap8 plasmid) The viral vector genome contains the following genomic elements in the 5' to 3' direction | |
| 5' ITR | 2 |
| CMV Enhancer and CBA PROMOTER (GENEBANK ACCESSION DD215332 FROM BP 1 to BP 161) | 22 |
| ADDED KOZAK | 5 |
| HUMAN RLBP1 GENE CDS | 6 |
| SV40 POLYA | 8 |
| REVERSE COMPLEMENT OF RLBP1 INTRONIC SEQUENCE AS STUFFER SEQUENCE (NT 010274.17) | 23 |
| 3' ITR | 9 |
| CAPSID PROTEIN SEQUENCE OF NVS8 | |
| AAV8 CAPSID SEQUENCE | 21, 70, and 71 (Encoded by 20) |
| Viral Vector NVS9 (Generated from plasmid TM040 and AAVRep2/Cap2 plasmid) The viral vector genome contains the following genomic elements in the 5' to 3' direction | |
| 5' ITR | 2 |
| HUMAN RLBP1 PROMOTER (short) | 3 |
| MODIFIED SV40 INTRON | 4 |
| ADDED KOZAK | 5 |
| HUMAN RLBP1 GENE CDS | 6 |
| SV40 POLYA | 8 |
| REVERSE COMPLEMENT OF RLBP1 INTRONIC SEQUENCE AS STUFFER SEQUENCE (NT_010274.17) | 23 |
| 3' ITR | 9 |
| CAPSID PROTEIN SEQUENCE OF NVS9 | |
| AAV2 CAPSID SEQUENCE | 19, 68 and 69 (Encoded by 18) |
| Viral Vector NVS10 (Generated from plasmid TM040 and AAVRep2/Cap8 plasmid) The viral vector genome contains the following genomic elements in the 5' to 3' direction | |
| 5' ITR | 2 |
| HUMAN RLBP1 PROMOTER (short) | 3 |
| MODIFIED SV40 INTRON | 4 |
| ADDED KOZAK | 5 |
| HUMAN RLBP1 GENE CDS | 6 |
| SV40 POLYA | 8 |

TABLE 4-continued

Viral Vector Composition: Vector Genome and Caspid

| SEQUENCE ELEMENTS | SEQUENCE IDENTIFIER (SEQ. ID. NO:) |
|---|---|
| REVERSE COMPLEMENT OF RLBP1 INTRONIC SEQUENCE AS STUFFER SEQUENCE (NT_010274.17) | 23 |
| 3' ITR | 9 |
| CAPSID PROTEIN SEQUENCE OF NVS10 | |
| AAV8 CAPSID SEQUENCE | 21, 70, and 71 (Encoded by 20) |
| Viral vector scAAV8-pRLBP1 (short)-eGFP (eGFP Reporter viral vector generated from plasmid TM016 and AAVRep2/Cap8 plasmid) The viral vector contains a self complementary genome with the following genomic elements in the 5' to 3' direction packaged in the viral capsid AAV8. | |
| SC5'ITR | 36 |
| Reverse Complementary sequence of SV40polyA | 62 |
| Reverse Complementary sequence of eGFP | 67 |
| Reverse Complementary sequence of Added KOZAK | 64 |
| Reverse Complementary sequence of Modified SV40INTRON | 65 |
| Reverse Complementary sequence of Human RLBP1 PROMOTER (short) | 66 |
| ΔITR | 1 |
| HUMAN RLBP1 PROMOTER (short) | 3 |
| MODIFIED SV40 INTRON | 4 |
| ADDED KOZAK | 5 |
| eGFP | 24 |
| SV40 POLYA | 8 |
| 3' ITR | 9 |
| CAPSID PROTEIN SEQUENCE OF Viral vector scAAV8-pRLBP1(short)-eGFP | |
| AAV8 CAPSID SEQUENCE | 21, 70, and 71 (Encoded by 20) |
| Viral Vector AAV8-pRLBP1(long)-eGFP (eGFP Reporter viral vector generated from plasmid TM035 and AAVRep2/Cap8 plasmid) The viral vector genome contains the following genomic elements in the 5' to 3' direction | |
| 5' ITR | 2 |
| HUMAN RLBP1 PROMOTER (long) | 10 |
| ADDED KOZAK | 5 |
| eGFP | 24 |
| SV40 POLYA | 8 |
| 3' ITR | 9 |
| CAPSID PROTEIN SEQUENCE OF Viral Vector AAV8-pRLBP1(long)-eGFP | |
| AAV8 CAPSID SEQUENCE | 21, 70, and 71 (Encoded by 20) |

TABLE 4-continued

Viral Vector Composition: Vector Genome and Caspid

| SEQUENCE ELEMENTS | SEQUENCE IDENTIFIER (SEQ. ID. NO:) |
|---|---|
| Viral Vector AAV8-pRPE65-eGFP (eGFP Reporter viral vector generated from plasmid AG004 and AAVRep2/Cap8 plasmid) The viral vector genome contains the following genomic elements in the 5' to 3' direction | |
| 5' ITR | 2 |
| HUMAN RPE65 PROMOTER | 11 |
| ADDED KOZAK | 5 |
| eGFP | 24 |
| SV40 POLYA | 8 |
| RLBP1 INTRONIC SEQUENCE AS STUFFER SEQUENCE (NT_010274.17) | 14 |
| 3' ITR | 9 |
| CAPSID PROTEIN SEQUENCE OF Viral Vector AAV8-pRPE65-eGFP | |
| AAV8 CAPSID SEQUENCE | 21, 70, and 71 (Encoded by 20) |
| Viral Vector AAV8-pVMD2-eGFP (eGFP Reporter viral vector generated from plasmid AG006 and AAVRep2/Cap8 plasmid) The viral vector genome contains the following genomic elements in the 5' to 3' direction | |
| 5' ITR | 2 |
| HUMAN VMD2 PROMOTER | 12 |
| ADDED KOZAK | 5 |
| eGFP | 24 |
| SV40 POLYA | 8 |
| RLBP1 INTRONIC SEQUENCE AS STUFFER SEQUENCE (NT_010274.17) | 14 |
| 3' ITR | 9 |
| CAPSID PROTEIN SEQUENCE OF Viral Vector AAV8-pVMD2-eGFP | |
| AAV8 CAPSID SEQUENCE | 21, 70, and 71 (Encoded by 20) |
| Viral Vector NVS11 (Generated from plasmid AG012 and AAVRep2/Cap8 plasmid) The viral vector genome contains the following genomic elements in the 5' to 3' direction | |
| 5' ITR | 2 |
| SYNUCLEIN INTRONIC SEQUENCE AS STUFFER SEQUENCE | 13 |
| SV40 POLYA | 8 |
| RLBP1 INTRONIC SEQUENCE AS STUFFER SEQUENCE (NT_010274.17) | 14 |
| 3' ITR | 9 |
| CAPSID PROTEIN SEQUENCE OF NVS11 | |
| AAV8 CAPSID SEQUENCE | 21, 70, and 71 (Encoded by 20) |

Example 2

Subretinal Injection of rAAV Vectors in Mice 2.1 Subretinal Injection of rAAV Vectors in Mice Subretinal injection of an rAAV vector can achieve efficient transduction of RPE and other retinal cells because subretinal injection induces a bleb of concentrated virus in intimate contact with RPE cells and the neural retina. In addition, the subretinal space has a relatively high degree of immunoprivilege and typically very little evidence of inflammation is seen in the vicinity of the injection site. Thus, subretinal injection was a preferred route for delivery of rAAV vectors in mouse retina. However, other routes of delivery may be used, for example, intravitreal injection.

Supplies/Reagents:

- Leica M844 F40 Ophthalmic Surgical Microscope
- 1% cyclopentolate: Bausch & Lomb Cat#965911
- 2.5%-10% phenylephrine: Altaire Pharmaceuticals Cat#05626
- 0.5% Proparacaine: Bausch & Lomb Cat#NDC 54799-500-12
- 10 μl Hamilton syringe: VWR Cat#89184-476
- 33G blunt-ended needle: Hamilton Cat#7803-05
- Fluorescein sodium salt: Sigma Cat#F6377

Test Articles Used in this Example:

- scAAV8-pRLBP1(short)-eGFP viral vector $1\times10^9$ vg/eye
- AAV8-pRLBP1(long)-eGFP viral vector $1\times10^9$ vg/eye
- AAV8-pRPE-eGFP viral vector $1\times10^9$ vg/eye
- AAV8-VMD2-eGFP viral vector $1\times10^9$ vg/eye Protocol:

The subretinal injection was performed either in both eyes or unilaterally in the right eye. All procedures were performed under aseptic conditions, using sterile reagents, syringes and appropriate personal protection equipment.

Subretinal Injection Procedures:

- The mouse pupils were dilated by 1 drop of 1% cyclopentolate and followed by 1 drop of 2.5%-10% phenylephrine
- The mouse was anesthetized by using Avertin (250 mg/kg) i.p. and a drop of 0.5% Proparacine topically (local anesthetic) in the eye
- An approximately 0.5 mm incision was made nasally, posterior to the limbus with a microscalpel
- The blunt-ended needle on the 10 μl Hamilton syringe was inserted tangentially through the scleral incision toward the temporal retina. The needle was advanced until resistance was felt. The 1 μl of diluted rAAV vector (containing fluorescein with the concentration of 1:50) was then injected slowly into the subretinal space, and the needle is withdrawn through the incision
- The eye was examined and the success of the subretinal injection was confirmed by visualization of a bleb containing fluorescein. The success of injection and the degree of retinal damage (hemorrhage) were scored.
- An antibiotic ointment was applied to the eye immediately after the injection 2.2. rAAV Vectors Induced GFP Expression and its Cell-Type Specifics in Mouse Retina To study the rAAV vector-induced gene transduction and cell-type specifics in the mouse retina, the eGFP expression in retinal cross sections and RPE/retina flatmounts were examined. One approach used to identify the eGFP expressing cell types was to co-label eGFP positive cells with retinal cell markers by immunocytochemistry staining in cryosections.

Supplies/Reagents:

Primary Antibodies for Immunocytochemistry Staining:

- Anti-CRALBP antibody: Thermo cat#MA1-813
- Anti-GFAP antibody: Covance cat#SMI-21
- Anti-Opsin Blue antibody: Millipore cat#AB 5407
- Anti-Opsin Red antibody: Millipore cat#AB5405
- Anti-Vimentin antibody: Santa Cruz cat#sc-7557
- Anti-PKC α antibody: C-20 Santa Cruz cat#sc-208

Secondary Antibodies for Immunocytochemistry Staining:

- Goat anti-mouse IgG: Invitrogen Cat#A11005
- Goat anti-rat IgG: Invitrogen Cat#A11007
- Donkey anti-rabbit IgG: Invitrogen Cat#A21207

Other Supplies/Reagents:

- Vectashield Mounting Medium with DAPI: Vector Laboratories, Burlingame Cat#H-1200),
- Zeiss Imaging system, AxioVision Software
- Zeiss LSM 510 confocal microscope, ZEN version of the Zeiss software Protocol:

The mouse eyeball was removed and placed in 4% PFA (paraformaldehyde) for 2 hours at 25° C. and then in PBS buffer for 1-3 days in 4° C. till dissection. The cornea, lens and vitreous were removed from the eye ball and the retinal and RPE/choroid was flatmounted with Vectashield mounting medium on to the slide. The GFP expression in flatmount was captured by Zeiss Imaging system and quantified using AxioVision Software. After imaging, the slides with retinal flatmounts were placed in 0.25% triton buffer at 25° C. for 30 min and then the retinal flatmounts were removed from the slides. The eGFP positive areas of the retina flatmounts were cut and embedded in OCT and then cryosectioned. The immunocytochemistry staining using retinal cell markers was applied in the cryosections. The images were captured by Zeiss LSM 510 confocal microscope and ZEN version of the Zeiss software.

The Immunocytochemistry Staining Procedures:

Day 1.

- air dry sections at room temperature 1 hour.
- place slides in PBS+0.25% Triton 15 min×2
- block in 1% BSA+PBS+0.25% Triton 90 min
- incubate slides with primary antibody in 1% BSA+PBS+0.25% Triton at 4° C. overnight Day 2.

- take out slides from 4° C., leave them at 25° C. for 30 min
- wash slides in PBS+0.25% Triton 15 min×2
- incubate slides with secondary 1:800 at 25° C. for 90 min
- wash slides in PBS+0.25% Triton 15 min×2
- mount slides with Vectashield Mounting Medium with DAPI

TABLE 5

The retinal cell markers and dilutions used in the study

| Cell Type | Cell Marker | Dilutions |
|---|---|---|
| Muller cell | Anti-CRALBP | 1:1000 |
| | Anti-Vimentin | 1:100 |
| | Anti-GFAP | 1:1000 |
| Photoreceptor | Anti-Opsin Red/Green | 1:250 |
| | Anti-Opsin Blue | 1:250 |
| Neuron in INL | Anti-PKCα | 1:200 |
| Astrocytes | Anti-GFAP | 1:1000 |

TABLE 6

Immunohistochemistry results that describe the transduction of cell types by test viral vectors.

| Cell Type | Cell Marker | scAAV8-pRLBP1(short)-eGFP | AAV8-pRLBP1(long)-eGFP | AAV8-pRPE65-eGFP | AAV8 pVMD2-eGFP |
|---|---|---|---|---|---|
| RPE | | + | + | + | + |
| Muller cell | CRALBP | + | + | − | − |
| | Vimentin | + | + | − | − |
| | GFAP | + | + | − | − |
| Photoreceptor | Opsin Red/Green | − | + | + | + |
| | Opsin Blue | − | − | + | + |
| | Recoverin | ND | ND | + | ND |
| Neuron in INL | PKCα | − | − | − | − |
| Ganglion Cell | NeuN | − | ND | ND | ND |
| Astrocytes | GFAP | − | − | − | − |

+, indicates expression of GFP in a given cell type
−, no GFP expression
ND, Not Determined Results:

- All tested viral vectors were functional in the mouse retina.
- scAAV8-pRLBP1(short)-eGFP vector leads to selective expression of GFP in RPE and the Müller cells in the neural retina.
- AAV8-pRLBP1(long)-eGFP leads to expression of GFP in RPE, Müller cells and photoreceptors in the neural retina.
- AAV8-pRPE65-eGFP and AAV8-pVMD2-eGFP lead to GFP expression in RPE and photoreceptors in the neural retina.

Conclusion

These results demonstrate that the combination of promoter, AAV genome conformation and AAV capsid sequence can lead to different transduction properties in specific cell types, to achieve the desired effect. Expression of the RLBP1 gene product in RPE and Müller cells of the retina, represents the desired on-target cell type expression. RLBP1 short promoter packaged in a self-complementary genome in conjunction with an AAV8 serotype capsid induces gene expression in RPE and Müller cells in the neural retina without off-target cell expression.

The RLBP1-long promoter packaged in a single-stranded genome in conjunction with an AAV8 serotype capsid induces gene expression in RPE and Müller cells, which are on-target cell types, and also in photoreceptors, which is an off-target cell type.

The RPE65 and VMD2 promoter packaged in a single-stranded genome in conjunction with an AAV8 serotype capsid induces gene expression in RPE cells but also in photoreceptors, which is an off-target cell type.

Example 3 mRNA Based Assay to Measure Vector-Mediated Expression of a Human RLBP1 Transgene Relative to Endogenous Mouse RLBP1 mRNA Expression The expression levels and tissue specificity of an rAAV-transduced transgene will vary depending on the vector serotype, the vector genome, the tissue-specific promoter used and the dose injected. A goal of gene replacement therapy is to achieve a level of expression that is sufficient to compensate for the missing endogenous gene expression while not over expressing the gene to toxic levels.

An assay has been developed to measure the vector-mediated expression of human RLBP1 mRNA relative to the endogenous levels of mouse RLBP1 mRNA following sub-retinal injections of various AAV vectors at different doses in wild-type mice. This assay utilized Taqman® Gene Expression Assays containing primers and probes for specifically detecting human or mouse RLBP1 cDNA. Prior to performing the experiment the Taqman® Gene Expression Assays were tested for species specificity using plasmid DNA containing either human or mouse RLBP1 cDNA sequences. In brief, Taqman® reagents were used to co-amplify either mouse or human RLBP1 cDNA with mouse GAPDH cDNA as an endogenous control. The levels of the mouse or human RLBP1 were normalized to the internal GAPDH control and then these normalized levels were compared with one another.

Supplies/Reagents:

- RNA extraction
  - Qiagen RNeasy micro kit (Qiagen cat #74004)
  - Qiagen RNase-Free DNase Set (Qiagen cat#79254)
  - Beta-Mercaptoethanol (Sigma cat#63689)
  - Qiagen Stainless-Steel 5 mm beads (Qiagen cat#69989)
  - 2.0 ml Seal Rite Microcentrifuge tube (USA Scientific cat#1620-2700)
  - Qiagen TissueLyser II (cat#85300)
- cDNA synthesis
  - High Capacity cDNA Reverse Transcription Kit (Applied Biosystems cat#4368814)
  - RNase Inhibitor (Applied Biosystems cat#N8080119)
  - BioRad Thermal cycler
- Relative Quantitation PCR
  - 2× TaqMan® Universal PCR Master Mix (Applied Biosystems cat#4304437)
  - 20× TaqMan® Gene Expression Assay for human RLBP1 (Applied Biosystems cat#4331182: Hs00165632.m1)
  - 20× TaqMan® Gene Expression Assay for mouse RLBP1 (Applied Biosystems cat#4331182: Mm00445129.m1)
  - 20× Applied Biosystems® Mouse GAPD (GAPDH) Endogenous Control (VIC®/MGB Probe, Primer Limited) (Applied Biosystems cat#4352339E)
  - Applied Biosystems Real-Time PCR machine model 7900HT.

Test articles used in this example:

NVS8 viral vector

NVS10 viral vector

NVS4 viral vector

NVS2 viral vector

NVS6 viral vector

Protocol:

At the termination of the in vivo experiment neural retina was dissected out of the eyes, placed in a 2 ml microcentrifuge tube and flash frozen on dry ice. The remaining eye cup (minus retina and lens) was frozen in a separate tube. Samples were stored at −80° C. until RNA isolation. Total RNA was extracted using a Qiagen RNeasy micro kit with DNase treatment. For tissue homogenization and lysis, a Qiagen TissueLyzer was used. In particular, a 5 mm stainless-steel bead was added to each tissue-containing tube while on dry ice. Samples were transferred to room temperature and 350 μl of buffer RLT containing 1% beta-mercaptoethanol was added. Samples were processed on the TissueLyzer with a shaking frequency of 30 Hz for two 2 minute cycles. The standard Qiagen RNeasy micro kit protocol for RNA extraction with DNase treatment was then followed with one minor modification. Prior to elution the RNA column was allowed to air dry for >10 minutes to ensure elimination of residual ethanol. Total RNA was stored at −80° C. until ready for cDNA synthesis.

Total RNA concentration was determined using a Nanodrop spectrophotometer. Each sample was adjusted to a final concentration of 50 ng/μl. cDNA was generated using the Applied Biosystems High Capacity cDNA reverse transcriptase kit. A master mix of reagents from the High Capacity cDNA RT kit was prepared such that each 10 μl contained 2 μl of 10× High Capacity RT buffer, 0.8 μl of 25× dNTPs (100 mM), 2 μl of Reverse Transcriptase random primers, 0.4 μl of RNase inhibitor, 1 μl of Multiscribe Reverse transcriptase and 3.8 μl of RNAse-free water. 10 μl of the 50 ng/μl stock of each total RNA was dispensed into a well of a 96-well PCR amplification plate and then 10 μl of the RT master mix was added to each well. The plate was placed in a Bio-Rad thermal cycler and operated using the following parameters: 25° C. for 10 min, 37° C. for 120 min., 85° C. for 5 min then hold at 4 degrees until terminate program. cDNA was stored at −20° C. prior to Relative quantitative PCR reaction set-up.

The cDNA concentration was adjusted to a final concentration of 20 ng/μl by adding 5 μl of RNAse-free water to each well of the cDNA reaction (this is based on the initial total RNA concentration and assuming 100% conversion to cDNA). For each cDNA sample set up two different multiplex qPCR reactions; one using the mouse RLBP1 Taqman Expression Assay probes with the mouse GAPDH endogenous control, and the other using the human RLBP1 Taqman Expression Assay probes with the mouse GAPDH endogenous control. Each of these two reactions were performed in duplicate for each sample. For each sample, 5 μl of the 20 ng/μl cDNA sample was dispensed into a well of a 385-well plate. Two separate master mixes were prepared, one for the mouse RLBP1 Taqman assay and one for the human RLBP1 assay such that each 15 μl of mixture contained 10 μl of 2× TaqMan® Universal PCR Master Mix, 1 μl of 20× TaqMan® Gene Expression Assay for either mouse or human RLBP1, 1 μl of 20× Applied Biosystems® Mouse GAPD (GAPDH) Endogenous Control, and 3 μl of RNAse-free water. 15 μl of the appropriate master mix was dispensed into the well containing the cDNA. The plate was placed in an ABI 7900HT Real Time PCR machine and run using the relative quantitation program with the following parameters: an initial incubation at 50° C. for 2 min then 40 cycles of the following two steps, 15 sec. at 95° C. and 1 min. at 60° C.

The relative quantitation plate results were imported into a RQ study document using the ABI RQ Manager 1.2. The data were analyzed using the automatic threshold setting to generate average and average ΔCt which is the difference in Ct readings of the RLBP1 cDNA (mouse or human) minus the Ct of the internal endogenous GAPDH. The data were exported into Microsoft Excel and used to calculate the ΔΔCt value by subtracting the mouse RLBP1 ΔCt value from the human RLBP1 ΔCt for each sample. The relative expression was calculated using the calculation $2^{\Delta\Delta Ct}$ this expresses the relative expression of human RLBP1 as a fold change of the mouse endogenous RLBP1 expression. To portray the results as expression of human RLBP1 as a percent of the mouse endogenous expression the relative expression value was multiplied by 100.

Results: mRNA Expression.

FIG. 1A illustrates that NVS8, NVS4, NVS2 and NVS6 successfully transduce both the neural retina cells and the RPE cells in the posterior eyecup. Vector NVS10 transduces the RPE cells but barely at the level of detection limit in the neural retina.

Figure 1B:
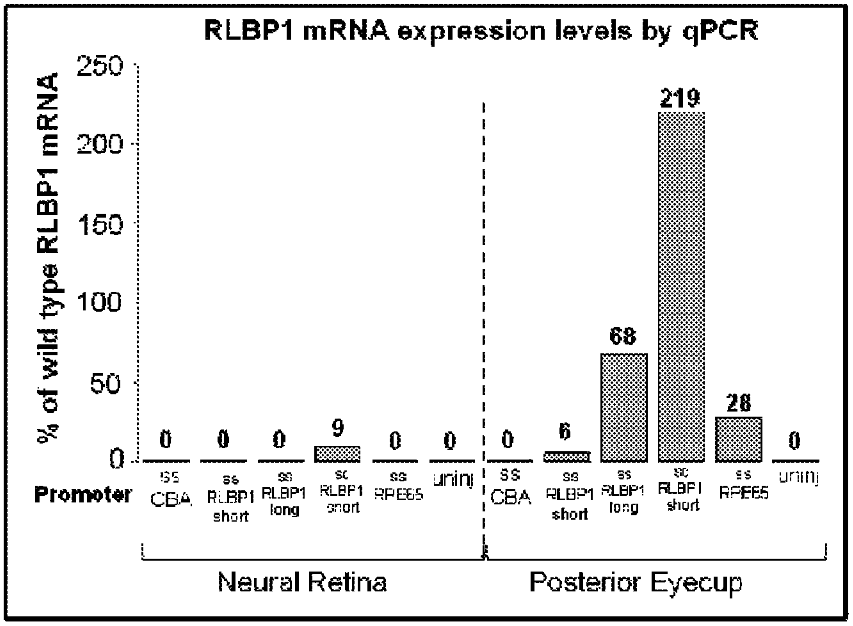

FIG. 1B illustrates that NVS2 is the only vector to show mRNA expression in the neural retina at a lower dose of $1\times10^8$ vg/eye.

Conclusion

These surprising results demonstrated that the specific combination of promoter, AAV genome conformation, and AAV capsid sequence can lead to different transduction properties in different cell types in the retina. In general, all tested vectors successfully lead to vector-mediated human RLBP1 mRNA expression. More specifically, NVS2 is the most potent vector in expressing human RLBP1 mRNA in the RPE cells (in the posterior eyecup) and in the neural retina in both doses tested ($1\times10^9$ and $1\times10^8$ vg/eye), while NVS4 and NVS6 lead to detectable vector-mediated human RLBP1 mRNA expression at the dose of $1\times10^9$ vg/eye, and only in the RPE at the dose of $1\times10^8$ vg/eye. NVS8 and NVS10 lead to detectable mRNA expression in the RPE and neural retina at the dose of $1\times10^9$ vg/eye but almost at the detection limit at the dose of $1\times10^8$ vg/eye.

Example 4

Electroretinogram-Based Dark Adaptation Assay

One approach for assessing treatments that modify the visual cycle is to quantify the recovery of visual function in the dark following a bright light exposure (i.e. dark adaptation). Dark adaptation after extensive light exposure is driven largely by the ability of the eye to regenerate photopigment via the visual cycle. Modifications to the visual cycle achieved through treatment will therefore lead to a change in the kinetics of dark adaptation.

An assay has been developed to monitor the recovery of visual function in mice that is based on quantifying dark adaptation using an electroretinogram (ERG). The ERG-based assay typically proceeds over two days with an initial baseline and subsequent follow-up measurement to assess recovery after exposure to light that bleaches a fraction of the photopigment (photobleach). This procedure developed for testing the invention first determines the maximum electrical response of each eye 5 ms after a flash of light during the a-wave portion of the ERG trace. The test subsequently compares the 5 ms a-wave amplitude 4 hours after a photobleach to assess the fraction of maximum amplitude recovered in that time. If the visual cycle is functioning normally, the ERG amplitude will approach baseline values in 4 hours. A delayed visual cycle will result in lower recovery of photopigment with a corresponding reduction in ERG a-wave amplitude recovery after photobleach.

Supplies/Reagents:

- ERG system: Diagnosys, Espion E2 console with Color-Dome full field ganzfeld stimulator
- Ketamine
- Xylazine
- 2.5% phenylephrine
- 1% cyclopentolate
- 0.5% proparacaine
- Active electrode: Gold loop contact lens electrode (Mayo, part number N30)
- Reference electrode: Nasopharyngeal electrode (Grass, part number F-ERG-G)
- Ground electrode: Platinum needle electrode (Grass, part number F-E2)
- Hydrating drops: Novartis, Genteel Mild to Moderate
- Syringe pump: Harvard Apparatus, part number Pump 11 Plus Protocol:

Mice are placed in the dark overnight for approximately 20 hours before baseline ERGs are recorded. Immediately preceding recording, eyes are dilated with 1-2 drops of 1% cyclopentolate and 1-2 drops of 2.5% phenylephrine. 1-2 drops of 0.5% proparacaine (a topical anesthetic) are also applied. Mice are then anesthetized with an intraperitoneal injection of a cocktail of ketamine and xylazine (100-150 mg/kg and 5-10 mg/kg, respectively). Three electrodes are then placed to enable recording an ERG from one eye per mouse. The active electrode on the eye is a gold loop contact lens, the reference is a nasopharyngeal electrode placed in the mouth and the ground is a subdermal platinum needle electrode placed on the back just behind the head. Eyes are kept moist and electrical contact is maintained through continuous application of hydrating drops with a syringe pump (300 μl/hour). ERG amplitude is recorded by averaging the electrical response to three white flashes (2.7 log scotopic candela second per square meter) delivered by the xenon lamp in the ganzfeld dome. A-wave amplitude reported is the voltage measured 5 ms after the xenon flash as assessed using software analysis routines developed for this purpose (Mathworks, Matlab).

Dark adaptation is assessed by quantifying the ERG a-wave amplitude 4 hours after a photobleach. These experiments typically occur 48 hours after baseline determination. Mice are first housed in the dark overnight just as with the baseline measurements so that ERG recordings occur approximately 20 hours later. Eyes are dilated with 1-2 drops of 2.5% phenylephrine and 1-2 drops of 1% cyclopentolate immediately preceding photobleach. A sequence of 16 flashes of light (3.7 log scotopic candela second per square meter) is then delivered to the eye resulting in a photopigment bleach. Mice are placed back in the dark for 4 hours to recover visual function. ERGs are then recorded utilizing the same protocol used for the baseline determination. The recovery of visual function for each eye is defined as:

$$DA = \frac{a - \text{wave amplitude 4 hours post} - \text{bleach}}{\text{baseline } a - \text{wave amplitude}}$$

Figure 2:
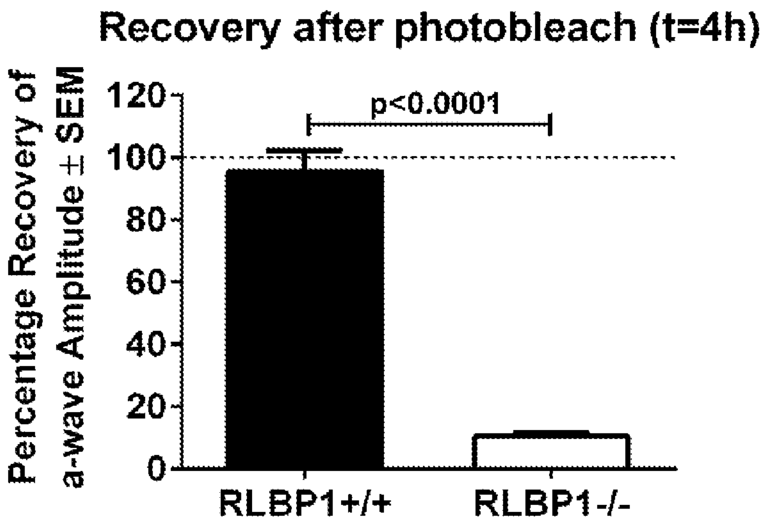
FIG. 2. Dark adaptation in RLBP1 KO (−/−) and wild-type (+/+) mice.

FIG. 2 illustrates the results of the assay when applied to RLBP1−/− and RLBP1+/+ mice. RLBP1+/+ mice exhibit nearly full recovery (up to 96%) 4 hours post-bleach. In contrast, RLBP1−/− mice recover minimal visual function (11%) at the same time point due to severely delayed visual cycle kinetics (Saari et al 2001). This 8-9 fold window between RLBP1+/+ and −/− mice is the assay window achievable for testing vectors injected into RLBP1−/− mice.

Using the ERG-based dark adaptation assay described above, the improvement of dark adaptation efficiency is tested in RLBP1 knockout (KO) mice where therapeutic vectors are introduced subretinally. Since the subretinal injection involves the displacement of neural retina from the RPE, it is crucial to determine if the neural retina is reattached to the RPE to avoid false negative results for the test articles in the ERG assay. One week after subretinal injection of viral vectors into mouse eyes, optical coherence tomography (OCT) is performed to visualize the condition of the retina. Eyes with unresolved retinal detachment were excluded from ERG measurement.

At each time point, mice were dark adapted overnight (>12 hours) and the ERG a-wave amplitude from each eye was established as the maximum dark adapted response to light (100%). The fully dark adapted eyes were then exposed to a series of bright flashes (as described in previous section) and a-wave amplitude was quantified 4 hours later. The term "percentage of normal" is defined as the percentage of the second a-wave recovery measurement with respect to the value obtained from the maximum a-wave recovery measurement.

Positive efficacy, or efficacious effect, is defined as the difference between test measurement and negative (naïve) control being statistically significant at a given time point post-injection.

Test articles used in this example includes:

- NVS1 viral vector
- NVS2 viral vector
- NVS3 viral vector
- NVS4 viral vector
- NVS5 viral vector
- NVS11 viral vector FIGS. 3A-D illustrate that viral vectors expressing RLBP1 improve the rate of dark adaptation in RLBP1 KO mice. Efficacy assessments were performed for each group vs. naïve controls with statistics calculated using a one way ANOVA with a Newman-Keuls multiple comparison test. The mean+3 standard deviations (SD) for naïve (uninjected) eyes and eyes receiving $1\times10^9$ vg/eye of the negative control AAV-null vector (NVS11) for all related studies are shown to indicate the approximate threshold for efficacy (a-wave recoveries above this line typically exhibit statistically significant efficacy). This approach for displaying the degree of efficacy is similar to that presented in gene therapy publications (Jacobson et al. 2006 and Roman et al. 2007).

Figure 3A:
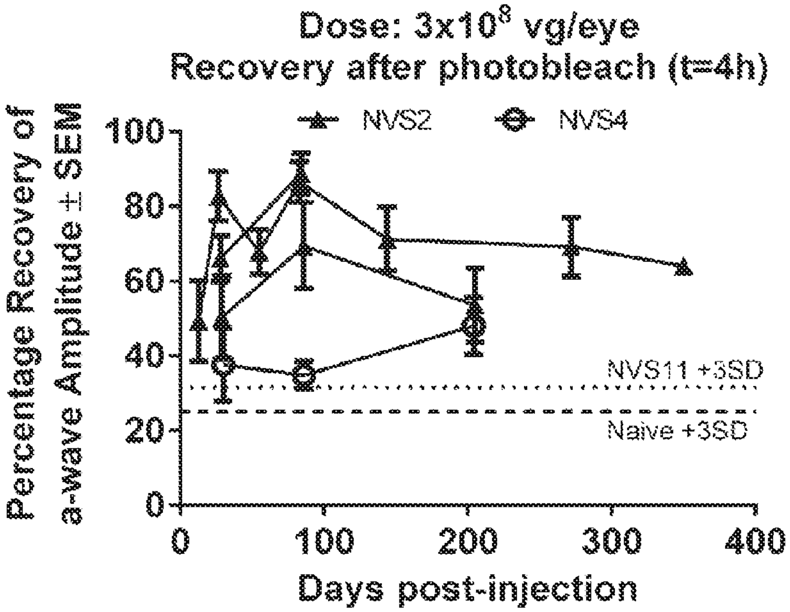
FIGS. 3A-3D. Measurement of rate of dark adaptation of RLBP1 KO mice treated with various viral vectors: NVS1 (3B), NVS3 (3A and 3C), NVS3 (3B and 3D), NVS4 (3A and 3C) and NVS5 (3B and 3D).

FIG. 3A shows that at a dose of $3\times10^8$ vg/eye, NVS2 is efficacious in improving the rate of dark adaptation as early as 14 days post treatment, and the efficacy endures at least 350 days. A dose of $3\times10^8$ vg/eye of NVS4 is also efficacious for at least 30-204 days post-treatment. NVS2 at the dose of approximately $3\times10^8$ vg/eye has been tested in RLBP1 KO mouse model in 3 independent experiments. In each experiment at all time points tested up to 350 days post injection the vector demonstrated efficacy.

Figure 3B:
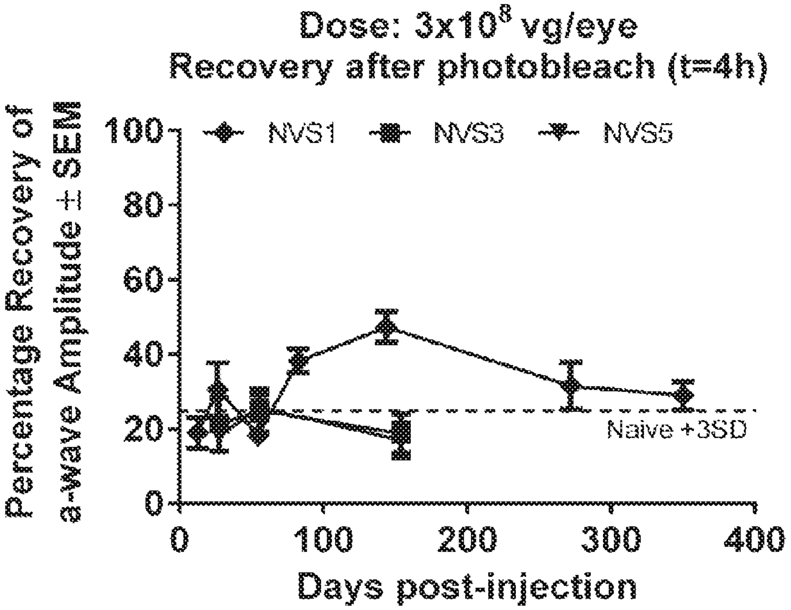

FIG. 3B shows that NVS1 at the same dose ($3\times10^8$ vg/eye) demonstrated efficacy starting 84 days post-injection, with efficacy enduring to at least 350 days. NVS5 and NVS3 at the same dose did not demonstrate efficacy for up to 154 days post drug administration. Data presented in FIGS. 3A and 3B suggested that even though the viral vector genome is equivalent, the vector can be of different potency when packaged in different AAV capsid serotype (NVS1 versus NVS2). In addition, the specific combination of vector serotype, promoter, and vector genome conformation can affect the potency of the vector (NVS1 carries a self-complementary genome while NVS3 and NVS4 carry a single-stranded genome, all with different promoter sequences). This result further confirms that the combination of genome conformation and capsid serotype can affect the efficiency of recovery outcome.

Figure 3C:
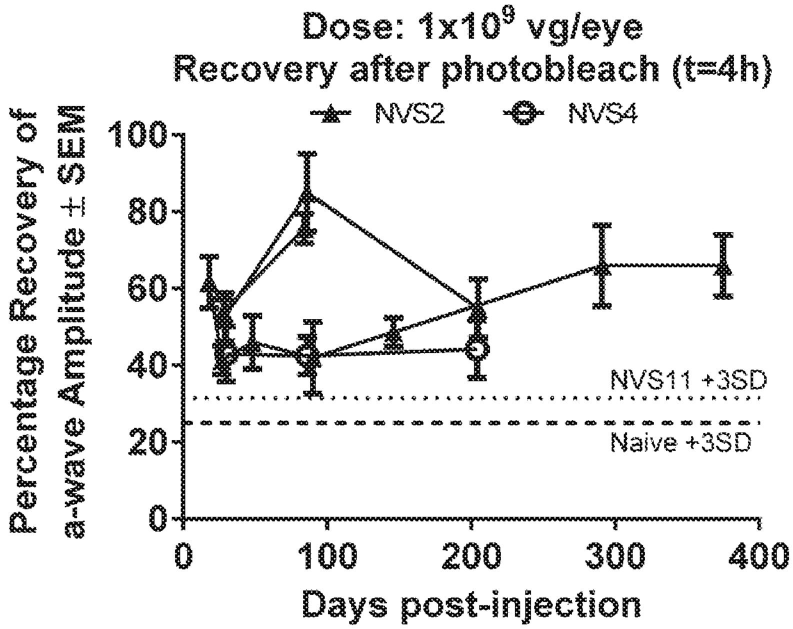

FIG. 3C shows that, at the dose of $1\times10^9$ vg/eye, NVS2 is efficacious as early as 18 days post treatment, and the efficacy endures at least 375 days. At the dose of $1\times10^9$ vg/eye, NVS11, which is a negative control AAV-null vector, did not show significant difference in improvement of rate of dark adaptation when compared to uninjected control (individual data points not shown, but the historical mean+3SD line is displayed for comparison). A dose of $1\times10^9$ vg/eye of NVS4 is also efficacious for at least 30-204 days post-treatment.

Figure 3D:
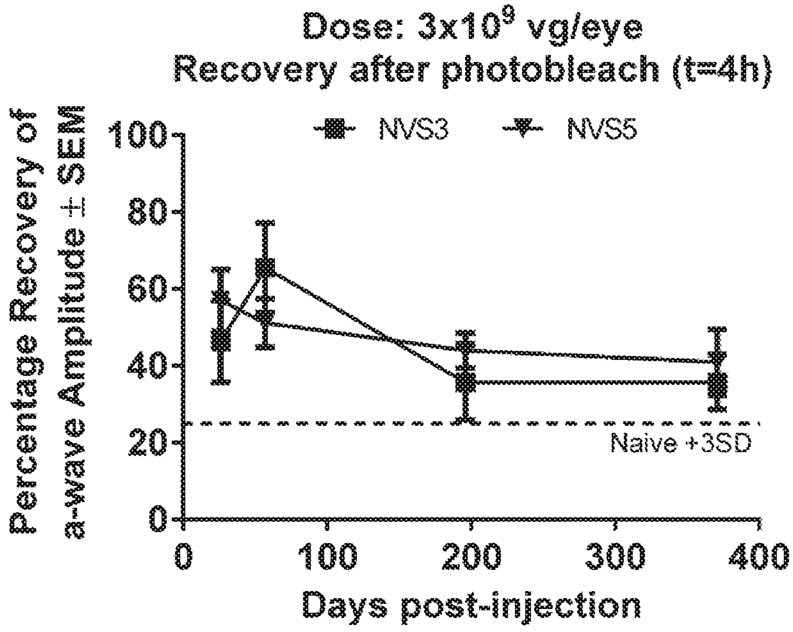

FIG. 3D shows that at a dose of $3\times10^9$ vg/eye, NVS3 and NVS5, respectively, are efficacious in improving the rate of dark adaptation as early as day 26 post-treatment, and the efficacy endures at least 371 days.

Figure 4A:
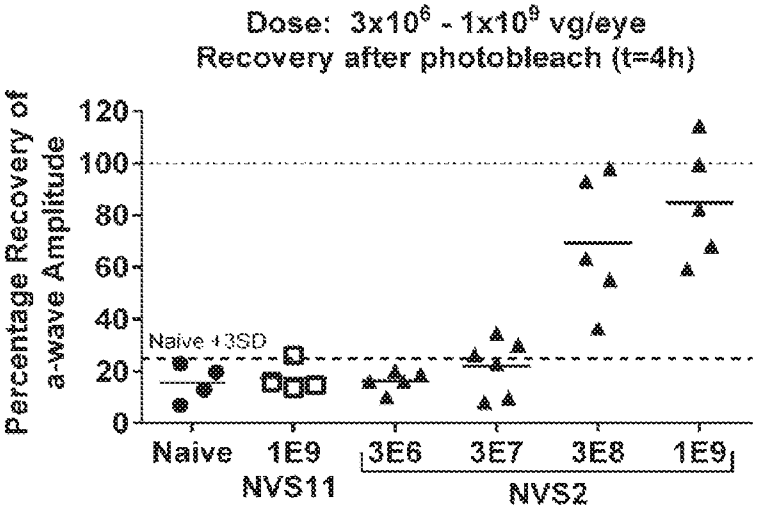
FIGS. 4A-4B. Measurement of increased rate of dark adaptation of RLBP1 KO mice treated with various doses of NVS2 and NVS11 is shown in panel 4A. Panel 4B illustrates treatment efficacy of NVS2. Horizontal axis doses are indicated in scientific notation (for example, 3E6=$3\times10^6$).
Figure 4B:
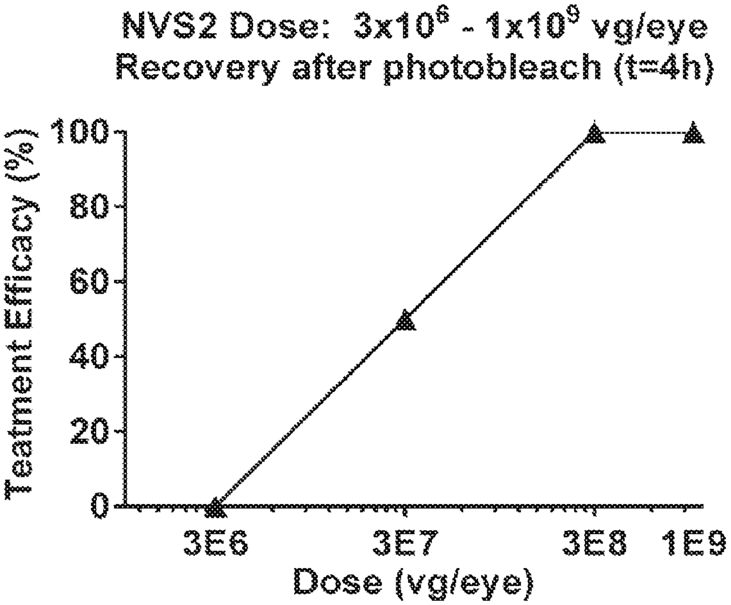

FIG. 4A demonstrates that NVS2 at multiple doses is efficacious at improving the rate of dark adaptation for at least 94 days post-injection. Both the $3\times10^8$ and $1\times10^9$ vg/eye groups were efficacious compared to naïve controls based on a one way ANOVA with a Newman-Keuls multiple comparison test. FIG. 4B displays the data from FIG. 4A in a different format. In this case, the plot displays the percentage of eyes/group with an a-wave recovery greater than that defined by the mean+3SD of the naïve group from several experiments. The results indicate that for NVS2, 50% of $3\times10^7$ vg/eye treated eyes and 100% of $3\times10^8$ and $1\times10^9$ vg/eye treated eyes demonstrated efficacious a-wave recovery, and that a dose-response curve is established.

Figure 5A:
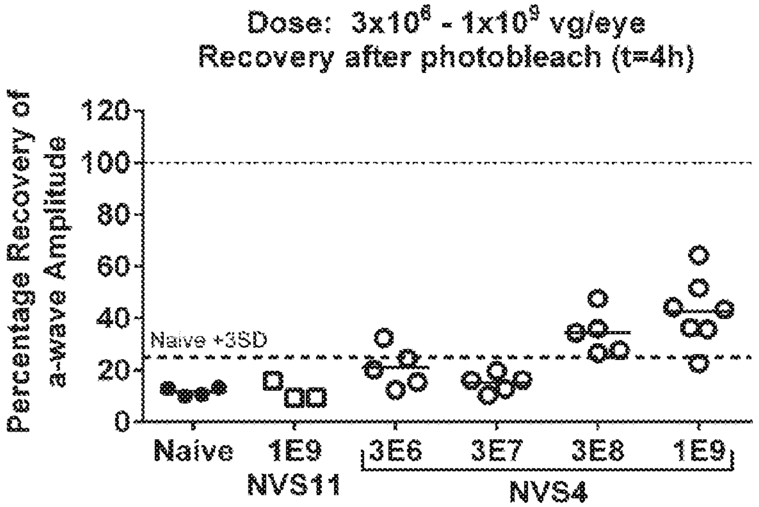
FIGS. 5A-5B. Measurement of increased rate of dark adaptation of RLBP1 KO mice treated with various doses of NVS4 and NVS11 is shown in panel 5A. Panel 5B illustrates treatment efficacy of NVS4. Horizontal axis doses are indicated in scientific notation (for example, 3E6=$3\times10^6$).
Figure 5B:
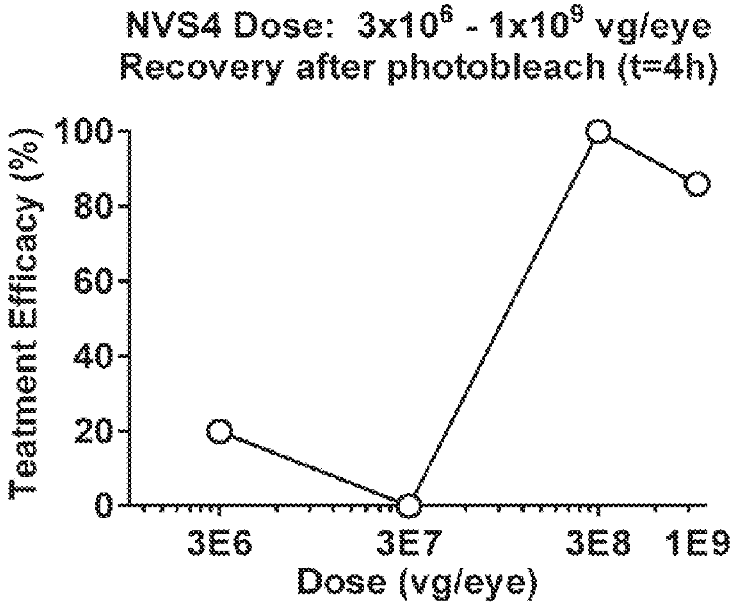

FIG. 5A demonstrates that NVS4 at multiple doses is efficacious at improving the rate of dark adaptation for at least 93 days post-injection. Both the $3\times10^8$ and $1\times10^9$ vg/eye groups were efficacious compared to naïve controls based on a one way ANOVA with a Newman-Keuls multiple comparison test. FIG. 5B displays the data from FIG. 5A in a different format. In this case, the plot displays the percentage of eyes/group with an a-wave recovery greater than that defined by the mean+3SD of the naïve group from several experiments. The results suggest that for NVS4, ≥85% of eyes treated with $3\times10^8$ and $1\times10^9$ vg/eye exhibited an increase in dark adaptation rate.

Figure 6:
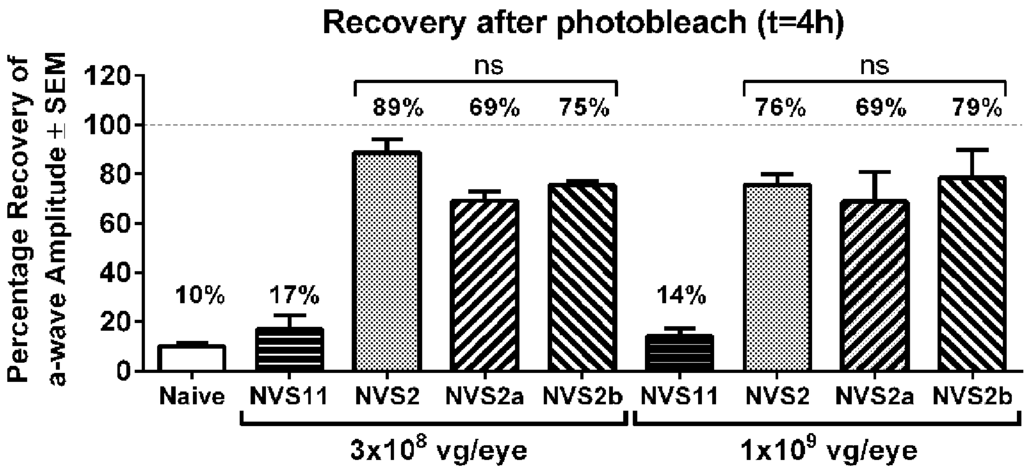
FIG. 6. Measurement of increased rate of dark adaptation of RLBP1 KO mice treated with NVS2 prepared with different purification methods.

FIG. 6 demonstrates the increase in dark adaptation rate achieved with vector NVS2 generated by various production methods. NVS2 and NVS2a were both produced using two different CsCl gradient centrifugation methods while NVS2b was purified using column chromatography. Efficacy achieved 84 days post-injection with all three purification methods is indistinguishable based on a one way ANOVA with a Tukey's test. This result indicates that 3 independent productions of NVS2 in 2 independent laboratories yielded functional material resulting in similar efficacy in RLBP1 KO mice.

Summary of Example 4 Results:

- Eyes injected with viral vector NVS2 exhibit an increased rate of dark adaption at doses ranging from $\geq3\times10^7$ to $1\times10^9$ vg/eye, where efficacy lasts for at least 350 days post injection in the RLBP1 KO mouse model.
- Eyes injected with viral vector NVS4 exhibit an increased rate of dark adaption at doses ranging from $3\times10^8$ to $1\times10^9$ vg/eye and the efficacy endures at least 204 days at both doses.
- Eyes injected with viral vector NVS1 exhibit an increased rate of dark adaptation at the dose of $3\times10^8$ vg/eye and the efficacy endures at least 350 days.
- Eyes injected with viral vector NVS3 and NVS5 exhibit an increased rate of dark adaptation at the dose of $3\times10^9$ vg/eye and efficacy endures at least 371 days. Efficacy of NVS3 and NVS5 was not observed at $3\times10^8$ vg/eye for any time point tested.

Conclusion

Viral vector NVS2 exhibits higher maximum recovery than equivalent doses of the other vectors tested. Additionally, the NVS2 vector-mediated efficacy appears to be indistinguishable when prepared using CsCl or column chromatography purification.

Summary of Results:

The results demonstrated that self-complementary AAV8-pRLBP1(short)-eGFP vector, the reporter gene surrogate version of the therapeutic vector NVS2, leads to RPE and Müller cell type specific expression with no detectable off-target expression, where the therapeutic vector NVS2 leads to at least 350 days of visual function recovery measured by a-wave recovery in RLBP1 mice at doses ranging from $\geq3\times10^7$ to $1\times10^9$ vg/eye. This specific gene cassette when packaged in a single-stranded genome and packaged with the same serotype capsid 8 exhibits significantly lower level of gene expression in mice, as demonstrated by the measurement of mRNA expression level. The same self-complementary genome as NVS2 and packaged in AAV2 capsid, which is NVS1, demonstrated efficacious a-wave recovery (i.e.: an increased rate of dark adaption) at the dose of $3\times10^8$ vg/eye for at least 350 days. This result suggests that NVS2 is a more potent viral vector than NVS1, which is likely due to the more efficient infection of AAV8 capsid than AAV2 capsid to the target cell types.

The results also demonstrated that AAV8-pRLBP1(long)-eGFP vector, the reporter gene surrogate version of the therapeutic vector NVS4, leads to RPE and Müller cell expression but also to photoreceptors. The therapeutic vector NVS4 leads to at least 204 days of efficacy at doses ranging from $3\times10^8$ to $1\times10^9$ vg/eye. The same genome in NVS4 but packaged in AAV 2 capsid, which is NVS3, leads to efficacious a-wave recovery at the dose of $3\times10^9$ but not at lower dose tested ($3\times10^8$ vg/eye). The results demonstrated that AAV8-pRPE65-eGFP vector, the reporter gene surrogate version of the therapeutic vector NVS6, leads to RPE cell type expression with extensive photoreceptor off-target expression. When therapeutic vector NVS5, which carries the same genome as NVS6 but packaged into AAV2 capsid, is tested in RLBP1 KO mouse efficacy model, the results demonstrated that NVS5 endures positive a-wave recovery efficacy at the dose of $3\times10^9$ vg/eye but not at lower dose tested ($3\times10^8$ vg/eye).

REFERENCES

Burstedt M S, Forsman-Semb K, Golovleva I, et al (2001) Ocular phenotype of Bothnia dystrophy, an autosomal recessive retinitis pigmentosa associated with an R234W mutation in the RLBP1 gene. Arch Ophthalmol; 119:260-267.

Burstedt M S and Mönestam E (2010) Self-reported quality of life in patients with retinitis pigmentosa and maculopathy of Bothnia type. Clin Ophthalmol; 4:147-54.

Choi V W, Asokan A, Haberman R A, and Samulski R J (2007) Production of Recombinant Adeno-Associated Viral Vectors for In Vitro and In Vivo Use. CURRENT PROTOCOLS IN MOLECULAR BIOLOGY. 16:25, Supplement 78.

Choi V W, McCarty D M, and Samulski R J (2005) AAV Hybrid Serotypes: Improved Vectors for Gene Delivery. Curr Gene Ther; 5(3):299-310.

Demirci F Y K, Rigatti B W, Mah T S, et al (2004) A novel compound heterozygous mutation in the cellular retinaldehyde-binding protein gene (RLBP1) in a patient with retinitis *punctata albescens*. Am J Ophthalmol.; 138:171-173.

Eichers E R, Green J S, Stockton D W, et al (2002) Newfoundland rod-cone dystrophy, an early-onset retinal dystrophy, is caused by splice-junction mutations in RLBP1. Am J Hum Genet; 70:955-964.

Ferrari F K, Xiao X, McCarty D et al (1997) New developments in the generation of Ad-free, high-titer rAAV gene therapy vectors. Nat Med 3(11); 1295-1297.

Fishman G A, Roberts M F, Derlacki D J, et al (2004) Novel mutations in the cellular retinaldehyde-binding protein gene (RLBP1) associated with retinitis *punctata albescens*: evidence of interfamilial genetic heterogeneity and fundus changes in heterozygotes. Arch Ophthalmol.; 122: 70-75.

Golovleva I and Burstedt M (2012) Retinitis Pigmentosa in Northern Sweden—From Gene to Treatment. March 2012. Advances in Ophthalmology, chapter 25, p. 451-472. Published by InTech.

Golovleva I, Köhn L, Burstedt M, et al (2010) Mutation spectra in autosomal dominant and recessive retinitis pigmentosa in northern Sweden. Adv Exp Med Biol. 664:255-262.

Grieger J C, Choi V W and Samulski R J. (2006) Production and characterization of adeno-associated viral vectors. Nat Protoc. 1(3); 1412-1428.

He X, Lobsiger J and Stocker A (2009) Bothnia dystrophy is caused by domino-like rearrangements in cellular retinaldehyde-binding protein mutant R234W. Proc. Natl Acad Sci USA. 106(44): 18545-50.

Jacobson S G, Acland G M, Aguirre G D et al (2006) Safety of Recombinant Adeno-Associated Virus Type 2-RPE65 Vector Delivered by Ocular Subretinal Injection. Molecular Therapy. 13(6); 1074-1084.

Katsanis N, Shroyer N F, Lewis R A, et al (2001) Fundus albipunctatus and retinitis *punctata albescens* in a pedigree with an R150Q mutation in RLBP1. Clin Genet; 59:424-429.

Köhn L, Burstedt M S, Jonsson F, et al (2008) Carrier of R14W in carbonic anhydrase IV presents Bothnia dystrophy phenotype caused by two allelic mutations in RLBP1. Invest Opthalmol Vis Sci. 49(7): 3172-3177.

Lock M, Alvira M, Vandenberghe L H, et al. (2010) Rapid, Simple, and Versatile Manufacturing of Recombinant Adeno-Associated Viral Vectors at scale. Human Gene Therapy. 21; 1-13.

Maw M A, Kennedy B, Knight A, et al (1997) Mutation of the gene encoding cellular retinaldehyde-binding protein in autosomal recessive retinitis pigmentosa. Nat Genet; 17:198-200.

McCarty D M (2008) Self-Complementary AAV Vectors; Advances and Applications. Molecular Therapy. 16(10): 1648-1656.

McCarty D M, Fu H, Monohan P E et al (2003) Adeno-associated virus terminal repeat (TR) mutant generates self-complementary vectors to overcome the rate-limiting step t transduction in vivo. Gene Therapy. 10; 2112-2118.

Morimura H, Berson E L, Dryja T P (1999) Recessive mutations in the RLBP1 gene encoding cellular retinaldehyde-binding protein in a form of retinitis *punctata albescens*. Invest Ophthalmol Visual Sci; 40:1000-1004.

Muzyczka N and Berns K I (2001) Chapter 69, Fields Virology. Lippincott Williams & Wilkins.

Naz S, Ali S, Riazuddin S A, et al (2011) Mutations in RLBP1 associated with fundus albipunctatus in consanguineous Pakistani families. Br J Ophthalmol; 95:1019-24.

Nojima K, Hosono K, Zhao Y, et al (2011) Clinical features of a Japanese case with Bothnia dystrophy. Ophthalmic Genet [Epub ahead of print]

Phelan J K and Bok D (2000) A Brief Review of Retinitis Pigmentosa and the Identified Retinitis Pigmentosa Genes. Mol Vis; 6:116-124.

Roman A J, Boye S L, Aleman T S, et al (2007) Electroretinographic Analyses of RPE65-mutant rd12 Mice: Developing an In Vivo Bioassay for Human Gene Therapy Trials of Leber Congenital Amaurosis. Mol Vis. 13; 1701-1710.

Saari J C, Huang J, Possin D E, et al (1997) Cellular retinaldehyde-binding protein is expressed by oligodendrocytes in optic nerve and brain. Glia.; 21:259-268.

SAMBROOK et al (1989) MOLECULAR CLONING: A LABORATORY MANUAL 2nd Ed. (Cold Spring Harbor, N.Y)

Saari J C, Nawrot M, Kennedy B N et al. (2001) Visual Cycle Impairment in Cellular Retinaldehyde Binding Protein (CRALBP) Knockout Mice Results in Delayed Dark Adaptation. Neuron; 29:739-748.

Samulski R J, Srivastava A, Berns K I, et al. (1983) Rescue of adeno-associated virus from recombinant plasmids: gene correction within the terminal repeats of AAV. Cell. 33(1):135-143.

Schmidt M, Vouteaakis A, Afione S et al. (2008) Adeno-Associated Virus Type 12 (AAV12): a Novel AAV Serotype with Sialic Acid- and Heparan Sulfate Proteoglycan-Independent Transduction Activity. J of Virology. 82(3): 1399-1406.

Smith R H, Levy J R and Kotin R M. (2009) A Simplified Baculovirus-AAV Expression Vector System Coupled with One-Step Affinity Purification Yields High-Titer rAAV Stocks from Insect Cells. Molecular Therapy. 17(11); 1888-1896.

Travis G H, Golczak M, Moise A R, et al (2007) Diseases caused by defects in the visual cycle: retinoids as potential therapeutic agents. Annu Rev Pharmacol Toxicol.; 47: 469-512.

Vandenberghe L H, Xiao R, Lock M, et al. (2010) Efficient Serotype-Dependent Release of Functional Vector into the Culture Medium During Adeno-Associated Virus Manufacturing. Human Gene Therapy. 21; 1251-1257.

Wang J and Kefalov J V (2011) The Cone-specific visual cycle. Progress in retinal and eye research. 30: 115-128.

The invention claimed is:

1. A viral vector comprising:

a vector genome comprising the nucleic acid sequences of SEQ ID NOs:5, 6, 8, and 9; and an adeno-associated virus (AAV) serotype 2 or 8 capsid.

2. The viral vector of claim 1, wherein the vector genome further comprises a 5' inverted terminal repeat (ITR) comprising the nucleic acid sequence of SEQ ID NO:1.

3. The viral vector of claim 1, wherein the vector genome further comprises a retinaldehyde binding protein 1 (RLBP1) promoter comprising the nucleic acid sequence of SEQ ID NO:3.

4. The viral vector of claim 1, wherein the vector comprises an AAV2 capsid.

5. The viral vector of claim 4, wherein the AAV2 capsid is encoded by a nucleic acid sequence comprising the sequence of SEQ ID NO:18.

6. The viral vector of claim 1, wherein the vector comprises an AAV8 capsid.

7. The viral vector of claim 6, wherein the AAV8 capsid is encoded by a nucleic acid sequence comprising the sequence of SEQ ID NO:20.

8. The viral vector of claim 1, wherein the vector genome further comprises a plasmid sequence comprising the nucleic acid sequence of SEQ ID NO:26, 27, 28, 29, 30, or 50.

9. A composition comprising the viral vector of claim 1.

10. The composition of claim 9 further comprising a pharmaceutically acceptable excipient.

11. The viral vector of claim 1, wherein the vector genome further comprises a 5' inverted terminal repeat (ITR) comprising the nucleic acid sequence of SEQ ID NO:2.

12. The viral vector of claim 1, wherein the vector genome further comprises a RLBP1 promoter comprising the nucleic acid sequence of SEQ ID NO:10.

* * * * *

UNITED STATES PATENT AND TRADEMARK OFFICE

CERTIFICATE OF CORRECTION

PATENT NO. : 9,803,217 B2
APPLICATION NO. : 14/881960
DATED : October 31, 2017
INVENTOR(S) : Vivian Choi et al.

It is certified that error appears in the above-identified patent and that said Letters Patent is hereby corrected as shown below:

On the Title Page

At Column 1, item (71) (Applicants:), should read:
Vivian Choi, Waltham, MA (US); Chad Eric Bigelow, Somerville, MA (US), Thaddeus Peter Dryja, Milton, MA (US), Seshidhar Reddy Police, Burlington, MA (US), Akshata Ninad Gujar, Waltham, MA (US), Shawn Michael Hanks, Sudbury, MA (US), Terri McGee, Walpole, MA (US) and Joanna Vrouvlianis, Melrose, MA (US)

At Column 1, item (72) (Inventors:), should read:
Vivian Choi, Waltham, MA (US); Chad Eric Bigelow, Somerville, MA (US), Thaddeus Peter Dryja, Milton, MA (US), Seshidhar Reddy Police, Burlington, MA (US), Akshata Ninad Gujar, Waltham, MA (US), Shawn Michael Hanks, Sudbury, MA (US), Terri McGee, Walpole, MA (US) and Joanna Vrouvlianis, Melrose, MA (US)

Signed and Sealed this
Second Day of August, 2022

Katherine Kelly Vidal

Katherine Kelly Vidal
*Director of the United States Patent and Trademark Office*

SEQUENCE LISTING

<160> NUMBER OF SEQ ID NOS: 71

<210> SEQ ID NO 1
<211> LENGTH: 103
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1
cgcgctcgct cgctcactga ggccgcccgg gcaaagcccg ggcgtcgggc gacctttggt 60
cgcccggcct cagtgagcga gcgagcgcgc agagagggag tgg 103

<210> SEQ ID NO 2
<211> LENGTH: 119
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 2
ctgcgcgctc gctcgctcac tgaggccgcc cgggcgtcgg gcgacctttg gtcgcccggc 60
ctcagtgagc gagcgagcgc gcagagaggg agtggccaac tccatcacta ggggttcct 119

<210> SEQ ID NO 3
<211> LENGTH: 590
<212> TYPE: DNA
<213> ORGANISM: Homo sapiens

<400> SEQUENCE: 3
ttgtcctctc cctgcttggc cttaaccagc cacatttctc aactgacccc actcactgca 60
gaggtgaaaa ctaccatgcc aggtcctgct ggctggggga ggggtgggca ataggcctgg 120
atttgccaga gctgccactg tagatgtagt catatttacg atttcccttc acctcttatt 180
accctggtgg tggtggtggg gggggggggg tgctctctca gcaaccccac cccgggatct 240
tgaggagaaa gagggcagag aaaagaggga atgggactgg cccagatccc agccccacag 300
ccgggcttcc acatggccga gcaggaactc cagagcagga gcacacaaag gagggctttg 360
atgcgcctcc agccaggccc aggcctctcc cctctcccct ttctctctgg gtcttccttt 420
gccccactga gggcctcctg tgagcccgat ttaacggaaa ctgtgggcgg tgagaagttc 480
cttatgacac actaatccca acctgctgac cggaccacgc ctccagcgga gggaacctct 540
agagctccag gacattcagg taccaggtag ccccaaggag gagctgccga 590

<210> SEQ ID NO 4
<211> LENGTH: 183
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 4
aactgaaaaa ccagaaagtt aactggtaag tttagtcttt ttgtctttta tttcaggtcc 60
cggatccggt ggtggtgcaa atcaaagaac tgctcctcag tggatgttgc ctttacttct 120
aggcctgtac ggaagtgtta cttctgctct aaaagctgcg gaattgtacc cgccccggga 180
tcc 183

<210> SEQ ID NO 5
<211> LENGTH: 6
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 5 gccacc 6

<210> SEQ ID NO 6
<211> LENGTH: 954
<212> TYPE: DNA
<213> ORGANISM: Homo sapiens

<400> SEQUENCE: 6
atgtcagaag gggtgggcac gttccgcatg gtacctgaag aggaacagga gctccgtgcc 60
caactggagc agctcacaac caaggaccat ggacctgtct ttggcccgtg cagccagctg 120
ccccgccaca ccttgcagaa ggccaaggat gagctgaacg agagagagga gacccgggag 180
gaggcagtgc gagagctgca ggagatggtg caggcgcagg cggcctcggg ggaggagctg 240
gcggtggccg tggcggagag ggtgcaagag aaggacagcg gcttcttcct gcgcttcatc 300
cgcgcacgga agttcaacgt gggccgtgcc tatgagctgc tcagaggcta tgtgaatttc 360
cggctgcagt accctgagct ctttgacagc ctgtccccag aggctgtccg ctgcaccatt 420
gaagctggct accctggtgt cctctctagt cgggacaagt atggccgagt ggtcatgctc 480
ttcaacattg agaactggca aagtcaagaa atcacctttg atgagatctt gcaggcatat 540
tgcttcatcc tggagaagct gctggagaat gaggaaactc aaatcaatgg cttctgcatc 600
attgagaact tcaagggctt taccatgcag caggctgcta gtctccggac ttcagatctc 660
aggaagatgg tggacatgct ccaggattcc ttcccagccc ggttcaaagc catccacttc 720
atccaccagc catggtactt caccacgacc tacaatgtgg tcaagccctt cttgaagagc 780
aagctgcttg agagggtctt tgtccacggg gatgaccttt ctggtttcta ccaggagatc 840
gatgagaaca tcctgccctc tgacttcggg ggcacgctgc ccaagtatga tggcaaggcc 900
gttgctgagc agctctttgg cccccaggcc caagctgaga acacagcctt ctga 954

<210> SEQ ID NO 7
<211> LENGTH: 317
<212> TYPE: PRT
<213> ORGANISM: Homo sapiens

<400> SEQUENCE: 7

Met Ser Glu Gly Val Gly Thr Phe Arg Met Val Pro Glu Glu Glu Gln
1 5 10 15

Glu Leu Arg Ala Gln Leu Glu Gln Leu Thr Thr Lys Asp His Gly Pro
20 25 30

Val Phe Gly Pro Cys Ser Gln Leu Pro Arg His Thr Leu Gln Lys Ala
35 40 45

Lys Asp Glu Leu Asn Glu Arg Glu Glu Thr Arg Glu Glu Ala Val Arg
50 55 60

Glu Leu Gln Glu Met Val Gln Ala Gln Ala Ala Ser Gly Glu Glu Leu
65 70 75 80

Ala Val Ala Val Ala Glu Arg Val Gln Glu Lys Asp Ser Gly Phe Phe
85 90 95

```
Leu Arg Phe Ile Arg Ala Arg Lys Phe Asn Val Gly Arg Ala Tyr Glu
            100                 105                 110

Leu Leu Arg Gly Tyr Val Asn Phe Arg Leu Gln Tyr Pro Glu Leu Phe
        115                 120                 125

Asp Ser Leu Ser Pro Glu Ala Val Arg Cys Thr Ile Glu Ala Gly Tyr
    130                 135                 140

Pro Gly Val Leu Ser Ser Arg Asp Lys Tyr Gly Arg Val Val Met Leu
145                 150                 155                 160

Phe Asn Ile Glu Asn Trp Gln Ser Gln Glu Ile Thr Phe Asp Glu Ile
                165                 170                 175

Leu Gln Ala Tyr Cys Phe Ile Leu Glu Lys Leu Leu Glu Asn Glu Glu
            180                 185                 190

Thr Gln Ile Asn Gly Phe Cys Ile Ile Glu Asn Phe Lys Gly Phe Thr
        195                 200                 205

Met Gln Gln Ala Ala Ser Leu Arg Thr Ser Asp Leu Arg Lys Met Val
    210                 215                 220

Asp Met Leu Gln Asp Ser Phe Pro Ala Arg Phe Lys Ala Ile His Phe
225                 230                 235                 240

Ile His Gln Pro Trp Tyr Phe Thr Thr Thr Tyr Asn Val Val Lys Pro
                245                 250                 255

Phe Leu Lys Ser Lys Leu Leu Glu Arg Val Phe Val His Gly Asp Asp
            260                 265                 270

Leu Ser Gly Phe Tyr Gln Glu Ile Asp Glu Asn Ile Leu Pro Ser Asp
        275                 280                 285

Phe Gly Gly Thr Leu Pro Lys Tyr Asp Gly Lys Ala Val Ala Glu Gln
    290                 295                 300

Leu Phe Gly Pro Gln Ala Gln Ala Glu Asn Thr Ala Phe
305                 310                 315


<210> SEQ ID NO 8
<211> LENGTH: 236
<212> TYPE: DNA
<213> ORGANISM: Simian virus 40

<400> SEQUENCE: 8

gatcataatc agccatacca catttgtaga ggttttactt gctttaaaaa acctcccaca      60

cctccccctg aacctgaaac ataaaatgaa tgcaattgtt gttgttaact tgtttattgc     120

agcttataat ggttacaaat aaagcaatag catcacaaat ttcacaaata aagcattttt     180

ttcactgcat tctagttgtg gtttgtccaa actcatcaat gtatcttatc atgtct         236


<210> SEQ ID NO 9
<211> LENGTH: 130
<212> TYPE: DNA
<213> ORGANISM: Adeno-associated virus

<400> SEQUENCE: 9

aggaacccct agtgatggag ttggccactc cctctctgcg cgctcgctcg ctcactgagg      60

ccgggcgacc aaaggtcgcc cgacgcccgg gctttgcccg ggcggcctca gtgagcgagc     120

gagcgcgcag                                                            130


<210> SEQ ID NO 10
<211> LENGTH: 3157
<212> TYPE: DNA
<213> ORGANISM: Homo sapiens

<400> SEQUENCE: 10
```

```
ttgtcctctc cctgcttggc cttaaccagc cacatttctc aactgacccc actcactgca      60
gaggtgaaaa ctaccatgcc aggtcctgct ggctggggga ggggtgggca ataggcctgg     120
atttgccaga gctgccactg tagatgtagt catatttacg atttcccttc acctcttatt     180
accctggtgg tggtggtggg gggggggggg tgctctctca gcaaccccac cccgggatct     240
tgaggagaaa gagggcagag aaaagaggga atgggactgg cccagatccc agccccacag     300
ccgggcttcc acatggccga gcaggaactc cagagcagga gcacacaaag gagggctttg     360
atgcgcctcc agccaggccc aggcctctcc cctctcccct ttctctctgg gtcttccttt     420
gccccactga gggcctcctg tgagcccgat ttaacggaaa ctgtgggcgg tgagaagttc     480
cttatgacac actaatccca acctgctgac cggaccacgc ctccagcgga gggaacctct     540
agagctccag gacattcagg taccaggtag ccccaaggag gagctgccga cctggcaggt     600
aagtcaatac ctggggcttg cctgggccag ggagcccagg actggggtga ggactcaggg     660
gagcagggag accacgtccc aagatgcctg taaaactgaa accacctggc cattctccag     720
gttgagccag accaatttga tggcagattt agcaaataaa aatacaggac acccagttaa     780
atgtgaattt cagatgaaca gcaaatactt ttttagtatt aaaaaagttc acatttaggc     840
tcacgcctgt aatcccagca ctttgggagg ccgaggcagg cagatcacct gaggtcagga     900
gttcgagacc agcctggcca acatggtgaa accccatctc cactaaaaat accaaaaatt     960
agccaggcgt gctggtgggc acctgtagtt ccagctactc aggaggctaa ggcaggagaa    1020
ttgcttgaac ctgggaggca gaggttgcag tgagctgaga tcgcaccatt gcactctagc    1080
ctgggcgaca agaacaaaac tccatctcaa aaaaaaaaaa aaaaaaaaag ttcacattta    1140
actgggcatt ctgtatttaa ttggtaatct gagatggcag ggaacagcat cagcatggtg    1200
tgagggatag gcattttttc attgtgtaca gcttgtaaat cagtattttt aaaactcaaa    1260
gttaatggct tgggcatatt tagaaaagag ttgccgcacg gacttgaacc ctgtattcct    1320
aaaatctagg atcttgttct gatggtctgc acaactggct gggggtgtcc agccactgtc    1380
cctcttgcct gggctcccca gggcagttct gtcagcctct ccatttccat tcctgttcca    1440
gcaaaaccca actgatagca cagcagcatt tcagcctgtc tacctctgtg cccacatacc    1500
tggatgtcta ccagccagaa aggtggctta gatttggttc ctgtgggtgg attatggccc    1560
ccagaacttc cctgtgcttg ctgggggtgt ggagtggaaa gagcaggaaa tgggggaccc    1620
tccgatactc tatgggggtc ctccaagtct ctttgtgcaa gttagggtaa taatcaatat    1680
ggagctaaga aagagaaggg gaactatgct ttagaacagg acactgtgcc aggagcattg    1740
cagaaattat atggttttca cgacagttct ttttggtagg tactgttatt atcctcagtt    1800
tgcagatgag gaaactgaga cccagaaagg ttaaataact tgctagggtc acacaagtca    1860
taactgacaa agcctgattc aaacccaggt ctccctaacc tttaaggttt ctatgacgcc    1920
agctctccta gggagtttgt cttcagatgt cttggctcta ggtgtcaaaa aaagacttgg    1980
tgtcaggcag gcataggttc aagtcccaac tctgtcactt accaactgtg actaggtgat    2040
tgaactgacc atggaacctg gtcacatgca ggagcaggat ggtgaagggt tcttgaaggc    2100
acttaggcag gacatttagg caggagagaa aacctggaaa cagaagagct gtctccaaaa    2160
atacccactg gggaagcagg ttgtcatgtg ggccatgaat gggacctgtt ctggtaacca    2220
agcattgctt atgtgtccat tacatttcat aacacttcca tcctacttta cagggaacaa    2280
ccaagactgg ggttaaatct cacagcctgc aagtggaaga gaagaacttg aacccaggtc    2340
```

```
caacttttgc gccacagcag gctgcctctt ggtcctgaca ggaagtcaca acttgggtct   2400
gagtactgat ccctggctat tttttggctg tgttaccttg gacaagtcac ttattcctcc   2460
tcccgtttcc tcctatgtaa aatggaaata ataatgttga ccctgggtct gagagagtgg   2520
atttgaaagt acttagtgca tcacaaagca cagaacacac ttccagtctc gtgattatgt   2580
acttatgtaa ctggtcatca cccatcttga gaatgaatgc attggggaaa gggccatcca   2640
ctaggctgcg aagtttctga gggactcctt cgggctggag aaggatggcc acaggaggga   2700
ggagagattg ccttatcctg cagtgatcat gtcattgaga acagagccag attctttttt   2760
tcctggcagg gccaacttgt tttaacatct aaggactgag ctatttgtgt ctgtgccctt   2820
tgtccaagca gtgtttccca aagtgtagcc caagaaccat ctccctcaga gccaccagga   2880
agtgctttaa attgcaggtt cctaggccac agcctgcacc tgcagagtca gaatcatgga   2940
ggttgggacc caggcacctg cgtttctaac aaatgcctcg ggtgattctg atgcaattga   3000
aagtttgaga tccacagttc tgagacaata acagaatggt tttctaacc cctgcagccc    3060
tgacttccta tcctagggaa ggggccggct ggagaggcca ggacagagaa agcagatccc   3120
ttctttttcc aaggactctg tgtcttccat aggcaac                             3157
```

<210> SEQ ID NO 11
<211> LENGTH: 1585
<212> TYPE: DNA
<213> ORGANISM: Homo sapiens

<400> SEQUENCE: 11

```
tacgtaatat ttattgaagt ttaatattgt gtttgtgata cagaagtatt tgctttaatt     60
ctaaataaaa attttatgct tttattgctg gtttaagaag atttggatta tccttgtact    120
ttgaggagaa gtttcttatt tgaaatattt tggaaacagg tcttttaatg tggaaagata    180
gatattaatc tcctcttcta ttactctcca agatccaaca aaagtgatta tacccccaa     240
aatatgatgg tagtatctta tactaccatc attttatagg catagggctc ttagctgcaa    300
ataatggaac taactctaat aaagcagaac gcaaatattg taaatattag agagctaaca    360
atctctggga tggctaaagg atggagcttg gaggctaccc agccagtaac aatattccgg    420
gctccactgt tgaatggaga cactacaact gccttggatg ggcagagata ttatggatgc    480
taagccccag gtgctaccat taggacttct accactgtcc ctaacgggtg gagcccatca    540
catgcctatg ccctcactgt aaggaaatga agctactgtt gtatatcttg ggaagcactt    600
ggattaattg ttatacagtt ttgttgaaga agacccctag ggtaagtagc cataactgca    660
cactaaattt aaaattgtta atgagtttct caaaaaaaat gttaaggttg ttagctggta    720
tagtatatat cttgcctgtt ttccaaggac ttctttgggc agtaccttgt ctgtgctggc    780
aagcaactga gacttaatga aagagtattg gagatatgaa tgaattgatg ctgtatactc    840
tcagagtgcc aaacatatac caatggacaa gaaggtgagg cagagagcag acaggcatta    900
gtgacaagca aagatatgca gaatttcatt ctcagcaaat caaaagtcct caacctggtt    960
ggaagaatat tggcactgaa tggtatcaat aaggttgcta gagagggtta gaggtgcaca   1020
atgtgcttcc ataacatttt atacttctcc aatcttagca ctaatcaaac atggttgaat   1080
actttgttta ctataactct tacagagtta taagatctgt gaagacaggg acaggacaa    1140
tacccatctc tgtctggttc ataggtggta tgtaatagat atttttaaaa ataagtgagt   1200
taatgaatga gggtgagaat gaaggcacag aggtattagg gggaggtggg ccccagagaa   1260
tggtgccaag gtccagtggg gtgactggga tcagctcagg cctgacgctg gccactccca   1320
```

-continued cctagctcct ttctttctaa tctgttctca ttctccttgg gaaggattga ggtctctgga 1380
aaacagccaa acaactgtta tgggaacagc aagcccaaat aaagccaagc atcaggggga 1440
tctgagagct gaaagcaact tctgttcccc ctccctcagc tgaaggggtg gggaagggct 1500
cccaaagcca taactccttt taagggattt agaaggcata aaaaggcccc tggctgagaa 1560
cttccttctt cattctgcag ttggt 1585

<210> SEQ ID NO 12
<211> LENGTH: 628
<212> TYPE: DNA
<213> ORGANISM: Homo sapiens

<400> SEQUENCE: 12
tacgtaattc tgtcatttta ctagggtgat gaaattccca agcaacacca tccttttcag 60
ataagggcac tgaggctgag agaggagctg aaacctaccc ggcgtcacca cacacaggtg 120
gcaaggctgg gaccagaaac caggactgtt gactgcagcc cggtattcat tctttccata 180
gcccacaggg ctgtcaaaga ccccagggcc tagtcagagg ctcctccttc ctggagagtt 240
cctggcacag aagttgaagc tcagcacagc cccctaaccc ccaactctct ctgcaaggcc 300
tcaggggtca gaacactggt ggagcagatc ctttagcctc tggattttag ggccatggta 360
gagggggtgt tgccctaaat tccagccctg gtctcagccc aacaccctcc aagaagaaat 420
tagaggggcc atggccaggc tgtgctagcc gttgcttctg agcagattac aagaagggac 480
taagacaagg actcctttgt ggaggtcctg gcttagggag tcaagtgacg gcggctcagc 540
actcacgtgg gcagtgccag cctctaagag tgggcagggg cactggccac agagtcccag 600
ggagtcccac cagcctagtc gccagacc 628

<210> SEQ ID NO 13
<211> LENGTH: 2454
<212> TYPE: DNA
<213> ORGANISM: Homo sapiens

<400> SEQUENCE: 13
gggccccggt gttatctcat tctttttttct cctctgtaag ttgacatgtg atgtgggaac 60
aaaggggata aagtcattat tttgtgctaa aatcgtaatt ggagaggacc tcctgttagc 120
tgggctttct tctatttatt gtggtggtta ctggagttcc ttcttctagt tttaggatat 180
atatatatat tttttttttt tctttccctg aagatataat aatatatata cttctgaaga 240
ttgagatttt taaattagtt gtattgaaaa ctagctaatc agcaatttaa ggctagcttg 300
agacttatgt cttgaatttg tttttgtagg ctccaaaacc aaggagggag tggtgcatgg 360
tgtggcaaca ggtaagctcc attgtgctta tatccaaaga tgatatttaa agtatctagt 420
gattagtgtg gcccagtatt caagattcct atgaaattgt aaaacaatca ctgagcattc 480
taagaacata tcagtcttat tgaaactgaa ttctttataa agtattttta aaaaggtaaa 540
tattgattat aaataaaaaa tatacttgcc aagaataatg agggctttga attgataagc 600
tatgtttaat ttatagtaag tgggcattta aatattctga ccaaaaaatgt attgacaaac 660 tgctgacaaa aataaaatgt gaatattgcc ataattttaa aaaaagagta aaatttctgt 720
tgattacagt aaaatatttt gaccttaaat tatgttgatt acaatattcc tttgataatt 780
cagagtgcat ttcaggaaac acccttggac agtcagtaaa ttgtttattg tatttatctt 840
tgtattgtta tggtatagct atttgtacaa atattattgt gcaattatta catttctgat 900

-continued

```
tatattattc atttggccta aatttaccaa gaatttgaac aagtcaatta ggtttacaat    960
caagaaatat caaaaatgat gaaaaggatg ataatcatca tcagatgttg aggaagatga   1020
cgatgagagt gccagaaata gagaaatcaa aggagaacca aaatttaaca aattaaaagc   1080
ccacagactt gctgtaatta agttttctgt tgtaagtact ccacgtttcc tggcagatgt   1140
ggtgaagcaa aagatataat cagaaatata atttatatga tcggaaagca ttaaacacaa   1200
tagtgcctat acaaataaaa tgttcctatc actgacttct aaaatggaaa tgaggacaat   1260
gatatgggaa tcttaataca gtgttgtgga taggactaaa aacacaggag tcagatcttc   1320
ttggttcaac ttcctgctta ctccttacca gctgtgtgtt ttttgcaagg ttcttcacct   1380
ctatgtgatt tagcttcctc atctataaaa taattcagtg aattaatgta cacaaaacat   1440
ctggaaaaca aaagcaaaca atatgtattt tataagtgtt acttatagtt ttatagtgaa   1500
ctttcttgtg caacattttt acaactagtg gagaaaaata tttctttaaa tgaatacttt   1560
tgatttaaaa atcagagtgt aaaaataaaa cagactcctt tgaaactagt tctgttagaa   1620
gttaattgtg cacctttaat gggctctgtt gcaatccaac agagaagtag ttaagtaagt   1680
ggactatgat ggcttctagg gacctcctat aaatatgata ttgtgaagca tgattataat   1740
aagaactaga taacagacag gtggagactc cactatctga agagggtcaa cctagatgaa   1800
tggtgttcca tttagtagtt gaggaagaac ccatgaggtt tagaaagcag acaagcatgt   1860
ggcaagttct ggagtcagtg gtaaaaatta aagaacccaa ctattactgt cacctaatga   1920
tctaatggag actgtggaga tgggctgcat ttttttaatc ttctccagaa tgccaaaatg   1980
taaacacata tctgtgtgtg tgtgtgtgtg tgtgtgtgtg tgtgagagag agagagagag   2040
agagagagac tgaagtttgt acaattagac attttataaa atgttttctg aaggacagtg   2100
gctcacaatc ttaagtttct aacattgtac aatgttggga gactttgtat actttatttt   2160
ctctttagca tattaaggaa tctgagatgt cctacagtaa agaaatttgc attacatagt   2220
taaaatcagg gttattcaaa ctttttgatt attgaaacct ttcttcatta gttactaggg   2280
ttgaatgaaa ctagtgttcc acagaaaact atgggaaatg ttgctaggca gtaaggacat   2340
ggtgatttca gcatgtgcaa tatttacagc gattgcaccc atggaccacc ctggcagtag   2400
tgaaataacc aaaaatgctg tcataactag tatggctatg agaaacacat tggg         2454
```

<210> SEQ ID NO 14
<211> LENGTH: 1503
<212> TYPE: DNA
<213> ORGANISM: Homo sapiens

<400> SEQUENCE: 14

```
attctccagg ttgagccaga ccaatttgat ggtagattta gcaaataaaa atacaggaca     60
cccagttaaa tgtgaatttc cgatgaacag caaatacttt tttagtatta aaaaagttca    120
catttaggct cacgcctgta atcccagcac tttgggaggc cgaggcaggc agatcacctg    180
aggtcaggag ttcgagacca gcctggccaa catggtgaaa ccccatctcc actaaaaata    240
ccaaaaatta gccaggcgtg ctggtgggca cctgtagttc cagctactca ggaggctaag    300
gcaggagaat tgcttgaacc tgggaggcag aggttgcagt gagctgagat cgcaccattg    360
cactctagcc tgggcgacaa gaacaaaact ccatctcaaa aaaaaaaaaa aaaaaaaagt    420
tcacatttaa ctgggcattc tgtatttaat tggtaatctg agatggcagg gaacagcatc    480
agcatggtgt gagggatagg catttttca ttgtgtacag cttgtaaatc agtattttta    540
aaactcaaag ttaatggctt gggcatattt agaaaagagt tgccgcacgg acttgaaccc    600
```

tgtattccta aaatctagga tcttgttctg atggtctgca caactggctg gggtgtcca 660 gccactgtcc ctcttgcctg ggctccccag ggcagttctg tcagcctctc catttccatt 720
cctgttccag caaaacccaa ctgatagcac agcagcattt cagcctgtct acctctgtgc 780
ccacatacct ggatgtctac cagccagaaa ggtggcttag atttggttcc tgtgggtgga 840
ttatggcccc cagaacttcc ctgtgcttgc tgggggtgtg gagtggaaag agcaggaaat 900
gggggaccct ccgatactct atgggggtcc tccaagtctc tttgtgcaag ttagggtaat 960
aatcaatatg gagctaagaa agagaagggg aactatgctt tagaacagga cactgtgcca 1020
ggagcattgc agaaattata tggttttcac gacagttctt tttggtaggt actgttatta 1080
tcctcagttt gcagatgagg aaactgagac ccagaaaggt taaataactt gctagggtca 1140
cacaagtcat aactgacaaa gcctgattca aacccaggtc tccctaacct ttaaggtttc 1200
tatgacgcca gctctcctag ggagtttgtc ttcagatgtc ttggctctag gtgtcaaaaa 1260
aagacttggt gtcaggcagg cataggttca agtcccaact ctgtcactta ccaactgtga 1320
ctaggtgatt gaactgacca tggaacctgg tcacatgcag gagcaggatg gtgaagggtt 1380
cttgaaggca cttaggcagg acatttaggc aggagagaaa acctggaaac agaagagctg 1440
tctccaaaaa tacccactgg ggaagcaggt tgtcatgtgg gccatgaatg ggacctgttc 1500
tgg 1503

<210> SEQ ID NO 15
<211> LENGTH: 2619
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
ctgcctgcag gggcgcctga tgcggtattt tctccttacg catctgtgcg gtatttcaca 60
ccgcatacgt caaagcaacc atagtacgcg ccctgtagcg gcgcattaag cgcggcgggt 120
gtggtggtta cgcgcagcgt gaccgctaca cttgccagcg ccttagcgcc cgctcctttc 180
gctttcttcc cttcctttct cgccacgttc gccggctttc cccgtcaagc tctaaatcgg 240
gggctccctt tagggttccg atttagtgct ttacggcacc tcgaccccaa aaaacttgat 300
ttgggtgatg gttcacgtag tgggccatcg ccctgataga cggtttttcg ccctttgacg 360
ttggagtcca cgttctttaa tagtggactc ttgttccaaa ctggaacaac actcaactct 420
atctcgggct attcttttga tttataaggg attttgccga tttcggtcta ttggttaaaa 480
aatgagctga tttaacaaaa atttaacgcg aattttaaca aaatattaac gtttacaatt 540
ttatggtgca ctctcagtac aatctgctct gatgccgcat agttaagcca gccccgacac 600
ccgccaacac ccgctgacgc gccctgacgg gcttgtctgc tcccggcatc cgcttacaga 660
caagctgtga ccgtctccgg gagctgcatg tgtcagaggt tttcaccgtc atcaccgaaa 720
cgcgcgagac gaaagggcct cgtgatacgc ctatttttat aggttaatgt catgataata 780
atggtttctt agacgtcagg tggcactttt cggggaaatg tgcgcggaac ccctatttgt 840
ttatttttct aaatacattc aaatatgtat ccgctcatga gacaataacc ctgataaatg 900
cttcaataat attgaaaaag gaagagtatg agtattcaac atttccgtgt cgcccttatt 960
cccttttttg cggcattttg ccttcctgtt tttgctcacc cagaaacgct ggtgaaagta 1020
aaagatgctg aagatcagtt gggtgcacga gtgggttaca tcgaactgga tctcaacagc 1080
ggtaagatcc ttgagagttt tcgccccgaa gaacgttttc caatgatgag cacttttaaa 1140
gttctgctat gtggcgcggt attatcccgt attgacgccg ggcaagagca actcggtcgc 1200
cgcatacact attctcagaa tgacttggtt gagtactcac cagtcacaga aaagcatctt 1260
acggatggca tgacagtaag agaattatgc agtgctgcca taaccatgag tgataacact 1320
gcggccaact tacttctgac aacgatcgga ggaccgaagg agctaaccgc ttttttgcac 1380
aacatggggg atcatgtaac tcgccttgat cgttgggaac cggagctgaa tgaagccata 1440
ccaaacgacg agcgtgacac cacgatgcct gtagcaatgg caacaacgtt gcgcaaacta 1500
ttaactggcg aactacttac tctagcttcc cggcaacaat taatagactg gatggaggcg 1560
gataaagttg caggaccact tctgcgctcg gcccttccgg ctggctggtt tattgctgat 1620
aaatctggag ccggtgagcg tgggtctcgc ggtatcattg cagcactggg gccagatggt 1680
aagccctccc gtatcgtagt tatctacacg acggggagtc aggcaactat ggatgaacga 1740
aatagacaga tcgctgagat aggtgcctca ctgattaagc attggtaact gtcagaccaa 1800
gtttactcat atatacttta gattgattta aaacttcatt tttaatttaa aaggatctag 1860
gtgaagatcc tttttgataa tctcatgacc aaaatccctt aacgtgagtt ttcgttccac 1920
tgagcgtcag accccgtaga aaagatcaaa ggatcttctt gaaatccttt ttttctgcgc 1980
gtaatctgct gcttgcaaac aaaaaaacca ccgctaccag cggtggtttg tttgccggat 2040
caagagctac caactctttt tccgaaggta actggcttca gcagagcgca gataccaaat 2100
actgttcttc tagtgtagcc gtagttaggc caccacttca agaactctgt agcaccgcct 2160
acatacctcg ctctgctaat cctgttacca gtggctgctg ccagtggcga taagtcgtgt 2220
cttaccgggt tggactcaag acgatagtta ccggataagg cgcagcggtc gggctgaacg 2280
gggggttcgt gcacacagcc cagcttggag cgaacgacct acaccgaact gagataccta 2340
cagcgtgagc tatgagaaag cgccacgctt cccgaaggga gaaaggcgga caggtatccg 2400
gtaagcggca gggtcggaac aggagagcgc acgagggagc ttccaggggg aaacgcctgg 2460
tatctttata gtcctgtcgg gtttcgccac ctctgacttg agcgtcgatt tttgtgatgc 2520
tcgtcagggg ggcggagcct atggaaaaac gccagcaacg cggccttttt acggttcctg 2580
gccttttgct ggccttttgc tcacatgtcc tgcaggcag 2619

<210> SEQ ID NO 16
<211> LENGTH: 130
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 16
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct 130

<210> SEQ ID NO 17
<211> LENGTH: 145
<212> TYPE: DNA
<213> ORGANISM: Adeno-associated virus

<400> SEQUENCE: 17
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcct 145

<210> SEQ ID NO 18
<211> LENGTH: 2208
<212> TYPE: DNA
<213> ORGANISM: Adeno-associated virus

<400> SEQUENCE: 18
atggctgccg atggttatct tccagattgg ctcgaggaca ctctctctga aggaataaga 60
cagtggtgga agctcaaacc tggcccacca ccaccaaagc ccgcagagcg gcataaggac 120
gacagcaggg gtcttgtgct tcctgggtac aagtacctcg gacccttcaa cggactcgac 180
aagggagagc cggtcaacga ggcagacgcc gcggccctcg agcacgacaa agcctacgac 240
cggcagctcg acagcggaga caacccgtac ctcaagtaca accacgccga cgcggagttt 300
caggagcgcc ttaaagaaga tacgtctttt gggggcaacc tcggacgagc agtcttccag 360
gcgaaaaaga gggttcttga acctctgggc ctggttgagg aacctgttaa gacggctccg 420
ggaaaaaaga ggccggtaga gcactctcct gtggagccag actcctcctc gggaaccgga 480
aaggcgggcc agcagcctgc aagaaaaaga ttgaattttg gtcagactgg agacgcagac 540
tcagtacctg acccccagcc tctcggacag ccaccagcag ccccctctgg tctgggaact 600
aatacgatgg ctacaggcag tggcgcacca atggcagaca ataacgaggg cgccgacgga 660
gtgggtaatt cctcgggaaa ttggcattgc gattccacat ggatgggcga cagagtcatc 720
accaccagca cccgaacctg ggccctgccc acctacaaca accacctcta caaacaaatt 780
tccagccaat caggagcctc gaacgacaat cactactttg gctacagcac cccttggggg 840
tattttgact tcaacagatt ccactgccac ttttcaccac gtgactggca aagactcatc 900
aacaacaact ggggattccg acccaagaga ctcaacttca agctctttaa cattcaagtc 960
aaagaggtca cgcagaatga cggtacgacg acgattgcca ataaccttac cagcacggtt 1020
caggtgttta ctgactcgga gtaccagctc ccgtacgtcc tcggctcggc gcatcaagga 1080
tgcctcccgc cgttcccagc agacgtcttc atggtgccac agtatggata cctcaccctg 1140
aacaacggga gtcaggcagt aggacgctct tcattttact gcctggagta ctttccttct 1200
cagatgctgc gtaccggaaa caactttacc ttcagctaca cttttgagga cgttcctttc 1260
cacagcagct acgctcacag ccagagtctg gaccgtctca tgaatcctct catcgaccag 1320
tacctgtatt acttgagcag aacaaacact ccaagtggaa ccaccacgca gtcaaggctt 1380
cagttttctc aggccggagc gagtgacatt cgggaccagt ctaggaactg gcttcctgga 1440
ccctgttacc gccagcagcg agtatcaaag acatctgcgg ataacaacaa cagtgaatac 1500
tcgtggactg gagctaccaa gtaccacctc aatggcagag actctctggt gaatccgggc 1560
ccggccatgg caagccacaa ggacgatgaa gaaaagtttt ttcctcagag cggggttctc 1620
atctttggga agcaaggctc agagaaaaca aatgtggaca ttgaaaaggt catgattaca 1680
gacgaagagg aaatcaggac aaccaatccc gtggctacgg agcagtatgg ttctgtatct 1740
accaacctcc agagaggcaa cagacaagca gctaccgcag atgtcaacac acaaggcgtt 1800
cttccaggca tggtctggca ggacagagat gtgtaccttc aggggcccat ctgggcaaag 1860
attccacaca cggacggaca ttttcacccc tctcccctca tgggtggatt cggacttaaa 1920
caccctcctc cacagattct catcaagaac accccggtac ctgcgaatcc ttcgaccacc 1980

-continued

```
ttcagtgcgg caaagtttgc ttccttcatc acacagtact ccacgggaca ggtcagcgtg   2040

gagatcgagt gggagctgca gaaggaaaac agcaaacgct ggaatcccga aattcagtac   2100

acttccaact acaacaagtc tgttaatgtg gactttactg tggacactaa tggcgtgtat   2160

tcagagcctc gccccattgg caccagatac ctgactcgta atctgtaa                2208


<210> SEQ ID NO 19
<211> LENGTH: 735
<212> TYPE: PRT
<213> ORGANISM: Adeno-associated virus

<400> SEQUENCE: 19

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335
```

```
Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735
```

<210> SEQ ID NO 20
<211> LENGTH: 2217
<212> TYPE: DNA

<213> ORGANISM: Adeno-associated virus

<400> SEQUENCE: 20

```
atggctgccg atggttatct tccagattgg ctcgaggaca acctctctga gggcattcgc     60
gagtggtggg cgctgaaacc tggagccccg aagcccaaag ccaaccagca aaagcaggac    120
gacggccggg gtctggtgct tcctggctac aagtacctcg gacccttcaa cggactcgac    180
aagggggagc ccgtcaacgc ggcggacgca gcggccctcg agcacgacaa ggcctacgac    240
cagcagctgc aggcgggtga caatccgtac ctgcggtata accacgccga cgccgagttt    300
caggagcgtc tgcaagaaga tacgtctttt gggggcaacc tcgggcgagc agtcttccag    360
gccaagaagc gggttctcga acctctcggt ctggttgagg aaggcgctaa gacggctcct    420
ggaaagaaga gaccggtaga gccatcaccc cagcgttctc cagactcctc tacgggcatc    480
ggcaagaaag gccaacagcc cgccagaaaa agactcaatt ttggtcagac tggcgactca    540
gagtcagttc cagaccctca acctctcgga gaacctccag cagcgccctc tggtgtggga    600
cctaatacaa tggctgcagg cggtggcgca ccaatggcag acaataacga aggcgccgac    660
ggagtgggta gttcctcggg aaattggcat tgcgattcca catggctggg cgacagagtc    720
atcaccacca gcacccgaac ctgggccctg cccacctaca acaaccacct ctacaagcaa    780
atctccaacg ggacatcggg aggagccacc aacgacaaca cctacttcgg ctacagcacc    840
ccctgggggt attttgactt taacagattc cactgccact tttcaccacg tgactggcag    900
cgactcatca acaacaactg gggattccgg cccaagagac tcagcttcaa gctcttcaac    960
atccaggtca aggaggtcac gcagaatgaa ggcaccaaga ccatcgccaa taacctcacc   1020
agcaccatcc aggtgtttac ggactcggag taccagctgc cgtacgttct cggctctgcc   1080
caccagggct gcctgcctcc gttcccggcg gacgtgttca tgattcccca gtacggctac   1140
ctaacactca acaacggtag tcaggccgtg ggacgctcct ccttctactg cctggaatac   1200
tttccttcgc agatgctgag aaccggcaac aacttccagt ttacttacac cttcgaggac   1260
gtgcctttcc acagcagcta cgcccacagc cagagcttgg accggctgat gaatcctctg   1320
attgaccagt acctgtacta cttgtctcgg actcaaacaa caggaggcac ggcaaatacg   1380
cagactctgg gcttcagcca aggtgggcct aatacaatgg ccaatcaggc aaagaactgg   1440
ctgccaggac cctgttaccg ccaacaacgc gtctcaacga caaccgggca aaacaacaat   1500
agcaactttg cctggactgc tgggaccaaa taccatctga atggaagaaa ttcattggct   1560
aatcctggca tcgctatggc aacacacaaa gacgacgagg agcgtttttt tcccagtaac   1620
gggatcctga tttttggcaa acaaaatgct gccagagaca atgcggatta cagcgatgtc   1680
atgctcacca gcgaggaaga aatcaaaacc actaaccctg tggctacaga ggaatacggt   1740
atcgtggcag ataacttgca gcagcaaaac acggctcctc aaattggaac tgtcaacagc   1800
caggggggcct tacccggtat ggtctggcag aaccgggacg tgtacctgca gggtcccatc   1860
tgggccaaga ttcctcacac ggacggcaac ttccacccgt ctccgctgat gggcggcttt   1920
ggcctgaaac atcctccgcc tcagatcctg atcaagaaca cgcctgtacc tgcggatcct   1980
ccgaccacct tcaaccagtc aaagctgaac tctttcatca cgcaatacag caccggacag   2040
gtcagcgtgg aaattgaatg ggagctgcag aaggaaaaca gcaagcgctg gaaccccgag   2100
atccagtaca cctccaacta ctacaaatct acaagtgtgg actttgctgt taatacagaa   2160
ggcgtgtact ctgaaccccg ccccattggc acccgttacc tcacccgtaa tctgtaa      2217
```

```
<210> SEQ ID NO 21
<211> LENGTH: 738
<212> TYPE: PRT
<213> ORGANISM: Adeno-associated virus

<400> SEQUENCE: 21

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380
```

```
Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu
```

<210> SEQ ID NO 22
<211> LENGTH: 1616
<212> TYPE: DNA
<213> ORGANISM: Unknown
<220> FEATURE:
<223> OTHER INFORMATION: Description of Unknown: CVM enhancer and CBA promoter polynucleotide

<400> SEQUENCE: 22

-continued

```
actagttatt aatagtaatc aattacgggg tcattagttc atagcccata tatggagttc     60
cgcgttacat aacttacggt aaatggcccg cctggctgac cgcccaacga cccccgccca    120
ttgacgtcaa taatgacgta tgttcccata gtaacgccaa tagggacttt ccattgacgt    180
caatgggtgg agtatttacg gtaaactgcc cacttggcag tacatcaagt gtatcatatg    240
ccaagtacgc cccctattga cgtcaatgac ggtaaatggc ccgcctggca ttatgcccag    300
tacatgacct tatgggactt tcctacttgg cagtacatct acgtattagt catcgctatt    360
accatggtcg aggtgagccc cacgttctgc ttcactctcc ccatctcccc cccctcccca    420
cccccaattt tgtatttatt tattttttaa ttattttgtg cagcgatggg ggcggggggg    480
gggggggggc gcgcgccagg cggggcgggg cggggcgagg ggcggggcgg ggcgaggcgg    540
agaggtgcgg cggcagccaa tcagagcggc gcgctccgaa agtttccttt tatggcgagg    600
cggcggcggc ggcggcccta taaaaagcga agcgcgcggc gggcggggag tcgctgcgac    660
gctgccttcg ccccgtgccc cgctccgccg ccgcctcgcg ccgcccgccc cggctctgac    720
tgaccgcgtt actcccacag gtgagcgggc gggacggccc ttctcctccg ggctgtaatt    780
agcgcttggt ttaatgacgg cttgtttctt ttctgtggct gcgtgaaagc cttgaggggc    840
tccgggaggg ccctttgtgc ggggggagcg gctcgggggg tgcgtgcgtg tgtgtgtgcg    900
tggggagcgc cgcgtgcggc tccgcgctgc ccggcggctg tgagcgctgc gggcgcggcg    960
cggggctttg tgcgctccgc agtgtgcgcg aggggagcgc ggccgggggc ggtgccccgc   1020
ggtgcggggg gggctgcgag gggaacaaag gctgcgtgcg gggtgtgtgc gtgggggggt   1080
gagcaggggg tgtgggcgcg tcggtcgggc tgcaaccccc cctgcacccc cctccccgag   1140
ttgctgagca cggcccggct tcgggtgcgg ggctccgtac ggggcgtggc gcggggctcg   1200
ccgtgccggg cgggggggtgg cggcaggtgg gggtgccggg cggggcgggg ccgcctcggg   1260
ccggggaggg ctcgggggag ggcgcggcgg gccccccggag cgccggcggc tgtcgaggcg   1320
cggcgagccg cagccattgc cttttatggt aatcgtgcga gagggcgcag ggacttcctt   1380
tgtcccaaat ctgtgcggag ccgaaatctg ggaggcgccg ccgcaccccc tctagcgggc   1440
gcggggcgaa gcggtgcggc gccggcagga aggaaatggg cggggagggc cttcgtgcgt   1500
cgccgcgccg ccgtcccctt ctccctctcc agcctcgggg ctgtccgcgg ggggacggct   1560
gccttcgggg gggacggggc agggcggggt tcggcttctg gcgtgtgacc ggcggc       1616
```

<210> SEQ ID NO 23
<211> LENGTH: 1503
<212> TYPE: DNA
<213> ORGANISM: Homo sapiens

<400> SEQUENCE: 23

```
ccagaacagg tcccattcat ggcccacatg acaacctgct tccccagtgg gtatttttgg     60
agacagctct tctgtttcca ggttttctct cctgcctaaa tgtcctgcct aagtgccttc    120
aagaaccctt caccatcctg ctcctgcatg tgaccaggtt ccatggtcag ttcaatcacc    180
tagtcacagt tggtaagtga cagagttggg acttgaacct atgcctgcct gacaccaagt    240
cttttttga cacctagagc caagacatct gaagacaaac tccctaggag agctggcgtc    300
atagaaacct taaaggttag ggagacctgg gtttgaatca ggctttgtca gttatgactt    360
gtgtgaccct agcaagttat ttaacctttc tgggtctcag tttcctcatc tgcaaactga    420
ggataataac agtacctacc aaaaagaact gtcgtgaaaa ccatataatt tctgcaatgc    480
tcctggcaca gtgtcctgtt ctaaagcata gttccccttc tctttcttag ctccatattg    540
```

attattaccc taacttgcac aaagagactt ggaggacccc catagagtat cggagggtcc 600
cccatttcct gctctttcca ctccacaccc ccagcaagca cagggaagtt ctgggggcca 660
taatccaccc acaggaacca aatctaagcc acctttctgg ctggtagaca tccaggtatg 720
tgggcacaga ggtagacagg ctgaaatgct gctgtgctat cagttgggtt ttgctggaac 780
aggaatggaa atggagaggc tgacagaact gccctgggga gcccaggcaa gagggacagt 840
ggctggacac ccccagccag ttgtgcagac catcagaaca agatcctaga ttttaggaat 900
acagggttca agtccgtgcg gcaactcttt tctaaatatg cccaagccat taactttgag 960
ttttaaaaat actgatttac aagctgtaca caatgaaaaa atgcctatcc ctcacaccat 1020
gctgatgctg ttccctgcca tctcagatta ccaattaaat acagaatgcc cagttaaatg 1080
tgaacttttt tttttttttt ttttttgaga tggagttttg ttcttgtcgc ccaggctaga 1140
gtgcaatggt gcgatctcag ctcactgcaa cctctgcctc ccaggttcaa gcaattctcc 1200
tgccttagcc tcctgagtag ctggaactac aggtgcccac cagcacgcct ggctaatttt 1260
tggtattttt agtggagatg gggtttcacc atgttggcca ggctggtctc gaactcctga 1320
cctcaggtga tctgcctgcc tcggcctccc aaagtgctgg gattacaggc gtgagcctaa 1380
atgtgaactt ttttaatact aaaaaagtat ttgctgttca tcggaaattc acatttaact 1440
gggtgtcctg tatttttatt tgctaaatct accatcaaat tggtctggct caacctggag 1500
aat 1503

<210> SEQ ID NO 24
<211> LENGTH: 720
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagtaa 720

<210> SEQ ID NO 25
<211> LENGTH: 239
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 26
<211> LENGTH: 4949
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
ctgcgcgctc gctcgctcac tgaggccgcc cgggcaaagc ccgggcgtcg ggcgaccttt 60
ggtcgcccgg cctcagtgag cgagcgagcg cgcagagagg gagtggggta ccacgcgttt 120
gtcctctccc tgcttggcct taaccagcca catttctcaa ctgaccccac tcactgcaga 180
ggtgaaaact accatgccag gtcctgctgg ctgggggagg ggtgggcaat aggcctggat 240
ttgccagagc tgccactgta gatgtagtca tatttacgat ttcccttcac ctcttattac 300
cctggtggtg gtggtggggg gggggggtg ctctctcagc aaccccaccc cgggatcttg 360
aggagaaaga gggcagagaa aagagggaat gggactggcc cagatcccag ccccacagcc 420
gggcttccac atggccgagc aggaactcca gagcaggagc acacaaagga gggctttgat 480
gcgcctccag ccaggcccag gcctctcccc tctccccttt ctctctgggt cttcctttgc 540
cccactgagg gcctcctgtg agcccgattt aacggaaact gtgggcggtg agaagttcct 600
tatgacacac taatcccaac ctgctgaccg gaccacgcct ccagcggagg gaacctctag 660

-continued

```
agctccagga cattcaggta ccaggtagcc ccaaggagga gctgccgaat cgatggatcg    720
ggaactgaaa aaccagaaag ttaactggta agtttagtct tttgtcttt tatttcaggt    780
cccggatccg gtggtggtgc aaatcaaaga actgctcctc agtggatgtt gcctttactt    840
ctaggcctgt acggaagtgt tacttctgct ctaaaagctg cggaattgta cccgccccgg    900
gatccatcga ttgaattcgc caccatgtca gaaggggtgg gcacgttccg catggtacct    960
gaagaggaac aggagctccg tgcccaactg gagcagctca caaccaagga ccatggacct   1020
gtctttggcc cgtgcagcca gctgccccgc cacaccttgc agaaggccaa ggatgagctg   1080
aacgagagag aggagacccg ggaggaggca gtgcgagagc tgcaggagat ggtgcaggcg   1140
caggcggcct cgggggagga gctggcggtg gccgtggcgg agagggtgca agagaaggac   1200
agcggcttct tcctgcgctt catccgcgca cggaagttca acgtgggccg tgcctatgag   1260
ctgctcagag gctatgtgaa tttccggctg cagtaccctg agctctttga cagcctgtcc   1320
ccagaggctg tccgctgcac cattgaagct ggctaccctg gtgtcctctc tagtcgggac   1380
aagtatggcc gagtggtcat gctcttcaac attgagaact ggcaaagtca agaaatcacc   1440
tttgatgaga tcttgcaggc atattgcttc atcctggaga agctgctgga gaatgaggaa   1500
actcaaatca atggcttctg catcattgag aacttcaagg gctttaccat gcagcaggct   1560
gctagtctcc ggacttcaga tctcaggaag atggtggaca tgctccagga ttccttccca   1620
gcccggttca aagccatcca cttcatccac cagccatggt acttcaccac gacctacaat   1680
gtggtcaagc ccttcttgaa gagcaagctg cttgagaggg tctttgtcca cggggatgac   1740
ctttctggtt tctaccagga gatcgatgag aacatcctgc cctctgactt cgggggcacg   1800
ctgcccaagt atgatggcaa ggccgttgct gagcagctct ttggccccca ggcccaagct   1860
gagaacacag ccttctgagg atcgtaccgg tcgacctgca gaagcttgcc tcgagcagcg   1920
ctgctcgaga gatctggatc ataatcagcc ataccacatt tgtagaggtt ttacttgctt   1980
taaaaaacct cccacacctc cccctgaacc tgaaacataa aatgaatgca attgttgttg   2040
ttaacttgtt tattgcagct tataatggtt acaaataaag caatagcatc acaaatttca   2100
caaataaagc atttttttca ctgcattcta gttgtggttt gtccaaactc atcaatgtat   2160
cttatcatgt ctggtaacca cgtgcggacc gagcggccgc aggaacccct agtgatggag   2220
ttggccactc cctctctgcg cgctcgctcg ctcactgagg ccgggcgacc aaaggtcgcc   2280
cgacgcccgg gctttgcccg ggcggcctca gtgagcgagc gagcgcgcag ctgcctgcag   2340
gggcgcctga tgcggtattt tctccttacg catctgtgcg gtatttcaca ccgcatacgt   2400
caaagcaacc atagtacgcg ccctgtagcg gcgcattaag cgcggcgggt gtggtggtta   2460
cgcgcagcgt gaccgctaca cttgccagcg ccttagcgcc cgctcctttc gctttcttcc   2520
cttcctttct cgccacgttc gccggctttc cccgtcaagc tctaaatcgg gggctccctt   2580
tagggttccg atttagtgct ttacggcacc tcgaccccaa aaaacttgat ttgggtgatg   2640
gttcacgtag tgggccatcg ccctgataga cggtttttcg ccctttgacg ttggagtcca   2700
cgttctttaa tagtggactc ttgttccaaa ctggaacaac actcaactct atctcgggct   2760
attcttttga tttataaggg attttgccga tttcggtcta ttggttaaaa aatgagctga   2820
tttaacaaaa atttaacgcg aattttaaca aaatattaac gtttacaatt ttatggtgca   2880
ctctcagtac aatctgctct gatgccgcat agttaagcca gccccgacac ccgccaacac   2940
ccgctgacgc gccctgacgg gcttgtctgc tcccggcatc cgcttacaga caagctgtga   3000
```

ccgtctccgg gagctgcatg tgtcagaggt tttcaccgtc atcaccgaaa cgcgcgagac 3060
gaaagggcct cgtgatacgc ctatttttat aggttaatgt catgataata atggtttctt 3120
agacgtcagg tggcactttt cggggaaatg tgcgcggaac ccctatttgt ttatttttct 3180
aaatacattc aaatatgtat ccgctcatga gacaataacc ctgataaatg cttcaataat 3240
attgaaaaag gaagagtatg agtattcaac atttccgtgt cgcccttatt cccttttttg 3300
cggcattttg ccttcctgtt tttgctcacc cagaaacgct ggtgaaagta aaagatgctg 3360
aagatcagtt gggtgcacga gtgggttaca tcgaactgga tctcaacagc ggtaagatcc 3420
ttgagagttt tcgccccgaa gaacgttttc caatgatgag cacttttaaa gttctgctat 3480
gtggcgcggt attatcccgt attgacgccg ggcaagagca actcggtcgc cgcatacact 3540
attctcagaa tgacttggtt gagtactcac cagtcacaga aaagcatctt acggatggca 3600
tgacagtaag agaattatgc agtgctgcca taaccatgag tgataacact gcggccaact 3660
tacttctgac aacgatcgga ggaccgaagg agctaaccgc ttttttgcac aacatggggg 3720
atcatgtaac tcgccttgat cgttgggaac cggagctgaa tgaagccata ccaaacgacg 3780
agcgtgacac cacgatgcct gtagcaatgg caacaacgtt gcgcaaacta ttaactggcg 3840
aactacttac tctagcttcc cggcaacaat taatagactg gatggaggcg gataaagttg 3900
caggaccact tctgcgctcg gcccttccgg ctggctggtt tattgctgat aaatctggag 3960
ccggtgagcg tgggtctcgc ggtatcattg cagcactggg gccagatggt aagccctccc 4020
gtatcgtagt tatctacacg acggggagtc aggcaactat ggatgaacga aatagacaga 4080
tcgctgagat aggtgcctca ctgattaagc attggtaact gtcagaccaa gtttactcat 4140
atatacttta gattgattta aaacttcatt tttaatttaa aaggatctag gtgaagatcc 4200
tttttgataa tctcatgacc aaaatccctt aacgtgagtt ttcgttccac tgagcgtcag 4260
accccgtaga aaagatcaaa ggatcttctt gaaatccttt ttttctgcgc gtaatctgct 4320
gcttgcaaac aaaaaaacca ccgctaccag cggtggtttg tttgccggat caagagctac 4380
caactctttt tccgaaggta actggcttca gcagagcgca gataccaaat actgttcttc 4440
tagtgtagcc gtagttaggc caccacttca agaactctgt agcaccgcct acatacctcg 4500
ctctgctaat cctgttacca gtggctgctg ccagtggcga taagtcgtgt cttaccgggt 4560
tggactcaag acgatagtta ccggataagg cgcagcggtc gggctgaacg gggggttcgt 4620
gcacacagcc cagcttggag cgaacgacct acaccgaact gagataccta cagcgtgagc 4680
tatgagaaag cgccacgctt cccgaaggga gaaaggcgga caggtatccg gtaagcggca 4740
gggtcggaac aggagagcgc acgagggagc ttccaggggg aaacgcctgg tatctttata 4800
gtcctgtcgg gtttcgccac ctctgacttg agcgtcgatt tttgtgatgc tcgtcagggg 4860
ggcggagcct atggaaaaac gccagcaacg cggccttttt acggttcctg gccttttgct 4920
ggccttttgc tcacatgtcc tgcaggcag 4949

<210> SEQ ID NO 27
<211> LENGTH: 7330
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 27
ctgcgcgctc gctcgctcac tgaggccgcc cgggcgtcgg gcgacctttg gtcgcccggc 60

-continued

```
ctcagtgagc gagcgagcgc gcagagaggg agtggccaac tccatcacta ggggttcctg    120
cggccgcacg cagcttttgt cctctccctg cttggcctta accagccaca tttctcaact    180
gaccccactc actgcagagg tgaaaactac catgccaggt cctgctggct gggggagggg    240
tgggcaatag gcctggattt gccagagctg ccactgtaga tgtagtcata tttacgattt    300
cccttcacct cttattaccc tggtggtggt ggtggggggg ggggggtgct ctctcagcaa    360
ccccaccccg ggatcttgag gagaaagagg gcagagaaaa gagggaatgg gactggccca    420
gatcccagcc ccacagccgg gcttccacat ggccgagcag gaactccaga gcaggagcac    480
acaaaggagg gctttgatgc gcctccagcc aggcccaggc ctctcccctc tcccctttct    540
ctctgggtct tcctttgccc cactgagggc ctcctgtgag cccgatttaa cggaaactgt    600
gggcggtgag aagttcctta tgacacacta atcccaacct gctgaccgga ccacgcctcc    660
agcggaggga acctctagag ctccaggaca ttcaggtacc aggtagcccc aaggaggagc    720
tgccgacctg gcaggtaagt caatacctgg ggcttgcctg ggccagggag cccaggactg    780
gggtgaggac tcaggggagc agggagacca cgtcccaaga tgcctgtaaa actgaaacca    840
cctggccatt ctccaggttg agccagacca atttgatggc agatttagca aataaaaata    900
caggacaccc agttaaatgt gaatttcaga tgaacagcaa atactttttt agtattaaaa    960
aagttcacat ttaggctcac gcctgtaatc ccagcacttt gggaggccga ggcaggcaga   1020
tcacctgagg tcaggagttc gagaccagcc tggccaacat ggtgaaaccc catctccact   1080
aaaaatacca aaaattagcc aggcgtgctg gtgggcacct gtagttccag ctactcagga   1140
ggctaaggca ggagaattgc ttgaacctgg gaggcagagg ttgcagtgag ctgagatcgc   1200
accattgcac tctagcctgg gcgacaagaa caaaactcca tctcaaaaaa aaaaaaaaaa   1260
aaaaagttca catttaactg ggcattctgt atttaattgg taatctgaga tggcagggaa   1320
cagcatcagc atggtgtgag ggataggcat tttttcattg tgtacagctt gtaaatcagt   1380
atttttaaaa ctcaaagtta atggcttggg catatttaga aaagagttgc cgcacggact   1440
tgaaccctgt attcctaaaa tctaggatct tgttctgatg gtctgcacaa ctggctgggg   1500
gtgtccagcc actgtccctc ttgcctgggc tccccagggc agttctgtca gcctctccat   1560
ttccattcct gttccagcaa aacccaactg atagcacagc agcatttcag cctgtctacc   1620
tctgtgccca catacctgga tgtctaccag ccagaaaggt ggcttagatt tggttcctgt   1680
gggtggatta tggcccccag aacttccctg tgcttgctgg gggtgtggag tggaaagagc   1740
aggaaatggg ggaccctccg atactctatg gggtcctcc aagtctcttt gtgcaagtta   1800
gggtaataat caatatggag ctaagaaaga gaaggggaac tatgctttag aacaggacac   1860
tgtgccagga gcattgcaga aattatatgg ttttcacgac agttcttttt ggtaggtact   1920
gttattatcc tcagtttgca gatgaggaaa ctgagaccca gaaaggttaa ataacttgct   1980
agggtcacac aagtcataac tgacaaagcc tgattcaaac ccaggtctcc ctaaccttta   2040
aggtttctat gacgccagct ctcctaggga gtttgtcttc agatgtcttg gctctaggtg   2100
tcaaaaaaag acttggtgtc aggcaggcat aggttcaagt cccaactctg tcacttacca   2160
actgtgacta ggtgattgaa ctgaccatgg aacctggtca catgcaggag caggatggtg   2220
aagggttctt gaaggcactt aggcaggaca tttaggcagg agagaaaacc tggaaacaga   2280
agagctgtct ccaaaaatac ccactgggga agcaggttgt catgtgggcc atgaatggga   2340
cctgttctgg taaccaagca ttgcttatgt gtccattaca tttcataaca cttccatcct   2400
actttacagg gaacaaccaa gactggggtt aaatctcaca gcctgcaagt ggaagagaag   2460
```

-continued

```
aacttgaacc caggtccaac ttttgcgcca cagcaggctg cctcttggtc ctgacaggaa   2520
gtcacaactt gggtctgagt actgatccct ggctattttt tggctgtgtt accttggaca   2580
agtcacttat tcctcctccc gtttcctcct atgtaaaatg gaaataataa tgttgaccct   2640
gggtctgaga gagtggattt gaaagtactt agtgcatcac aaagcacaga acacacttcc   2700
agtctcgtga ttatgtactt atgtaactgg tcatcaccca tcttgagaat gaatgcattg   2760
gggaaagggc catccactag gctgcgaagt ttctgaggga ctccttcggg ctggagaagg   2820
atggccacag gagggaggag agattgcctt atcctgcagt gatcatgtca ttgagaacag   2880
agccagattc tttttttcct ggcagggcca acttgtttta acatctaagg actgagctat   2940
ttgtgtctgt gccctttgtc caagcagtgt ttcccaaagt gtagcccaag aaccatctcc   3000
ctcagagcca ccaggaagtg ctttaaattg caggttccta ggccacagcc tgcacctgca   3060
gagtcagaat catggaggtt gggacccagg cacctgcgtt tctaacaaat gcctcgggtg   3120
attctgatgc aattgaaagt ttgagatcca cagttctgag acaataacag aatggttttt   3180
ctaacccctg cagccctgac ttcctatcct agggaagggg ccggctggag aggccaggac   3240
agagaaagca gatcccttct tttccaagg actctgtgtc ttccataggc aacgaattcg   3300
ccaccatgtc agaaggggtg ggcacgttcc gcatggtacc tgaagaggaa caggagctcc   3360
gtgcccaact ggagcagctc acaaccaagg accatggacc tgtctttggc ccgtgcagcc   3420
agctgccccg ccacaccttg cagaaggcca aggatgagct gaacgagaga gaggagaccc   3480
gggaggaggc agtgcgagag ctgcaggaga tggtgcaggc gcaggcggcc tcgggggagg   3540
agctggcggt ggccgtggcg gagagggtgc aagagaagga cagcggcttc ttcctgcgct   3600
tcatccgcgc acggaagttc aacgtgggcc gtgcctatga gctgctcaga ggctatgtga   3660
atttccggct gcagtaccct gagctctttg acagcctgtc cccagaggct gtccgctgca   3720
ccattgaagc tggctaccct ggtgtcctct ctagtcggga caagtatggc cgagtggtca   3780
tgctcttcaa cattgagaac tggcaaagtc aagaaatcac ctttgatgag atcttgcagg   3840
catattgctt catcctggag aagctgctgg agaatgagga aactcaaatc aatggcttct   3900
gcatcattga gaacttcaag ggctttacca tgcagcaggc tgctagtctc cggacttcag   3960
atctcaggaa gatggtggac atgctccagg attccttccc agcccggttc aaagccatcc   4020
acttcatcca ccagccatgg tacttcacca cgacctacaa tgtggtcaag cccttcttga   4080
agagcaagct gcttgagagg gtctttgtcc acggggatga cctttctggt ttctaccagg   4140
agatcgatga gaacatcctg ccctctgact tcgggggcac gctgcccaag tatgatggca   4200
aggccgttgc tgagcagctc tttggccccc aggcccaagc tgagaacaca gccttctgag   4260
gatcgtaccg gtcgacctgc agaagcttgc ctcgagcagc gctgctcgag agatctggat   4320
cataatcagc cataccacat ttgtagaggt tttacttgct ttaaaaaacc tcccacacct   4380
ccccctgaac ctgaaacata aaatgaatgc aattgttgtt gttaacttgt ttattgcagc   4440
ttataatggt tacaaataaa gcaatagcat cacaaatttc acaaataaag catttttttc   4500
actgcattct agttgtggtt tgtccaaact catcaatgta tcttatcatg tctggtaacc   4560
acgtgcggac cgagcggccg caggaacccc tagtgatgga gttggccact ccctctctgc   4620
gcgctcgctc gctcactgag gccgggcgac caaaggtcgc ccgacgcccg ggctttgccc   4680
gggcggcctc agtgagcgag cgagcgcgca gctgcctgca ggggcgcctg atgcggtatt   4740
ttctccttac gcatctgtgc ggtatttcac accgcatacg tcaaagcaac catagtacgc   4800
```

-continued gccctgtagc ggcgcattaa gcgcggcggg tgtggtggtt acgcgcagcg tgaccgctac 4860
acttgccagc gccttagcgc ccgctccttt cgctttcttc ccttcctttc tcgccacgtt 4920
cgccggcttt ccccgtcaag ctctaaatcg ggggctccct ttagggttcc gatttagtgc 4980
tttacggcac ctcgacccca aaaaacttga tttgggtgat ggttcacgta gtgggccatc 5040
gccctgatag acggtttttc gccctttgac gttggagtcc acgttcttta atagtggact 5100
cttgttccaa actggaacaa cactcaactc tatctcgggc tattcttttg atttataagg 5160
gattttgccg atttcggtct attggttaaa aaatgagctg atttaacaaa aatttaacgc 5220
gaattttaac aaaatattaa cgtttacaat tttatggtgc actctcagta caatctgctc 5280
tgatgccgca tagttaagcc agccccgaca cccgccaaca cccgctgacg cgccctgacg 5340
ggcttgtctg ctcccggcat ccgcttacag acaagctgtg accgtctccg ggagctgcat 5400
gtgtcagagg ttttcaccgt catcaccgaa acgcgcgaga cgaaagggcc tcgtgatacg 5460
cctattttta taggttaatg tcatgataat aatggtttct tagacgtcag gtggcacttt 5520
tcggggaaat gtgcgcggaa cccctatttg tttatttttc taaatacatt caaatatgta 5580
tccgctcatg agacaataac cctgataaat gcttcaataa tattgaaaaa ggaagagtat 5640
gagtattcaa catttccgtg tcgcccttat tccctttttt gcggcatttt gccttcctgt 5700
ttttgctcac ccagaaacgc tggtgaaagt aaaagatgct gaagatcagt tgggtgcacg 5760
agtgggttac atcgaactgg atctcaacag cggtaagatc cttgagagtt ttcgccccga 5820
agaacgtttt ccaatgatga gcacttttaa agttctgcta tgtggcgcgg tattatcccg 5880
tattgacgcc gggcaagagc aactcggtcg ccgcatacac tattctcaga atgacttggt 5940
tgagtactca ccagtcacag aaaagcatct tacggatggc atgacagtaa gagaattatg 6000
cagtgctgcc ataaccatga gtgataacac tgcggccaac ttacttctga caacgatcgg 6060
aggaccgaag gagctaaccg cttttttgca caacatgggg gatcatgtaa ctcgccttga 6120
tcgttgggaa ccggagctga atgaagccat accaaacgac gagcgtgaca ccacgatgcc 6180
tgtagcaatg gcaacaacgt tgcgcaaact attaactggc gaactactta ctctagcttc 6240
ccggcaacaa ttaatagact ggatggaggc ggataaagtt gcaggaccac ttctgcgctc 6300
ggcccttccg gctggctggt ttattgctga taaatctgga gccggtgagc gtgggtctcg 6360
cggtatcatt gcagcactgg ggccagatgg taagccctcc cgtatcgtag ttatctacac 6420
gacggggagt caggcaacta tggatgaacg aaatagacag atcgctgaga taggtgcctc 6480
actgattaag cattggtaac tgtcagacca agtttactca tatatacttt agattgattt 6540
aaaacttcat ttttaattta aaaggatcta ggtgaagatc ctttttgata atctcatgac 6600
caaaatccct taacgtgagt tttcgttcca ctgagcgtca gaccccgtag aaaagatcaa 6660
aggatcttct tgaaatcctt tttttctgcg cgtaatctgc tgcttgcaaa caaaaaaacc 6720
accgctacca gcggtggttt gtttgccgga tcaagagcta ccaactcttt ttccgaaggt 6780
aactggcttc agcagagcgc agataccaaa tactgttctt ctagtgtagc cgtagttagg 6840
ccaccacttc aagaactctg tagcaccgcc tacatacctc gctctgctaa tcctgttacc 6900
agtggctgct gccagtggcg ataagtcgtg tcttaccggg ttggactcaa gacgatagtt 6960
accggataag gcgcagcggt cgggctgaac ggggggttcg tgcacacagc ccagcttgga 7020
gcgaacgacc tacaccgaac tgagatacct acagcgtgag ctatgagaaa gcgccacgct 7080
tcccgaaggg agaaaggcgg acaggtatcc ggtaagcggc agggtcggaa caggagagcg 7140
cacgagggag cttccagggg gaaacgcctg gtatctttat agtcctgtcg ggtttcgcca 7200
cctctgactt gagcgtcgat ttttgtgatg ctcgtcaggg gggcggagcc tatggaaaaa 7260
cgccagcaac gcggcctttt tacggttcct ggccttttgc tggccttttg ctcacatgtc 7320
ctgcaggcag 7330

<210> SEQ ID NO 28
<211> LENGTH: 7264
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 28
ctgcgcgctc gctcgctcac tgaggccgcc cgggcgtcgg gcgacctttg gtcgcccggc 60
ctcagtgagc gagcgagcgc gcagagaggg agtggccaac tccatcacta ggggttcctg 120
cggccgcacg cgttacgtaa tatttattga agtttaatat tgtgtttgtg atacagaagt 180
atttgcttta attctaaata aaaattttat gcttttattg ctggtttaag aagatttgga 240
ttatccttgt actttgagga gaagtttctt atttgaaata ttttggaaac aggtctttta 300
atgtggaaag atagatatta atctcctctt ctattactct ccaagatcca acaaaagtga 360
ttataccccc caaaatatga tggtagtatc ttatactacc atcattttat aggcataggg 420
ctcttagctg caaataatgg aactaactct aataaagcag aacgcaaata ttgtaaatat 480
tagagagcta acaatctctg ggatggctaa aggatggagc ttggaggcta cccagccagt 540
aacaatattc cgggctccac tgttgaatgg agacactaca actgccttgg atgggcagag 600
atattatgga tgctaagccc caggtgctac cattaggact tctaccactg tccctaacgg 660
gtggagccca tcacatgcct atgccctcac tgtaaggaaa tgaagctact gttgtatatc 720
ttgggaagca cttggattaa ttgttataca gttttgttga agaagacccc tagggtaagt 780
agccataact gcacactaaa tttaaaattg ttaatgagtt tctcaaaaaa aatgttaagg 840
ttgttagctg gtatagtata tatcttgcct gttttccaag gacttctttg ggcagtacct 900
tgtctgtgct ggcaagcaac tgagacttaa tgaaagagta ttggagatat gaatgaattg 960
atgctgtata ctctcagagt gccaaacata taccaatgga caagaaggtg aggcagagag 1020
cagacaggca ttagtgacaa gcaaagatat gcagaatttc attctcagca aatcaaaagt 1080
cctcaacctg gttggaagaa tattggcact gaatggtatc aataaggttg ctagagaggg 1140
ttagaggtgc acaatgtgct tccataacat tttatacttc tccaatctta gcactaatca 1200
aacatggttg aatactttgt ttactataac tcttacagag ttataagatc tgtgaagaca 1260
gggacaggga caatacccat ctctgtctgg ttcataggtg gtatgtaata gatattttta 1320
aaaataagtg agttaatgaa tgagggtgag aatgaaggca cagaggtatt agggggaggt 1380
gggccccaga gaatggtgcc aaggtccagt ggggtgactg ggatcagctc aggcctgacg 1440
ctggccactc ccacctagct cctttctttc taatctgttc tcattctcct tgggaaggat 1500
tgaggtctct ggaaaacagc caaacaactg ttatgggaac agcaagccca aataaagcca 1560
agcatcaggg ggatctgaga gctgaaagca acttctgttc cccctccctc agctgaaggg 1620
gtggggaagg gctcccaaag ccataactcc ttttaaggga tttagaaggc ataaaaaggc 1680
ccctggctga gaacttcctt cttcattctg cagttggtga attcgccacc atgtcagaag 1740
gggtgggcac gttccgcatg gtacctgaag aggaacagga gctccgtgcc caactggagc 1800
agctcacaac caaggaccat ggacctgtct ttggcccgtg cagccagctg ccccgccaca 1860

-continued

```
ccttgcagaa ggccaaggat gagctgaacg agagagagga gacccgggag gaggcagtgc   1920
gagagctgca ggagatggtg caggcgcagg cggcctcggg ggaggagctg gcggtggccg   1980
tggcggagag ggtgcaagag aaggacagcg gcttcttcct gcgcttcatc cgcgcacgga   2040
agttcaacgt gggccgtgcc tatgagctgc tcagaggcta tgtgaatttc cggctgcagt   2100
accctgagct ctttgacagc ctgtccccag aggctgtccg ctgcaccatt gaagctggct   2160
accctggtgt cctctctagt cgggacaagt atggccgagt ggtcatgctc ttcaacattg   2220
agaactggca aagtcaagaa atcacctttg atgagatctt gcaggcatat tgcttcatcc   2280
tggagaagct gctggagaat gaggaaactc aaatcaatgg cttctgcatc attgagaact   2340
tcaagggctt taccatgcag caggctgcta gtctccggac ttcagatctc aggaagatgg   2400
tggacatgct ccaggattcc ttcccagccc ggttcaaagc catccacttc atccaccagc   2460
catggtactt caccacgacc tacaatgtgg tcaagccctt cttgaagagc aagctgcttg   2520
agagggtctt tgtccacggg gatgaccttt ctggtttcta ccaggagatc gatgagaaca   2580
tcctgccctc tgacttcggg ggcacgctgc ccaagtatga tggcaaggcc gttgctgagc   2640
agctctttgg cccccaggcc caagctgaga acacagcctt ctgaggatct accggtcgac   2700
ctgcagaagc ttgcctcgag cagcgctgct cgagagatct ggatcataat cagccatacc   2760
acatttgtag aggttttact tgctttaaaa aacctcccac acctccccct gaacctgaaa   2820
cataaaatga atgcaattgt tgttgttaac ttgtttattg cagcttataa tggttacaaa   2880
taaagcaata gcatcacaaa tttcacaaat aaagcatttt tttcactgca ttctagttgt   2940
ggtttgtcca aactcatcaa tgtatcttat catgtctggt aaccattctc caggttgagc   3000
cagaccaatt tgatggtaga tttagcaaat aaaaatacag gacacccagt taaatgtgaa   3060
tttccgatga acagcaaata ctttttagt attaaaaaag ttcacattta ggctcacgcc   3120
tgtaatccca gcactttggg aggccgaggc aggcagatca cctgaggtca ggagttcgag   3180
accagcctgg ccaacatggt gaaaccccat ctccactaaa aataccaaaa attagccagg   3240
cgtgctggtg ggcacctgta gttccagcta ctcaggaggc taaggcagga gaattgcttg   3300
aacctgggag gcagaggttg cagtgagctg agatcgcacc attgcactct agcctgggcg   3360
acaagaacaa aactccatct caaaaaaaaa aaaaaaaaaa aagttcacat ttaactgggc   3420
attctgtatt taattggtaa tctgagatgg cagggaacag catcagcatg gtgtgaggga   3480
taggcatttt ttcattgtgt acagcttgta aatcagtatt tttaaaactc aaagttaatg   3540
gcttgggcat atttagaaaa gagttgccgc acggacttga accctgtatt cctaaaatct   3600
aggatcttgt tctgatggtc tgcacaactg gctgggggtg tccagccact gtccctcttg   3660
cctgggctcc ccagggcagt tctgtcagcc tctccatttc cattcctgtt ccagcaaaac   3720
ccaactgata gcacagcagc atttcagcct gtctacctct gtgcccacat acctggatgt   3780
ctaccagcca gaaaggtggc ttagatttgg ttcctgtggg tggattatgg cccccagaac   3840
ttccctgtgc ttgctggggg tgtggagtgg aaagagcagg aaatggggga ccctccgata   3900
ctctatgggg gtcctccaag tctctttgtg caagttaggg taataatcaa tatggagcta   3960
agaaagagaa ggggaactat gctttagaac aggacactgt gccaggagca ttgcagaaat   4020
tatatggttt tcacgacagt tctttttggt aggtactgtt attatcctca gtttgcagat   4080
gaggaaactg agacccagaa aggttaaata acttgctagg gtcacacaag tcataactga   4140
caaagcctga ttcaaaccca ggtctcccta acctttaagg tttctatgac gccagctctc   4200
```

-continued

```
ctagggagtt tgtcttcaga tgtcttggct ctaggtgtca aaaaaagact tggtgtcagg   4260
caggcatagg ttcaagtccc aactctgtca cttaccaact gtgactaggt gattgaactg   4320
accatggaac ctggtcacat gcaggagcag gatggtgaag ggttcttgaa ggcacttagg   4380
caggacattt aggcaggaga gaaaacctgg aaacagaaga gctgtctcca aaaataccca   4440
ctggggaagc aggttgtcat gtgggccatg aatgggacct gttctggggt aaccacgtgc   4500
ggaccgagcg gccgcaggaa cccctagtga tggagttggc cactccctct ctgcgcgctc   4560
gctcgctcac tgaggccggg cgaccaaagg tcgcccgacg cccgggcttt gcccgggcgg   4620
cctcagtgag cgagcgagcg cgcagctgcc tgcaggggcg cctgatgcgg tattttctcc   4680
ttacgcatct gtgcggtatt tcacaccgca tacgtcaaag caaccatagt acgcgccctg   4740
tagcggcgca ttaagcgcgg cgggtgtggt ggttacgcgc agcgtgaccg ctacacttgc   4800
cagcgcctta gcgcccgctc ctttcgcttt cttcccttcc tttctcgcca cgttcgccgg   4860
ctttccccgt caagctctaa atcgggggct ccctttaggg ttccgattta gtgctttacg   4920
gcacctcgac cccaaaaaac ttgatttggg tgatggttca cgtagtgggc catcgccctg   4980
atagacggtt tttcgccctt tgacgttgga gtccacgttc tttaatagtg gactcttgtt   5040
ccaaactgga acaacactca actctatctc gggctattct tttgatttat aagggatttt   5100
gccgatttcg gtctattggt taaaaaatga gctgatttaa caaaaattta acgcgaattt   5160
taacaaaata ttaacgttta caattttatg gtgcactctc agtacaatct gctctgatgc   5220
cgcatagtta agccagcccc gacacccgcc aacacccgct gacgcgccct gacgggcttg   5280
tctgctcccg gcatccgctt acagacaagc tgtgaccgtc tccgggagct gcatgtgtca   5340
gaggttttca ccgtcatcac cgaaacgcgc gagacgaaag ggcctcgtga tacgcctatt   5400
tttataggtt aatgtcatga taataatggt ttcttagacg tcaggtggca cttttcgggg   5460
aaatgtgcgc ggaaccccta tttgtttatt tttctaaata cattcaaata tgtatccgct   5520
catgagacaa taaccctgat aaatgcttca ataatattga aaaaggaaga gtatgagtat   5580
tcaacatttc cgtgtcgccc ttattccctt ttttgcggca ttttgccttc ctgtttttgc   5640
tcacccagaa acgctggtga aagtaaaaga tgctgaagat cagttgggtg cacgagtggg   5700
ttacatcgaa ctggatctca acagcggtaa gatccttgag agttttcgcc ccgaagaacg   5760
ttttccaatg atgagcactt ttaaagttct gctatgtggc gcggtattat cccgtattga   5820
cgccgggcaa gagcaactcg gtcgccgcat acactattct cagaatgact tggttgagta   5880
ctcaccagtc acagaaaagc atcttacgga tggcatgaca gtaagagaat tatgcagtgc   5940
tgccataacc atgagtgata acactgcggc caacttactt ctgacaacga tcggaggacc   6000
gaaggagcta accgcttttt tgcacaacat gggggatcat gtaactcgcc ttgatcgttg   6060
ggaaccggag ctgaatgaag ccataccaaa cgacgagcgt gacaccacga tgcctgtagc   6120
aatggcaaca acgttgcgca aactattaac tggcgaacta cttactctag cttcccggca   6180
acaattaata gactggatgg aggcggataa agttgcagga ccacttctgc gctcggccct   6240
tccggctggc tggtttattg ctgataaatc tggagccggt gagcgtgggt ctcgcggtat   6300
cattgcagca ctggggccag atggtaagcc ctcccgtatc gtagttatct acacgacggg   6360
gagtcaggca actatggatg aacgaaatag acagatcgct gagataggtg cctcactgat   6420
taagcattgg taactgtcag accaagttta ctcatatata ctttagattg atttaaaact   6480
tcatttttaa tttaaaagga tctaggtgaa gatccttttt gataatctca tgaccaaaat   6540
cccttaacgt gagttttcgt tccactgagc gtcagacccc gtagaaaaga tcaaaggatc   6600
```

```
ttcttgaaat cctttttttc tgcgcgtaat ctgctgcttg caaacaaaaa aaccaccgct   6660

accagcggtg gtttgtttgc cggatcaaga gctaccaact ctttttccga aggtaactgg   6720

cttcagcaga gcgcagatac caaatactgt tcttctagtg tagccgtagt taggccacca   6780

cttcaagaac tctgtagcac cgcctacata cctcgctctg ctaatcctgt taccagtggc   6840

tgctgccagt ggcgataagt cgtgtcttac cgggttggac tcaagacgat agttaccgga   6900

taaggcgcag cggtcgggct gaacgggggg ttcgtgcaca cagcccagct tggagcgaac   6960

gacctacacc gaactgagat acctacagcg tgagctatga gaaagcgcca cgcttcccga   7020

agggagaaag gcggacaggt atccggtaag cggcagggtc ggaacaggag agcgcacgag   7080

ggagcttcca gggggaaacg cctggtatct ttatagtcct gtcgggtttc gccacctctg   7140

acttgagcgt cgatttttgt gatgctcgtc aggggggcgg agcctatgga aaaacgccag   7200

caacgcggcc tttttacggt tcctggcctt ttgctggcct tttgctcaca tgtcctgcag   7260

gcag                                                                7264
```

```
<210> SEQ ID NO 29
<211> LENGTH: 7321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

ctgcgcgctc gctcgctcac tgaggccgcc cgggcgtcgg gcgacctttg gtcgcccggc     60

ctcagtgagc gagcgagcgc gcagagaggg agtggccaac tccatcacta ggggttcctg    120

cggccgcacg cgtactagtt attaatagta atcaattacg gggtcattag ttcatagccc    180

atatatggag ttccgcgtta cataacttac ggtaaatggc ccgcctggct gaccgcccaa    240

cgacccccgc ccattgacgt caataatgac gtatgttccc atagtaacgc caatagggac    300

tttccattga cgtcaatggg tggagtattt acggtaaact gcccacttgg cagtacatca    360

agtgtatcat atgccaagta cgccccctat tgacgtcaat gacggtaaat ggcccgcctg    420

gcattatgcc cagtacatga ccttatggga ctttcctact tggcagtaca tctacgtatt    480

agtcatcgct attaccatgg tcgaggtgag ccccacgttc tgcttcactc tccccatctc    540

ccccccctcc ccacccccaa ttttgtattt atttattttt taattatttt gtgcagcgat    600

gggggcgggg gggggggggg ggcgcgcgcc aggcggggcg gggcggggcg aggggcgggg    660

cggggcgagg cggagaggtg cggcggcagc caatcagagc ggcgcgctcc gaaagtttcc    720

ttttatggcg aggcggcggc ggcggcggcc ctataaaaag cgaagcgcgc ggcgggcggg    780

gagtcgctgc gacgctgcct tcgccccgtg ccccgctccg ccgccgcctc gcgccgcccg    840

ccccggctct gactgaccgc gttactccca caggtgagcg ggcgggacgg cccttctcct    900

ccgggctgta attagcgctt ggtttaatga cggcttgttt cttttctgtg gctgcgtgaa    960

agccttgagg ggctccggga gggccctttg tgcgggggga gcggctcggg gggtgcgtgc   1020

gtgtgtgtgt gcgtggggag cgccgcgtgc ggctccgcgc tgcccggcgg ctgtgagcgc   1080

tgcgggcgcg gcgcggggct ttgtgcgctc cgcagtgtgc gcgaggggag cgcggccggg   1140

ggcggtgccc cgcggtgcgg ggggggctgc gaggggaaca aaggctgcgt gcggggtgtg   1200

tgcgtggggg ggtgagcagg gggtgtgggc gcgtcggtcg ggctgcaacc ccccctgcac   1260

ccccctcccc gagttgctga gcacggcccg gcttcgggtg cggggctccg tacggggcgt   1320
```

-continued

```
ggcgcggggc tcgccgtgcc gggcgggggg tggcggcagg tgggggtgcc gggcggggcg   1380
gggccgcctc gggccgggga gggctcgggg gaggggcgcg gcggcccccg gagcgccggc   1440
ggctgtcgag gcgcggcgag ccgcagccat tgccttttat ggtaatcgtg cgagagggcg   1500
cagggacttc ctttgtccca aatctgtgcg gagccgaaat ctgggaggcg ccgccgcacc   1560
ccctctagcg ggcgcggggc gaagcggtgc ggcgccggca ggaaggaaat gggcggggag   1620
ggccttcgtg cgtcgccgcg ccgccgtccc cttctccctc tccagcctcg gggctgtccg   1680
cggggggacg gctgccttcg ggggggacgg ggcagggcgg ggttcggctt ctggcgtgtg   1740
accggcggca tcgattgaat tcgccaccat gtcagaaggg gtgggcacgt tccgcatggt   1800
acctgaagag gaacaggagc tccgtgccca actggagcag ctcacaacca aggaccatgg   1860
acctgtcttt ggcccgtgca gccagctgcc ccgccacacc ttgcagaagg ccaaggatga   1920
gctgaacgag agagaggaga cccgggagga ggcagtgcga gagctgcagg agatggtgca   1980
ggcgcaggcg gcctcggggg aggagctggc ggtggccgtg gcggagaggg tgcaagagaa   2040
ggacagcggc ttcttcctgc gcttcatccg cgcacggaag ttcaacgtgg gccgtgccta   2100
tgagctgctc agaggctatg tgaatttccg gctgcagtac cctgagctct ttgacagcct   2160
gtccccagag gctgtccgct gcaccattga agctggctac cctggtgtcc tctctagtcg   2220
ggacaagtat ggccgagtgg tcatgctctt caacattgag aactggcaaa gtcaagaaat   2280
cacctttgat gagatcttgc aggcatattg cttcatcctg gagaagctgc tggagaatga   2340
ggaaactcaa atcaatggct tctgcatcat tgagaacttc aagggcttta ccatgcagca   2400
ggctgctagt ctccggactt cagatctcag gaagatggtg gacatgctcc aggattcctt   2460
cccagcccgg ttcaaagcca tccacttcat ccaccagcca tggtacttca ccacgaccta   2520
caatgtggtc aagcccttct tgaagagcaa gctgcttgag agggtctttg tccacgggga   2580
tgacctttct ggtttctacc aggagatcga tgagaacatc ctgccctctg acttcggggg   2640
cacgctgccc aagtatgatg gcaaggccgt tgctgagcag ctctttggcc cccaggccca   2700
agctgagaac acagccttct gaggatcgta ccggtcgacc tgcagaagct tgcctcgagc   2760
agcgctgctc gagagatctg gatcataatc agccatacca catttgtaga ggttttactt   2820
gctttaaaaa acctcccaca cctccccctg aacctgaaac ataaaatgaa tgcaattgtt   2880
gttgttaact tgtttattgc agcttataat ggttacaaat aaagcaatag catcacaaat   2940
ttcacaaata aagcattttt ttcactgcat tctagttgtg gtttgtccaa actcatcaat   3000
gtatcttatc atgtctggta ctagggttac cccagaacag gtcccattca tggcccacat   3060
gacaacctgc ttccccagtg ggtatttttg gagacagctc ttctgtttcc aggttttctc   3120
tcctgcctaa atgtcctgcc taagtgcctt caagaaccct tcaccatcct gctcctgcat   3180
gtgaccaggt tccatggtca gttcaatcac ctagtcacag ttggtaagtg acagagttgg   3240
gacttgaacc tatgcctgcc tgacaccaag tcttttttttg acacctagag ccaagacatc   3300
tgaagacaaa ctccctagga gagctggcgt catagaaacc ttaaaggtta gggagacctg   3360
ggtttgaatc aggctttgtc agttatgact tgtgtgaccc tagcaagtta tttaaccttt   3420
ctgggtctca gtttcctcat ctgcaaactg aggataataa cagtacctac caaaaagaac   3480
tgtcgtgaaa accatataat ttctgcaatg ctcctggcac agtgtcctgt tctaaagcat   3540
agttcccctt ctctttctta gctccatatt gattattacc ctaacttgca caaagagact   3600
tggaggaccc ccatagagta tcggagggtc ccccatttcc tgctctttcc actccacacc   3660
```

-continued

```
cccagcaagc acagggaagt tctgggggcc ataatccacc cacaggaacc aaatctaagc   3720
cacctttctg gctggtagac atccaggtat gtgggcacag aggtagacag gctgaaatgc   3780
tgctgtgcta tcagttgggt tttgctggaa caggaatgga aatggagagg ctgacagaac   3840
tgccctgggg agcccaggca agagggacag tggctggaca cccccagcca gttgtgcaga   3900
ccatcagaac aagatcctag attttaggaa tacagggttc aagtccgtgc ggcaactctt   3960
ttctaaatat gcccaagcca ttaactttga gttttaaaaa tactgattta caagctgtac   4020
acaatgaaaa aatgcctatc cctcacacca tgctgatgct gttccctgcc atctcagatt   4080
accaattaaa tacagaatgc ccagttaaat gtgaactttt tttttttttt tttttttgag   4140
atggagtttt gttcttgtcg cccaggctag agtgcaatgg tgcgatctca gctcactgca   4200
acctctgcct cccaggttca agcaattctc ctgccttagc ctcctgagta gctggaacta   4260
caggtgccca ccagcacgcc tggctaattt ttggtatttt tagtggagat ggggtttcac   4320
catgttggcc aggctggtct cgaactcctg acctcaggtg atctgcctgc ctcggcctcc   4380
caaagtgctg ggattacagg cgtgagccta aatgtgaact tttttaatac taaaaaagta   4440
tttgctgttc atcggaaatt cacatttaac tgggtgtcct gtatttttat ttgctaaatc   4500
taccatcaaa ttggtctggc tcaacctgga gaatggttac cctaggtaac cacgtgcgga   4560
ccgagcggcc gcaggaaccc ctagtgatgg agttggccac tccctctctg cgcgctcgct   4620
cgctcactga ggccgggcga ccaaaggtcg cccgacgccc gggctttgcc cgggcggcct   4680
cagtgagcga gcgagcgcgc agctgcctgc aggggcgcct gatgcggtat tttctcctta   4740
cgcatctgtg cggtatttca caccgcatac gtcaaagcaa ccatagtacg cgccctgtag   4800
cggcgcatta agcgcggcgg gtgtggtggt tacgcgcagc gtgaccgcta cacttgccag   4860
cgccttagcg cccgctcctt tcgctttctt cccttccttt ctcgccacgt tcgccggctt   4920
tccccgtcaa gctctaaatc gggggctccc tttagggttc cgatttagtg ctttacggca   4980
cctcgacccc aaaaaacttg atttgggtga tggttcacgt agtgggccat cgccctgata   5040
gacggttttt cgccctttga cgttggagtc cacgttcttt aatagtggac tcttgttcca   5100
aactggaaca acactcaact ctatctcggg ctattctttt gatttataag ggattttgcc   5160
gatttcggtc tattggttaa aaaatgagct gatttaacaa aaatttaacg cgaattttaa   5220
caaaatatta acgtttacaa ttttatggtg cactctcagt acaatctgct ctgatgccgc   5280
atagttaagc cagccccgac acccgccaac acccgctgac gcgccctgac gggcttgtct   5340
gctcccggca tccgcttaca gacaagctgt gaccgtctcc gggagctgca tgtgtcagag   5400
gttttcaccg tcatcaccga aacgcgcgag acgaaagggc ctcgtgatac gcctattttt   5460
ataggttaat gtcatgataa taatggtttc ttagacgtca ggtggcactt ttcggggaaa   5520
tgtgcgcgga acccctattt gtttattttt ctaaatacat tcaaatatgt atccgctcat   5580
gagacaataa ccctgataaa tgcttcaata atattgaaaa aggaagagta tgagtattca   5640
acatttccgt gtcgccctta ttcccttttt tgcggcattt tgccttcctg tttttgctca   5700
cccagaaacg ctggtgaaag taaaagatgc tgaagatcag ttgggtgcac gagtgggtta   5760
catcgaactg gatctcaaca gcggtaagat ccttgagagt tttcgccccg aagaacgttt   5820
tccaatgatg agcactttta aagttctgct atgtggcgcg gtattatccc gtattgacgc   5880
cgggcaagag caactcggtc gccgcataca ctattctcag aatgacttgg ttgagtactc   5940
accagtcaca gaaaagcatc ttacggatgg catgacagta agagaattat gcagtgctgc   6000
cataaccatg agtgataaca ctgcggccaa cttacttctg acaacgatcg gaggaccgaa   6060
```

ggagctaacc gctttttgc acaacatggg ggatcatgta actcgccttg atcgttggga 6120
accggagctg aatgaagcca taccaaacga cgagcgtgac accacgatgc ctgtagcaat 6180
ggcaacaacg ttgcgcaaac tattaactgg cgaactactt actctagctt cccggcaaca 6240
attaatagac tggatggagg cggataaagt tgcaggacca cttctgcgct cggcccttcc 6300
ggctggctgg tttattgctg ataaatctgg agccggtgag cgtgggtctc gcggtatcat 6360
tgcagcactg gggccagatg gtaagccctc ccgtatcgta gttatctaca cgacggggag 6420
tcaggcaact atggatgaac gaaatagaca gatcgctgag ataggtgcct cactgattaa 6480
gcattggtaa ctgtcagacc aagtttactc atatatactt tagattgatt taaaacttca 6540
tttttaattt aaaaggatct aggtgaagat cctttttgat aatctcatga ccaaaatccc 6600
ttaacgtgag ttttcgttcc actgagcgtc agaccccgta gaaaagatca aaggatcttc 6660
ttgaaatcct ttttttctgc gcgtaatctg ctgcttgcaa acaaaaaaac caccgctacc 6720
agcggtggtt tgtttgccgg atcaagagct accaactctt tttccgaagg taactggctt 6780
cagcagagcg cagataccaa atactgttct tctagtgtag ccgtagttag gccaccactt 6840
caagaactct gtagcaccgc ctacatacct cgctctgcta atcctgttac cagtggctgc 6900
tgccagtggc gataagtcgt gtcttaccgg gttggactca agacgatagt taccggataa 6960
ggcgcagcgg tcgggctgaa cggggggttc gtgcacacag cccagcttgg agcgaacgac 7020
ctacaccgaa ctgagatacc tacagcgtga gctatgagaa agcgccacgc ttcccgaagg 7080
gagaaaggcg gacaggtatc cggtaagcgg cagggtcgga acaggagagc gcacgaggga 7140
gcttccaggg ggaaacgcct ggtatcttta tagtcctgtc gggtttcgcc acctctgact 7200
tgagcgtcga tttttgtgat gctcgtcagg ggggcggagc ctatggaaaa acgccagcaa 7260
cgcggccttt ttacggttcc tggccttttg ctggcctttt gctcacatgt cctgcaggca 7320
g 7321

<210> SEQ ID NO 30
<211> LENGTH: 6492
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 30
ctgcgcgctc gctcgctcac tgaggccgcc cgggcgtcgg gcgacctttg gtcgcccggc 60
ctcagtgagc gagcgagcgc gcagagaggg agtggccaac tccatcacta ggggttcctg 120
cggccgcacg cgtttgtcct ctccctgctt ggccttaacc agccacattt ctcaactgac 180
cccactcact gcagaggtga aaactaccat gccaggtcct gctggctggg ggaggggtgg 240
gcaataggcc tggatttgcc agagctgcca ctgtagatgt agtcatattt acgatttccc 300
ttcacctctt attaccctgg tggtggtggt gggggggggg gggtgctctc tcagcaaccc 360
caccccggga tcttgaggag aaagagggca gagaaaagag ggaatgggac tggcccagat 420
cccagcccca cagccgggct tccacatggc cgagcaggaa ctccagagca ggagcacaca 480
aaggagggct ttgatgcgcc tccagccagg cccaggcctc tcccctctcc cctttctctc 540
tgggtcttcc tttgccccac tgagggcctc ctgtgagccc gatttaacgg aaactgtggg 600
cggtgagaag ttccttatga cacactaatc ccaacctgct gaccggacca cgcctccagc 660
ggagggaacc tctagagctc caggacattc aggtaccagg tagccccaag gaggagctgc 720

-continued

```
cgaatcgatg gatcgggaac tgaaaaacca gaaagttaac tggtaagttt agtctttttg    780
tcttttattt caggtcccgg atccggtggt ggtgcaaatc aaagaactgc tcctcagtgg    840
atgttgcctt tacttctagg cctgtacgga agtgttactt ctgctctaaa agctgcggaa    900
ttgtacccgc cccgggatcc atcgattgaa ttcgccacca tgtcagaagg ggtgggcacg    960
ttccgcatgg tacctgaaga ggaacaggag ctccgtgccc aactggagca gctcacaacc   1020
aaggaccatg gacctgtctt tggcccgtgc agccagctgc cccgccacac cttgcagaag   1080
gccaaggatg agctgaacga gagagaggag acccgggagg aggcagtgcg agagctgcag   1140
gagatggtgc aggcgcaggc ggcctcgggg gaggagctgg cggtggccgt ggcggagagg   1200
gtgcaagaga aggacagcgg cttcttcctg cgcttcatcc gcgcacggaa gttcaacgtg   1260
ggccgtgcct atgagctgct cagaggctat gtgaatttcc ggctgcagta ccctgagctc   1320
tttgacagcc tgtccccaga ggctgtccgc tgcaccattg aagctggcta ccctggtgtc   1380
ctctctagtc gggacaagta tggccgagtg gtcatgctct tcaacattga gaactggcaa   1440
agtcaagaaa tcacctttga tgagatcttg caggcatatt gcttcatcct ggagaagctg   1500
ctggagaatg aggaaactca aatcaatggc ttctgcatca ttgagaactt caagggcttt   1560
accatgcagc aggctgctag tctccggact tcagatctca ggaagatggt ggacatgctc   1620
caggattcct tcccagcccg gttcaaagcc atccacttca tccaccagcc atggtacttc   1680
accacgacct acaatgtggt caagcccttc ttgaagagca agctgcttga gagggtcttt   1740
gtccacgggg atgacctttc tggtttctac caggagatcg atgagaacat cctgccctct   1800
gacttcgggg gcacgctgcc caagtatgat ggcaaggccg ttgctgagca gctctttggc   1860
ccccaggccc aagctgagaa cacagccttc tgaggatcgt accggtcgac ctgcagaagc   1920
ttgcctcgag cagcgctgct cgagagatct ggatcataat cagccatacc acatttgtag   1980
aggttttact tgctttaaaa aacctcccac acctcccct gaacctgaaa cataaaatga   2040
atgcaattgt tgttgttaac ttgtttattg cagcttataa tggttacaaa taaagcaata   2100
gcatcacaaa tttcacaaat aaagcatttt tttcactgca ttctagttgt ggtttgtcca   2160
aactcatcaa tgtatcttat catgtctggt actagggtta ccccagaaca ggtcccattc   2220
atggcccaca tgacaacctg cttccccagt gggtattttt ggagacagct cttctgtttc   2280
caggttttct ctcctgccta aatgtcctgc ctaagtgcct tcaagaaccc ttcaccatcc   2340
tgctcctgca tgtgaccagg ttccatggtc agttcaatca cctagtcaca gttggtaagt   2400
gacagagttg ggacttgaac ctatgcctgc ctgacaccaa gtcttttttt gacacctaga   2460
gccaagacat ctgaagacaa actccctagg agagctggcg tcatagaaac cttaaaggtt   2520
agggagacct gggtttgaat caggctttgt cagttatgac ttgtgtgacc ctagcaagtt   2580
atttaacctt tctgggtctc agtttcctca tctgcaaact gaggataata acagtaccta   2640
ccaaaaagaa ctgtcgtgaa aaccatataa tttctgcaat gctcctggca cagtgtcctg   2700
ttctaaagca tagttcccct tctctttctt agctccatat tgattattac cctaacttgc   2760
acaaagagac ttggaggacc cccatagagt atcggagggt cccccatttc ctgctctttc   2820
cactccacac ccccagcaag cacagggaag ttctgggggc cataatccac ccacaggaac   2880
caaatctaag ccacctttct ggctggtaga catccaggta tgtgggcaca gaggtagaca   2940
ggctgaaatg ctgctgtgct atcagttggg ttttgctgga acaggaatgg aaatggagag   3000
gctgacagaa ctgccctggg gagcccaggc aagagggaca gtggctggac acccccagcc   3060
```

-continued

```
agttgtgcag accatcagaa caagatccta gattttagga atacagggtt caagtccgtg   3120
cggcaactct tttctaaata tgcccaagcc attaactttg agttttaaaa atactgattt   3180
acaagctgta cacaatgaaa aaatgcctat ccctcacacc atgctgatgc tgttccctgc   3240
catctcagat taccaattaa atacagaatg cccagttaaa tgtgaacttt ttttttttt    3300
tttttttga gatggagttt tgttcttgtc gcccaggcta gagtgcaatg gtgcgatctc    3360
agctcactgc aacctctgcc tcccaggttc aagcaattct cctgccttag cctcctgagt   3420
agctggaact acaggtgccc accagcacgc ctggctaatt tttggtattt ttagtggaga   3480
tggggtttca ccatgttggc caggctggtc tcgaactcct gacctcaggt gatctgcctg   3540
cctcggcctc ccaaagtgct gggattacag gcgtgagcct aaatgtgaac tttttaata    3600
ctaaaaaagt atttgctgtt catcggaaat tcacatttaa ctgggtgtcc tgtattttta   3660
tttgctaaat ctaccatcaa attggtctgg ctcaacctgg agaatggtta ccctaggtaa   3720
ccacgtgcgg accgagcggc cgcaggaacc cctagtgatg gagttggcca ctccctctct   3780
gcgcgctcgc tcgctcactg aggccgggcg accaaaggtc gcccgacgcc cgggctttgc   3840
ccgggcggcc tcagtgagcg agcgagcgcg cagctgcctg caggggcgcc tgatgcggta   3900
ttttctcctt acgcatctgt gcggtatttc acaccgcata cgtcaaagca accatagtac   3960
gcgccctgta gcggcgcatt aagcgcggcg ggtgtggtgg ttacgcgcag cgtgaccgct   4020
acacttgcca gcgccttagc gcccgctcct ttcgctttct tcccttcctt tctcgccacg   4080
ttcgccggct ttccccgtca agctctaaat cgggggctcc ctttagggtt ccgatttagt   4140
gctttacggc acctcgaccc caaaaaactt gatttgggtg atggttcacg tagtgggcca   4200
tcgccctgat agacggtttt tcgccctttg acgttggagt ccacgttctt taatagtgga   4260
ctcttgttcc aaactggaac aacactcaac tctatctcgg gctattcttt tgatttataa   4320
gggattttgc cgatttcggt ctattggtta aaaaatgagc tgatttaaca aaaatttaac   4380
gcgaatttta acaaaatatt aacgtttaca attttatggt gcactctcag tacaatctgc   4440
tctgatgccg catagttaag ccagccccga cacccgccaa cacccgctga cgcgccctga   4500
cgggcttgtc tgctcccggc atccgcttac agacaagctg tgaccgtctc cgggagctgc   4560
atgtgtcaga ggttttcacc gtcatcaccg aaacgcgcga gacgaaaggg cctcgtgata   4620
cgcctatttt tataggttaa tgtcatgata ataatggttt cttagacgtc aggtggcact   4680
tttcggggaa atgtgcgcgg aacccctatt tgtttatttt tctaaataca ttcaaatatg   4740
tatccgctca tgagacaata accctgataa atgcttcaat aatattgaaa aaggaagagt   4800
atgagtattc aacatttccg tgtcgccctt attccctttt ttgcggcatt ttgccttcct   4860
gtttttgctc acccagaaac gctggtgaaa gtaaaagatg ctgaagatca gttgggtgca   4920
cgagtgggtt acatcgaact ggatctcaac agcggtaaga tccttgagag ttttcgcccc   4980
gaagaacgtt ttccaatgat gagcactttt aaagttctgc tatgtggcgc ggtattatcc   5040
cgtattgacg ccgggcaaga gcaactcggt cgccgcatac actattctca gaatgacttg   5100
gttgagtact caccagtcac agaaaagcat cttacggatg gcatgacagt aagagaatta   5160
tgcagtgctg ccataaccat gagtgataac actgcggcca acttacttct gacaacgatc   5220
ggaggaccga aggagctaac cgcttttttg cacaacatgg gggatcatgt aactcgcctt   5280
gatcgttggg aaccggagct gaatgaagcc ataccaaacg acgagcgtga caccacgatg   5340
cctgtagcaa tggcaacaac gttgcgcaaa ctattaactg gcgaactact tactctagct   5400
tcccggcaac aattaataga ctggatggag gcggataaag ttgcaggacc acttctgcgc   5460
```

```
tcggcccttc cggctggctg gtttattgct gataaatctg gagccggtga gcgtgggtct   5520

cgcggtatca ttgcagcact ggggccagat ggtaagccct cccgtatcgt agttatctac   5580

acgacgggga gtcaggcaac tatggatgaa cgaaatagac agatcgctga gataggtgcc   5640

tcactgatta agcattggta actgtcagac caagtttact catatatact ttagattgat   5700

ttaaaacttc atttttaatt taaaaggatc taggtgaaga tcctttttga taatctcatg   5760

accaaaatcc cttaacgtga gttttcgttc cactgagcgt cagaccccgt agaaaagatc   5820

aaaggatctt cttgaaatcc tttttttctg cgcgtaatct gctgcttgca aacaaaaaaa   5880

ccaccgctac cagcggtggt ttgtttgccg gatcaagagc taccaactct ttttccgaag   5940

gtaactggct tcagcagagc gcagatacca aatactgttc ttctagtgta gccgtagtta   6000

ggccaccact tcaagaactc tgtagcaccg cctacatacc tcgctctgct aatcctgtta   6060

ccagtggctg ctgccagtgg cgataagtcg tgtcttaccg ggttggactc aagacgatag   6120

ttaccggata aggcgcagcg gtcgggctga acggggggtt cgtgcacaca gcccagcttg   6180

gagcgaacga cctacaccga actgagatac ctacagcgtg agctatgaga aagcgccacg   6240

cttcccgaag ggagaaaggc ggacaggtat ccggtaagcg gcagggtcgg aacaggagag   6300

cgcacgaggg agcttccagg gggaaacgcc tggtatcttt atagtcctgt cgggtttcgc   6360

cacctctgac ttgagcgtcg atttttgtga tgctcgtcag gggggcggag cctatggaaa   6420

aacgccagca acgcggcctt tttacggttc ctggcctttt gctggccttt tgctcacatg   6480

tcctgcaggc ag                                                       6492
```

<210> SEQ ID NO 31
<211> LENGTH: 4741
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31

```
cgcgctcgct cgctcactga ggccgcccgg gcaaagcccg ggcgtcgggc gacctttggt     60

cgcccggcct cagtgagcga gcgagcgcgc agagagggag tggggtacca cgcgtttgtc    120

ctctccctgc ttggccttaa ccagccacat ttctcaactg accccactca ctgcagaggt    180

gaaaactacc atgccaggtc ctgctggctg ggggaggggt gggcaatagg cctggatttg    240

ccagagctgc cactgtagat gtagtcatat ttacgatttc ccttcacctc ttattaccct    300

ggtggtggtg gtgggggggg gggggtgctc tctcagcaac cccaccccgg gatcttgagg    360

agaaagaggg cagagaaaag agggaatggg actggcccag atcccagccc cacagccggg    420

cttccacatg gccgagcagg aactccagag caggagcaca caaaggaggg ctttgatgcg    480

cctccagcca ggcccaggcc tctcccctct cccctttctc tctgggtctt cctttgcccc    540

actgagggcc tcctgtgagc ccgatttaac ggaaactgtg ggcggtgaga agttccttat    600

gacacactaa tcccaacctg ctgaccggac cacgcctcca gcggagggaa cctctagagc    660

tccaggacat tcaggtacca ggtagcccca aggaggagct gccgaatcga tggatcggga    720

actgaaaaac cagaaagtta actggtaagt ttagtctttt tgtcttttat ttcaggtccc    780

ggatccggtg gtggtgcaaa tcaaagaact gctcctcagt ggatgttgcc tttacttcta    840

ggcctgtacg gaagtgttac ttctgctcta aaagctgcgg aattgtaccc gccccgggat    900

ccatcgattg aattccccgg ggatcctcta gagtcgaaat tcgccaccat ggtgagcaag    960
```

-continued

```
ggcgaggagc tgttcaccgg ggtggtgccc atcctggtcg agctggacgg cgacgtaaac   1020
ggccacaagt tcagcgtgtc cggcgagggc gagggcgatg ccacctacgg caagctgacc   1080
ctgaagttca tctgcaccac cggcaagctg cccgtgccct ggcccaccct cgtgaccacc   1140
ctgacctacg gcgtgcagtg cttcagccgc taccccgacc acatgaagca gcacgacttc   1200
ttcaagtccg ccatgcccga aggctacgtc caggagcgca ccatcttctt caaggacgac   1260
ggcaactaca agacccgcgc cgaggtgaag ttcgagggcg acaccctggt gaaccgcatc   1320
gagctgaagg gcatcgactt caaggaggac ggcaacatcc tggggcacaa gctggagtac   1380
aactacaaca gccacaacgt ctatatcatg gccgacaagc agaagaacgg catcaaggtg   1440
aacttcaaga tccgccacaa catcgaggac ggcagcgtgc agctcgccga ccactaccag   1500
cagaacaccc ccatcggcga cggccccgtg ctgctgcccg acaaccacta cctgagcacc   1560
cagtccgccc tgagcaaaga ccccaacgag aagcgcgatc acatggtcct gctggagttc   1620
gtgaccgccg ccgggatcac tctcggcatg gacgagctgt acaagtaata gggtaccggt   1680
cgacctgcag aagcttgcct cgagcagcgc tgctcgagag atctggatca taatcagcca   1740
taccacattt gtagaggttt tacttgcttt aaaaaacctc ccacacctcc ccctgaacct   1800
gaaacataaa atgaatgcaa ttgttgttgt taacttgttt attgcagctt ataatggtta   1860
caaataaagc aatagcatca caaatttcac aaataaagca tttttttcac tgcattctag   1920
ttgtggtttg tccaaactca tcaatgtatc ttatcatgtc tggtaaccac gtgcggaccg   1980
agcggccgca ggaaccccta gtgatggagt tggccactcc ctctctgcgc gctcgctcgc   2040
tcactgaggc cgggcgacca aaggtcgccc gacgcccggg ctttgcccgg gcggcctcag   2100
tgagcgagcg agcgcgcagc tgcctgcagg ggcgcctgat gcggtatttt ctccttacgc   2160
atctgtgcgg tatttcacac cgcatacgtc aaagcaacca tagtacgcgc cctgtagcgg   2220
cgcattaagc gcggcgggtg tggtggttac gcgcagcgtg accgctacac ttgccagcgc   2280
cttagcgccc gctcctttcg ctttcttccc ttcctttctc gccacgttcg ccggctttcc   2340
ccgtcaagct ctaaatcggg ggctcccttt agggttccga tttagtgctt tacggcacct   2400
cgaccccaaa aaacttgatt tgggtgatgg ttcacgtagt gggccatcgc cctgatagac   2460
ggtttttcgc cctttgacgt tggagtccac gttctttaat agtggactct tgttccaaac   2520
tggaacaaca ctcaactcta tctcgggcta ttcttttgat ttataaggga ttttgccgat   2580
ttcggtctat tggttaaaaa atgagctgat ttaacaaaaa tttaacgcga attttaacaa   2640
aatattaacg tttacaattt tatggtgcac tctcagtaca atctgctctg atgccgcata   2700
gttaagccag ccccgacacc cgccaacacc cgctgacgcg ccctgacggg cttgtctgct   2760
cccggcatcc gcttacagac aagctgtgac cgtctccggg agctgcatgt gtcagaggtt   2820
ttcaccgtca tcaccgaaac gcgcgagacg aaagggcctc gtgatacgcc tatttttata   2880
ggttaatgtc atgataataa tggtttctta gacgtcaggt ggcacttttc ggggaaatgt   2940
gcgcggaacc cctatttgtt tatttttcta aatacattca aatatgtatc cgctcatgag   3000
acaataaccc tgataaatgc ttcaataata ttgaaaaagg aagagtatga gtattcaaca   3060
tttccgtgtc gcccttattc ccttttttgc ggcattttgc cttcctgttt ttgctcaccc   3120
agaaacgctg gtgaaagtaa aagatgctga agatcagttg ggtgcacgag tgggttacat   3180
cgaactggat ctcaacagcg gtaagatcct tgagagtttt cgccccgaag aacgttttcc   3240
aatgatgagc acttttaaag ttctgctatg tggcgcggta ttatcccgta ttgacgccgg   3300
```

gcaagagcaa ctcggtcgcc gcatacacta ttctcagaat gacttggttg agtactcacc 3360
agtcacagaa aagcatctta cggatggcat gacagtaaga gaattatgca gtgctgccat 3420
aaccatgagt gataacactg cggccaactt acttctgaca acgatcggag gaccgaagga 3480
gctaaccgct tttttgcaca acatgggga tcatgtaact cgccttgatc gttgggaacc 3540
ggagctgaat gaagccatac caaacgacga gcgtgacacc acgatgcctg tagcaatggc 3600
aacaacgttg cgcaaactat taactggcga actacttact ctagcttccc ggcaacaatt 3660
aatagactgg atggaggcgg ataaagttgc aggaccactt ctgcgctcgg cccttccggc 3720
tggctggttt attgctgata aatctggagc cggtgagcgt gggtctcgcg gtatcattgc 3780
agcactgggg ccagatggta agccctcccg tatcgtagtt atctacacga cggggagtca 3840
ggcaactatg gatgaacgaa atagacagat cgctgagata ggtgcctcac tgattaagca 3900
ttggtaactg tcagaccaag tttactcata tatactttag attgatttaa aacttcattt 3960
ttaatttaaa aggatctagg tgaagatcct ttttgataat ctcatgacca aaatccctta 4020
acgtgagttt tcgttccact gagcgtcaga ccccgtagaa aagatcaaag gatcttcttg 4080
aaatcctttt tttctgcgcg taatctgctg cttgcaaaca aaaaaaccac cgctaccagc 4140
ggtggtttgt ttgccggatc aagagctacc aactcttttt ccgaaggtaa ctggcttcag 4200
cagagcgcag ataccaaata ctgttcttct agtgtagccg tagttaggcc accacttcaa 4260
gaactctgta gcaccgccta catacctcgc tctgctaatc ctgttaccag tggctgctgc 4320
cagtggcgat aagtcgtgtc ttaccgggtt ggactcaaga cgatagttac cggataaggc 4380
gcagcggtcg ggctgaacgg ggggttcgtg cacacagccc agcttggagc gaacgaccta 4440
caccgaactg agatacctac agcgtgagct atgagaaagc gccacgcttc ccgaagggag 4500
aaaggcggac aggtatccgg taagcggcag ggtcggaaca ggagagcgca cgagggagct 4560
tccaggggga aacgcctggt atctttatag tcctgtcggg tttcgccacc tctgacttga 4620
gcgtcgattt ttgtgatgct cgtcaggggg gcggagccta tggaaaaacg ccagcaacgc 4680
ggccttttta cggttcctgg ccttttgctg gccttttgct cacatgtcct gcaggcagct 4740
g 4741

<210> SEQ ID NO 32
<211> LENGTH: 7122
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 32
ctgcgcgctc gctcgctcac tgaggccgcc cgggcgtcgg gcgacctttg gtcgcccggc 60
ctcagtgagc gagcgagcgc gcagagaggg agtggccaac tccatcacta ggggttcctg 120
cggccgcacg cagcttttgt cctctccctg cttggcctta accagccaca tttctcaact 180
gaccccactc actgcagagg tgaaaactac catgccaggt cctgctggct gggggagggg 240
tgggcaatag gcctggattt gccagagctg ccactgtaga tgtagtcata tttacgattt 300
cccttcacct cttattaccc tggtggtggt ggtggggggg ggggggtgct ctctcagcaa 360
ccccaccccg ggatcttgag gagaaagagg gcagagaaaa gagggaatgg gactggccca 420
gatcccagcc ccacagccgg gcttccacat ggccgagcag gaactccaga gcaggagcac 480
acaaaggagg gctttgatgc gcctccagcc aggcccaggc ctctcccctc tcccctttct 540

-continued

```
ctctgggtct tcctttgccc cactgagggc ctcctgtgag cccgatttaa cggaaactgt    600
gggcggtgag aagttcctta tgacacacta atcccaacct gctgaccgga ccacgcctcc    660
agcggaggga acctctagag ctccaggaca ttcaggtacc aggtagcccc aaggaggagc    720
tgccgacctg gcaggtaagt caatacctgg ggcttgcctg ggccagggag cccaggactg    780
gggtgaggac tcaggggagc agggagacca cgtcccaaga tgcctgtaaa actgaaacca    840
cctggccatt ctccaggttg agccagacca atttgatggc agatttagca aataaaaata    900
caggacaccc agttaaatgt gaatttcaga tgaacagcaa atactttttt agtattaaaa    960
aagttcacat ttaggctcac gcctgtaatc ccagcacttt gggaggccga ggcaggcaga   1020
tcacctgagg tcaggagttc gagaccagcc tggccaacat ggtgaaaccc catctccact   1080
aaaaatacca aaaattagcc aggcgtgctg gtgggcacct gtagttccag ctactcagga   1140
ggctaaggca ggagaattgc ttgaacctgg gaggcagagg ttgcagtgag ctgagatcgc   1200
accattgcac tctagcctgg gcgacaagaa caaaactcca tctcaaaaaa aaaaaaaaaa   1260
aaaaagttca catttaactg ggcattctgt atttaattgg taatctgaga tggcagggaa   1320
cagcatcagc atggtgtgag ggataggcat tttttcattg tgtacagctt gtaaatcagt   1380
atttttaaaa ctcaaagtta atggcttggg catatttaga aaagagttgc cgcacggact   1440
tgaaccctgt attcctaaaa tctaggatct tgttctgatg gtctgcacaa ctggctgggg   1500
gtgtccagcc actgtccctc ttgcctgggc tccccagggc agttctgtca gcctctccat   1560
ttccattcct gttccagcaa aacccaactg atagcacagc agcatttcag cctgtctacc   1620
tctgtgccca catacctgga tgtctaccag ccagaaaggt ggcttagatt tggttcctgt   1680
gggtggatta tggcccccag aacttccctg tgcttgctgg gggtgtggag tggaaagagc   1740
aggaaatggg ggaccctccg atactctatg ggggtcctcc aagtctcttt gtgcaagtta   1800
gggtaataat caatatggag ctaagaaaga gaaggggaac tatgctttag aacaggacac   1860
tgtgccagga gcattgcaga aattatatgg ttttcacgac agttcttttt ggtaggtact   1920
gttattatcc tcagtttgca gatgaggaaa ctgagaccca gaaaggttaa ataacttgct   1980
agggtcacac aagtcataac tgacaaagcc tgattcaaac ccaggtctcc ctaaccttta   2040
aggtttctat gacgccagct ctcctaggga gtttgtcttc agatgtcttg gctctaggtg   2100
tcaaaaaaag acttggtgtc aggcaggcat aggttcaagt cccaactctg tcacttacca   2160
actgtgacta ggtgattgaa ctgaccatgg aacctggtca catgcaggag caggatggtg   2220
aagggttctt gaaggcactt aggcaggaca tttaggcagg agagaaaacc tggaaacaga   2280
agagctgtct ccaaaaatac ccactgggga agcaggttgt catgtgggcc atgaatggga   2340
cctgttctgg taaccaagca ttgcttatgt gtccattaca tttcataaca cttccatcct   2400
actttacagg gaacaaccaa gactggggtt aaatctcaca gcctgcaagt ggaagagaag   2460
aacttgaacc caggtccaac ttttgcgcca cagcaggctg cctcttggtc ctgacaggaa   2520
gtcacaactt gggtctgagt actgatccct ggctattttt tggctgtgtt accttggaca   2580
agtcacttat tcctcctccc gtttcctcct atgtaaaatg gaaataataa tgttgaccct   2640
gggtctgaga gagtggattt gaaagtactt agtgcatcac aaagcacaga acacacttcc   2700
agtctcgtga ttatgtactt atgtaactgg tcatcaccca tcttgagaat gaatgcattg   2760
gggaaagggc catccactag gctgcgaagt ttctgaggga ctccttcggg ctggagaagg   2820
atggccacag gagggaggag agattgcctt atcctgcagt gatcatgtca ttgagaacag   2880
agccagattc tttttttcct ggcagggcca acttgtttta acatctaagg actgagctat   2940
```

-continued

```
ttgtgtctgt gccctttgtc caagcagtgt ttcccaaagt gtagcccaag aaccatctcc   3000
ctcagagcca ccaggaagtg ctttaaattg caggttccta ggccacagcc tgcacctgca   3060
gagtcagaat catggaggtt gggacccagg cacctgcgtt tctaacaaat gcctcgggtg   3120
attctgatgc aattgaaagt ttgagatcca cagttctgag acaataacag aatggttttt   3180
ctaacccctg cagccctgac ttcctatcct agggaagggg ccggctggag aggccaggac   3240
agagaaagca gatcccttct tttccaagg actctgtgtc ttccataggc aacgaattcc   3300
ccggggatcc tctagagtcg aaattcgcca ccatggtgag caagggcgag gagctgttca   3360
ccggggtggt gcccatcctg gtcgagctgg acggcgacgt aaacggccac aagttcagcg   3420
tgtccggcga gggcgagggc gatgccacct acggcaagct gaccctgaag ttcatctgca   3480
ccaccggcaa gctgcccgtg ccctggccca ccctcgtgac caccctgacc tacggcgtgc   3540
agtgcttcag ccgctacccc gaccacatga agcagcacga cttcttcaag tccgccatgc   3600
ccgaaggcta cgtccaggag cgcaccatct tcttcaagga cgacggcaac tacaagaccc   3660
gcgccgaggt gaagttcgag ggcgacaccc tggtgaaccg catcgagctg aagggcatcg   3720
acttcaagga ggacggcaac atcctggggc acaagctgga gtacaactac aacagccaca   3780
acgtctatat catggccgac aagcagaaga acggcatcaa ggtgaacttc aagatccgcc   3840
acaacatcga ggacggcagc gtgcagctcg ccgaccacta ccagcagaac acccccatcg   3900
gcgacggccc cgtgctgctg cccgacaacc actacctgag cacccagtcc gccctgagca   3960
aagaccccaa cgagaagcgc gatcacatgg tcctgctgga gttcgtgacc gccgccggga   4020
tcactctcgg catggacgag ctgtacaagt aatagggtac cggtcgacct gcagaagctt   4080
gcctcgagca gcgctgctcg agagatctgg atcataatca gccataccac atttgtagag   4140
gttttacttg ctttaaaaaa cctcccacac ctccccctga acctgaaaca taaaatgaat   4200
gcaattgttg ttgttaactt gtttattgca gcttataatg gttacaaata aagcaatagc   4260
atcacaaatt tcacaaataa agcatttttt tcactgcatt ctagttgtgg tttgtccaaa   4320
ctcatcaatg tatcttatca tgtctggtaa ccacgtgcgg accgagcggc cgcaggaacc   4380
cctagtgatg gagttggcca ctccctctct gcgcgctcgc tcgctcactg aggccgggcg   4440
accaaaggtc gcccgacgcc cgggctttgc ccgggcggcc tcagtgagcg agcgagcgcg   4500
cagctgcctg caggggcgcc tgatgcggta ttttctcctt acgcatctgt gcggtatttc   4560
acaccgcata cgtcaaagca accatagtac gcgccctgta gcggcgcatt aagcgcggcg   4620
ggtgtggtgg ttacgcgcag cgtgaccgct acacttgcca gcgccttagc gcccgctcct   4680
ttcgctttct tcccttcctt tctcgccacg ttcgccggct ttccccgtca agctctaaat   4740
cgggggctcc ctttagggtt ccgatttagt gctttacggc acctcgaccc caaaaaactt   4800
gatttgggtg atggttcacg tagtgggcca tcgccctgat agacggtttt tcgccctttg   4860
acgttggagt ccacgttctt taatagtgga ctcttgttcc aaactggaac aacactcaac   4920
tctatctcgg gctattcttt tgatttataa gggattttgc cgatttcggt ctattggtta   4980
aaaaatgagc tgatttaaca aaaatttaac gcgaatttta acaaaatatt aacgtttaca   5040
attttatggt gcactctcag tacaatctgc tctgatgccg catagttaag ccagccccga   5100
cacccgccaa cacccgctga cgcgccctga cgggcttgtc tgctcccggc atccgcttac   5160
agacaagctg tgaccgtctc cgggagctgc atgtgtcaga ggttttcacc gtcatcaccg   5220
aaacgcgcga gacgaaaggg cctcgtgata cgcctatttt tataggttaa tgtcatgata   5280
```

-continued

```
ataatggttt cttagacgtc aggtggcact tttcggggaa atgtgcgcgg aacccctatt   5340

tgtttatttt tctaaataca ttcaaatatg tatccgctca tgagacaata accctgataa   5400

atgcttcaat aatattgaaa aaggaagagt atgagtattc aacatttccg tgtcgccctt   5460

attccctttt ttgcggcatt ttgccttcct gtttttgctc acccagaaac gctggtgaaa   5520

gtaaaagatg ctgaagatca gttgggtgca cgagtgggtt acatcgaact ggatctcaac   5580

agcggtaaga tccttgagag ttttcgcccc gaagaacgtt ttccaatgat gagcactttt   5640

aaagttctgc tatgtggcgc ggtattatcc cgtattgacg ccgggcaaga gcaactcggt   5700

cgccgcatac actattctca gaatgacttg gttgagtact caccagtcac agaaaagcat   5760

cttacggatg gcatgacagt aagagaatta tgcagtgctg ccataaccat gagtgataac   5820

actgcggcca acttacttct gacaacgatc ggaggaccga aggagctaac cgcttttttg   5880

cacaacatgg gggatcatgt aactcgcctt gatcgttggg aaccggagct gaatgaagcc   5940

ataccaaacg acgagcgtga caccacgatg cctgtagcaa tggcaacaac gttgcgcaaa   6000

ctattaactg gcgaactact tactctagct tcccggcaac aattaataga ctggatggag   6060

gcggataaag ttgcaggacc acttctgcgc tcggcccttc cggctggctg gtttattgct   6120

gataaatctg gagccggtga gcgtgggtct cgcggtatca ttgcagcact ggggccagat   6180

ggtaagccct cccgtatcgt agttatctac acgacgggga gtcaggcaac tatggatgaa   6240

cgaaatagac agatcgctga gataggtgcc tcactgatta agcattggta actgtcagac   6300

caagtttact catatatact ttagattgat ttaaaacttc atttttaatt taaaaggatc   6360

taggtgaaga tcctttttga taatctcatg accaaaatcc cttaacgtga gttttcgttc   6420

cactgagcgt cagaccccgt agaaaagatc aaaggatctt cttgaaatcc tttttttctg   6480

cgcgtaatct gctgcttgca aacaaaaaaa ccaccgctac cagcggtggt ttgtttgccg   6540

gatcaagagc taccaactct ttttccgaag gtaactggct tcagcagagc gcagatacca   6600

aatactgttc ttctagtgta gccgtagtta ggccaccact tcaagaactc tgtagcaccg   6660

cctacatacc tcgctctgct aatcctgtta ccagtggctg ctgccagtgg cgataagtcg   6720

tgtcttaccg ggttggactc aagacgatag ttaccggata aggcgcagcg gtcgggctga   6780

acggggggtt cgtgcacaca gcccagcttg gagcgaacga cctacaccga actgagatac   6840

ctacagcgtg agctatgaga aagcgccacg cttcccgaag ggagaaaggc ggacaggtat   6900

ccggtaagcg gcagggtcgg aacaggagag cgcacgaggg agcttccagg gggaaacgcc   6960

tggtatcttt atagtcctgt cgggtttcgc cacctctgac ttgagcgtcg atttttgtga   7020

tgctcgtcag gggggcggag cctatggaaa aacgccagca acgcggcctt tttacggttc   7080

ctggcctttt gctggccttt tgctcacatg tcctgcaggc ag                      7122
```

<210> SEQ ID NO 33
<211> LENGTH: 7162
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 33

```
ctgcgcgctc gctcgctcac tgaggccgcc cgggcgtcgg gcgacctttg gtcgcccggc     60

ctcagtgagc gagcgagcgc gcagagaggg agtggccaac tccatcacta ggggttcctg    120

cggccgcacg cgtgacgtcg tttaaacggg ccccggtgtt atctcattct tttttctcct    180
```

-continued

```
ctgtaagttg acatgtgatg tgggaacaaa ggggataaag tcattatttt gtgctaaaat    240
cgtaattgga gaggacctcc tgttagctgg gctttcttct atttattgtg gtggttactg    300
gagttccttc ttctagtttt aggatatata tatatatttt ttttttttct ttccctgaag    360
atataataat atatatactt ctgaagattg agatttttaa attagttgta ttgaaaacta    420
gctaatcagc aatttaaggc tagcttgaga cttatgtctt gaatttgttt ttgtaggctc    480
caaaaccaag gagggagtgg tgcatggtgt ggcaacaggt aagctccatt gtgcttatat    540
ccaaagatga tatttaaagt atctagtgat tagtgtggcc cagtattcaa gattcctatg    600
aaattgtaaa acaatcactg agcattctaa gaacatatca gtcttattga aactgaattc    660
tttataaagt atttttaaaa aggtaaatat tgattataaa taaaaaatat acttgccaag    720
aataatgagg gctttgaatt gataagctat gtttaattta tagtaagtgg gcatttaaat    780
attctgacca aaaatgtatt gacaaactgc tgacaaaaat aaaatgtgaa tattgccata    840
attttaaaaa aagagtaaaa tttctgttga ttacagtaaa atattttgac cttaaattat    900
gttgattaca atattccttt gataattcag agtgcatttc aggaaacacc cttggacagt    960
cagtaaattg tttattgtat ttatctttgt attgttatgg tatagctatt tgtacaaata   1020
ttattgtgca attattacat ttctgattat attattcatt tggcctaaat ttaccaagaa   1080
tttgaacaag tcaattaggt ttacaatcaa gaaatatcaa aaatgatgaa aaggatgata   1140
atcatcatca gatgttgagg aagatgacga tgagagtgcc agaaatagag aaatcaaagg   1200
agaaccaaaa tttaacaaat taaaagccca cagacttgct gtaattaagt tttctgttgt   1260
aagtactcca cgtttcctgg cagatgtggt gaagcaaaag atataatcag aaatataatt   1320
tatatgatcg gaaagcatta aacacaatag tgcctataca aataaaatgt tcctatcact   1380
gacttctaaa atggaaatga ggacaatgat atgggaatct taatacagtg ttgtggatag   1440
gactaaaaac acaggagtca gatcttcttg gttcaacttc ctgcttactc cttaccagct   1500
gtgtgttttt tgcaaggttc ttcacctcta tgtgatttag cttcctcatc tataaaataa   1560
ttcagtgaat taatgtacac aaaacatctg gaaaacaaaa gcaaacaata tgtattttat   1620
aagtgttact tatagtttta tagtgaactt tcttgtgcaa catttttaca actagtggag   1680
aaaaatattt ctttaaatga atacttttga tttaaaaatc agagtgtaaa aataaaacag   1740
actcctttga aactagttct gttagaagtt aattgtgcac ctttaatggg ctctgttgca   1800
atccaacaga gaagtagtta agtaagtgga ctatgatggc ttctagggac ctcctataaa   1860
tatgatattg tgaagcatga ttataataag aactagataa cagacaggtg gagactccac   1920
tatctgaaga gggtcaacct agatgaatgg tgttccattt agtagttgag gaagaaccca   1980
tgaggtttag aaagcagaca agcatgtggc aagttctgga gtcagtggta aaaattaaag   2040
aacccaacta ttactgtcac ctaatgatct aatggagact gtggagatgg gctgcatttt   2100
tttaatcttc tccagaatgc caaaatgtaa acacatatct gtgtgtgtgt gtgtgtgtgt   2160
gtgtgtgtgt gagagagaga gagagagaga gagagactga agtttgtaca attagacatt   2220
ttataaaatg ttttctgaag gacagtggct cacaatctta agtttctaac attgtacaat   2280
gttgggagac tttgtatact ttattttctc tttagcatat taaggaatct gagatgtcct   2340
acagtaaaga aatttgcatt acatagttaa aatcagggtt attcaaactt tttgattatt   2400
gaaacctttc ttcattagtt actagggttg aatgaaacta gtgttccaca gaaaactatg   2460
ggaaatgttg ctaggcagta aggacatggt gatttcagca tgtgcaatat ttacagcgat   2520
tgcacccatg gaccaccctg gcagtagtga aataaccaaa aatgctgtca taactagtat   2580
```

```
ggctatgaga aacacattgg gcagaagctt gcctcgagca gcgctgctcg agagatctgg   2640
atcataatca gccataccac atttgtagag gttttacttg ctttaaaaaa cctcccacac   2700
ctccccctga acctgaaaca taaaatgaat gcaattgttg ttgttaactt gtttattgca   2760
gcttataatg gttacaaata aagcaatagc atcacaaatt tcacaaataa agcatttttt   2820
tcactgcatt ctagttgtgg tttgtccaaa ctcatcaatg tatcttatca tgtctggtaa   2880
ccattctcca ggttgagcca gaccaatttg atggtagatt tagcaaataa aaatacagga   2940
cacccagtta aatgtgaatt tccgatgaac agcaaatact tttttagtat taaaaaagtt   3000
cacatttagg ctcacgcctg taatcccagc actttgggag gccgaggcag gcagatcacc   3060
tgaggtcagg agttcgagac cagcctggcc aacatggtga aaccccatct ccactaaaaa   3120
taccaaaaat tagccaggcg tgctggtggg cacctgtagt tccagctact caggaggcta   3180
aggcaggaga attgcttgaa cctgggaggc agaggttgca gtgagctgag atcgcaccat   3240
tgcactctag cctgggcgac aagaacaaaa ctccatctca aaaaaaaaaa aaaaaaaaaa   3300
gttcacattt aactgggcat tctgtattta attggtaatc tgagatggca gggaacagca   3360
tcagcatggt gtgagggata ggcatttttt cattgtgtac agcttgtaaa tcagtatttt   3420
taaaactcaa agttaatggc ttgggcatat ttagaaaaga gttgccgcac ggacttgaac   3480
cctgtattcc taaaatctag gatcttgttc tgatggtctg cacaactggc tgggggtgtc   3540
cagccactgt ccctcttgcc tgggctcccc agggcagttc tgtcagcctc tccatttcca   3600
ttcctgttcc agcaaaaccc aactgatagc acagcagcat ttcagcctgt ctacctctgt   3660
gcccacatac ctggatgtct accagccaga aaggtggctt agatttggtt cctgtgggtg   3720
gattatggcc cccagaactt ccctgtgctt gctgggggtg tggagtggaa agagcaggaa   3780
atgggggacc ctccgatact ctatggggt cctccaagtc tctttgtgca agttagggta   3840
ataatcaata tggagctaag aaagagaagg ggaactatgc tttagaacag gacactgtgc   3900
caggagcatt gcagaaatta tatggttttc acgacagttc tttttggtag gtactgttat   3960
tatcctcagt ttgcagatga ggaaactgag acccagaaag gttaaataac ttgctagggt   4020
cacacaagtc ataactgaca aagcctgatt caaacccagg tctccctaac ctttaaggtt   4080
tctatgacgc cagctctcct agggagtttg tcttcagatg tcttggctct aggtgtcaaa   4140
aaaagacttg gtgtcaggca ggcataggtt caagtcccaa ctctgtcact taccaactgt   4200
gactaggtga ttgaactgac catggaacct ggtcacatgc aggagcagga tggtgaaggg   4260
ttcttgaagg cacttaggca ggacatttag gcaggagaga aaacctggaa acagaagagc   4320
tgtctccaaa aatacccact ggggaagcag gttgtcatgt gggccatgaa tgggacctgt   4380
tctggggtaa ccacgtgcgg accgagcggc cgcaggaacc cctagtgatg gagttggcca   4440
ctccctctct gcgcgctcgc tcgctcactg aggccgggcg accaaaggtc gcccgacgcc   4500
cgggctttgc ccgggcggcc tcagtgagcg agcgagcgcg cagctgcctg caggggcgcc   4560
tgatgcggta ttttctcctt acgcatctgt gcggtatttc acaccgcata cgtcaaagca   4620
accatagtac gcgccctgta gcggcgcatt aagcgcggcg ggtgtggtgg ttacgcgcag   4680
cgtgaccgct acacttgcca gcgccttagc gcccgctcct ttcgctttct tcccttcctt   4740
tctcgccacg ttcgccggct ttccccgtca agctctaaat cgggggctcc ctttagggtt   4800
ccgatttagt gctttacggc acctcgaccc caaaaaactt gatttgggtg atggttcacg   4860
tagtgggcca tcgccctgat agacggtttt tcgccctttg acgttggagt ccacgttctt   4920
```

-continued

```
taatagtgga ctcttgttcc aaactggaac aacactcaac tctatctcgg gctattcttt   4980
tgatttataa gggattttgc cgatttcggt ctattggtta aaaaatgagc tgatttaaca   5040
aaaatttaac gcgaatttta acaaaatatt aacgtttaca attttatggt gcactctcag   5100
tacaatctgc tctgatgccg catagttaag ccagccccga cacccgccaa cacccgctga   5160
cgcgccctga cgggcttgtc tgctcccggc atccgcttac agacaagctg tgaccgtctc   5220
cgggagctgc atgtgtcaga ggttttcacc gtcatcaccg aaacgcgcga gacgaaaggg   5280
cctcgtgata cgcctatttt tataggttaa tgtcatgata ataatggttt cttagacgtc   5340
aggtggcact tttcggggaa atgtgcgcgg aacccctatt tgtttatttt tctaaataca   5400
ttcaaatatg tatccgctca tgagacaata accctgataa atgcttcaat aatattgaaa   5460
aaggaagagt atgagtattc aacatttccg tgtcgccctt attccctttt ttgcggcatt   5520
ttgccttcct gtttttgctc acccagaaac gctggtgaaa gtaaaagatg ctgaagatca   5580
gttgggtgca cgagtgggtt acatcgaact ggatctcaac agcggtaaga tccttgagag   5640
ttttcgcccc gaagaacgtt ttccaatgat gagcactttt aaagttctgc tatgtggcgc   5700
ggtattatcc cgtattgacg ccgggcaaga gcaactcggt cgccgcatac actattctca   5760
gaatgacttg gttgagtact caccagtcac agaaaagcat cttacggatg gcatgacagt   5820
aagagaatta tgcagtgctg ccataaccat gagtgataac actgcggcca acttacttct   5880
gacaacgatc ggaggaccga aggagctaac cgcttttttg cacaacatgg gggatcatgt   5940
aactcgcctt gatcgttggg aaccggagct gaatgaagcc ataccaaacg acgagcgtga   6000
caccacgatg cctgtagcaa tggcaacaac gttgcgcaaa ctattaactg gcgaactact   6060
tactctagct tcccggcaac aattaataga ctggatggag gcggataaag ttgcaggacc   6120
acttctgcgc tcggcccttc cggctggctg gtttattgct gataaatctg gagccggtga   6180
gcgtgggtct cgcggtatca ttgcagcact ggggccagat ggtaagccct cccgtatcgt   6240
agttatctac acgacgggga gtcaggcaac tatggatgaa cgaaatagac agatcgctga   6300
gataggtgcc tcactgatta agcattggta actgtcagac caagtttact catatatact   6360
ttagattgat ttaaaacttc atttttaatt taaaaggatc taggtgaaga tcctttttga   6420
taatctcatg accaaaatcc cttaacgtga gttttcgttc cactgagcgt cagaccccgt   6480
agaaaagatc aaaggatctt cttgaaatcc tttttttctg cgcgtaatct gctgcttgca   6540
aacaaaaaaa ccaccgctac cagcggtggt ttgtttgccg gatcaagagc taccaactct   6600
ttttccgaag gtaactggct tcagcagagc gcagatacca aatactgttc ttctagtgta   6660
gccgtagtta ggccaccact tcaagaactc tgtagcaccg cctacatacc tcgctctgct   6720
aatcctgtta ccagtggctg ctgccagtgg cgataagtcg tgtcttaccg ggttggactc   6780
aagacgatag ttaccggata aggcgcagcg gtcgggctga acggggggtt cgtgcacaca   6840
gcccagcttg gagcgaacga cctacaccga actgagatac ctacagcgtg agctatgaga   6900
aagcgccacg cttcccgaag ggagaaaggc ggacaggtat ccggtaagcg gcagggtcgg   6960
aacaggagag cgcacgaggg agcttccagg gggaaacgcc tggtatcttt atagtcctgt   7020
cgggtttcgc cacctctgac ttgagcgtcg atttttgtga tgctcgtcag gggggcggag   7080
cctatggaaa aacgccagca acgcggcctt tttacggttc ctggcctttt gctggccttt   7140
tgctcacatg tcctgcaggc ag                                             7162
```

<210> SEQ ID NO 34
<211> LENGTH: 7057

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 34
ctgcgcgctc gctcgctcac tgaggccgcc cgggcgtcgg gcgacctttg gtcgcccggc 60
ctcagtgagc gagcgagcgc gcagagaggg agtggccaac tccatcacta ggggttcctg 120
cggccgcacg cgttacgtaa tatttattga agtttaatat tgtgtttgtg atacagaagt 180
atttgcttta attctaaata aaaattttat gcttttattg ctggtttaag aagatttgga 240
ttatccttgt actttgagga gaagtttctt atttgaaata ttttggaaac aggtctttta 300
atgtggaaag atagatatta atctcctctt ctattactct ccaagatcca acaaaagtga 360
ttataccccc caaaatatga tggtagtatc ttatactacc atcattttat aggcataggg 420
ctcttagctg caaataatgg aactaactct aataaagcag aacgcaaata ttgtaaatat 480
tagagagcta acaatctctg ggatggctaa aggatggagc ttggaggcta cccagccagt 540
aacaatattc cgggctccac tgttgaatgg agacactaca actgccttgg atgggcagag 600
atattatgga tgctaagccc caggtgctac cattaggact tctaccactg tccctaacgg 660
gtggagccca tcacatgcct atgccctcac tgtaaggaaa tgaagctact gttgtatatc 720
ttgggaagca cttggattaa ttgttataca gttttgttga agaagacccc tagggtaagt 780
agccataact gcacactaaa tttaaaattg ttaatgagtt tctcaaaaaa aatgttaagg 840
ttgttagctg gtatagtata tatcttgcct gttttccaag gacttctttg ggcagtacct 900
tgtctgtgct ggcaagcaac tgagacttaa tgaaagagta ttggagatat gaatgaattg 960
atgctgtata ctctcagagt gccaaacata taccaatgga caagaaggtg aggcagagag 1020
cagacaggca ttagtgacaa gcaaagatat gcagaatttc attctcagca aatcaaaagt 1080
cctcaacctg gttggaagaa tattggcact gaatggtatc aataaggttg ctagagaggg 1140
ttagaggtgc acaatgtgct tccataacat tttatacttc tccaatctta gcactaatca 1200
aacatggttg aatactttgt ttactataac tcttacagag ttataagatc tgtgaagaca 1260
gggacaggga caatacccat ctctgtctgg ttcataggtg gtatgtaata gatattttta 1320
aaaataagtg agttaatgaa tgagggtgag aatgaaggca cagaggtatt agggggaggt 1380
gggccccaga gaatggtgcc aaggtccagt ggggtgactg ggatcagctc aggcctgacg 1440
ctggccactc ccacctagct cctttctttc taatctgttc tcattctcct tgggaaggat 1500
tgaggtctct ggaaaacagc caaacaactg ttatgggaac agcaagccca aataaagcca 1560
agcatcaggg ggatctgaga gctgaaagca acttctgttc cccctccctc agctgaaggg 1620
gtggggaagg gctcccaaag ccataactcc ttttaaggga tttagaaggc ataaaaaggc 1680
ccctggctga gaacttcctt cttcattctg cagttggtga attccccggg gatcctctag 1740
agtcgaaatt cgccaccatg gtgagcaagg gcgaggagct gttcaccggg gtggtgccca 1800
tcctggtcga gctggacggc gacgtaaacg gccacaagtt cagcgtgtcc ggcgagggcg 1860
agggcgatgc cacctacggc aagctgaccc tgaagttcat ctgcaccacc ggcaagctgc 1920
ccgtgccctg gcccaccctc gtgaccaccc tgacctacgg cgtgcagtgc ttcagccgct 1980
accccgacca catgaagcag cacgacttct tcaagtccgc catgcccgaa ggctacgtcc 2040
aggagcgcac catcttcttc aaggacgacg gcaactacaa gacccgcgcc gaggtgaagt 2100
tcgagggcga caccctggtg aaccgcatcg agctgaaggg catcgacttc aaggaggacg 2160

-continued gcaacatcct ggggcacaag ctggagtaca actacaacag ccacaacgtc tatatcatgg 2220
ccgacaagca gaagaacggc atcaaggtga acttcaagat ccgccacaac atcgaggacg 2280
gcagcgtgca gctcgccgac cactaccagc agaacacccc catcggcgac ggccccgtgc 2340
tgctgcccga caaccactac ctgagcaccc agtccgccct gagcaaagac cccaacgaga 2400
agcgcgatca catggtcctg ctggagttcg tgaccgccgc cgggatcact ctcggcatgg 2460
acgagctgta caagtaatag ggtaccggtc gacctgcaga agcttgcctc gagcagcgct 2520
gctcgagaga tctggatcat aatcagccat accacatttg tagaggtttt acttgcttta 2580
aaaaacctcc cacacctccc cctgaacctg aaacataaaa tgaatgcaat tgttgttgtt 2640
aacttgttta ttgcagctta taatggttac aaataaagca atagcatcac aaatttcaca 2700
aataaagcat ttttttcact gcattctagt tgtggtttgt ccaaactcat caatgtatct 2760
tatcatgtct ggtaaccatt ctccaggttg agccagacca atttgatggt agatttagca 2820
aataaaaata caggacaccc agttaaatgt gaatttccga tgaacagcaa atactttttt 2880
agtattaaaa aagttcacat ttaggctcac gcctgtaatc ccagcacttt gggaggccga 2940
ggcaggcaga tcacctgagg tcaggagttc gagaccagcc tggccaacat ggtgaaaccc 3000
catctccact aaaaatacca aaaattagcc aggcgtgctg gtgggcacct gtagttccag 3060
ctactcagga ggctaaggca ggagaattgc ttgaacctgg gaggcagagg ttgcagtgag 3120
ctgagatcgc accattgcac tctagcctgg gcgacaagaa caaaactcca tctcaaaaaa 3180
aaaaaaaaaa aaaaagttca catttaactg ggcattctgt atttaattgg taatctgaga 3240
tggcagggaa cagcatcagc atggtgtgag ggataggcat tttttcattg tgtacagctt 3300
gtaaatcagt atttttaaaa ctcaaagtta atggcttggg catatttaga aaagagttgc 3360
cgcacggact tgaaccctgt attcctaaaa tctaggatct tgttctgatg gtctgcacaa 3420
ctggctgggg gtgtccagcc actgtccctc ttgcctgggc tccccagggc agttctgtca 3480
gcctctccat ttccattcct gttccagcaa aacccaactg atagcacagc agcatttcag 3540
cctgtctacc tctgtgccca catacctgga tgtctaccag ccagaaaggt ggcttagatt 3600
tggttcctgt gggtggatta tggcccccag aacttccctg tgcttgctgg gggtgtggag 3660
tggaaagagc aggaaatggg ggaccctccg atactctatg gggtcctcc aagtctcttt 3720 gtgcaagtta gggtaataat caatatggag ctaagaaaga gaaggggaac tatgctttag 3780
aacaggacac tgtgccagga gcattgcaga aattatatgg ttttcacgac agttcttttt 3840
ggtaggtact gttattatcc tcagtttgca gatgaggaaa ctgagaccca gaaaggttaa 3900
ataacttgct agggtcacac aagtcataac tgacaaagcc tgattcaaac ccaggtctcc 3960
ctaaccttta aggtttctat gacgccagct ctcctaggga gtttgtcttc agatgtcttg 4020
gctctaggtg tcaaaaaaag acttggtgtc aggcaggcat aggttcaagt cccaactctg 4080
tcacttacca actgtgacta ggtgattgaa ctgaccatgg aacctggtca catgcaggag 4140
caggatggtg aagggttctt gaaggcactt aggcaggaca tttaggcagg agagaaaacc 4200
tggaaacaga agagctgtct ccaaaaatac ccactgggga agcaggttgt catgtgggcc 4260
atgaatggga cctgttctgg ggtaaccacg tgcggaccga gcggccgcag gaacccctag 4320
tgatggagtt ggccactccc tctctgcgcg ctcgctcgct cactgaggcc gggcgaccaa 4380
aggtcgcccg acgcccgggc tttgcccggg cggcctcagt gagcgagcga gcgcgcagct 4440
gcctgcaggg gcgcctgatg cggtattttc tccttacgca tctgtgcggt atttcacacc 4500

-continued gcatacgtca aagcaaccat agtacgcgcc ctgtagcggc gcattaagcg cggcgggtgt 4560
ggtggttacg cgcagcgtga ccgctacact tgccagcgcc ttagcgcccg ctcctttcgc 4620
tttcttccct tcctttctcg ccacgttcgc cggctttccc cgtcaagctc taaatcgggg 4680
gctcccttta gggttccgat ttagtgcttt acggcacctc gaccccaaaa aacttgattt 4740
gggtgatggt tcacgtagtg ggccatcgcc ctgatagacg gtttttcgcc ctttgacgtt 4800
ggagtccacg ttctttaata gtggactctt gttccaaact ggaacaacac tcaactctat 4860
ctcgggctat tcttttgatt tataagggat tttgccgatt tcggtctatt ggttaaaaaa 4920
tgagctgatt taacaaaaat ttaacgcgaa ttttaacaaa atattaacgt ttacaatttt 4980
atggtgcact ctcagtacaa tctgctctga tgccgcatag ttaagccagc cccgacaccc 5040
gccaacaccc gctgacgcgc cctgacgggc ttgtctgctc ccggcatccg cttacagaca 5100
agctgtgacc gtctccggga gctgcatgtg tcagaggttt tcaccgtcat caccgaaacg 5160
cgcgagacga aagggcctcg tgatacgcct atttttatag gttaatgtca tgataataat 5220
ggtttcttag acgtcaggtg gcacttttcg gggaaatgtg cgcggaaccc ctatttgttt 5280
atttttctaa atacattcaa atatgtatcc gctcatgaga caataaccct gataaatgct 5340
tcaataatat tgaaaaagga agagtatgag tattcaacat ttccgtgtcg cccttattcc 5400
cttttttgcg gcattttgcc ttcctgtttt tgctcaccca gaaacgctgg tgaaagtaaa 5460
agatgctgaa gatcagttgg gtgcacgagt gggttacatc gaactggatc tcaacagcgg 5520
taagatcctt gagagttttc gccccgaaga acgttttcca atgatgagca cttttaaagt 5580
tctgctatgt ggcgcggtat tatcccgtat tgacgccggg caagagcaac tcggtcgccg 5640
catacactat tctcagaatg acttggttga gtactcacca gtcacagaaa agcatcttac 5700
ggatggcatg acagtaagag aattatgcag tgctgccata accatgagtg ataacactgc 5760
ggccaactta cttctgacaa cgatcggagg accgaaggag ctaaccgctt ttttgcacaa 5820
catgggggat catgtaactc gccttgatcg ttgggaaccg gagctgaatg aagccatacc 5880
aaacgacgag cgtgacacca cgatgcctgt agcaatggca acaacgttgc gcaaactatt 5940
aactggcgaa ctacttactc tagcttcccg gcaacaatta atagactgga tggaggcgga 6000
taaagttgca ggaccacttc tgcgctcggc ccttccggct ggctggttta ttgctgataa 6060
atctggagcc ggtgagcgtg ggtctcgcgg tatcattgca gcactggggc cagatggtaa 6120
gccctcccgt atcgtagtta tctacacgac ggggagtcag gcaactatgg atgaacgaaa 6180
tagacagatc gctgagatag gtgcctcact gattaagcat tggtaactgt cagaccaagt 6240
ttactcatat atactttaga ttgatttaaa acttcatttt taatttaaaa ggatctaggt 6300
gaagatcctt tttgataatc tcatgaccaa aatcccttaa cgtgagtttt cgttccactg 6360
agcgtcagac cccgtagaaa agatcaaagg atcttcttga aatccttttt ttctgcgcgt 6420
aatctgctgc ttgcaaacaa aaaaaccacc gctaccagcg gtggtttgtt tgccggatca 6480
agagctacca actctttttc cgaaggtaac tggcttcagc agagcgcaga taccaaatac 6540
tgttcttcta gtgtagccgt agttaggcca ccacttcaag aactctgtag caccgcctac 6600
atacctcgct ctgctaatcc tgttaccagt ggctgctgcc agtggcgata agtcgtgtct 6660
taccgggttg gactcaagac gatagttacc ggataaggcg cagcggtcgg gctgaacggg 6720
gggttcgtgc acacagccca gcttggagcg aacgacctac accgaactga gatacctaca 6780
gcgtgagcta tgagaaagcg ccacgcttcc cgaagggaga aaggcggaca ggtatccggt 6840
aagcggcagg gtcggaacag gagagcgcac gagggagctt ccagggggaa acgcctggta 6900

-continued

```
tctttatagt cctgtcgggt ttcgccacct ctgacttgag cgtcgatttt tgtgatgctc   6960

gtcagggggg cggagcctat ggaaaaacgc cagcaacgcg gcctttttac ggttcctggc   7020

cttttgctgg ccttttgctc acatgtcctg caggcag                            7057
```

<210> SEQ ID NO 35
<211> LENGTH: 6100
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
ctgcgcgctc gctcgctcac tgaggccgcc cgggcgtcgg gcgacctttg gtcgcccggc     60

ctcagtgagc gagcgagcgc gcagagaggg agtggccaac tccatcacta ggggttcctg    120

cggccgcacg cgttacgtaa ttctgtcatt ttactagggt gatgaaattc ccaagcaaca    180

ccatcctttt cagataaggg cactgaggct gagagaggag ctgaaaccta cccggcgtca    240

ccacacacag gtggcaaggc tgggaccaga aaccaggact gttgactgca gcccggtatt    300

cattctttcc atagcccaca gggctgtcaa agaccccagg gcctagtcag aggctcctcc    360

ttcctggaga gttcctggca cagaagttga agctcagcac agccccctaa cccccaactc    420

tctctgcaag gcctcagggg tcagaacact ggtggagcag atcctttagc ctctggattt    480

tagggccatg gtagaggggg tgttgcccta aattccagcc ctggtctcag cccaacaccc    540

tccaagaaga aattagaggg gccatggcca ggctgtgcta gccgttgctt ctgagcagat    600

tacaagaagg gactaagaca aggactcctt tgtggaggtc ctggcttagg gagtcaagtg    660

acggcggctc agcactcacg tgggcagtgc cagcctctaa gagtgggcag ggcactggc     720

cacagagtcc cagggagtcc caccagccta gtcgccagac cgaattcccc ggggatcctc    780

tagagtcgaa attcgccacc atggtgagca agggcgagga gctgttcacc ggggtggtgc    840

ccatcctggt cgagctggac ggcgacgtaa acggccacaa gttcagcgtg tccggcgagg    900

gcgagggcga tgccacctac ggcaagctga ccctgaagtt catctgcacc accggcaagc    960

tgcccgtgcc ctggcccacc ctcgtgacca ccctgaccta cggcgtgcag tgcttcagcc   1020

gctaccccga ccacatgaag cagcacgact tcttcaagtc cgccatgccc gaaggctacg   1080

tccaggagcg caccatcttc ttcaaggacg acggcaacta caagacccgc gccgaggtga   1140

agttcgaggg cgacaccctg gtgaaccgca tcgagctgaa gggcatcgac ttcaaggagg   1200

acggcaacat cctggggcac aagctggagt acaactacaa cagccacaac gtctatatca   1260

tggccgacaa gcagaagaac ggcatcaagg tgaacttcaa gatccgccac aacatcgagg   1320

acggcagcgt gcagctcgcc gaccactacc agcagaacac ccccatcggc gacggccccg   1380

tgctgctgcc cgacaaccac tacctgagca cccagtccgc cctgagcaaa gaccccaacg   1440

agaagcgcga tcacatggtc ctgctggagt tcgtgaccgc cgccgggatc actctcggca   1500

tggacgagct gtacaagtaa tagggtaccg gtcgacctgc agaagcttgc ctcgagcagc   1560

gctgctcgag agatctggat cataatcagc cataccacat ttgtagaggt tttacttgct   1620

ttaaaaaacc tcccacacct ccccctgaac ctgaaacata aaatgaatgc aattgttgtt   1680

gttaacttgt ttattgcagc ttataatggt tacaaataaa gcaatagcat cacaaatttc   1740

acaaataaag catttttttc actgcattct agttgtggtt tgtccaaact catcaatgta   1800

tcttatcatg tctggtaacc attctccagg ttgagccaga ccaatttgat ggtagattta   1860
```

-continued gcaaataaaa atacaggaca cccagttaaa tgtgaatttc cgatgaacag caaatacttt 1920
tttagtatta aaaaagttca catttaggct cacgcctgta atcccagcac tttgggaggc 1980
cgaggcaggc agatcacctg aggtcaggag ttcgagacca gcctggccaa catggtgaaa 2040
ccccatctcc actaaaaata ccaaaaatta gccaggcgtg ctggtgggca cctgtagttc 2100
cagctactca ggaggctaag gcaggagaat tgcttgaacc tgggaggcag aggttgcagt 2160
gagctgagat cgcaccattg cactctagcc tgggcgacaa gaacaaaact ccatctcaaa 2220
aaaaaaaaaa aaaaaaaagt tcacatttaa ctgggcattc tgtatttaat tggtaatctg 2280
agatggcagg gaacagcatc agcatggtgt gagggatagg catttttca ttgtgtacag 2340
cttgtaaatc agtattttta aaactcaaag ttaatggctt gggcatattt agaaaagagt 2400
tgccgcacgg acttgaaccc tgtattccta aaatctagga tcttgttctg atggtctgca 2460
caactggctg gggtgtcca gccactgtcc ctcttgcctg ggctccccag ggcagttctg 2520
tcagcctctc catttccatt cctgttccag caaaacccaa ctgatagcac agcagcattt 2580
cagcctgtct acctctgtgc ccacatacct ggatgtctac cagccagaaa ggtggcttag 2640
atttggttcc tgtgggtgga ttatggcccc cagaacttcc ctgtgcttgc tgggggtgtg 2700
gagtggaaag agcaggaaat gggggaccct ccgatactct atgggggtcc tccaagtctc 2760
tttgtgcaag ttagggtaat aatcaatatg gagctaagaa agagaagggg aactatgctt 2820
tagaacagga cactgtgcca ggagcattgc agaaattata tggttttcac gacagttctt 2880
tttggtaggt actgttatta tcctcagttt gcagatgagg aaactgagac ccagaaaggt 2940
taaataactt gctagggtca cacaagtcat aactgacaaa gcctgattca aacccaggtc 3000
tccctaacct ttaaggtttc tatgacgcca gctctcctag ggagtttgtc ttcagatgtc 3060
ttggctctag gtgtcaaaaa aagacttggt gtcaggcagg cataggttca agtcccaact 3120
ctgtcactta ccaactgtga ctaggtgatt gaactgacca tggaacctgg tcacatgcag 3180
gagcaggatg gtgaagggtt cttgaaggca cttaggcagg acatttaggc aggagagaaa 3240
acctggaaac agaagagctg tctccaaaaa tacccactgg ggaagcaggt tgtcatgtgg 3300
gccatgaatg ggacctgttc tggggtaacc acgtgcggac cgagcggccg caggaacccc 3360
tagtgatgga gttggccact ccctctctgc gcgctcgctc gctcactgag gccgggcgac 3420
caaaggtcgc ccgacgcccg ggctttgccc gggcggcctc agtgagcgag cgagcgcgca 3480
gctgcctgca ggggcgcctg atgcggtatt ttctccttac gcatctgtgc ggtatttcac 3540
accgcatacg tcaaagcaac catagtacgc gccctgtagc ggcgcattaa gcgcggcggg 3600
tgtggtggtt acgcgcagcg tgaccgctac acttgccagc gccttagcgc ccgctccttt 3660
cgctttcttc ccttcctttc tcgccacgtt cgccggcttt ccccgtcaag ctctaaatcg 3720
ggggctccct ttagggttcc gatttagtgc tttacggcac ctcgacccca aaaaacttga 3780
tttgggtgat ggttcacgta gtgggccatc gccctgatag acggtttttc gccctttgac 3840
gttggagtcc acgttcttta atagtggact cttgttccaa actggaacaa cactcaactc 3900
tatctcgggc tattcttttg atttataagg gattttgccg atttcggtct attggttaaa 3960
aaatgagctg atttaacaaa aatttaacgc gaattttaac aaaatattaa cgtttacaat 4020
tttatggtgc actctcagta caatctgctc tgatgccgca tagttaagcc agccccgaca 4080
cccgccaaca cccgctgacg cgccctgacg ggcttgtctg ctcccggcat ccgcttacag 4140
acaagctgtg accgtctccg ggagctgcat gtgtcagagg ttttcaccgt catcaccgaa 4200

-continued

```
acgcgcgaga cgaaagggcc tcgtgatacg cctattttta taggttaatg tcatgataat   4260

aatggtttct tagacgtcag gtggcacttt tcggggaaat gtgcgcggaa cccctatttg   4320

tttatttttc taaatacatt caaatatgta tccgctcatg agacaataac cctgataaat   4380

gcttcaataa tattgaaaaa ggaagagtat gagtattcaa catttccgtg tcgcccttat   4440

tccctttttt gcggcatttt gccttcctgt ttttgctcac ccagaaacgc tggtgaaagt   4500

aaaagatgct gaagatcagt tgggtgcacg agtgggttac atcgaactgg atctcaacag   4560

cggtaagatc cttgagagtt ttcgccccga agaacgtttt ccaatgatga gcacttttaa   4620

agttctgcta tgtggcgcgg tattatcccg tattgacgcc gggcaagagc aactcggtcg   4680

ccgcatacac tattctcaga atgacttggt tgagtactca ccagtcacag aaaagcatct   4740

tacggatggc atgacagtaa gagaattatg cagtgctgcc ataaccatga gtgataacac   4800

tgcggccaac ttacttctga caacgatcgg aggaccgaag gagctaaccg cttttttgca   4860

caacatgggg gatcatgtaa ctcgccttga tcgttgggaa ccggagctga atgaagccat   4920

accaaacgac gagcgtgaca ccacgatgcc tgtagcaatg gcaacaacgt tgcgcaaact   4980

attaactggc gaactactta ctctagcttc ccggcaacaa ttaatagact ggatggaggc   5040

ggataaagtt gcaggaccac ttctgcgctc ggcccttccg gctggctggt ttattgctga   5100

taaatctgga gccggtgagc gtgggtctcg cggtatcatt gcagcactgg ggccagatgg   5160

taagccctcc cgtatcgtag ttatctacac gacggggagt caggcaacta tggatgaacg   5220

aaatagacag atcgctgaga taggtgcctc actgattaag cattggtaac tgtcagacca   5280

agtttactca tatatacttt agattgattt aaaacttcat ttttaattta aaaggatcta   5340

ggtgaagatc ctttttgata atctcatgac caaaatccct taacgtgagt tttcgttcca   5400

ctgagcgtca gaccccgtag aaaagatcaa aggatcttct tgaaatcctt tttttctgcg   5460

cgtaatctgc tgcttgcaaa caaaaaaacc accgctacca gcggtggttt gtttgccgga   5520

tcaagagcta ccaactcttt ttccgaaggt aactggcttc agcagagcgc agataccaaa   5580

tactgttctt ctagtgtagc cgtagttagg ccaccacttc aagaactctg tagcaccgcc   5640

tacatacctc gctctgctaa tcctgttacc agtggctgct gccagtggcg ataagtcgtg   5700

tcttaccggg ttggactcaa gacgatagtt accggataag gcgcagcggt cgggctgaac   5760

ggggggttcg tgcacacagc ccagcttgga gcgaacgacc tacaccgaac tgagatacct   5820

acagcgtgag ctatgagaaa gcgccacgct tcccgaaggg agaaaggcgg acaggtatcc   5880

ggtaagcggc agggtcggaa caggagagcg cacgagggag cttccagggg gaaacgcctg   5940

gtatctttat agtcctgtcg ggtttcgcca cctctgactt gagcgtcgat ttttgtgatg   6000

ctcgtcaggg gggcggagcc tatggaaaaa cgccagcaac gcggcctttt tacggttcct   6060

ggccttttgc tggccttttg ctcacatgtc ctgcaggcag                         6100
```

<210> SEQ ID NO 36
<211> LENGTH: 130
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120
```

aggggttcct 130

<210> SEQ ID NO 37
<211> LENGTH: 954
<212> TYPE: DNA
<213> ORGANISM: Macaca mulatta

<400> SEQUENCE: 37
atgtcagaag gggtgggcac gttccgcatg gtacctgaag aggaacagga gctccgtgcc 60
caactggagc agctcacaac caaggaccat ggacctgtct ttggcccgtg cagccagctg 120
ccccgccaca ccttgcagaa ggccaaagat gagctgaatg agagagagga gacccgggag 180
gaggcagtgc gagagctgca ggagatggtg caggcgcagg cggcctcggg ggaggagctg 240
gccgtggccg tggcggagag ggtgcaagag aaggacagcg gcttcttcct gcgcttcatc 300
cgcgcgcgaa agttcaacgt gggccgtgcc tatgagctgc tcagaggcta tgtgaatttc 360
cggctgcagt accctgagct ctttgacagc ctgtccccag aggctgtccg ctgtaccatt 420
gaagctggct accctggtgt cctctctagt cgggacaagt atggccgagt ggtcatgctc 480
ttcaacattg agaactggca aagtcaagaa atcaccttcg atgagatctt gcaggcatat 540
tgcttcatcc tggagaagct gctggagaat gaggaaactc aaattaatgg attctgcatc 600
attgagaact tcaagggctt taccatgcag caggctgcta gtctccgcac ttcagatctc 660
aggaagatgg tggacatgct ccaggattcc ttcccagccc ggttcaaagc catccacttc 720
atccaccagc catggtactt caccacgacc tacaatgtgg tcaagccctt cttgaagagc 780
aagctgcttg agagggtctt tgtccacggg gaggacctct ctggtttcta ccaggagatt 840
gatgagaaca tcctgccctc tgactttggg ggcacgctgc ccaagtatga tggcaaagct 900
gttgctgagc agctctttgg cccccgggcc caagctgaga acacagcctt ctga 954

<210> SEQ ID NO 38
<211> LENGTH: 317
<212> TYPE: PRT
<213> ORGANISM: Macaca mulatta

<400> SEQUENCE: 38

Met Ser Glu Gly Val Gly Thr Phe Arg Met Val Pro Glu Glu Glu Gln
1 5 10 15

Glu Leu Arg Ala Gln Leu Glu Gln Leu Thr Thr Lys Asp His Gly Pro
20 25 30

Val Phe Gly Pro Cys Ser Gln Leu Pro Arg His Thr Leu Gln Lys Ala
35 40 45

Lys Asp Glu Leu Asn Glu Arg Glu Glu Thr Arg Glu Glu Ala Val Arg
50 55 60

Glu Leu Gln Glu Met Val Gln Ala Gln Ala Ala Ser Gly Glu Glu Leu
65 70 75 80

Ala Val Ala Val Ala Glu Arg Val Gln Glu Lys Asp Ser Gly Phe Phe
85 90 95

Leu Arg Phe Ile Arg Ala Arg Lys Phe Asn Val Gly Arg Ala Tyr Glu
100 105 110

Leu Leu Arg Gly Tyr Val Asn Phe Arg Leu Gln Tyr Pro Glu Leu Phe
115 120 125

Asp Ser Leu Ser Pro Glu Ala Val Arg Cys Thr Ile Glu Ala Gly Tyr
130 135 140

Pro Gly Val Leu Ser Ser Arg Asp Lys Tyr Gly Arg Val Val Met Leu
145 150 155 160

```
Phe Asn Ile Glu Asn Trp Gln Ser Gln Glu Ile Thr Phe Asp Glu Ile
                165                 170                 175

Leu Gln Ala Tyr Cys Phe Ile Leu Glu Lys Leu Leu Glu Asn Glu Glu
            180                 185                 190

Thr Gln Ile Asn Gly Phe Cys Ile Ile Glu Asn Phe Lys Gly Phe Thr
        195                 200                 205

Met Gln Gln Ala Ala Ser Leu Arg Thr Ser Asp Leu Arg Lys Met Val
    210                 215                 220

Asp Met Leu Gln Asp Ser Phe Pro Ala Arg Phe Lys Ala Ile His Phe
225                 230                 235                 240

Ile His Gln Pro Trp Tyr Phe Thr Thr Thr Tyr Asn Val Val Lys Pro
                245                 250                 255

Phe Leu Lys Ser Lys Leu Leu Glu Arg Val Phe Val His Gly Glu Asp
            260                 265                 270

Leu Ser Gly Phe Tyr Gln Glu Ile Asp Glu Asn Ile Leu Pro Ser Asp
        275                 280                 285

Phe Gly Gly Thr Leu Pro Lys Tyr Asp Gly Lys Ala Val Ala Glu Gln
    290                 295                 300

Leu Phe Gly Pro Arg Ala Gln Ala Glu Asn Thr Ala Phe
305                 310                 315


<210> SEQ ID NO 39
<211> LENGTH: 954
<212> TYPE: DNA
<213> ORGANISM: Bos taurus

<400> SEQUENCE: 39

atgtcagagg gggcgggcac gttccgcatg gtccctgaag aggaacagga gctccgtgcc     60

caactggaga ggcttacgac caaagaccat ggacctgtct ttggcccgtg cagccagctg    120

ccccgccaca ccttgcagaa ggccaaggac gagctgaatg aaaaggaaga gacccgggaa    180

gaggcagtgc gggagctaca ggagctggtg caggcggagg ccgcctcggg gcaggagctg    240

gccgtggccg tggcggagag ggtgcaggga aaagacagtg ccttcttcct gcgcttcatc    300

cgcgcgcgca agttccacgt ggggcgcgcc tacgagctgc tcagaggcta cgtgaacttc    360

cggctgcagt acccagagct cttcgacagc ctgtccccag aggctgtccg ctgcaccgtt    420

gaggctggct accctggtgt cctctccacg cgggacaagt atggccgagt ggtcatgctc    480

ttcaatattg agaactggga ctctgaagaa atcacctttg atgagatctt gcaggcatac    540

tgcgtcatcc tggagaagct actggagaat gaggagactc aaattaatgg cttttgcatc    600

attgagaact tcaagggctt caccatgcag caggctgccg gacttcggcc ttccgatctc    660

agaaagatgg tggacatgct ccaggattcc ttcccagctc ggttcaaagc catccacttc    720

atctaccagc cctggtactt caccaccacc tacaacgtgg tcaagccctt cttgaagagc    780

aaattgctcc agagggtatt tgtccatgga gaagacctct ccagcttcta ccaggagttt    840

gacgaggaca tcctgccctc cgactttggg ggtacactgc ccaagtatga tggcaaggcc    900

gttgctgagc agctctttgg tcctcgggac caaactgaga acacagcctt ctga          954


<210> SEQ ID NO 40
<211> LENGTH: 317
<212> TYPE: PRT
<213> ORGANISM: Bos taurus

<400> SEQUENCE: 40
```

-continued

```
Met Ser Glu Gly Ala Gly Thr Phe Arg Met Val Pro Glu Glu Glu Gln
1               5                   10                  15

Glu Leu Arg Ala Gln Leu Glu Arg Leu Thr Thr Lys Asp His Gly Pro
            20                  25                  30

Val Phe Gly Pro Cys Ser Gln Leu Pro Arg His Thr Leu Gln Lys Ala
        35                  40                  45

Lys Asp Glu Leu Asn Glu Lys Glu Glu Thr Arg Glu Glu Ala Val Arg
    50                  55                  60

Glu Leu Gln Glu Leu Val Gln Ala Glu Ala Ala Ser Gly Gln Glu Leu
65                  70                  75                  80

Ala Val Ala Val Ala Glu Arg Val Gln Gly Lys Asp Ser Ala Phe Phe
                85                  90                  95

Leu Arg Phe Ile Arg Ala Arg Lys Phe His Val Gly Arg Ala Tyr Glu
            100                 105                 110

Leu Leu Arg Gly Tyr Val Asn Phe Arg Leu Gln Tyr Pro Glu Leu Phe
        115                 120                 125

Asp Ser Leu Ser Pro Glu Ala Val Arg Cys Thr Val Glu Ala Gly Tyr
    130                 135                 140

Pro Gly Val Leu Ser Thr Arg Asp Lys Tyr Gly Arg Val Val Met Leu
145                 150                 155                 160

Phe Asn Ile Glu Asn Trp Asp Ser Glu Glu Ile Thr Phe Asp Glu Ile
                165                 170                 175

Leu Gln Ala Tyr Cys Val Ile Leu Glu Lys Leu Leu Glu Asn Glu Glu
            180                 185                 190

Thr Gln Ile Asn Gly Phe Cys Ile Ile Glu Asn Phe Lys Gly Phe Thr
        195                 200                 205

Met Gln Gln Ala Ala Gly Leu Arg Pro Ser Asp Leu Arg Lys Met Val
    210                 215                 220

Asp Met Leu Gln Asp Ser Phe Pro Ala Arg Phe Lys Ala Ile His Phe
225                 230                 235                 240

Ile Tyr Gln Pro Trp Tyr Phe Thr Thr Thr Tyr Asn Val Val Lys Pro
                245                 250                 255

Phe Leu Lys Ser Lys Leu Leu Gln Arg Val Phe Val His Gly Glu Asp
            260                 265                 270

Leu Ser Ser Phe Tyr Gln Glu Phe Asp Glu Asp Ile Leu Pro Ser Asp
        275                 280                 285

Phe Gly Gly Thr Leu Pro Lys Tyr Asp Gly Lys Ala Val Ala Glu Gln
    290                 295                 300

Leu Phe Gly Pro Arg Asp Gln Thr Glu Asn Thr Ala Phe
305                 310                 315
```

<210> SEQ ID NO 41
<211> LENGTH: 954
<212> TYPE: DNA
<213> ORGANISM: Canis lupus

<400> SEQUENCE: 41

```
atgtcagaag gcgtgggcac attccgtgtg gtccctgaag aggaacagga gctccgtgcc     60

cagctggagc ggcttacaac caaggaccat gggcctgtct ttggcccttg cagccagctc    120

cctcgtcata ccttacagaa ggccaaggac gagctgaacg agagggagga gacccgggag    180

gaggtggtgc gagagctgca ggagctggtg caggcacagg ctgccaccgg gcaggagctg    240

gccagggcgg tggctgagag ggtgcaggga agggacagtg ccttcttcct gcgcttcatc    300

cgcgcgcgga agttccatgt ggggcgtgcc tacgagctgc ttcgaggcta cgtgaacttc    360
```

```
cggctgcagt acccagagct cttcgacagc ctgtccctgg aggctgtccg ttgcaccgtc    420

gaggccggct atcctggggt cctccccagt cgggacaagt atggccgagt ggtcatgctc    480

ttcaacatcg agaactggga ctccgaagaa atcaccttcg atgagatctt gcaggcatat    540

tgtttcatcc tggagaagct actagagaat gaggaaactc aaattaatgg cttctgcatt    600

attgagaact ttaagggctt taccatgcag caggctgctg gacttcgggc ttccgatctc    660

aggaagatgg tggacatgct ccaggattcc ttcccagcgc ggttcaaagc catccacttc    720

attcaccaac catggtactt caccaccacc tacaacatgg tcaagcccct cctgaagaac    780

aagctgctcc aaagagtctt tgtccatgga gatgacctct ctggcttctt ccaggagatt    840

gatgaagaca tactgcccgc tgactttggg ggcacactgc ccaagtatga tggcaaggtg    900

gttgctgagc agctctttgg cccccgggcc caagctgaga acacagcctt ctga          954
```

```
<210> SEQ ID NO 42
<211> LENGTH: 317
<212> TYPE: PRT
<213> ORGANISM: Canis lupus

<400> SEQUENCE: 42

Met Ser Glu Gly Val Gly Thr Phe Arg Val Val Pro Glu Glu Glu Gln
1               5                   10                  15

Glu Leu Arg Ala Gln Leu Glu Arg Leu Thr Thr Lys Asp His Gly Pro
            20                  25                  30

Val Phe Gly Pro Cys Ser Gln Leu Pro Arg His Thr Leu Gln Lys Ala
        35                  40                  45

Lys Asp Glu Leu Asn Glu Arg Glu Glu Thr Arg Glu Glu Val Val Arg
    50                  55                  60

Glu Leu Gln Glu Leu Val Gln Ala Gln Ala Ala Thr Gly Gln Glu Leu
65                  70                  75                  80

Ala Arg Ala Val Ala Glu Arg Val Gln Gly Arg Asp Ser Ala Phe Phe
                85                  90                  95

Leu Arg Phe Ile Arg Ala Arg Lys Phe His Val Gly Arg Ala Tyr Glu
            100                 105                 110

Leu Leu Arg Gly Tyr Val Asn Phe Arg Leu Gln Tyr Pro Glu Leu Phe
        115                 120                 125

Asp Ser Leu Ser Leu Glu Ala Val Arg Cys Thr Val Glu Ala Gly Tyr
    130                 135                 140

Pro Gly Val Leu Pro Ser Arg Asp Lys Tyr Gly Arg Val Val Met Leu
145                 150                 155                 160

Phe Asn Ile Glu Asn Trp Asp Ser Glu Glu Ile Thr Phe Asp Glu Ile
                165                 170                 175

Leu Gln Ala Tyr Cys Phe Ile Leu Glu Lys Leu Leu Glu Asn Glu Glu
            180                 185                 190

Thr Gln Ile Asn Gly Phe Cys Ile Ile Glu Asn Phe Lys Gly Phe Thr
        195                 200                 205

Met Gln Gln Ala Ala Gly Leu Arg Ala Ser Asp Leu Arg Lys Met Val
    210                 215                 220

Asp Met Leu Gln Asp Ser Phe Pro Ala Arg Phe Lys Ala Ile His Phe
225                 230                 235                 240

Ile His Gln Pro Trp Tyr Phe Thr Thr Thr Tyr Asn Met Val Lys Pro
                245                 250                 255

Leu Leu Lys Asn Lys Leu Leu Gln Arg Val Phe Val His Gly Asp Asp
            260                 265                 270
```

```
Leu Ser Gly Phe Phe Gln Glu Ile Asp Glu Asp Ile Leu Pro Ala Asp
        275                 280                 285

Phe Gly Gly Thr Leu Pro Lys Tyr Asp Gly Lys Val Val Ala Glu Gln
    290                 295                 300

Leu Phe Gly Pro Arg Ala Gln Ala Glu Asn Thr Ala Phe
305                 310                 315
```

<210> SEQ ID NO 43
<211> LENGTH: 954
<212> TYPE: DNA
<213> ORGANISM: Rattus norvegicus

<400> SEQUENCE: 43

```
atgtcagagg gggtgggcac attccgaatg gtccctgaag aggagcagga gctccgggca      60

cagctagaac agctcacaac caaggatcat ggtcctgtct ttggcccatg cagccagctg     120

ccccgccaca ctttgcagaa ggctaaggat gagctgaatg aaagggagga aacccgggat     180

gaggcggtga gggagctaca ggagctggtc caggcacagg cagcttctgg ggaagagttg     240

gccgtggcag tggctgagag ggtgcaggca agagacagcg ccttcctcct gcgcttcatc     300

cgtgcccgaa agtttgatgt gggccgggct tatgagctgc tcaaaggcta tgtgaacttc     360

cggctccagt accctgaact cttcgatagc ctatctatgg aggctctccg ctgcactatc     420

gaggccggtt accctggtgt cctttccagt cgggacaagt atggtcgagt ggttatgctc     480

ttcaacattg aaaactggca ctgtgaagaa gtcacctttg atgagatctt acaggcatat     540

tgtttcattc tggagaaact gctggagaac gaggaaaccc aaatcaacgg cttctgtatt     600

gtggagaact tcaagggctt caccatgcag caggccgcgg gactccgccc ctccgatctc     660

aagaagatgg tggacatgct ccaggattca ttcccagcca ggttcaaagc tatccacttc     720

atccaccaac catggtactt caccaccact tacaatgtgg tcaagccctt cttgaagaac     780

aagttgctac agagggtctt cgttcatgga gatgacctgg acggcttctt ccaggagatt     840

gatgagaata tcttgcctgc tgactttggg ggtacactgc ccaagtatga cggcaaagtt     900

gtcgctgagc agctcttcgg tccccgggtt gaggttgaga acacagcctt gtga           954
```

<210> SEQ ID NO 44
<211> LENGTH: 317
<212> TYPE: PRT
<213> ORGANISM: Rattus norvegicus

<400> SEQUENCE: 44

```
Met Ser Glu Gly Val Gly Thr Phe Arg Met Val Pro Glu Glu Glu Gln
1               5                   10                  15

Glu Leu Arg Ala Gln Leu Glu Gln Leu Thr Thr Lys Asp His Gly Pro
            20                  25                  30

Val Phe Gly Pro Cys Ser Gln Leu Pro Arg His Thr Leu Gln Lys Ala
        35                  40                  45

Lys Asp Glu Leu Asn Glu Arg Glu Glu Thr Arg Asp Glu Ala Val Arg
    50                  55                  60

Glu Leu Gln Glu Leu Val Gln Ala Gln Ala Ala Ser Gly Glu Glu Leu
65                  70                  75                  80

Ala Val Ala Val Ala Glu Arg Val Gln Ala Arg Asp Ser Ala Phe Leu
                85                  90                  95

Leu Arg Phe Ile Arg Ala Arg Lys Phe Asp Val Gly Arg Ala Tyr Glu
            100                 105                 110
```

-continued

```
Leu Leu Lys Gly Tyr Val Asn Phe Arg Leu Gln Tyr Pro Glu Leu Phe
        115                 120                 125

Asp Ser Leu Ser Met Glu Ala Leu Arg Cys Thr Ile Glu Ala Gly Tyr
    130                 135                 140

Pro Gly Val Leu Ser Ser Arg Asp Lys Tyr Gly Arg Val Val Met Leu
145                 150                 155                 160

Phe Asn Ile Glu Asn Trp His Cys Glu Glu Val Thr Phe Asp Glu Ile
                165                 170                 175

Leu Gln Ala Tyr Cys Phe Ile Leu Glu Lys Leu Leu Glu Asn Glu Glu
            180                 185                 190

Thr Gln Ile Asn Gly Phe Cys Ile Val Glu Asn Phe Lys Gly Phe Thr
        195                 200                 205

Met Gln Gln Ala Ala Gly Leu Arg Pro Ser Asp Leu Lys Lys Met Val
    210                 215                 220

Asp Met Leu Gln Asp Ser Phe Pro Ala Arg Phe Lys Ala Ile His Phe
225                 230                 235                 240

Ile His Gln Pro Trp Tyr Phe Thr Thr Thr Tyr Asn Val Val Lys Pro
                245                 250                 255

Phe Leu Lys Asn Lys Leu Leu Gln Arg Val Phe Val His Gly Asp Asp
            260                 265                 270

Leu Asp Gly Phe Phe Gln Glu Ile Asp Glu Asn Ile Leu Pro Ala Asp
        275                 280                 285

Phe Gly Gly Thr Leu Pro Lys Tyr Asp Gly Lys Val Val Ala Glu Gln
    290                 295                 300

Leu Phe Gly Pro Arg Val Glu Val Glu Asn Thr Ala Leu
305                 310                 315


<210> SEQ ID NO 45
<211> LENGTH: 954
<212> TYPE: DNA
<213> ORGANISM: Mus musculus

<400> SEQUENCE: 45

atgtcagacg gggtgggcac tttccgcatg gttcctgaag aggagcagga gctccgagca      60

caactggagc agctcacaac caaggatcat ggtcctgtct ttggcccatg cagccagctg     120

ccccgccaca ctttgcagaa ggccaaggat gagctgaatg aaaaggagga gacccgggag     180

gaagcggtga gggagctaca ggagctggta caggcacagg cagcttctgg cgaggaattg     240

gccctggcag tggctgagag ggtgcaggca agagacagcg ccttcctcct gcgcttcatc     300

cgtgcccgca agttcgatgt gggtcgtgct tatgagctgc tcaaaggcta tgtgaacttc     360

cgcctccagt accctgaact cttcgatagt ctctccatgg aggctctccg ctgcactatc     420

gaggccggat accctggtgt cctttccagt cgggacaagt atggtcgagt ggttatgctc     480

ttcaacatcg aaaactggca ctgtgaagaa gtgacctttg atgagatctt acaggcatat     540

tgtttcattt tggagaaact gctggaaaat gaggaaaccc aaatcaacgg cttctgtatt     600

gttgagaact tcaagggctt caccatgcag caggcagcag ggctccgccc ctcggatctc     660

aagaagatgg tggacatgct ccaggattca ttcccagcca ggttcaaagc tatccacttc     720

atccaccagc catggtactt caccaccacc tataatgtgg tcaagccctt cttgaagaac     780

aagctgctac agagggtctt tgttcacgga gatgacctgg atggcttctt ccaggagatt     840

gatgagaaca tcctgcctgc tgactttggg ggtacactgc ccaagtacga cggcaaagtt     900

gttgctgagc agctctttgg tccccgggct gaagttgaga acacagcctt atga           954
```

<210> SEQ ID NO 46
<211> LENGTH: 317
<212> TYPE: PRT
<213> ORGANISM: Mus musculus

<400> SEQUENCE: 46

```
Met Ser Asp Gly Val Gly Thr Phe Arg Met Val Pro Glu Glu Glu Gln
1               5                   10                  15

Glu Leu Arg Ala Gln Leu Glu Gln Leu Thr Thr Lys Asp His Gly Pro
            20                  25                  30

Val Phe Gly Pro Cys Ser Gln Leu Pro Arg His Thr Leu Gln Lys Ala
        35                  40                  45

Lys Asp Glu Leu Asn Glu Lys Glu Glu Thr Arg Glu Glu Ala Val Arg
    50                  55                  60

Glu Leu Gln Glu Leu Val Gln Ala Gln Ala Ala Ser Gly Glu Glu Leu
65                  70                  75                  80

Ala Leu Ala Val Ala Glu Arg Val Gln Ala Arg Asp Ser Ala Phe Leu
                85                  90                  95

Leu Arg Phe Ile Arg Ala Arg Lys Phe Asp Val Gly Arg Ala Tyr Glu
            100                 105                 110

Leu Leu Lys Gly Tyr Val Asn Phe Arg Leu Gln Tyr Pro Glu Leu Phe
        115                 120                 125

Asp Ser Leu Ser Met Glu Ala Leu Arg Cys Thr Ile Glu Ala Gly Tyr
    130                 135                 140

Pro Gly Val Leu Ser Ser Arg Asp Lys Tyr Gly Arg Val Val Met Leu
145                 150                 155                 160

Phe Asn Ile Glu Asn Trp His Cys Glu Glu Val Thr Phe Asp Glu Ile
                165                 170                 175

Leu Gln Ala Tyr Cys Phe Ile Leu Glu Lys Leu Leu Glu Asn Glu Glu
            180                 185                 190

Thr Gln Ile Asn Gly Phe Cys Ile Val Glu Asn Phe Lys Gly Phe Thr
        195                 200                 205

Met Gln Gln Ala Ala Gly Leu Arg Pro Ser Asp Leu Lys Lys Met Val
    210                 215                 220

Asp Met Leu Gln Asp Ser Phe Pro Ala Arg Phe Lys Ala Ile His Phe
225                 230                 235                 240

Ile His Gln Pro Trp Tyr Phe Thr Thr Thr Tyr Asn Val Val Lys Pro
                245                 250                 255

Phe Leu Lys Asn Lys Leu Leu Gln Arg Val Phe Val His Gly Asp Asp
            260                 265                 270

Leu Asp Gly Phe Phe Gln Glu Ile Asp Glu Asn Ile Leu Pro Ala Asp
        275                 280                 285

Phe Gly Gly Thr Leu Pro Lys Tyr Asp Gly Lys Val Val Ala Glu Gln
    290                 295                 300

Leu Phe Gly Pro Arg Ala Glu Val Glu Asn Thr Ala Leu
305                 310                 315
```

<210> SEQ ID NO 47
<211> LENGTH: 951
<212> TYPE: DNA
<213> ORGANISM: Gallus gallus

<400> SEQUENCE: 47

```
atgtctgctg ttacgggcac cttccgcatt gtctcggaag aggagcaggc gctgcgcacc      60

aaactggagc gcctcaccac caaggaccac ggccctgttt ttgggaggtg ccagcagatc     120
```

```
cccccctcaca ccctgcagaa ggcaaaagat gagctgaatg agacggagga gcagagggag    180

gcagcggtca aagcgctgcg ggagctggtg caggagcggg ccggcagcga ggatgtctgc    240

aaggcagtgg cagagaagat gcaggggaag gacgattcct tcttcctccg cttcatccgt    300

gcccgcaagt ttgacgtgca cagggcctac gacctgctga aaggctatgt gaactttcgc    360

cagcaatacc ctgaactctt tgacaacctg acccccgagg ccgtgcgcag caccatcgag    420

gcgggctacc ccggcatcct ggccagcagg gacaaatacg ggcgggtagt gatgctcttc    480

aacatcgaga actgggacta cgaggagatc acctttgatg agatccttcg tgcctactgc    540

gttatcttgg agaagctgct ggaaaacgaa gagacccaga tcaatgggtt ctgcatcatt    600

gagaacttca agggcttcac catgcagcag gcatcaggga tcaaaccctc cgagctcaag    660

aagatggtgg acatgctaca ggactccttc ccagcgcggt tcaaagctgt ccacttcatc    720

caccagccct ggtacttcac cactacctac aacgtggtca aaccgttcct gaagagcaag    780

ctgctggaga gggtgtttgt gcacggcgag gagctggagt ccttctacca ggagatcgat    840

gctgacatac tgccagcaga cttcggtggc aacctgccca agtacgacgg caaagcaact    900

gcagagcagc tctttgggcc ccgcattgag gctgaagaca cggcacttta a              951


<210> SEQ ID NO 48
<211> LENGTH: 316
<212> TYPE: PRT
<213> ORGANISM: Gallus gallus

<400> SEQUENCE: 48

Met Ser Ala Val Thr Gly Thr Phe Arg Ile Val Ser Glu Glu Glu Gln
1               5                   10                  15

Ala Leu Arg Thr Lys Leu Glu Arg Leu Thr Thr Lys Asp His Gly Pro
            20                  25                  30

Val Phe Gly Arg Cys Gln Gln Ile Pro Pro His Thr Leu Gln Lys Ala
        35                  40                  45

Lys Asp Glu Leu Asn Glu Thr Glu Glu Gln Arg Glu Ala Ala Val Lys
    50                  55                  60

Ala Leu Arg Glu Leu Val Gln Glu Arg Ala Gly Ser Glu Asp Val Cys
65                  70                  75                  80

Lys Ala Val Ala Glu Lys Met Gln Gly Lys Asp Asp Ser Phe Phe Leu
                85                  90                  95

Arg Phe Ile Arg Ala Arg Lys Phe Asp Val His Arg Ala Tyr Asp Leu
            100                 105                 110

Leu Lys Gly Tyr Val Asn Phe Arg Gln Gln Tyr Pro Glu Leu Phe Asp
        115                 120                 125

Asn Leu Thr Pro Glu Ala Val Arg Ser Thr Ile Glu Ala Gly Tyr Pro
    130                 135                 140

Gly Ile Leu Ala Ser Arg Asp Lys Tyr Gly Arg Val Val Met Leu Phe
145                 150                 155                 160

Asn Ile Glu Asn Trp Asp Tyr Glu Glu Ile Thr Phe Asp Glu Ile Leu
                165                 170                 175

Arg Ala Tyr Cys Val Ile Leu Glu Lys Leu Leu Glu Asn Glu Glu Thr
            180                 185                 190

Gln Ile Asn Gly Phe Cys Ile Ile Glu Asn Phe Lys Gly Phe Thr Met
        195                 200                 205

Gln Gln Ala Ser Gly Ile Lys Pro Ser Glu Leu Lys Lys Met Val Asp
    210                 215                 220
```

-continued

```
Met Leu Gln Asp Ser Phe Pro Ala Arg Phe Lys Ala Val His Phe Ile
225                 230                 235                 240

His Gln Pro Trp Tyr Phe Thr Thr Thr Tyr Asn Val Val Lys Pro Phe
                245                 250                 255

Leu Lys Ser Lys Leu Leu Glu Arg Val Phe Val His Gly Glu Glu Leu
            260                 265                 270

Glu Ser Phe Tyr Gln Glu Ile Asp Ala Asp Ile Leu Pro Ala Asp Phe
        275                 280                 285

Gly Gly Asn Leu Pro Lys Tyr Asp Gly Lys Ala Thr Ala Glu Gln Leu
    290                 295                 300

Phe Gly Pro Arg Ile Glu Ala Glu Asp Thr Ala Leu
305                 310                 315
```

```
<210> SEQ ID NO 49
<211> LENGTH: 2659
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

ctgcctgcag ggttccatcc caatggcgcg tcaattcact ggccgtcgtt ttacaacgtc     60

gtgactggga aaaccctggc gttacccaac ttaatcgcct tgcagcacat ccccctttcg    120

ccagctggcg taatagcgaa gaggcccgca ccgatcgccc ttcccaacag ttgcgcagcc    180

tgaatggcga atggcgcctg atgcggtatt ttctccttac gcatctgtgc ggtatttcac    240

accgcatatg gtgcactctc agtacaatct gctctgatgc cgcatagtta agccagcccc    300

gacacccgcc aacacccgct gacgcgccct gacgggcttg tctgctcccg gcatccgctt    360

acagacaagc tgtgaccgtc tccgggagct gcatgtgtca gaggttttca ccgtcatcac    420

cgaaacgcgc gagacgaaag ggcctcgtga tacgcctatt tttataggtt aatgtcatga    480

taataatggt ttcttagacg tcaggtggca cttttcgggg aaatgtgcgc ggaaccccta    540

tttgtttatt tttctaaata cattcaaata tgtatccgct catgagacaa taaccctgat    600

aaatgcttca ataatattga aaaaggaaga gtatgagcca tattcaacgg gaaacgtctt    660

gctctaggcc gcgattaaat tccaacatgg atgctgattt atatgggtat aaatgggctc    720

gcgataatgt cgggcaatca ggtgcgacaa tctatcgatt gtatgggaag cccgatgcgc    780

cagagttgtt tctgaaacat ggcaaaggta gcgttgccaa tgatgttaca gatgagatgg    840

tcagactaaa ctggctgacg gaatttatgc ctcttccgac catcaagcat tttatccgta    900

ctcctgatga tgcatggtta ctcaccactg cgatccctgg gaaaacagca ttccaggtat    960

tagaagaata tcctgattca ggtgaaaata ttgttgatgc gctggcagtg ttcctgcgcc   1020

ggttgcattc gattcctgtt tgtaattgtc cttttaacag cgatcgcgta tttcgtctcg   1080

ctcaggcgca atcacgaatg aataacggtt tggttgatgc gagtgatttt gatgacgagc   1140

gtaatggctg gcctgttgaa caagtctgga aagaaatgca taaacttttg ccattctcac   1200

cggattcagt cgtcactcat ggtgatttct cacttgataa ccttattttt gacgagggga   1260

aattaatagg ttgtattgat gttggacgag tcggaatcgc agaccgatac caggatcttg   1320

ccatcctatg gaactgcctc ggtgagtttt ctccttcatt acagaaacgg ctttttcaaa   1380

aatatggtat tgataatcct gatatgaata aattgcagtt tcatttgatg ctcgatgagt   1440

ttttctaact gtcagaccaa gtttactcat atatacttta gattgattta aaacttcatt   1500
```

tttaatttaa aaggatctag gtgaagatcc tttttgataa tctcatgacc aaaatccctt 1560
aacgtgagtt ttcgttccac tgagcgtcag accccgtaga aaagatcaaa ggatcttctt 1620
gagatccttt ttttctgcgc gtaatctgct gcttgcaaac aaaaaaacca ccgctaccag 1680
cggtggtttg tttgccggat caagagctac caactctttt tccgaaggta actggcttca 1740
gcagagcgca gataccaaat actgttcttc tagtgtagcc gtagttaggc caccacttca 1800
agaactctgt agcaccgcct acatacctcg ctctgctaat cctgttacca gtggctgctg 1860
ccagtggcga taagtcgtgt cttaccgggt tggactcaag acgatagtta ccggataagg 1920
cgcagcggtc gggctgaacg gggggttcgt gcacacagcc cagcttggag cgaacgacct 1980
acaccgaact gagataccta cagcgtgagc tatgagaaag cgccacgctt cccgaaggga 2040
gaaaggcgga caggtatccg gtaagcggca gggtcggaac aggagagcgc acgagggagc 2100
ttccaggggg aaacgcctgg tatctttata gtcctgtcgg gtttcgccac ctctgacttg 2160
agcgtcgatt tttgtgatgc tcgtcagggg ggcggagcct atggaaaaac gccagcaacg 2220
cggccttttt acggttcctg gccttttgct ggccttttgc tcacatgttc tttcctgcgt 2280
tatcccctga ttctgtggat aaccgtatta ccgcctttga gtgagctgat accgctcgcc 2340
gcagccgaac gaccgagcgc agcgagtcag tgagcgagga agcggaagag cgcccaatac 2400
gcaaaccgcc tctccccgcg cgttggccga ttcattaatg cagctggcac gacaggtttc 2460
ccgactggaa agcgggcagt gagcgcaacg caattaatgt gagttagctc actcattagg 2520
caccccaggc tttacacttt atgcttccgg ctcgtatgtt gtgtggaatt gtgagcggat 2580
aacaatttca cacaggaaac agctatgacc atgattacgc caagctcggc gcgccattgg 2640
gatggaaccc tgcaggcag 2659

<210> SEQ ID NO 50
<211> LENGTH: 4989
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 50
ctgcgcgctc gctcgctcac tgaggccgcc cgggcaaagc ccgggcgtcg ggcgaccttt 60
ggtcgcccgg cctcagtgag cgagcgagcg cgcagagagg gagtggggta ccacgcgttt 120
gtcctctccc tgcttggcct taaccagcca catttctcaa ctgaccccac tcactgcaga 180
ggtgaaaact accatgccag gtcctgctgg ctgggggagg ggtgggcaat aggcctggat 240
ttgccagagc tgccactgta gatgtagtca tatttacgat ttcccttcac ctcttattac 300
cctggtggtg gtggtggggg gggggggtg ctctctcagc aaccccaccc cgggatcttg 360
aggagaaaga gggcagagaa aagagggaat gggactggcc cagatcccag ccccacagcc 420
gggcttccac atggccgagc aggaactcca gagcaggagc acacaaagga gggctttgat 480
gcgcctccag ccaggcccag gcctctcccc tctccccttt ctctctgggt cttcctttgc 540
cccactgagg gcctcctgtg agcccgattt aacggaaact gtgggcggtg agaagttcct 600
tatgacacac taatcccaac ctgctgaccg gaccacgcct ccagcggagg gaacctctag 660
agctccagga cattcaggta ccaggtagcc ccaaggagga gctgccgaat cgatggatcg 720
ggaactgaaa aaccagaaag ttaactggta agtttagtct tttgtcttt tatttcaggt 780 cccggatccg gtggtggtgc aaatcaaaga actgctcctc agtggatgtt gcctttactt 840

```
ctaggcctgt acggaagtgt tacttctgct ctaaaagctg cggaattgta cccgccccgg    900
gatccatcga ttgaattcgc caccatgtca gaaggggtgg gcacgttccg catggtacct    960
gaagaggaac aggagctccg tgcccaactg gagcagctca caaccaagga ccatggacct   1020
gtctttggcc cgtgcagcca gctgccccgc cacaccttgc agaaggccaa ggatgagctg   1080
aacgagagag aggagacccg ggaggaggca gtgcgagagc tgcaggagat ggtgcaggcg   1140
caggcggcct cgggggagga gctggcggtg gccgtggcgg agagggtgca agagaaggac   1200
agcggcttct tcctgcgctt catccgcgca cggaagttca acgtgggccg tgcctatgag   1260
ctgctcagag gctatgtgaa tttccggctg cagtaccctg agctctttga cagcctgtcc   1320
ccagaggctg tccgctgcac cattgaagct ggctaccctg gtgtcctctc tagtcgggac   1380
aagtatggcc gagtggtcat gctcttcaac attgagaact ggcaaagtca agaaatcacc   1440
tttgatgaga tcttgcaggc atattgcttc atcctggaga agctgctgga gaatgaggaa   1500
actcaaatca atggcttctg catcattgag aacttcaagg gctttaccat gcagcaggct   1560
gctagtctcc ggacttcaga tctcaggaag atggtggaca tgctccagga ttccttccca   1620
gcccggttca aagccatcca cttcatccac cagccatggt acttcaccac gacctacaat   1680
gtggtcaagc ccttcttgaa gagcaagctg cttgagaggg tctttgtcca cggggatgac   1740
ctttctggtt tctaccagga gatcgatgag aacatcctgc cctctgactt cgggggcacg   1800
ctgcccaagt atgatggcaa ggccgttgct gagcagctct ttggccccca ggcccaagct   1860
gagaacacag ccttctgagg atcgtaccgg tcgacctgca gaagcttgcc tcgagcagcg   1920
ctgctcgaga gatctggatc ataatcagcc ataccacatt tgtagaggtt ttacttgctt   1980
taaaaaacct cccacacctc cccctgaacc tgaaacataa aatgaatgca attgttgttg   2040
ttaacttgtt tattgcagct tataatggtt acaaataaag caatagcatc acaaatttca   2100
caaataaagc atttttttca ctgcattcta gttgtggttt gtccaaactc atcaatgtat   2160
cttatcatgt ctggtaacca cgtgcggacc gagcggccgc aggaacccct agtgatggag   2220
ttggccactc cctctctgcg cgctcgctcg ctcactgagg ccgggcgacc aaaggtcgcc   2280
cgacgcccgg gctttgcccg ggcggcctca gtgagcgagc gagcgcgcag ctgcctgcag   2340
ggttccatcc caatggcgcg tcaattcact ggccgtcgtt ttacaacgtc gtgactggga   2400
aaaccctggc gttacccaac ttaatcgcct tgcagcacat ccccctttcg ccagctggcg   2460
taatagcgaa gaggcccgca ccgatcgccc ttcccaacag ttgcgcagcc tgaatggcga   2520
atggcgcctg atgcggtatt ttctccttac gcatctgtgc ggtatttcac accgcatatg   2580
gtgcactctc agtacaatct gctctgatgc cgcatagtta agccagcccc gacacccgcc   2640
aacacccgct gacgcgccct gacgggcttg tctgctcccg gcatccgctt acagacaagc   2700
tgtgaccgtc tccgggagct gcatgtgtca gaggttttca ccgtcatcac cgaaacgcgc   2760
gagacgaaag ggcctcgtga tacgcctatt tttataggtt aatgtcatga taataatggt   2820
ttcttagacg tcaggtggca cttttcgggg aaatgtgcgc ggaaccccta tttgtttatt   2880
tttctaaata cattcaaata tgtatccgct catgagacaa taaccctgat aaatgcttca   2940
ataatattga aaaaggaaga gtatgagcca tattcaacgg gaaacgtctt gctctaggcc   3000
gcgattaaat tccaacatgg atgctgattt atatgggtat aaatgggctc gcgataatgt   3060
cgggcaatca ggtgcgacaa tctatcgatt gtatgggaag cccgatgcgc cagagttgtt   3120
tctgaaacat ggcaaaggta gcgttgccaa tgatgttaca gatgagatgg tcagactaaa   3180
ctggctgacg gaatttatgc ctcttccgac catcaagcat tttatccgta ctcctgatga   3240
```

```
tgcatggtta ctcaccactg cgatccctgg gaaaacagca ttccaggtat tagaagaata   3300

tcctgattca ggtgaaaata ttgttgatgc gctggcagtg ttcctgcgcc ggttgcattc   3360

gattcctgtt tgtaattgtc cttttaacag cgatcgcgta tttcgtctcg ctcaggcgca   3420

atcacgaatg aataacggtt tggttgatgc gagtgatttt gatgacgagc gtaatggctg   3480

gcctgttgaa caagtctgga aagaaatgca taaacttttg ccattctcac cggattcagt   3540

cgtcactcat ggtgatttct cacttgataa ccttattttt gacgagggga aattaatagg   3600

ttgtattgat gttggacgag tcggaatcgc agaccgatac caggatcttg ccatcctatg   3660

gaactgcctc ggtgagtttt ctccttcatt acagaaacgg ctttttcaaa aatatggtat   3720

tgataatcct gatatgaata aattgcagtt tcatttgatg ctcgatgagt ttttctaact   3780

gtcagaccaa gtttactcat atatacttta gattgattta aaacttcatt tttaatttaa   3840

aaggatctag gtgaagatcc tttttgataa tctcatgacc aaaatccctt aacgtgagtt   3900

ttcgttccac tgagcgtcag accccgtaga aaagatcaaa ggatcttctt gagatccttt   3960

ttttctgcgc gtaatctgct gcttgcaaac aaaaaaacca ccgctaccag cggtggtttg   4020

tttgccggat caagagctac caactctttt tccgaaggta actggcttca gcagagcgca   4080

gataccaaat actgttcttc tagtgtagcc gtagttaggc caccacttca agaactctgt   4140

agcaccgcct acatacctcg ctctgctaat cctgttacca gtggctgctg ccagtggcga   4200

taagtcgtgt cttaccgggt tggactcaag acgatagtta ccggataagg cgcagcggtc   4260

gggctgaacg gggggttcgt gcacacagcc cagcttggag cgaacgacct acaccgaact   4320

gagataccta cagcgtgagc tatgagaaag cgccacgctt cccgaaggga gaaaggcgga   4380

caggtatccg gtaagcggca gggtcggaac aggagagcgc acgagggagc ttccaggggg   4440

aaacgcctgg tatctttata gtcctgtcgg gtttcgccac ctctgacttg agcgtcgatt   4500

tttgtgatgc tcgtcagggg ggcggagcct atggaaaaac gccagcaacg cggccttttt   4560

acggttcctg gccttttgct ggccttttgc tcacatgttc tttcctgcgt tatcccctga   4620

ttctgtggat aaccgtatta ccgcctttga gtgagctgat accgctcgcc gcagccgaac   4680

gaccgagcgc agcgagtcag tgagcgagga agcggaagag cgcccaatac gcaaaccgcc   4740

tctccccgcg cgttggccga ttcattaatg cagctggcac gacaggtttc ccgactggaa   4800

agcgggcagt gagcgcaacg caattaatgt gagttagctc actcattagg caccccaggc   4860

tttacacttt atgcttccgg ctcgtatgtt gtgtggaatt gtgagcggat aacaatttca   4920

cacaggaaac agctatgacc atgattacgc caagctcggc gcgccattgg gatggaaccc   4980

tgcaggcag                                                           4989
```

```
<210> SEQ ID NO 51
<211> LENGTH: 2327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
```

```
cgcgctcgct cgctcactga ggccgcccgg gcaaagcccg ggcgtcgggc gacctttggt     60

cgcccggcct cagtgagcga gcgagcgcgc agagagggag tggggtacca cgcgtttgtc    120

ctctccctgc ttggccttaa ccagccacat ttctcaactg accccactca ctgcagaggt    180

gaaaactacc atgccaggtc ctgctggctg ggggaggggt gggcaatagg cctggatttg    240
```

-continued

```
ccagagctgc cactgtagat gtagtcatat ttacgatttc ccttcacctc ttattaccct    300
ggtggtggtg gtgggggggg gggggtgctc tctcagcaac ccccaccccgg gatcttgagg   360
agaaagaggg cagagaaaag agggaatggg actggcccag atcccagccc cacagccggg    420
cttccacatg gccgagcagg aactccagag caggagcaca caaaggaggg ctttgatgcg    480
cctccagcca ggcccaggcc tctcccctct cccctttctc tctgggtctt cctttgcccc    540
actgagggcc tcctgtgagc ccgatttaac ggaaactgtg ggcggtgaga agttccttat    600
gacacactaa tcccaacctg ctgaccggac cacgcctcca gcggagggaa cctctagagc    660
tccaggacat tcaggtacca ggtagcccca aggaggagct gccgaatcga tggatcggga    720
actgaaaaac cagaaagtta actggtaagt ttagtctttt tgtcttttat ttcaggtccc    780
ggatccggtg gtggtgcaaa tcaaagaact gctcctcagt ggatgttgcc tttacttcta    840
ggcctgtacg gaagtgttac ttctgctcta aaagctgcgg aattgtaccc gccccgggat    900
ccatcgattg aattcgccac catgtcagaa ggggtgggca cgttccgcat ggtacctgaa    960
gaggaacagg agctccgtgc ccaactggag cagctcacaa ccaaggacca tggacctgtc   1020
tttggcccgt gcagccagct gccccgccac accttgcaga aggccaagga tgagctgaac   1080
gagagagagg agacccggga ggaggcagtg cgagagctgc aggagatggt gcaggcgcag   1140
gcggcctcgg gggaggagct ggcggtggcc gtggcggaga gggtgcaaga gaaggacagc   1200
ggcttcttcc tgcgcttcat ccgcgcacgg aagttcaacg tgggccgtgc ctatgagctg   1260
ctcagaggct atgtgaattt ccggctgcag taccctgagc tctttgacag cctgtcccca   1320
gaggctgtcc gctgcaccat tgaagctggc taccctggtg tcctctctag tcgggacaag   1380
tatggccgag tggtcatgct cttcaacatt gagaactggc aaagtcaaga aatcaccttt   1440
gatgagatct tgcaggcata ttgcttcatc ctggagaagc tgctggagaa tgaggaaact   1500
caaatcaatg gcttctgcat cattgagaac ttcaagggct ttaccatgca gcaggctgct   1560
agtctccgga cttcagatct caggaagatg gtggacatgc tccaggattc cttcccagcc   1620
cggttcaaag ccatccactt catccaccag ccatggtact tcaccacgac ctacaatgtg   1680
gtcaagccct tcttgaagag caagctgctt gagagggtct ttgtccacgg ggatgacctt   1740
tctggtttct accaggagat cgatgagaac atcctgccct ctgacttcgg gggcacgctg   1800
cccaagtatg atggcaaggc cgttgctgag cagctctttg gcccccaggc ccaagctgag   1860
aacacagcct tctgaggatc gtaccggtcg acctgcagaa gcttgcctcg agcagcgctg   1920
ctcgagagat ctggatcata atcagccata ccacatttgt agaggtttta cttgctttaa   1980
aaaacctccc acacctcccc ctgaacctga aacataaaat gaatgcaatt gttgttgtta   2040
acttgtttat tgcagcttat aatggttaca aataaagcaa tagcatcaca aatttcacaa   2100
ataaagcatt tttttcactg cattctagtt gtggtttgtc caaactcatc aatgtatctt   2160
atcatgtctg gtaaccacgt gcggaccgag cggccgcagg aacccctagt gatggagttg   2220
gccactccct ctctgcgcgc tcgctcgctc actgaggccg ggcgaccaaa ggtcgcccga   2280
cgcccgggct ttgcccgggc ggcctcagtg agcgagcgag cgcgcag                 2327
```

<210> SEQ ID NO 52
<211> LENGTH: 4711
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 52
ctgcgcgctc gctcgctcac tgaggccgcc cgggcgtcgg gcgacctttg gtcgcccggc 60
ctcagtgagc gagcgagcgc gcagagaggg agtggccaac tccatcacta ggggttcctg 120
cggccgcacg cagcttttgt cctctccctg cttggcctta accagccaca tttctcaact 180
gaccccactc actgcagagg tgaaaactac catgccaggt cctgctggct gggggagggg 240
tgggcaatag gcctggattt gccagagctg ccactgtaga tgtagtcata tttacgattt 300
cccttcacct cttattaccc tggtggtggt ggtggggggg ggggggtgct ctctcagcaa 360
ccccaccccg ggatcttgag gagaaagagg gcagagaaaa gagggaatgg gactggccca 420
gatcccagcc ccacagccgg gcttccacat ggccgagcag gaactccaga gcaggagcac 480
acaaaggagg gctttgatgc gcctccagcc aggcccaggc ctctcccctc tccccttct 540
ctctgggtct tcctttgccc cactgagggc ctcctgtgag cccgatttaa cggaaactgt 600
gggcggtgag aagttcctta tgacacacta atcccaacct gctgaccgga ccacgcctcc 660
agcggaggga acctctagag ctccaggaca ttcaggtacc aggtagcccc aaggaggagc 720
tgccgacctg gcaggtaagt caatacctgg ggcttgcctg ggccagggag cccaggactg 780
gggtgaggac tcaggggagc agggagacca cgtcccaaga tgcctgtaaa actgaaacca 840
cctggccatt ctccaggttg agccagacca atttgatggc agatttagca aataaaaata 900
caggacaccc agttaaatgt gaatttcaga tgaacagcaa atactttttt agtattaaaa 960
aagttcacat ttaggctcac gcctgtaatc ccagcacttt gggaggccga ggcaggcaga 1020
tcacctgagg tcaggagttc gagaccagcc tggccaacat ggtgaaaccc catctccact 1080
aaaaatacca aaaattagcc aggcgtgctg gtgggcacct gtagttccag ctactcagga 1140
ggctaaggca ggagaattgc ttgaacctgg gaggcagagg ttgcagtgag ctgagatcgc 1200
accattgcac tctagcctgg gcgacaagaa caaaactcca tctcaaaaaa aaaaaaaaaa 1260
aaaaagttca catttaactg ggcattctgt atttaattgg taatctgaga tggcagggaa 1320
cagcatcagc atggtgtgag ggataggcat tttttcattg tgtacagctt gtaaatcagt 1380
atttttaaaa ctcaaagtta atggcttggg catatttaga aaagagttgc cgcacggact 1440
tgaaccctgt attcctaaaa tctaggatct tgttctgatg gtctgcacaa ctggctgggg 1500
gtgtccagcc actgtccctc ttgcctgggc tccccagggc agttctgtca gcctctccat 1560
ttccattcct gttccagcaa aacccaactg atagcacagc agcatttcag cctgtctacc 1620
tctgtgccca catacctgga tgtctaccag ccagaaaggt ggcttagatt tggttcctgt 1680
gggtggatta tggcccccag aacttccctg tgcttgctgg gggtgtggag tggaaagagc 1740
aggaaatggg ggaccctccg atactctatg gggtcctcc aagtctcttt gtgcaagtta 1800
gggtaataat caatatggag ctaagaaaga gaaggggaac tatgctttag aacaggacac 1860
tgtgccagga gcattgcaga aattatatgg ttttcacgac agttcttttt ggtaggtact 1920
gttattatcc tcagtttgca gatgaggaaa ctgagaccca gaaaggttaa ataacttgct 1980
agggtcacac aagtcataac tgacaaagcc tgattcaaac ccaggtctcc ctaaccttta 2040
aggtttctat gacgccagct ctcctaggga gtttgtcttc agatgtcttg gctctaggtg 2100
tcaaaaaaag acttggtgtc aggcaggcat aggttcaagt cccaactctg tcacttacca 2160
actgtgacta ggtgattgaa ctgaccatgg aacctggtca catgcaggag caggatggtg 2220
aagggttctt gaaggcactt aggcaggaca tttaggcagg agagaaaacc tggaaacaga 2280
agagctgtct ccaaaaatac ccactgggga agcaggttgt catgtgggcc atgaatggga 2340
cctgttctgg taaccaagca ttgcttatgt gtccattaca tttcataaca cttccatcct 2400
actttacagg gaacaaccaa gactggggtt aaatctcaca gcctgcaagt ggaagagaag 2460
aacttgaacc caggtccaac ttttgcgcca cagcaggctg cctcttggtc ctgacaggaa 2520
gtcacaactt gggtctgagt actgatccct ggctattttt tggctgtgtt accttggaca 2580
agtcacttat tcctcctccc gtttcctcct atgtaaaatg gaaataataa tgttgaccct 2640
gggtctgaga gagtggattt gaaagtactt agtgcatcac aaagcacaga acacacttcc 2700
agtctcgtga ttatgtactt atgtaactgg tcatcaccca tcttgagaat gaatgcattg 2760
gggaaagggc catccactag gctgcgaagt ttctgaggga ctccttcggg ctggagaagg 2820
atggccacag gagggaggag agattgcctt atcctgcagt gatcatgtca ttgagaacag 2880
agccagattc tttttttcct ggcagggcca acttgtttta acatctaagg actgagctat 2940
ttgtgtctgt gccctttgtc caagcagtgt ttcccaaagt gtagcccaag aaccatctcc 3000
ctcagagcca ccaggaagtg ctttaaattg caggttccta ggccacagcc tgcacctgca 3060
gagtcagaat catggaggtt gggacccagg cacctgcgtt tctaacaaat gcctcgggtg 3120
attctgatgc aattgaaagt ttgagatcca cagttctgag acaataacag aatggttttt 3180
ctaacccctg cagccctgac ttcctatcct agggaagggg ccggctggag aggccaggac 3240
agagaaagca gatcccttct ttttccaagg actctgtgtc ttccataggc aacgaattcg 3300
ccaccatgtc agaaggggtg ggcacgttcc gcatggtacc tgaagaggaa caggagctcc 3360
gtgcccaact ggagcagctc acaaccaagg accatggacc tgtctttggc ccgtgcagcc 3420
agctgccccg ccacaccttg cagaaggcca aggatgagct gaacgagaga gaggagaccc 3480
gggaggaggc agtgcgagag ctgcaggaga tggtgcaggc gcaggcggcc tcgggggagg 3540
agctggcggt ggccgtggcg gagagggtgc aagagaagga cagcggcttc ttcctgcgct 3600
tcatccgcgc acggaagttc aacgtgggcc gtgcctatga gctgctcaga ggctatgtga 3660
atttccggct gcagtaccct gagctctttg acagcctgtc cccagaggct gtccgctgca 3720
ccattgaagc tggctaccct ggtgtcctct ctagtcggga caagtatggc cgagtggtca 3780
tgctcttcaa cattgagaac tggcaaagtc aagaaatcac ctttgatgag atcttgcagg 3840
catattgctt catcctggag aagctgctgg agaatgagga aactcaaatc aatggcttct 3900
gcatcattga gaacttcaag ggctttacca tgcagcaggc tgctagtctc cggacttcag 3960
atctcaggaa gatggtggac atgctccagg attccttccc agcccggttc aaagccatcc 4020
acttcatcca ccagccatgg tacttcacca cgacctacaa tgtggtcaag cccttcttga 4080
agagcaagct gcttgagagg gtctttgtcc acggggatga cctttctggt ttctaccagg 4140
agatcgatga gaacatcctg ccctctgact tcgggggcac gctgcccaag tatgatggca 4200
aggccgttgc tgagcagctc tttggccccc aggcccaagc tgagaacaca gccttctgag 4260
gatcgtaccg gtcgacctgc agaagcttgc ctcgagcagc gctgctcgag agatctggat 4320
cataatcagc cataccacat ttgtagaggt tttacttgct ttaaaaaacc tcccacacct 4380
ccccctgaac ctgaaacata aaatgaatgc aattgttgtt gttaacttgt ttattgcagc 4440
ttataatggt tacaaataaa gcaatagcat cacaaatttc acaaataaag catttttttc 4500
actgcattct agttgtggtt tgtccaaact catcaatgta tcttatcatg tctggtaacc 4560
acgtgcggac cgagcggccg caggaacccc tagtgatgga gttggccact ccctctctgc 4620
gcgctcgctc gctcactgag gccgggcgac caaaggtcgc ccgacgcccg ggctttgccc 4680
gggcggcctc agtgagcgag cgagcgcgca g 4711

<210> SEQ ID NO 53
<211> LENGTH: 4645
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 53
ctgcgcgctc gctcgctcac tgaggccgcc cgggcgtcgg gcgacctttg gtcgcccggc 60
ctcagtgagc gagcgagcgc gcagagaggg agtggccaac tccatcacta ggggttcctg 120
cggccgcacg cgttacgtaa tatttattga agtttaatat tgtgtttgtg atacagaagt 180
atttgcttta attctaaata aaaattttat gcttttattg ctggtttaag aagatttgga 240
ttatccttgt actttgagga gaagtttctt atttgaaata ttttggaaac aggtctttta 300
atgtggaaag atagatatta atctcctctt ctattactct ccaagatcca acaaaagtga 360
ttataccccc caaaatatga tggtagtatc ttatactacc atcattttat aggcataggg 420
ctcttagctg caaataatgg aactaactct aataaagcag aacgcaaata ttgtaaatat 480
tagagagcta acaatctctg ggatggctaa aggatggagc ttggaggcta cccagccagt 540
aacaatattc cgggctccac tgttgaatgg agacactaca actgccttgg atgggcagag 600
atattatgga tgctaagccc caggtgctac cattaggact tctaccactg tccctaacgg 660
gtggagccca tcacatgcct atgccctcac tgtaaggaaa tgaagctact gttgtatatc 720
ttgggaagca cttggattaa ttgttataca gttttgttga agaagacccc tagggtaagt 780
agccataact gcacactaaa tttaaaattg ttaatgagtt tctcaaaaaa aatgttaagg 840
ttgttagctg gtatagtata tatcttgcct gttttccaag gacttctttg ggcagtacct 900
tgtctgtgct ggcaagcaac tgagacttaa tgaaagagta ttggagatat gaatgaattg 960
atgctgtata ctctcagagt gccaaacata taccaatgga caagaaggtg aggcagagag 1020
cagacaggca ttagtgacaa gcaaagatat gcagaatttc attctcagca aatcaaaagt 1080
cctcaacctg gttggaagaa tattggcact gaatggtatc aataaggttg ctagagaggg 1140
ttagaggtgc acaatgtgct tccataacat tttatacttc tccaatctta gcactaatca 1200
aacatggttg aatactttgt ttactataac tcttacagag ttataagatc tgtgaagaca 1260
gggacaggga caatacccat ctctgtctgg ttcataggtg gtatgtaata gatattttta 1320
aaaataagtg agttaatgaa tgagggtgag aatgaaggca cagaggtatt agggggaggt 1380
gggccccaga gaatggtgcc aaggtccagt ggggtgactg ggatcagctc aggcctgacg 1440
ctggccactc ccacctagct cctttctttc taatctgttc tcattctcct tgggaaggat 1500
tgaggtctct ggaaaacagc caaacaactg ttatgggaac agcaagccca aataaagcca 1560
agcatcaggg ggatctgaga gctgaaagca acttctgttc cccctccctc agctgaaggg 1620
gtggggaagg gctcccaaag ccataactcc ttttaaggga tttagaaggc ataaaaaggc 1680
ccctggctga gaacttcctt cttcattctg cagttggtga attcgccacc atgtcagaag 1740
gggtgggcac gttccgcatg gtacctgaag aggaacagga gctccgtgcc caactggagc 1800
agctcacaac caaggaccat ggacctgtct ttggcccgtg cagccagctg ccccgccaca 1860
ccttgcagaa ggccaaggat gagctgaacg agagagagga gacccgggag gaggcagtgc 1920
gagagctgca ggagatggtg caggcgcagg cggcctcggg ggaggagctg gcggtggccg 1980

-continued

```
tggcggagag ggtgcaagag aaggacagcg gcttcttcct gcgcttcatc cgcgcacgga   2040
agttcaacgt gggccgtgcc tatgagctgc tcagaggcta tgtgaatttc cggctgcagt   2100
accctgagct ctttgacagc ctgtccccag aggctgtccg ctgcaccatt gaagctggct   2160
accctggtgt cctctctagt cgggacaagt atggccgagt ggtcatgctc ttcaacattg   2220
agaactggca aagtcaagaa atcacctttg atgagatctt gcaggcatat tgcttcatcc   2280
tggagaagct gctggagaat gaggaaactc aaatcaatgg cttctgcatc attgagaact   2340
tcaagggctt taccatgcag caggctgcta gtctccggac ttcagatctc aggaagatgg   2400
tggacatgct ccaggattcc ttcccagccc ggttcaaagc catccacttc atccaccagc   2460
catggtactt caccacgacc tacaatgtgg tcaagccctt cttgaagagc aagctgcttg   2520
agagggtctt tgtccacggg gatgaccttt ctggtttcta ccaggagatc gatgagaaca   2580
tcctgccctc tgacttcggg ggcacgctgc ccaagtatga tggcaaggcc gttgctgagc   2640
agctctttgg cccccaggcc caagctgaga acacagcctt ctgaggatct accggtcgac   2700
ctgcagaagc ttgcctcgag cagcgctgct cgagagatct ggatcataat cagccatacc   2760
acatttgtag aggttttact tgctttaaaa aacctcccac acctcccct gaacctgaaa   2820
cataaaatga atgcaattgt tgttgttaac ttgtttattg cagcttataa tggttacaaa   2880
taaagcaata gcatcacaaa tttcacaaat aaagcatttt tttcactgca ttctagttgt   2940
ggtttgtcca aactcatcaa tgtatcttat catgtctggt aaccattctc caggttgagc   3000
cagaccaatt tgatggtaga tttagcaaat aaaaatacag gacacccagt taaatgtgaa   3060
tttccgatga acagcaaata ctttttagt attaaaaaag ttcacattta ggctcacgcc   3120
tgtaatccca gcactttggg aggccgaggc aggcagatca cctgaggtca ggagttcgag   3180
accagcctgg ccaacatggt gaaaccccat ctccactaaa aataccaaaa attagccagg   3240
cgtgctggtg ggcacctgta gttccagcta ctcaggaggc taaggcagga gaattgcttg   3300
aacctgggag gcagaggttg cagtgagctg agatcgcacc attgcactct agcctgggcg   3360
acaagaacaa aactccatct caaaaaaaaa aaaaaaaaaa aagttcacat ttaactgggc   3420
attctgtatt taattggtaa tctgagatgg cagggaacag catcagcatg gtgtgaggga   3480
taggcatttt ttcattgtgt acagcttgta aatcagtatt tttaaaactc aaagttaatg   3540
gcttgggcat atttagaaaa gagttgccgc acggacttga accctgtatt cctaaaatct   3600
aggatcttgt tctgatggtc tgcacaactg gctgggggtg tccagccact gtccctcttg   3660
cctgggctcc ccagggcagt tctgtcagcc tctccatttc cattcctgtt ccagcaaaac   3720
ccaactgata gcacagcagc atttcagcct gtctacctct gtgcccacat acctggatgt   3780
ctaccagcca gaaaggtggc ttagatttgg ttcctgtggg tggattatgg cccccagaac   3840
ttccctgtgc ttgctggggg tgtggagtgg aaagagcagg aaatggggga ccctccgata   3900
ctctatgggg gtcctccaag tctctttgtg caagttaggg taataatcaa tatggagcta   3960
agaaagagaa ggggaactat gctttagaac aggacactgt gccaggagca ttgcagaaat   4020
tatatggttt tcacgacagt tctttttggt aggtactgtt attatcctca gtttgcagat   4080
gaggaaactg agacccagaa aggttaaata acttgctagg gtcacacaag tcataactga   4140
caaagcctga ttcaaaccca ggtctcccta acctttaagg tttctatgac gccagctctc   4200
ctagggagtt tgtcttcaga tgtcttggct ctaggtgtca aaaaaagact tggtgtcagg   4260
caggcatagg ttcaagtccc aactctgtca cttaccaact gtgactaggt gattgaactg   4320
```

-continued

```
accatggaac ctggtcacat gcaggagcag gatggtgaag ggttcttgaa ggcacttagg   4380

caggacattt aggcaggaga gaaaacctgg aaacagaaga gctgtctcca aaaataccca   4440

ctggggaagc aggttgtcat gtgggccatg aatgggacct gttctggggt aaccacgtgc   4500

ggaccgagcg gccgcaggaa cccctagtga tggagttggc cactccctct ctgcgcgctc   4560

gctcgctcac tgaggccggg cgaccaaagg tcgcccgacg cccgggcttt gcccgggcgg   4620

cctcagtgag cgagcgagcg cgcag                                         4645
```

<210> SEQ ID NO 54
<211> LENGTH: 4702
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 54

```
ctgcgcgctc gctcgctcac tgaggccgcc cgggcgtcgg gcgacctttg gtcgcccggc     60

ctcagtgagc gagcgagcgc gcagagaggg agtggccaac tccatcacta ggggttcctg    120

cggccgcacg cgtactagtt attaatagta atcaattacg gggtcattag ttcatagccc    180

atatatggag ttccgcgtta cataacttac ggtaaatggc ccgcctggct gaccgcccaa    240

cgacccccgc ccattgacgt caataatgac gtatgttccc atagtaacgc caatagggac    300

tttccattga cgtcaatggg tggagtattt acggtaaact gcccacttgg cagtacatca    360

agtgtatcat atgccaagta cgccccctat tgacgtcaat gacggtaaat ggcccgcctg    420

gcattatgcc cagtacatga ccttatggga ctttcctact tggcagtaca tctacgtatt    480

agtcatcgct attaccatgg tcgaggtgag ccccacgttc tgcttcactc tccccatctc    540

ccccccctcc ccacccccaa ttttgtattt atttattttt taattatttt gtgcagcgat    600

gggggcgggg gggggggggg ggcgcgcgcc aggcggggcg gggcggggcg aggggcgggg    660

cggggcgagg cggagaggtg cggcggcagc caatcagagc ggcgcgctcc gaaagtttcc    720

ttttatggcg aggcggcggc ggcggcggcc ctataaaaag cgaagcgcgc ggcgggcggg    780

gagtcgctgc gacgctgcct tcgccccgtg ccccgctccg ccgccgcctc gcgccgcccg    840

ccccggctct gactgaccgc gttactccca caggtgagcg ggcgggacgg cccttctcct    900

ccgggctgta attagcgctt ggtttaatga cggcttgttt cttttctgtg gctgcgtgaa    960

agccttgagg ggctccggga gggccctttg tgcgggggga gcggctcggg gggtgcgtgc   1020

gtgtgtgtgt gcgtggggag cgccgcgtgc ggctccgcgc tgcccggcgg ctgtgagcgc   1080

tgcgggcgcg gcgcggggct ttgtgcgctc cgcagtgtgc gcgaggggag cgcggccggg   1140

ggcggtgccc cgcggtgcgg ggggggctgc gaggggaaca aaggctgcgt gcggggtgtg   1200

tgcgtggggg ggtgagcagg gggtgtgggc gcgtcggtcg ggctgcaacc ccccctgcac   1260

ccccctcccc gagttgctga gcacggcccg gcttcgggtg cggggctccg tacggggcgt   1320

ggcgcggggc tcgccgtgcc gggcgggggg tggcggcagg tgggggtgcc gggcggggcg   1380

gggccgcctc gggccgggga gggctcgggg gaggggcgcg gcggcccccg gagcgccggc   1440

ggctgtcgag gcgcggcgag ccgcagccat tgccttttat ggtaatcgtg cgagagggcg   1500

cagggacttc ctttgtccca aatctgtgcg gagccgaaat ctgggaggcg ccgccgcacc   1560

ccctctagcg ggcgcggggc gaagcggtgc ggcgccggca ggaaggaaat gggcggggag   1620

ggccttcgtg cgtcgccgcg ccgccgtccc cttctccctc tccagcctcg gggctgtccg   1680
```

-continued

```
cggggggacg gctgccttcg ggggggacgg ggcagggcgg ggttcggctt ctggcgtgtg   1740
accggcggca tcgattgaat tcgccaccat gtcagaaggg gtgggcacgt tccgcatggt   1800
acctgaagag gaacaggagc tccgtgccca actggagcag ctcacaacca aggaccatgg   1860
acctgtcttt ggcccgtgca gccagctgcc ccgccacacc ttgcagaagg ccaaggatga   1920
gctgaacgag agagaggaga cccgggagga ggcagtgcga gagctgcagg agatggtgca   1980
ggcgcaggcg gcctcggggg aggagctggc ggtggccgtg gcggagaggg tgcaagagaa   2040
ggacagcggc ttcttcctgc gcttcatccg cgcacggaag ttcaacgtgg gccgtgccta   2100
tgagctgctc agaggctatg tgaatttccg gctgcagtac cctgagctct ttgacagcct   2160
gtccccagag gctgtccgct gcaccattga agctggctac cctggtgtcc tctctagtcg   2220
ggacaagtat ggccgagtgg tcatgctctt caacattgag aactggcaaa gtcaagaaat   2280
cacctttgat gagatcttgc aggcatattg cttcatcctg gagaagctgc tggagaatga   2340
ggaaactcaa atcaatggct tctgcatcat tgagaacttc aagggcttta ccatgcagca   2400
ggctgctagt ctccggactt cagatctcag gaagatggtg gacatgctcc aggattcctt   2460
cccagcccgg ttcaaagcca tccacttcat ccaccagcca tggtacttca ccacgaccta   2520
caatgtggtc aagcccttct tgaagagcaa gctgcttgag agggtctttg tccacgggga   2580
tgacctttct ggtttctacc aggagatcga tgagaacatc ctgccctctg acttcggggg   2640
cacgctgccc aagtatgatg gcaaggccgt tgctgagcag ctctttggcc cccaggccca   2700
agctgagaac acagccttct gaggatcgta ccggtcgacc tgcagaagct tgcctcgagc   2760
agcgctgctc gagagatctg gatcataatc agccatacca catttgtaga ggttttactt   2820
gctttaaaaa acctcccaca cctccccctg aacctgaaac ataaaatgaa tgcaattgtt   2880
gttgttaact tgtttattgc agcttataat ggttacaaat aaagcaatag catcacaaat   2940
ttcacaaata aagcattttt ttcactgcat tctagttgtg gtttgtccaa actcatcaat   3000
gtatcttatc atgtctggta ctagggttac cccagaacag gtcccattca tggcccacat   3060
gacaacctgc ttccccagtg ggtatttttg gagacagctc ttctgtttcc aggttttctc   3120
tcctgcctaa atgtcctgcc taagtgcctt caagaaccct tcaccatcct gctcctgcat   3180
gtgaccaggt tccatggtca gttcaatcac ctagtcacag ttggtaagtg acagagttgg   3240
gacttgaacc tatgcctgcc tgacaccaag tcttttttg acacctagag ccaagacatc   3300
tgaagacaaa ctccctagga gagctggcgt catagaaacc ttaaaggtta gggagacctg   3360
ggtttgaatc aggctttgtc agttatgact tgtgtgaccc tagcaagtta tttaaccttt   3420
ctgggtctca gtttcctcat ctgcaaactg aggataataa cagtacctac caaaaagaac   3480
tgtcgtgaaa accatataat ttctgcaatg ctcctggcac agtgtcctgt tctaaagcat   3540
agttcccctt ctctttctta gctccatatt gattattacc ctaacttgca caaagagact   3600
tggaggaccc ccatagagta tcggagggtc ccccatttcc tgctctttcc actccacacc   3660
cccagcaagc acagggaagt tctgggggcc ataatccacc cacaggaacc aaatctaagc   3720
cacctttctg gctggtagac atccaggtat gtgggcacag aggtagacag gctgaaatgc   3780
tgctgtgcta tcagttgggt tttgctggaa caggaatgga aatggagagg ctgacagaac   3840
tgccctgggg agcccaggca agagggacag tggctggaca cccccagcca gttgtgcaga   3900
ccatcagaac aagatcctag attttaggaa tacagggttc aagtccgtgc ggcaactctt   3960
ttctaaatat gcccaagcca ttaactttga gttttaaaaa tactgattta caagctgtac   4020
acaatgaaaa aatgcctatc cctcacacca tgctgatgct gttccctgcc atctcagatt   4080
```

accaattaaa tacagaatgc ccagttaaat gtgaactttt tttttttttt tttttttgag 4140
atggagtttt gttcttgtcg cccaggctag agtgcaatgg tgcgatctca gctcactgca 4200
acctctgcct cccaggttca agcaattctc ctgccttagc ctcctgagta gctggaacta 4260
caggtgccca ccagcacgcc tggctaattt ttggtatttt tagtggagat ggggtttcac 4320
catgttggcc aggctggtct cgaactcctg acctcaggtg atctgcctgc ctcggcctcc 4380
caaagtgctg ggattacagg cgtgagccta aatgtgaact tttttaatac taaaaaagta 4440
tttgctgttc atcggaaatt cacatttaac tgggtgtcct gtatttttat ttgctaaatc 4500
taccatcaaa ttggtctggc tcaacctgga gaatggttac cctaggtaac cacgtgcgga 4560
ccgagcggcc gcaggaaccc ctagtgatgg agttggccac tccctctctg cgcgctcgct 4620
cgctcactga ggccgggcga ccaaaggtcg cccgacgccc gggctttgcc cgggcggcct 4680
cagtgagcga gcgagcgcgc ag 4702

<210> SEQ ID NO 55
<211> LENGTH: 3873
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 55
ctgcgcgctc gctcgctcac tgaggccgcc cgggcgtcgg gcgacctttg gtcgcccggc 60
ctcagtgagc gagcgagcgc gcagagaggg agtggccaac tccatcacta ggggttcctg 120
cggccgcacg cgtttgtcct ctccctgctt ggccttaacc agccacattt ctcaactgac 180
cccactcact gcagaggtga aaactaccat gccaggtcct gctggctggg ggaggggtgg 240
gcaataggcc tggatttgcc agagctgcca ctgtagatgt agtcatattt acgatttccc 300
ttcacctctt attaccctgg tggtggtggt gggggggggg gggtgctctc tcagcaaccc 360
caccccggga tcttgaggag aaagagggca gagaaaagag ggaatgggac tggcccagat 420
cccagcccca cagccgggct tccacatggc cgagcaggaa ctccagagca ggagcacaca 480
aaggagggct ttgatgcgcc tccagccagg cccaggcctc tcccctctcc cctttctctc 540
tgggtcttcc tttgccccac tgagggcctc ctgtgagccc gatttaacgg aaactgtggg 600
cggtgagaag ttccttatga cacactaatc ccaacctgct gaccggacca cgcctccagc 660
ggagggaacc tctagagctc caggacattc aggtaccagg tagccccaag gaggagctgc 720
cgaatcgatg gatcgggaac tgaaaaacca gaaagttaac tggtaagttt agtctttttg 780
tcttttattt caggtcccgg atccggtggt ggtgcaaatc aaagaactgc tcctcagtgg 840
atgttgcctt tacttctagg cctgtacgga agtgttactt ctgctctaaa agctgcggaa 900
ttgtacccgc cccgggatcc atcgattgaa ttcgccacca tgtcagaagg ggtgggcacg 960
ttccgcatgg tacctgaaga ggaacaggag ctccgtgccc aactggagca gctcacaacc 1020
aaggaccatg gacctgtctt tggcccgtgc agccagctgc cccgccacac cttgcagaag 1080
gccaaggatg agctgaacga gagagaggag acccgggagg aggcagtgcg agagctgcag 1140
gagatggtgc aggcgcaggc ggcctcgggg gaggagctgg cggtggccgt ggcggagagg 1200
gtgcaagaga aggacagcgg cttcttcctg cgcttcatcc gcgcacggaa gttcaacgtg 1260
ggccgtgcct atgagctgct cagaggctat gtgaatttcc ggctgcagta ccctgagctc 1320
tttgacagcc tgtccccaga ggctgtccgc tgcaccattg aagctggcta ccctggtgtc 1380
ctctctagtc gggacaagta tggccgagtg gtcatgctct tcaacattga gaactggcaa 1440
agtcaagaaa tcacctttga tgagatcttg caggcatatt gcttcatcct ggagaagctg 1500
ctggagaatg aggaaactca aatcaatggc ttctgcatca ttgagaactt caagggcttt 1560
accatgcagc aggctgctag tctccggact tcagatctca ggaagatggt ggacatgctc 1620
caggattcct tcccagcccg gttcaaagcc atccacttca tccaccagcc atggtacttc 1680
accacgacct acaatgtggt caagcccttc ttgaagagca agctgcttga gagggtcttt 1740
gtccacgggg atgacctttc tggtttctac caggagatcg atgagaacat cctgccctct 1800
gacttcgggg gcacgctgcc caagtatgat ggcaaggccg ttgctgagca gctctttggc 1860
ccccaggccc aagctgagaa cacagccttc tgaggatcgt accggtcgac ctgcagaagc 1920
ttgcctcgag cagcgctgct cgagagatct ggatcataat cagccatacc acatttgtag 1980
aggttttact tgctttaaaa aacctcccac acctccccct gaacctgaaa cataaaatga 2040
atgcaattgt tgttgttaac ttgtttattg cagcttataa tggttacaaa taaagcaata 2100
gcatcacaaa tttcacaaat aaagcatttt tttcactgca ttctagttgt ggtttgtcca 2160
aactcatcaa tgtatcttat catgtctggt actagggtta ccccagaaca ggtcccattc 2220
atggcccaca tgacaacctg cttccccagt gggtattttt ggagacagct cttctgtttc 2280
caggttttct ctcctgccta aatgtcctgc ctaagtgcct tcaagaaccc ttcaccatcc 2340
tgctcctgca tgtgaccagg ttccatggtc agttcaatca cctagtcaca gttggtaagt 2400
gacagagttg ggacttgaac ctatgcctgc ctgacaccaa gtcttttttt gacacctaga 2460
gccaagacat ctgaagacaa actccctagg agagctggcg tcatagaaac cttaaaggtt 2520
agggagacct gggtttgaat caggctttgt cagttatgac ttgtgtgacc ctagcaagtt 2580
atttaacctt tctgggtctc agtttcctca tctgcaaact gaggataata acagtaccta 2640
ccaaaaagaa ctgtcgtgaa aaccatataa tttctgcaat gctcctggca cagtgtcctg 2700
ttctaaagca tagttcccct tctctttctt agctccatat tgattattac cctaacttgc 2760
acaaagagac ttggaggacc cccatagagt atcggagggt cccccatttc ctgctctttc 2820
cactccacac ccccagcaag cacagggaag ttctgggggc cataatccac ccacaggaac 2880
caaatctaag ccacctttct ggctggtaga catccaggta tgtgggcaca gaggtagaca 2940
ggctgaaatg ctgctgtgct atcagttggg ttttgctgga acaggaatgg aaatggagag 3000
gctgacagaa ctgccctggg gagcccaggc aagagggaca gtggctggac acccccagcc 3060
agttgtgcag accatcagaa caagatccta gattttagga atacagggtt caagtccgtg 3120
cggcaactct tttctaaata tgcccaagcc attaactttg agttttaaaa atactgattt 3180
acaagctgta cacaatgaaa aaatgcctat ccctcacacc atgctgatgc tgttccctgc 3240
catctcagat taccaattaa atacagaatg cccagttaaa tgtgaacttt tttttttttt 3300
ttttttttga gatggagttt tgttcttgtc gcccaggcta gagtgcaatg gtgcgatctc 3360
agctcactgc aacctctgcc tcccaggttc aagcaattct cctgccttag cctcctgagt 3420
agctggaact acaggtgccc accagcacgc ctggctaatt tttggtattt ttagtggaga 3480
tggggtttca ccatgttggc caggctggtc tcgaactcct gacctcaggt gatctgcctg 3540
cctcggcctc ccaaagtgct gggattacag gcgtgagcct aaatgtgaac ttttttaata 3600
ctaaaaaagt atttgctgtt catcggaaat tcacatttaa ctgggtgtcc tgtattttta 3660
tttgctaaat ctaccatcaa attggtctgg ctcaacctgg agaatggtta ccctaggtaa 3720
ccacgtgcgg accgagcggc cgcaggaacc cctagtgatg gagttggcca ctccctctct 3780
gcgcgctcgc tcgctcactg aggccgggcg accaaaggtc gcccgacgcc cgggctttgc 3840
ccgggcggcc tcagtgagcg agcgagcgcg cag 3873

<210> SEQ ID NO 56
<211> LENGTH: 2119
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56
cgcgctcgct cgctcactga ggccgcccgg gcaaagcccg ggcgtcgggc gacctttggt 60
cgcccggcct cagtgagcga gcgagcgcgc agagagggag tggggtacca cgcgtttgtc 120
ctctccctgc ttggccttaa ccagccacat ttctcaactg accccactca ctgcagaggt 180
gaaaactacc atgccaggtc ctgctggctg ggggaggggt gggcaatagg cctggatttg 240
ccagagctgc cactgtagat gtagtcatat ttacgatttc ccttcacctc ttattaccct 300
ggtggtggtg gtgggggggg gggggtgctc tctcagcaac cccaccccgg gatcttgagg 360
agaaagaggg cagagaaaag agggaatggg actggcccag atcccagccc cacagccggg 420
cttccacatg gccgagcagg aactccagag caggagcaca caaaggaggg ctttgatgcg 480
cctccagcca ggcccaggcc tctcccctct cccctttctc tctgggtctt cctttgcccc 540
actgagggcc tcctgtgagc ccgatttaac ggaaactgtg ggcggtgaga agttccttat 600
gacacactaa tcccaacctg ctgaccggac cacgcctcca gcggagggaa cctctagagc 660
tccaggacat tcaggtacca ggtagcccca aggaggagct gccgaatcga tggatcggga 720
actgaaaaac cagaaagtta actggtaagt ttagtctttt tgtcttttat ttcaggtccc 780
ggatccggtg gtggtgcaaa tcaaagaact gctcctcagt ggatgttgcc tttacttcta 840
ggcctgtacg gaagtgttac ttctgctcta aaagctgcgg aattgtaccc gccccgggat 900
ccatcgattg aattccccgg ggatcctcta gagtcgaaat tcgccaccat ggtgagcaag 960
ggcgaggagc tgttcaccgg ggtggtgccc atcctggtcg agctggacgg cgacgtaaac 1020
ggccacaagt tcagcgtgtc cggcgagggc gagggcgatg ccacctacgg caagctgacc 1080
ctgaagttca tctgcaccac cggcaagctg cccgtgccct ggcccaccct cgtgaccacc 1140
ctgacctacg gcgtgcagtg cttcagccgc taccccgacc acatgaagca gcacgacttc 1200
ttcaagtccg ccatgcccga aggctacgtc caggagcgca ccatcttctt caaggacgac 1260
ggcaactaca agacccgcgc cgaggtgaag ttcgagggcg acaccctggt gaaccgcatc 1320
gagctgaagg gcatcgactt caaggaggac ggcaacatcc tggggcacaa gctggagtac 1380
aactacaaca gccacaacgt ctatatcatg gccgacaagc agaagaacgg catcaaggtg 1440
aacttcaaga tccgccacaa catcgaggac ggcagcgtgc agctcgccga ccactaccag 1500
cagaacaccc ccatcggcga cggccccgtg ctgctgcccg acaaccacta cctgagcacc 1560
cagtccgccc tgagcaaaga ccccaacgag aagcgcgatc acatggtcct gctggagttc 1620
gtgaccgccg ccgggatcac tctcggcatg gacgagctgt acaagtaata gggtaccggt 1680
cgacctgcag aagcttgcct cgagcagcgc tgctcgagag atctggatca taatcagcca 1740
taccacattt gtagaggttt tacttgcttt aaaaaacctc ccacacctcc ccctgaacct 1800
gaaacataaa atgaatgcaa ttgttgttgt taacttgttt attgcagctt ataatggtta 1860
caaataaagc aatagcatca caaatttcac aaataaagca ttttttttcac tgcattctag 1920 ttgtggtttg tccaaactca tcaatgtatc ttatcatgtc tggtaaccac gtgcggaccg 1980
agcggccgca ggaacccta gtgatggagt tggccactcc ctctctgcgc gctcgctcgc 2040
tcactgaggc cgggcgacca aaggtcgccc gacgcccggg ctttgcccgg gcggcctcag 2100
tgagcgagcg agcgcgcag 2119

<210> SEQ ID NO 57
<211> LENGTH: 4503
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 57
ctgcgcgctc gctcgctcac tgaggccgcc cgggcgtcgg gcgacctttg gtcgcccggc 60
ctcagtgagc gagcgagcgc gcagagaggg agtggccaac tccatcacta ggggttcctg 120
cggccgcacg cagcttttgt cctctccctg cttggcctta accagccaca tttctcaact 180
gaccccactc actgcagagg tgaaaactac catgccaggt cctgctggct gggggagggg 240
tgggcaatag gcctggattt gccagagctg ccactgtaga tgtagtcata tttacgattt 300
cccttcacct cttattaccc tggtggtggt ggtggggggg ggggggtgct ctctcagcaa 360
ccccaccccg ggatcttgag gagaaagagg gcagagaaaa gagggaatgg gactggccca 420
gatcccagcc ccacagccgg gcttccacat ggccgagcag gaactccaga gcaggagcac 480
acaaaggagg gctttgatgc gcctccagcc aggcccaggc ctctcccctc tcccctttct 540
ctctgggtct tcctttgccc cactgagggc ctcctgtgag cccgatttaa cggaaactgt 600
gggcggtgag aagttcctta tgacacacta atcccaacct gctgaccgga ccacgcctcc 660
agcggaggga acctctagag ctccaggaca ttcaggtacc aggtagcccc aaggaggagc 720
tgccgacctg gcaggtaagt caatacctgg ggcttgcctg ggccagggag cccaggactg 780
gggtgaggac tcaggggagc agggagacca cgtcccaaga tgcctgtaaa actgaaacca 840
cctggccatt ctccaggttg agccagacca atttgatggc agatttagca aataaaaata 900
caggacaccc agttaaatgt gaatttcaga tgaacagcaa atactttttt agtattaaaa 960
aagttcacat ttaggctcac gcctgtaatc ccagcacttt gggaggccga ggcaggcaga 1020
tcacctgagg tcaggagttc gagaccagcc tggccaacat ggtgaaaccc catctccact 1080
aaaaatacca aaaattagcc aggcgtgctg gtgggcacct gtagttccag ctactcagga 1140
ggctaaggca ggagaattgc ttgaacctgg gaggcagagg ttgcagtgag ctgagatcgc 1200
accattgcac tctagcctgg gcgacaagaa caaaactcca tctcaaaaaa aaaaaaaaaa 1260
aaaaagttca catttaactg ggcattctgt atttaattgg taatctgaga tggcagggaa 1320
cagcatcagc atggtgtgag ggataggcat tttttcattg tgtacagctt gtaaatcagt 1380
atttttaaaa ctcaaagtta atggcttggg catatttaga aaagagttgc cgcacggact 1440
tgaaccctgt attcctaaaa tctaggatct tgttctgatg gtctgcacaa ctggctgggg 1500
gtgtccagcc actgtccctc ttgcctgggc tccccagggc agttctgtca gcctctccat 1560
ttccattcct gttccagcaa aacccaactg atagcacagc agcatttcag cctgtctacc 1620
tctgtgccca catacctgga tgtctaccag ccagaaaggt ggcttagatt tggttcctgt 1680
gggtggatta tggcccccag aacttccctg tgcttgctgg gggtgtggag tggaaagagc 1740

-continued

```
aggaaatggg ggaccctccg atactctatg ggggtcctcc aagtctcttt gtgcaagtta   1800
gggtaataat caatatggag ctaagaaaga gaaggggaac tatgctttag aacaggacac   1860
tgtgccagga gcattgcaga aattatatgg ttttcacgac agttcttttt ggtaggtact   1920
gttattatcc tcagtttgca gatgaggaaa ctgagaccca gaaaggttaa ataacttgct   1980
agggtcacac aagtcataac tgacaaagcc tgattcaaac ccaggtctcc ctaaccttta   2040
aggtttctat gacgccagct ctcctaggga gtttgtcttc agatgtcttg gctctaggtg   2100
tcaaaaaaag acttggtgtc aggcaggcat aggttcaagt cccaactctg tcacttacca   2160
actgtgacta ggtgattgaa ctgaccatgg aacctggtca catgcaggag caggatggtg   2220
aagggttctt gaaggcactt aggcaggaca tttaggcagg agagaaaacc tggaaacaga   2280
agagctgtct ccaaaaatac ccactgggga agcaggttgt catgtgggcc atgaatggga   2340
cctgttctgg taaccaagca ttgcttatgt gtccattaca tttcataaca cttccatcct   2400
actttacagg gaacaaccaa gactggggtt aaatctcaca gcctgcaagt ggaagagaag   2460
aacttgaacc caggtccaac ttttgcgcca cagcaggctg cctcttggtc ctgacaggaa   2520
gtcacaactt gggtctgagt actgatccct ggctattttt tggctgtgtt accttggaca   2580
agtcacttat tcctcctccc gtttcctcct atgtaaaatg gaaataataa tgttgaccct   2640
gggtctgaga gagtggattt gaaagtactt agtgcatcac aaagcacaga acacacttcc   2700
agtctcgtga ttatgtactt atgtaactgg tcatcaccca tcttgagaat gaatgcattg   2760
gggaaagggc catccactag gctgcgaagt ttctgaggga ctccttcggg ctggagaagg   2820
atggccacag gagggaggag agattgcctt atcctgcagt gatcatgtca ttgagaacag   2880
agccagattc tttttttcct ggcagggcca acttgtttta acatctaagg actgagctat   2940
ttgtgtctgt gccctttgtc caagcagtgt ttcccaaagt gtagcccaag aaccatctcc   3000
ctcagagcca ccaggaagtg ctttaaattg caggttccta ggccacagcc tgcacctgca   3060
gagtcagaat catggaggtt gggacccagg cacctgcgtt tctaacaaat gcctcgggtg   3120
attctgatgc aattgaaagt ttgagatcca cagttctgag acaataacag aatggttttt   3180
ctaacccctg cagccctgac ttcctatcct agggaagggg ccggctggag aggccaggac   3240
agagaaagca gatcccttct ttttccaagg actctgtgtc ttccataggc aacgaattcc   3300
ccggggatcc tctagagtcg aaattcgcca ccatggtgag caagggcgag gagctgttca   3360
ccggggtggt gcccatcctg gtcgagctgg acggcgacgt aaacggccac aagttcagcg   3420
tgtccggcga gggcgagggc gatgccacct acggcaagct gaccctgaag ttcatctgca   3480
ccaccggcaa gctgcccgtg ccctggccca ccctcgtgac caccctgacc tacggcgtgc   3540
agtgcttcag ccgctacccc gaccacatga agcagcacga cttcttcaag tccgccatgc   3600
ccgaaggcta cgtccaggag cgcaccatct tcttcaagga cgacggcaac tacaagaccc   3660
gcgccgaggt gaagttcgag ggcgacaccc tggtgaaccg catcgagctg aagggcatcg   3720
acttcaagga ggacggcaac atcctggggc acaagctgga gtacaactac aacagccaca   3780
acgtctatat catggccgac aagcagaaga acggcatcaa ggtgaacttc aagatccgcc   3840
acaacatcga ggacggcagc gtgcagctcg ccgaccacta ccagcagaac acccccatcg   3900
gcgacggccc cgtgctgctg cccgacaacc actacctgag cacccagtcc gccctgagca   3960
aagaccccaa cgagaagcgc gatcacatgg tcctgctgga gttcgtgacc gccgccggga   4020
tcactctcgg catggacgag ctgtacaagt aatagggtac cggtcgacct gcagaagctt   4080
gcctcgagca gcgctgctcg agagatctgg atcataatca gccataccac atttgtagag   4140
```

-continued gttttacttg ctttaaaaaa cctcccacac ctccccctga acctgaaaca taaaatgaat 4200
gcaattgttg ttgttaactt gtttattgca gcttataatg gttacaaata aagcaatagc 4260
atcacaaatt tcacaaataa agcatttttt tcactgcatt ctagttgtgg tttgtccaaa 4320
ctcatcaatg tatcttatca tgtctggtaa ccacgtgcgg accgagcggc cgcaggaacc 4380
cctagtgatg gagttggcca ctccctctct gcgcgctcgc tcgctcactg aggccgggcg 4440
accaaaggtc gcccgacgcc cgggctttgc ccgggcggcc tcagtgagcg agcgagcgcg 4500
cag 4503

<210> SEQ ID NO 58
<211> LENGTH: 4543
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 58
ctgcgcgctc gctcgctcac tgaggccgcc cgggcgtcgg gcgacctttg gtcgcccggc 60
ctcagtgagc gagcgagcgc gcagagaggg agtggccaac tccatcacta ggggttcctg 120
cggccgcacg cgtgacgtcg tttaaacggg ccccggtgtt atctcattct tttttctcct 180
ctgtaagttg acatgtgatg tgggaacaaa ggggataaag tcattatttt gtgctaaaat 240
cgtaattgga gaggacctcc tgttagctgg gctttcttct atttattgtg gtggttactg 300
gagttccttc ttctagtttt aggatatata tatatatttt tttttttct ttccctgaag 360 atataataat atatatactt ctgaagattg agatttttaa attagttgta ttgaaaacta 420
gctaatcagc aatttaaggc tagcttgaga cttatgtctt gaatttgttt ttgtaggctc 480
caaaaccaag gagggagtgg tgcatggtgt ggcaacaggt aagctccatt gtgcttatat 540
ccaaagatga tatttaaagt atctagtgat tagtgtggcc cagtattcaa gattcctatg 600
aaattgtaaa acaatcactg agcattctaa gaacatatca gtcttattga aactgaattc 660
tttataaagt atttttaaaa aggtaaatat tgattataaa taaaaaatat acttgccaag 720
aataatgagg gctttgaatt gataagctat gtttaattta tagtaagtgg gcatttaaat 780
attctgacca aaaatgtatt gacaaactgc tgacaaaaat aaaatgtgaa tattgccata 840
attttaaaaa aagagtaaaa tttctgttga ttacagtaaa atattttgac cttaaattat 900
gttgattaca atattccttt gataattcag agtgcatttc aggaaacacc cttggacagt 960
cagtaaattg tttattgtat ttatctttgt attgttatgg tatagctatt tgtacaaata 1020
ttattgtgca attattacat ttctgattat attattcatt tggcctaaat ttaccaagaa 1080
tttgaacaag tcaattaggt ttacaatcaa gaaatatcaa aaatgatgaa aaggatgata 1140
atcatcatca gatgttgagg aagatgacga tgagagtgcc agaaatagag aaatcaaagg 1200
agaaccaaaa tttaacaaat taaaagccca cagacttgct gtaattaagt tttctgttgt 1260
aagtactcca cgtttcctgg cagatgtggt gaagcaaaag atataatcag aaatataatt 1320
tatatgatcg gaaagcatta aacacaatag tgcctataca aataaaatgt tcctatcact 1380
gacttctaaa atggaaatga ggacaatgat atgggaatct taatacagtg ttgtggatag 1440
gactaaaaac acaggagtca gatcttcttg gttcaacttc ctgcttactc cttaccagct 1500
gtgtgttttt tgcaaggttc ttcacctcta tgtgatttag cttcctcatc tataaaataa 1560
ttcagtgaat taatgtacac aaaacatctg gaaaacaaaa gcaaacaata tgtattttat 1620

-continued

```
aagtgttact tatagtttta tagtgaactt tcttgtgcaa catttttaca actagtggag   1680
aaaaatattt ctttaaatga atacttttga tttaaaaatc agagtgtaaa aataaaacag   1740
actcctttga aactagttct gttagaagtt aattgtgcac ctttaatggg ctctgttgca   1800
atccaacaga gaagtagtta agtaagtgga ctatgatggc ttctagggac ctcctataaa   1860
tatgatattg tgaagcatga ttataataag aactagataa cagacaggtg gagactccac   1920
tatctgaaga gggtcaacct agatgaatgg tgttccattt agtagttgag gaagaaccca   1980
tgaggtttag aaagcagaca agcatgtggc aagttctgga gtcagtggta aaaattaaag   2040
aacccaacta ttactgtcac ctaatgatct aatggagact gtggagatgg gctgcatttt   2100
tttaatcttc tccagaatgc caaaatgtaa acacatatct gtgtgtgtgt gtgtgtgtgt   2160
gtgtgtgtgt gagagagaga gagagagaga gagagactga agtttgtaca attagacatt   2220
ttataaaatg ttttctgaag gacagtggct cacaatctta agtttctaac attgtacaat   2280
gttgggagac tttgtatact ttattttctc tttagcatat taaggaatct gagatgtcct   2340
acagtaaaga aatttgcatt acatagttaa aatcagggtt attcaaactt tttgattatt   2400
gaaacctttc ttcattagtt actagggttg aatgaaacta gtgttccaca gaaaactatg   2460
ggaaatgttg ctaggcagta aggacatggt gatttcagca tgtgcaatat ttacagcgat   2520
tgcacccatg gaccaccctg gcagtagtga aataaccaaa aatgctgtca taactagtat   2580
ggctatgaga aacacattgg gcagaagctt gcctcgagca gcgctgctcg agagatctgg   2640
atcataatca gccataccac atttgtagag gttttacttg ctttaaaaaa cctcccacac   2700
ctccccctga acctgaaaca taaaatgaat gcaattgttg ttgttaactt gtttattgca   2760
gcttataatg gttacaaata aagcaatagc atcacaaatt tcacaaataa agcatttttt   2820
tcactgcatt ctagttgtgg tttgtccaaa ctcatcaatg tatcttatca tgtctggtaa   2880
ccattctcca ggttgagcca gaccaatttg atggtagatt tagcaaataa aaatacagga   2940
cacccagtta aatgtgaatt tccgatgaac agcaaatact tttttagtat taaaaaagtt   3000
cacatttagg ctcacgcctg taatcccagc actttgggag gccgaggcag gcagatcacc   3060
tgaggtcagg agttcgagac cagcctggcc aacatggtga aaccccatct ccactaaaaa   3120
taccaaaaat tagccaggcg tgctggtggg cacctgtagt tccagctact caggaggcta   3180
aggcaggaga attgcttgaa cctgggaggc agaggttgca gtgagctgag atcgcaccat   3240
tgcactctag cctgggcgac aagaacaaaa ctccatctca aaaaaaaaaa aaaaaaaaaa   3300
gttcacattt aactgggcat tctgtattta attggtaatc tgagatggca gggaacagca   3360
tcagcatggt gtgagggata ggcatttttt cattgtgtac agcttgtaaa tcagtatttt   3420
taaaactcaa agttaatggc ttgggcatat ttagaaaaga gttgccgcac ggacttgaac   3480
cctgtattcc taaaatctag gatcttgttc tgatggtctg cacaactggc tgggggtgtc   3540
cagccactgt ccctcttgcc tgggctcccc agggcagttc tgtcagcctc tccatttcca   3600
ttcctgttcc agcaaaaccc aactgatagc acagcagcat ttcagcctgt ctacctctgt   3660
gcccacatac ctggatgtct accagccaga aaggtggctt agatttggtt cctgtgggtg   3720
gattatggcc cccagaactt ccctgtgctt gctgggggtg tggagtggaa agagcaggaa   3780
atgggggacc ctccgatact ctatgggggt cctccaagtc tctttgtgca agttagggta   3840
ataatcaata tggagctaag aaagagaagg ggaactatgc tttagaacag gacactgtgc   3900
caggagcatt gcagaaatta tatggttttc acgacagttc tttttggtag gtactgttat   3960
```

tatcctcagt ttgcagatga ggaaactgag acccagaaag gttaaataac ttgctagggt 4020
cacacaagtc ataactgaca aagcctgatt caaacccagg tctccctaac ctttaaggtt 4080
tctatgacgc cagctctcct agggagtttg tcttcagatg tcttggctct aggtgtcaaa 4140
aaaagacttg gtgtcaggca ggcataggtt caagtcccaa ctctgtcact taccaactgt 4200
gactaggtga ttgaactgac catggaacct ggtcacatgc aggagcagga tggtgaaggg 4260
ttcttgaagg cacttaggca ggacatttag gcaggagaga aaacctggaa acagaagagc 4320
tgtctccaaa aatacccact ggggaagcag gttgtcatgt gggccatgaa tgggacctgt 4380
tctggggtaa ccacgtgcgg accgagcggc cgcaggaacc cctagtgatg gagttggcca 4440
ctccctctct gcgcgctcgc tcgctcactg aggccgggcg accaaaggtc gcccgacgcc 4500
cgggctttgc ccgggcggcc tcagtgagcg agcgagcgcg cag 4543

<210> SEQ ID NO 59
<211> LENGTH: 4438
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 59
ctgcgcgctc gctcgctcac tgaggccgcc cgggcgtcgg gcgacctttg gtcgcccggc 60
ctcagtgagc gagcgagcgc gcagagaggg agtggccaac tccatcacta ggggttcctg 120
cggccgcacg cgttacgtaa tatttattga agtttaatat tgtgtttgtg atacagaagt 180
atttgcttta attctaaata aaaattttat gcttttattg ctggtttaag aagatttgga 240
ttatccttgt actttgagga gaagtttctt atttgaaata ttttggaaac aggtctttta 300
atgtggaaag atagatatta atctcctctt ctattactct ccaagatcca acaaaagtga 360
ttataccccc caaaatatga tggtagtatc ttatactacc atcattttat aggcataggg 420
ctcttagctg caaataatgg aactaactct aataaagcag aacgcaaata ttgtaaatat 480
tagagagcta acaatctctg ggatggctaa aggatggagc ttggaggcta cccagccagt 540
aacaatattc cgggctccac tgttgaatgg agacactaca actgccttgg atgggcagag 600
atattatgga tgctaagccc caggtgctac cattaggact tctaccactg tccctaacgg 660
gtggagccca tcacatgcct atgccctcac tgtaaggaaa tgaagctact gttgtatatc 720
ttgggaagca cttggattaa ttgttataca gttttgttga agaagacccc tagggtaagt 780
agccataact gcacactaaa tttaaaattg ttaatgagtt tctcaaaaaa aatgttaagg 840
ttgttagctg gtatagtata tatcttgcct gttttccaag gacttctttg ggcagtacct 900
tgtctgtgct ggcaagcaac tgagacttaa tgaaagagta ttggagatat gaatgaattg 960
atgctgtata ctctcagagt gccaaacata taccaatgga caagaaggtg aggcagagag 1020
cagacaggca ttagtgacaa gcaaagatat gcagaatttc attctcagca aatcaaaagt 1080
cctcaacctg gttggaagaa tattggcact gaatggtatc aataaggttg ctagagaggg 1140
ttagaggtgc acaatgtgct tccataacat tttatacttc tccaatctta gcactaatca 1200
aacatggttg aatactttgt ttactataac tcttacagag ttataagatc tgtgaagaca 1260
gggacaggga caatacccat ctctgtctgg ttcataggtg gtatgtaata gatattttta 1320
aaaataagtg agttaatgaa tgagggtgag aatgaaggca cagaggtatt agggggaggt 1380
gggccccaga gaatggtgcc aaggtccagt ggggtgactg ggatcagctc aggcctgacg 1440

-continued ctggccactc ccacctagct cctttctttc taatctgttc tcattctcct tgggaaggat 1500
tgaggtctct ggaaaacagc caaacaactg ttatgggaac agcaagccca aataaagcca 1560
agcatcaggg ggatctgaga gctgaaagca acttctgttc cccctccctc agctgaaggg 1620
gtggggaagg gctcccaaag ccataactcc ttttaaggga tttagaaggc ataaaaaggc 1680
ccctggctga gaacttcctt cttcattctg cagttggtga attccccggg gatcctctag 1740
agtcgaaatt cgccaccatg gtgagcaagg gcgaggagct gttcaccggg gtggtgccca 1800
tcctggtcga gctggacggc gacgtaaacg gccacaagtt cagcgtgtcc ggcgagggcg 1860
agggcgatgc cacctacggc aagctgaccc tgaagttcat ctgcaccacc ggcaagctgc 1920
ccgtgccctg gcccaccctc gtgaccaccc tgacctacgg cgtgcagtgc ttcagccgct 1980
accccgacca catgaagcag cacgacttct tcaagtccgc catgcccgaa ggctacgtcc 2040
aggagcgcac catcttcttc aaggacgacg gcaactacaa gacccgcgcc gaggtgaagt 2100
tcgagggcga caccctggtg aaccgcatcg agctgaaggg catcgacttc aaggaggacg 2160
gcaacatcct ggggcacaag ctggagtaca actacaacag ccacaacgtc tatatcatgg 2220
ccgacaagca gaagaacggc atcaaggtga acttcaagat ccgccacaac atcgaggacg 2280
gcagcgtgca gctcgccgac cactaccagc agaacacccc catcggcgac ggccccgtgc 2340
tgctgcccga caaccactac ctgagcaccc agtccgccct gagcaaagac cccaacgaga 2400
agcgcgatca catggtcctg ctggagttcg tgaccgccgc cgggatcact ctcggcatgg 2460
acgagctgta caagtaatag ggtaccggtc gacctgcaga agcttgcctc gagcagcgct 2520
gctcgagaga tctggatcat aatcagccat accacatttg tagaggtttt acttgcttta 2580
aaaaacctcc cacacctccc cctgaacctg aaacataaaa tgaatgcaat tgttgttgtt 2640
aacttgttta ttgcagctta taatggttac aaataaagca atagcatcac aaatttcaca 2700
aataaagcat ttttttcact gcattctagt tgtggtttgt ccaaactcat caatgtatct 2760
tatcatgtct ggtaaccatt ctccaggttg agccagacca atttgatggt agatttagca 2820
aataaaaata caggacaccc agttaaatgt gaatttccga tgaacagcaa atactttttt 2880
agtattaaaa aagttcacat ttaggctcac gcctgtaatc ccagcacttt gggaggccga 2940
ggcaggcaga tcacctgagg tcaggagttc gagaccagcc tggccaacat ggtgaaaccc 3000
catctccact aaaaatacca aaaattagcc aggcgtgctg gtgggcacct gtagttccag 3060
ctactcagga ggctaaggca ggagaattgc ttgaacctgg gaggcagagg ttgcagtgag 3120
ctgagatcgc accattgcac tctagcctgg gcgacaagaa caaaactcca tctcaaaaaa 3180
aaaaaaaaaa aaaaagttca catttaactg ggcattctgt atttaattgg taatctgaga 3240
tggcagggaa cagcatcagc atggtgtgag ggataggcat tttttcattg tgtacagctt 3300
gtaaatcagt atttttaaaa ctcaaagtta atggcttggg catatttaga aaagagttgc 3360
cgcacggact tgaaccctgt attcctaaaa tctaggatct tgttctgatg gtctgcacaa 3420
ctggctgggg gtgtccagcc actgtccctc ttgcctgggc tccccagggc agttctgtca 3480
gcctctccat ttccattcct gttccagcaa aacccaactg atagcacagc agcatttcag 3540
cctgtctacc tctgtgccca catacctgga tgtctaccag ccagaaaggt ggcttagatt 3600
tggttcctgt gggtggatta tggcccccag aacttccctg tgcttgctgg gggtgtggag 3660
tggaaagagc aggaaatggg ggaccctccg atactctatg ggggtcctcc aagtctcttt 3720
gtgcaagtta gggtaataat caatatggag ctaagaaaga gaaggggaac tatgctttag 3780
aacaggacac tgtgccagga gcattgcaga aattatatgg ttttcacgac agttcttttt 3840
ggtaggtact gttattatcc tcagtttgca gatgaggaaa ctgagaccca gaaaggttaa 3900
ataacttgct agggtcacac aagtcataac tgacaaagcc tgattcaaac ccaggtctcc 3960
ctaaccttta aggtttctat gacgccagct ctcctaggga gtttgtcttc agatgtcttg 4020
gctctaggtg tcaaaaaaag acttggtgtc aggcaggcat aggttcaagt cccaactctg 4080
tcacttacca actgtgacta ggtgattgaa ctgaccatgg aacctggtca catgcaggag 4140
caggatggtg aagggttctt gaaggcactt aggcaggaca tttaggcagg agagaaaacc 4200
tggaaacaga agagctgtct ccaaaaatac ccactgggga agcaggttgt catgtgggcc 4260
atgaatggga cctgttctgg ggtaaccacg tgcggaccga gcggccgcag gaacccctag 4320
tgatggagtt ggccactccc tctctgcgcg ctcgctcgct cactgaggcc gggcgaccaa 4380
aggtcgcccg acgcccgggc tttgcccggg cggcctcagt gagcgagcga gcgcgcag 4438

<210> SEQ ID NO 60
<211> LENGTH: 3481
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 60
ctgcgcgctc gctcgctcac tgaggccgcc cgggcgtcgg gcgacctttg gtcgcccggc 60
ctcagtgagc gagcgagcgc gcagagaggg agtggccaac tccatcacta ggggttcctg 120
cggccgcacg cgttacgtaa ttctgtcatt ttactagggt gatgaaattc ccaagcaaca 180
ccatcctttt cagataaggg cactgaggct gagagaggag ctgaaaccta cccggcgtca 240
ccacacacag gtggcaaggc tgggaccaga aaccaggact gttgactgca gcccggtatt 300
cattctttcc atagcccaca gggctgtcaa agaccccagg gcctagtcag aggctcctcc 360
ttcctggaga gttcctggca cagaagttga agctcagcac agccccctaa cccccaactc 420
tctctgcaag gcctcagggg tcagaacact ggtggagcag atcctttagc ctctggattt 480
tagggccatg gtagaggggg tgttgcccta aattccagcc ctggtctcag cccaacaccc 540
tccaagaaga aattagaggg gccatggcca ggctgtgcta gccgttgctt ctgagcagat 600
tacaagaagg gactaagaca aggactcctt tgtggaggtc ctggcttagg gagtcaagtg 660
acggcggctc agcactcacg tgggcagtgc cagcctctaa gagtgggcag gggcactggc 720
cacagagtcc cagggagtcc caccagccta gtcgccagac cgaattcccc ggggatcctc 780
tagagtcgaa attcgccacc atggtgagca agggcgagga gctgttcacc ggggtggtgc 840
ccatcctggt cgagctggac ggcgacgtaa acggccacaa gttcagcgtg tccggcgagg 900
gcgagggcga tgccacctac ggcaagctga ccctgaagtt catctgcacc accggcaagc 960
tgcccgtgcc ctggcccacc ctcgtgacca ccctgaccta cggcgtgcag tgcttcagcc 1020
gctaccccga ccacatgaag cagcacgact tcttcaagtc cgccatgccc gaaggctacg 1080
tccaggagcg caccatcttc ttcaaggacg acggcaacta caagacccgc gccgaggtga 1140
agttcgaggg cgacaccctg gtgaaccgca tcgagctgaa gggcatcgac ttcaaggagg 1200
acggcaacat cctggggcac aagctggagt acaactacaa cagccacaac gtctatatca 1260
tggccgacaa gcagaagaac ggcatcaagg tgaacttcaa gatccgccac aacatcgagg 1320
acggcagcgt gcagctcgcc gaccactacc agcagaacac ccccatcggc gacggccccg 1380
tgctgctgcc cgacaaccac tacctgagca cccagtccgc cctgagcaaa gaccccaacg 1440
agaagcgcga tcacatggtc ctgctggagt tcgtgaccgc cgccgggatc actctcggca 1500
tggacgagct gtacaagtaa tagggtaccg gtcgacctgc agaagcttgc ctcgagcagc 1560
gctgctcgag agatctggat cataatcagc cataccacat ttgtagaggt tttacttgct 1620
ttaaaaaacc tcccacacct ccccctgaac ctgaaacata aaatgaatgc aattgttgtt 1680
gttaacttgt ttattgcagc ttataatggt tacaaataaa gcaatagcat cacaaatttc 1740
acaaataaag catttttttc actgcattct agttgtggtt tgtccaaact catcaatgta 1800
tcttatcatg tctggtaacc attctccagg ttgagccaga ccaatttgat ggtagattta 1860
gcaaataaaa atacaggaca cccagttaaa tgtgaatttc cgatgaacag caaatacttt 1920
tttagtatta aaaaagttca catttaggct cacgcctgta atcccagcac tttgggaggc 1980
cgaggcaggc agatcacctg aggtcaggag ttcgagacca gcctggccaa catggtgaaa 2040
ccccatctcc actaaaaata ccaaaaatta gccaggcgtg ctggtgggca cctgtagttc 2100
cagctactca ggaggctaag gcaggagaat tgcttgaacc tgggaggcag aggttgcagt 2160
gagctgagat cgcaccattg cactctagcc tgggcgacaa gaacaaaact ccatctcaaa 2220
aaaaaaaaaa aaaaaaaagt tcacatttaa ctgggcattc tgtatttaat tggtaatctg 2280
agatggcagg gaacagcatc agcatggtgt gagggatagg catttttttca ttgtgtacag 2340 cttgtaaatc agtattttta aaactcaaag ttaatggctt gggcatattt agaaaagagt 2400
tgccgcacgg acttgaaccc tgtattccta aaatctagga tcttgttctg atggtctgca 2460
caactggctg gggtgtcca gccactgtcc ctcttgcctg ggctccccag ggcagttctg 2520
tcagcctctc catttccatt cctgttccag caaaacccaa ctgatagcac agcagcattt 2580
cagcctgtct acctctgtgc ccacatacct ggatgtctac cagccagaaa ggtggcttag 2640
atttggttcc tgtgggtgga ttatggcccc cagaacttcc ctgtgcttgc tgggggtgtg 2700
gagtggaaag agcaggaaat gggggaccct ccgatactct atgggggtcc tccaagtctc 2760
tttgtgcaag ttagggtaat aatcaatatg gagctaagaa agagaagggg aactatgctt 2820
tagaacagga cactgtgcca ggagcattgc agaaattata tggttttcac gacagttctt 2880
tttggtaggt actgttatta tcctcagttt gcagatgagg aaactgagac ccagaaaggt 2940
taaataactt gctagggtca cacaagtcat aactgacaaa gcctgattca aacccaggtc 3000
tccctaacct ttaaggtttc tatgacgcca gctctcctag ggagtttgtc ttcagatgtc 3060
ttggctctag gtgtcaaaaa aagacttggt gtcaggcagg cataggttca agtcccaact 3120
ctgtcactta ccaactgtga ctaggtgatt gaactgacca tggaacctgg tcacatgcag 3180
gagcaggatg gtgaagggtt cttgaaggca cttaggcagg acatttaggc aggagagaaa 3240
acctggaaac agaagagctg tctccaaaaa tacccactgg ggaagcaggt tgtcatgtgg 3300
gccatgaatg ggacctgttc tggggtaacc acgtgcggac cgagcggccg caggaacccc 3360
tagtgatgga gttggccact ccctctctgc gcgctcgctc gctcactgag gccgggcgac 3420
caaaggtcgc ccgacgcccg ggctttgccc gggcggcctc agtgagcgag cgagcgcgca 3480
g 3481

<210> SEQ ID NO 61
<211> LENGTH: 2327
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 61
cgcgctcgct cgctcactga ggccgcccgg gcaaagcccg ggcgtcgggc gacctttggt 60
cgcccggcct cagtgagcga gcgagcgcgc agagagggag tggggtacca cgcgtttgtc 120
ctctccctgc ttggccttaa ccagccacat ttctcaactg accccactca ctgcagaggt 180
gaaaactacc atgccaggtc ctgctggctg ggggaggggt gggcaatagg cctggatttg 240
ccagagctgc cactgtagat gtagtcatat ttacgatttc ccttcacctc ttattaccct 300
ggtggtggtg gtgggggggg gggggtgctc tctcagcaac ccccaccccgg gatcttgagg 360
agaaagaggg cagagaaaag agggaatggg actggcccag atcccagccc cacagccggg 420
cttccacatg gccgagcagg aactccagag caggagcaca caaaggaggg ctttgatgcg 480
cctccagcca ggcccaggcc tctcccctct cccctttctc tctgggtctt cctttgcccc 540
actgagggcc tcctgtgagc ccgatttaac ggaaactgtg ggcggtgaga agttccttat 600
gacacactaa tcccaacctg ctgaccggac cacgcctcca gcggagggaa cctctagagc 660
tccaggacat tcaggtacca ggtagcccca aggaggagct gccgaatcga tggatcggga 720
actgaaaaac cagaaagtta actggtaagt ttagtctttt tgtcttttat ttcaggtccc 780
ggatccggtg gtggtgcaaa tcaaagaact gctcctcagt ggatgttgcc tttacttcta 840
ggcctgtacg gaagtgttac ttctgctcta aaagctgcgg aattgtaccc gccccgggat 900
ccatcgattg aattcgccac catgtcagaa ggggtgggca cgttccgcat ggtacctgaa 960
gaggaacagg agctccgtgc ccaactggag cagctcacaa ccaaggacca tggacctgtc 1020
tttggcccgt gcagccagct gccccgccac accttgcaga aggccaagga tgagctgaac 1080
gagagagagg agacccggga ggaggcagtg cgagagctgc aggagatggt gcaggcgcag 1140
gcggcctcgg gggaggagct ggcggtggcc gtggcggaga gggtgcaaga gaaggacagc 1200
ggcttcttcc tgcgcttcat ccgcgcacgg aagttcaacg tgggccgtgc ctatgagctg 1260
ctcagaggct atgtgaattt ccggctgcag taccctgagc tctttgacag cctgtcccca 1320
gaggctgtcc gctgcaccat tgaagctggc taccctggtg tcctctctag tcgggacaag 1380
tatggccgag tggtcatgct cttcaacatt gagaactggc aaagtcaaga aatcaccttt 1440
gatgagatct tgcaggcata ttgcttcatc ctggagaagc tgctggagaa tgaggaaact 1500
caaatcaatg gcttctgcat cattgagaac ttcaagggct ttaccatgca gcaggctgct 1560
agtctccgga cttcagatct caggaagatg gtggacatgc tccaggattc cttcccagcc 1620
cggttcaaag ccatccactt catccaccag ccatggtact tcaccacgac ctacaatgtg 1680
gtcaagccct tcttgaagag caagctgctt gagagggtct ttgtccacgg ggatgacctt 1740
tctggtttct accaggagat cgatgagaac atcctgccct ctgacttcgg gggcacgctg 1800
cccaagtatg atggcaaggc cgttgctgag cagctctttg gcccccaggc ccaagctgag 1860
aacacagcct tctgaggatc gtaccggtcg acctgcagaa gcttgcctcg agcagcgctg 1920
ctcgagagat ctggatcata atcagccata ccacatttgt agaggtttta cttgctttaa 1980
aaaacctccc acacctcccc ctgaacctga aacataaaat gaatgcaatt gttgttgtta 2040
acttgtttat tgcagcttat aatggttaca aataaagcaa tagcatcaca aatttcacaa 2100
ataaagcatt tttttcactg cattctagtt gtggtttgtc caaactcatc aatgtatctt 2160
atcatgtctg gtaaccacgt gcggaccgag cggccgcagg aacccctagt gatggagttg 2220
gccactccct ctctgcgcgc tcgctcgctc actgaggccg ggcgaccaaa ggtcgcccga 2280
cgcccgggct ttgcccgggc ggcctcagtg agcgagcgag cgcgcag 2327

<210> SEQ ID NO 62
<211> LENGTH: 236
<212> TYPE: DNA
<213> ORGANISM: Simian virus 40

<400> SEQUENCE: 62
agacatgata agatacattg atgagtttgg acaaaccaca actagaatgc agtgaaaaaa 60
atgctttatt tgtgaaattt gtgatgctat tgctttattt gtaaccatta taagctgcaa 120
taaacaagtt aacaacaaca attgcattca ttttatgttt caggttcagg gggaggtgtg 180
ggaggttttt taaagcaagt aaaacctcta caaatgtggt atggctgatt atgatc 236

<210> SEQ ID NO 63
<211> LENGTH: 954
<212> TYPE: DNA
<213> ORGANISM: Homo sapiens

<400> SEQUENCE: 63
tcagaaggct gtgttctcag cttgggcctg ggggccaaag agctgctcag caacggcctt 60
gccatcatac ttgggcagcg tgcccccgaa gtcagagggc aggatgttct catcgatctc 120
ctggtagaaa ccagaaaggt catccccgtg gacaaagacc ctctcaagca gcttgctctt 180
caagaagggc ttgaccacat tgtaggtcgt ggtgaagtac catggctggt ggatgaagtg 240
gatggctttg aaccgggctg ggaaggaatc ctggagcatg tccaccatct tcctgagatc 300
tgaagtccgg agactagcag cctgctgcat ggtaaagccc ttgaagttct caatgatgca 360
gaagccattg atttgagttt cctcattctc cagcagcttc tccaggatga agcaatatgc 420
ctgcaagatc tcatcaaagg tgatttcttg actttgccag ttctcaatgt tgaagagcat 480
gaccactcgg ccatacttgt cccgactaga gaggacacca gggtagccag cttcaatggt 540
gcagcggaca gcctctgggg acaggctgtc aaagagctca gggtactgca gccggaaatt 600
cacatagcct ctgagcagct cataggcacg gcccacgttg aacttccgtg cgcggatgaa 660
gcgcaggaag aagccgctgt ccttctcttg caccctctcc gccacggcca ccgccagctc 720
ctcccccgag gccgcctgcg cctgcaccat ctcctgcagc tctcgcactg cctcctcccg 780
ggtctcctct ctctcgttca gctcatcctt ggccttctgc aaggtgtggc ggggcagctg 840
gctgcacggg ccaaagacag gtccatggtc cttggttgtg agctgctcca gttgggcacg 900
gagctcctgt tcctcttcag gtaccatgcg gaacgtgccc accccttctg acat 954

<210> SEQ ID NO 64
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 64 ggtggc 6

<210> SEQ ID NO 65
<211> LENGTH: 183
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65
ggatcccggg gcgggtacaa ttccgcagct tttagagcag aagtaacact tccgtacagg 60
cctagaagta aaggcaacat ccactgagga gcagttcttt gatttgcacc accaccggat 120
ccgggacctg aaataaaaga caaaaagact aaacttacca gttaactttc tggtttttca 180
gtt 183

<210> SEQ ID NO 66
<211> LENGTH: 590
<212> TYPE: DNA
<213> ORGANISM: Homo sapiens

<400> SEQUENCE: 66
tcggcagctc ctccttgggg ctacctggta cctgaatgtc ctggagctct agaggttccc 60
tccgctggag gcgtggtccg gtcagcaggt tgggattagt gtgtcataag gaacttctca 120
ccgcccacag tttccgttaa atcgggctca caggaggccc tcagtggggc aaaggaagac 180
ccagagagaa aggggagagg ggagaggcct gggcctggct ggaggcgcat caaagccctc 240
ctttgtgtgc tcctgctctg gagttcctgc tcggccatgt ggaagcccgg ctgtggggct 300
gggatctggg ccagtcccat tccctctttt ctctgccctc tttctcctca agatcccggg 360
gtggggttgc tgagagagca cccccccccc cccaccacca ccaccagggt aataagaggt 420
gaagggaaat cgtaaatatg actacatcta cagtggcagc tctggcaaat ccaggcctat 480
tgcccacccc tcccccagcc agcaggacct ggcatggtag ttttcacctc tgcagtgagt 540
ggggtcagtt gagaaatgtg gctggttaag gccaagcagg gagaggacaa 590

<210> SEQ ID NO 67
<211> LENGTH: 720
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67
ttacttgtac agctcgtcca tgccgagagt gatcccggcg gcggtcacga actccagcag 60
gaccatgtga tcgcgcttct cgttggggtc tttgctcagg gcggactggg tgctcaggta 120
gtggttgtcg ggcagcagca cggggccgtc gccgatgggg gtgttctgct ggtagtggtc 180
ggcgagctgc acgctgccgt cctcgatgtt gtggcggatc ttgaagttca ccttgatgcc 240
gttcttctgc ttgtcggcca tgatatagac gttgtggctg ttgtagttgt actccagctt 300
gtgccccagg atgttgccgt cctccttgaa gtcgatgccc ttcagctcga tgcggttcac 360
cagggtgtcg ccctcgaact tcacctcggc gcgggtcttg tagttgccgt cgtccttgaa 420
gaagatggtg cgctcctgga cgtagccttc gggcatggcg gacttgaaga agtcgtgctg 480
cttcatgtgg tcggggtagc ggctgaagca ctgcacgccg taggtcaggg tggtcacgag 540
ggtgggccag ggcacgggca gcttgccggt ggtgcagatg aacttcaggg tcagcttgcc 600
gtaggtggca tcgccctcgc cctcgccgga cacgctgaac ttgtggccgt ttacgtcgcc 660
gtccagctcg accaggatgg gcaccacccc ggtgaacagc tcctcgccct tgctcaccat 720

<210> SEQ ID NO 68
<211> LENGTH: 598
<212> TYPE: PRT
<213> ORGANISM: Adeno-associated virus

<400> SEQUENCE: 68

Met Ala Pro Gly Lys Lys Arg Pro Val Glu His Ser Pro Val Glu Pro
1               5                   10                  15

Asp Ser Ser Ser Gly Thr Gly Lys Ala Gly Gln Gln Pro Ala Arg Lys
            20                  25                  30

Arg Leu Asn Phe Gly Gln Thr Gly Asp Ala Asp Ser Val Pro Asp Pro
        35                  40                  45

Gln Pro Leu Gly Gln Pro Pro Ala Ala Pro Ser Gly Leu Gly Thr Asn
    50                  55                  60

Thr Met Ala Thr Gly Ser Gly Ala Pro Met Ala Asp Asn Asn Glu Gly
65                  70                  75                  80

Ala Asp Gly Val Gly Asn Ser Ser Gly Asn Trp His Cys Asp Ser Thr
                85                  90                  95

Trp Met Gly Asp Arg Val Ile Thr Thr Ser Thr Arg Thr Trp Ala Leu
            100                 105                 110

Pro Thr Tyr Asn Asn His Leu Tyr Lys Gln Ile Ser Ser Gln Ser Gly
        115                 120                 125

Ala Ser Asn Asp Asn His Tyr Phe Gly Tyr Ser Thr Pro Trp Gly Tyr
    130                 135                 140

Phe Asp Phe Asn Arg Phe His Cys His Phe Ser Pro Arg Asp Trp Gln
145                 150                 155                 160

Arg Leu Ile Asn Asn Asn Trp Gly Phe Arg Pro Lys Arg Leu Asn Phe
                165                 170                 175

Lys Leu Phe Asn Ile Gln Val Lys Glu Val Thr Gln Asn Asp Gly Thr
            180                 185                 190

Thr Thr Ile Ala Asn Asn Leu Thr Ser Thr Val Gln Val Phe Thr Asp
        195                 200                 205

Ser Glu Tyr Gln Leu Pro Tyr Val Leu Gly Ser Ala His Gln Gly Cys
    210                 215                 220

Leu Pro Pro Phe Pro Ala Asp Val Phe Met Val Pro Gln Tyr Gly Tyr
225                 230                 235                 240

Leu Thr Leu Asn Asn Gly Ser Gln Ala Val Gly Arg Ser Ser Phe Tyr
                245                 250                 255

Cys Leu Glu Tyr Phe Pro Ser Gln Met Leu Arg Thr Gly Asn Asn Phe
            260                 265                 270

Thr Phe Ser Tyr Thr Phe Glu Asp Val Pro Phe His Ser Ser Tyr Ala
        275                 280                 285

His Ser Gln Ser Leu Asp Arg Leu Met Asn Pro Leu Ile Asp Gln Tyr
    290                 295                 300

Leu Tyr Tyr Leu Ser Arg Thr Asn Thr Pro Ser Gly Thr Thr Thr Gln
305                 310                 315                 320

Ser Arg Leu Gln Phe Ser Gln Ala Gly Ala Ser Asp Ile Arg Asp Gln
                325                 330                 335

Ser Arg Asn Trp Leu Pro Gly Pro Cys Tyr Arg Gln Gln Arg Val Ser
            340                 345                 350

Lys Thr Ser Ala Asp Asn Asn Asn Ser Glu Tyr Ser Trp Thr Gly Ala
        355                 360                 365

Thr Lys Tyr His Leu Asn Gly Arg Asp Ser Leu Val Asn Pro Gly Pro
    370                 375                 380

Ala Met Ala Ser His Lys Asp Asp Glu Glu Lys Phe Phe Pro Gln Ser
385                 390                 395                 400

Gly Val Leu Ile Phe Gly Lys Gln Gly Ser Glu Lys Thr Asn Val Asp

```
                405                 410                 415

Ile Glu Lys Val Met Ile Thr Asp Glu Glu Glu Ile Arg Thr Thr Asn
            420                 425                 430

Pro Val Ala Thr Glu Gln Tyr Gly Ser Val Ser Thr Asn Leu Gln Arg
        435                 440                 445

Gly Asn Arg Gln Ala Ala Thr Ala Asp Val Asn Thr Gln Gly Val Leu
    450                 455                 460

Pro Gly Met Val Trp Gln Asp Arg Asp Val Tyr Leu Gln Gly Pro Ile
465                 470                 475                 480

Trp Ala Lys Ile Pro His Thr Asp Gly His Phe His Pro Ser Pro Leu
                485                 490                 495

Met Gly Gly Phe Gly Leu Lys His Pro Pro Pro Gln Ile Leu Ile Lys
            500                 505                 510

Asn Thr Pro Val Pro Ala Asn Pro Ser Thr Thr Phe Ser Ala Ala Lys
        515                 520                 525

Phe Ala Ser Phe Ile Thr Gln Tyr Ser Thr Gly Gln Val Ser Val Glu
    530                 535                 540

Ile Glu Trp Glu Leu Gln Lys Glu Asn Ser Lys Arg Trp Asn Pro Glu
545                 550                 555                 560

Ile Gln Tyr Thr Ser Asn Tyr Asn Lys Ser Val Asn Val Asp Phe Thr
                565                 570                 575

Val Asp Thr Asn Gly Val Tyr Ser Glu Pro Arg Pro Ile Gly Thr Arg
            580                 585                 590

Tyr Leu Thr Arg Asn Leu
        595


<210> SEQ ID NO 69
<211> LENGTH: 533
<212> TYPE: PRT
<213> ORGANISM: Adeno-associated virus

<400> SEQUENCE: 69

Met Ala Thr Gly Ser Gly Ala Pro Met Ala Asp Asn Asn Glu Gly Ala
1               5                   10                  15

Asp Gly Val Gly Asn Ser Ser Gly Asn Trp His Cys Asp Ser Thr Trp
            20                  25                  30

Met Gly Asp Arg Val Ile Thr Thr Ser Thr Arg Thr Trp Ala Leu Pro
        35                  40                  45

Thr Tyr Asn Asn His Leu Tyr Lys Gln Ile Ser Ser Gln Ser Gly Ala
    50                  55                  60

Ser Asn Asp Asn His Tyr Phe Gly Tyr Ser Thr Pro Trp Gly Tyr Phe
65                  70                  75                  80

Asp Phe Asn Arg Phe His Cys His Phe Ser Pro Arg Asp Trp Gln Arg
                85                  90                  95

Leu Ile Asn Asn Asn Trp Gly Phe Arg Pro Lys Arg Leu Asn Phe Lys
            100                 105                 110

Leu Phe Asn Ile Gln Val Lys Glu Val Thr Gln Asn Asp Gly Thr Thr
        115                 120                 125

Thr Ile Ala Asn Asn Leu Thr Ser Thr Val Gln Val Phe Thr Asp Ser
    130                 135                 140

Glu Tyr Gln Leu Pro Tyr Val Leu Gly Ser Ala His Gln Gly Cys Leu
145                 150                 155                 160

Pro Pro Phe Pro Ala Asp Val Phe Met Val Pro Gln Tyr Gly Tyr Leu
                165                 170                 175
```

```
Thr Leu Asn Asn Gly Ser Gln Ala Val Gly Arg Ser Ser Phe Tyr Cys
            180                 185                 190

Leu Glu Tyr Phe Pro Ser Gln Met Leu Arg Thr Gly Asn Asn Phe Thr
        195                 200                 205

Phe Ser Tyr Thr Phe Glu Asp Val Pro Phe His Ser Ser Tyr Ala His
    210                 215                 220

Ser Gln Ser Leu Asp Arg Leu Met Asn Pro Leu Ile Asp Gln Tyr Leu
225                 230                 235                 240

Tyr Tyr Leu Ser Arg Thr Asn Thr Pro Ser Gly Thr Thr Thr Gln Ser
                245                 250                 255

Arg Leu Gln Phe Ser Gln Ala Gly Ala Ser Asp Ile Arg Asp Gln Ser
            260                 265                 270

Arg Asn Trp Leu Pro Gly Pro Cys Tyr Arg Gln Gln Arg Val Ser Lys
        275                 280                 285

Thr Ser Ala Asp Asn Asn Asn Ser Glu Tyr Ser Trp Thr Gly Ala Thr
    290                 295                 300

Lys Tyr His Leu Asn Gly Arg Asp Ser Leu Val Asn Pro Gly Pro Ala
305                 310                 315                 320

Met Ala Ser His Lys Asp Asp Glu Glu Lys Phe Phe Pro Gln Ser Gly
                325                 330                 335

Val Leu Ile Phe Gly Lys Gln Gly Ser Glu Lys Thr Asn Val Asp Ile
            340                 345                 350

Glu Lys Val Met Ile Thr Asp Glu Glu Glu Ile Arg Thr Thr Asn Pro
        355                 360                 365

Val Ala Thr Glu Gln Tyr Gly Ser Val Ser Thr Asn Leu Gln Arg Gly
    370                 375                 380

Asn Arg Gln Ala Ala Thr Ala Asp Val Asn Thr Gln Gly Val Leu Pro
385                 390                 395                 400

Gly Met Val Trp Gln Asp Arg Asp Val Tyr Leu Gln Gly Pro Ile Trp
                405                 410                 415

Ala Lys Ile Pro His Thr Asp Gly His Phe His Pro Ser Pro Leu Met
            420                 425                 430

Gly Gly Phe Gly Leu Lys His Pro Pro Pro Gln Ile Leu Ile Lys Asn
        435                 440                 445

Thr Pro Val Pro Ala Asn Pro Ser Thr Thr Phe Ser Ala Ala Lys Phe
    450                 455                 460

Ala Ser Phe Ile Thr Gln Tyr Ser Thr Gly Gln Val Ser Val Glu Ile
465                 470                 475                 480

Glu Trp Glu Leu Gln Lys Glu Asn Ser Lys Arg Trp Asn Pro Glu Ile
                485                 490                 495

Gln Tyr Thr Ser Asn Tyr Asn Lys Ser Val Asn Val Asp Phe Thr Val
            500                 505                 510

Asp Thr Asn Gly Val Tyr Ser Glu Pro Arg Pro Ile Gly Thr Arg Tyr
        515                 520                 525

Leu Thr Arg Asn Leu
    530


<210> SEQ ID NO 70
<211> LENGTH: 601
<212> TYPE: PRT
<213> ORGANISM: Adeno-associated virus

<400> SEQUENCE: 70

Met Ala Pro Gly Lys Lys Arg Pro Val Glu Pro Ser Pro Gln Arg Ser
1               5                   10                  15
```

-continued

```
Pro Asp Ser Ser Thr Gly Ile Gly Lys Lys Gly Gln Gln Pro Ala Arg
            20                  25                  30

Lys Arg Leu Asn Phe Gly Gln Thr Gly Asp Ser Glu Ser Val Pro Asp
        35                  40                  45

Pro Gln Pro Leu Gly Glu Pro Pro Ala Ala Pro Ser Gly Val Gly Pro
    50                  55                  60

Asn Thr Met Ala Ala Gly Gly Gly Ala Pro Met Ala Asp Asn Asn Glu
65                  70                  75                  80

Gly Ala Asp Gly Val Gly Ser Ser Ser Gly Asn Trp His Cys Asp Ser
                85                  90                  95

Thr Trp Leu Gly Asp Arg Val Ile Thr Thr Ser Thr Arg Thr Trp Ala
            100                 105                 110

Leu Pro Thr Tyr Asn Asn His Leu Tyr Lys Gln Ile Ser Asn Gly Thr
        115                 120                 125

Ser Gly Gly Ala Thr Asn Asp Asn Thr Tyr Phe Gly Tyr Ser Thr Pro
    130                 135                 140

Trp Gly Tyr Phe Asp Phe Asn Arg Phe His Cys His Phe Ser Pro Arg
145                 150                 155                 160

Asp Trp Gln Arg Leu Ile Asn Asn Asn Trp Gly Phe Arg Pro Lys Arg
                165                 170                 175

Leu Ser Phe Lys Leu Phe Asn Ile Gln Val Lys Glu Val Thr Gln Asn
            180                 185                 190

Glu Gly Thr Lys Thr Ile Ala Asn Asn Leu Thr Ser Thr Ile Gln Val
        195                 200                 205

Phe Thr Asp Ser Glu Tyr Gln Leu Pro Tyr Val Leu Gly Ser Ala His
    210                 215                 220

Gln Gly Cys Leu Pro Pro Phe Pro Ala Asp Val Phe Met Ile Pro Gln
225                 230                 235                 240

Tyr Gly Tyr Leu Thr Leu Asn Asn Gly Ser Gln Ala Val Gly Arg Ser
                245                 250                 255

Ser Phe Tyr Cys Leu Glu Tyr Phe Pro Ser Gln Met Leu Arg Thr Gly
            260                 265                 270

Asn Asn Phe Gln Phe Thr Tyr Thr Phe Glu Asp Val Pro Phe His Ser
        275                 280                 285

Ser Tyr Ala His Ser Gln Ser Leu Asp Arg Leu Met Asn Pro Leu Ile
    290                 295                 300

Asp Gln Tyr Leu Tyr Tyr Leu Ser Arg Thr Gln Thr Thr Gly Gly Thr
305                 310                 315                 320

Ala Asn Thr Gln Thr Leu Gly Phe Ser Gln Gly Gly Pro Asn Thr Met
                325                 330                 335

Ala Asn Gln Ala Lys Asn Trp Leu Pro Gly Pro Cys Tyr Arg Gln Gln
            340                 345                 350

Arg Val Ser Thr Thr Thr Gly Gln Asn Asn Asn Ser Asn Phe Ala Trp
        355                 360                 365

Thr Ala Gly Thr Lys Tyr His Leu Asn Gly Arg Asn Ser Leu Ala Asn
    370                 375                 380

Pro Gly Ile Ala Met Ala Thr His Lys Asp Asp Glu Glu Arg Phe Phe
385                 390                 395                 400

Pro Ser Asn Gly Ile Leu Ile Phe Gly Lys Gln Asn Ala Ala Arg Asp
                405                 410                 415

Asn Ala Asp Tyr Ser Asp Val Met Leu Thr Ser Glu Glu Glu Ile Lys
            420                 425                 430
```

```
Thr Thr Asn Pro Val Ala Thr Glu Glu Tyr Gly Ile Val Ala Asp Asn
        435                 440                 445

Leu Gln Gln Gln Asn Thr Ala Pro Gln Ile Gly Thr Val Asn Ser Gln
    450                 455                 460

Gly Ala Leu Pro Gly Met Val Trp Gln Asn Arg Asp Val Tyr Leu Gln
465                 470                 475                 480

Gly Pro Ile Trp Ala Lys Ile Pro His Thr Asp Gly Asn Phe His Pro
                485                 490                 495

Ser Pro Leu Met Gly Gly Phe Gly Leu Lys His Pro Pro Pro Gln Ile
            500                 505                 510

Leu Ile Lys Asn Thr Pro Val Pro Ala Asp Pro Pro Thr Thr Phe Asn
        515                 520                 525

Gln Ser Lys Leu Asn Ser Phe Ile Thr Gln Tyr Ser Thr Gly Gln Val
    530                 535                 540

Ser Val Glu Ile Glu Trp Glu Leu Gln Lys Glu Asn Ser Lys Arg Trp
545                 550                 555                 560

Asn Pro Glu Ile Gln Tyr Thr Ser Asn Tyr Tyr Lys Ser Thr Ser Val
                565                 570                 575

Asp Phe Ala Val Asn Thr Glu Gly Val Tyr Ser Glu Pro Arg Pro Ile
            580                 585                 590

Gly Thr Arg Tyr Leu Thr Arg Asn Leu
        595                 600


<210> SEQ ID NO 71
<211> LENGTH: 535
<212> TYPE: PRT
<213> ORGANISM: Adeno-associated virus

<400> SEQUENCE: 71

Met Ala Ala Gly Gly Gly Ala Pro Met Ala Asp Asn Asn Glu Gly Ala
1               5                   10                  15

Asp Gly Val Gly Ser Ser Ser Gly Asn Trp His Cys Asp Ser Thr Trp
            20                  25                  30

Leu Gly Asp Arg Val Ile Thr Thr Ser Thr Arg Thr Trp Ala Leu Pro
        35                  40                  45

Thr Tyr Asn Asn His Leu Tyr Lys Gln Ile Ser Asn Gly Thr Ser Gly
    50                  55                  60

Gly Ala Thr Asn Asp Asn Thr Tyr Phe Gly Tyr Ser Thr Pro Trp Gly
65                  70                  75                  80

Tyr Phe Asp Phe Asn Arg Phe His Cys His Phe Ser Pro Arg Asp Trp
                85                  90                  95

Gln Arg Leu Ile Asn Asn Asn Trp Gly Phe Arg Pro Lys Arg Leu Ser
            100                 105                 110

Phe Lys Leu Phe Asn Ile Gln Val Lys Glu Val Thr Gln Asn Glu Gly
        115                 120                 125

Thr Lys Thr Ile Ala Asn Asn Leu Thr Ser Thr Ile Gln Val Phe Thr
    130                 135                 140

Asp Ser Glu Tyr Gln Leu Pro Tyr Val Leu Gly Ser Ala His Gln Gly
145                 150                 155                 160

Cys Leu Pro Pro Phe Pro Ala Asp Val Phe Met Ile Pro Gln Tyr Gly
                165                 170                 175

Tyr Leu Thr Leu Asn Asn Gly Ser Gln Ala Val Gly Arg Ser Ser Phe
            180                 185                 190

Tyr Cys Leu Glu Tyr Phe Pro Ser Gln Met Leu Arg Thr Gly Asn Asn
        195                 200                 205
```

```
Phe Gln Phe Thr Tyr Thr Phe Glu Asp Val Pro Phe His Ser Ser Tyr
    210                 215                 220

Ala His Ser Gln Ser Leu Asp Arg Leu Met Asn Pro Leu Ile Asp Gln
225                 230                 235                 240

Tyr Leu Tyr Tyr Leu Ser Arg Thr Gln Thr Thr Gly Gly Thr Ala Asn
                245                 250                 255

Thr Gln Thr Leu Gly Phe Ser Gln Gly Gly Pro Asn Thr Met Ala Asn
            260                 265                 270

Gln Ala Lys Asn Trp Leu Pro Gly Pro Cys Tyr Arg Gln Gln Arg Val
        275                 280                 285

Ser Thr Thr Thr Gly Gln Asn Asn Asn Ser Asn Phe Ala Trp Thr Ala
    290                 295                 300

Gly Thr Lys Tyr His Leu Asn Gly Arg Asn Ser Leu Ala Asn Pro Gly
305                 310                 315                 320

Ile Ala Met Ala Thr His Lys Asp Asp Glu Glu Arg Phe Phe Pro Ser
                325                 330                 335

Asn Gly Ile Leu Ile Phe Gly Lys Gln Asn Ala Ala Arg Asp Asn Ala
            340                 345                 350

Asp Tyr Ser Asp Val Met Leu Thr Ser Glu Glu Glu Ile Lys Thr Thr
        355                 360                 365

Asn Pro Val Ala Thr Glu Glu Tyr Gly Ile Val Ala Asp Asn Leu Gln
    370                 375                 380

Gln Gln Asn Thr Ala Pro Gln Ile Gly Thr Val Asn Ser Gln Gly Ala
385                 390                 395                 400

Leu Pro Gly Met Val Trp Gln Asn Arg Asp Val Tyr Leu Gln Gly Pro
                405                 410                 415

Ile Trp Ala Lys Ile Pro His Thr Asp Gly Asn Phe His Pro Ser Pro
            420                 425                 430

Leu Met Gly Gly Phe Gly Leu Lys His Pro Pro Pro Gln Ile Leu Ile
        435                 440                 445

Lys Asn Thr Pro Val Pro Ala Asp Pro Pro Thr Thr Phe Asn Gln Ser
    450                 455                 460

Lys Leu Asn Ser Phe Ile Thr Gln Tyr Ser Thr Gly Gln Val Ser Val
465                 470                 475                 480

Glu Ile Glu Trp Glu Leu Gln Lys Glu Asn Ser Lys Arg Trp Asn Pro
                485                 490                 495

Glu Ile Gln Tyr Thr Ser Asn Tyr Tyr Lys Ser Thr Ser Val Asp Phe
            500                 505                 510

Ala Val Asn Thr Glu Gly Val Tyr Ser Glu Pro Arg Pro Ile Gly Thr
        515                 520                 525

Arg Tyr Leu Thr Arg Asn Leu
    530                 535
```